United States Patent
Wells et al.

(10) Patent No.: US 11,939,379 B2
(45) Date of Patent: Mar. 26, 2024

(54) ANTIBODY CHEMICALLY INDUCED DIMERIZER (AbCID) AS MOLECULAR SWITCHES FOR REGULATING CELLULAR THERAPIES

(71) Applicant: The Regents of the University of California, Oakland, CA (US)

(72) Inventors: James A Wells, San Francisco, CA (US); Zachary B. Hill, San Francisco, CA (US); Alexander J. Martinko, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 12 days.

(21) Appl. No.: 16/614,786

(22) PCT Filed: May 21, 2018

(86) PCT No.: PCT/US2018/033750
§ 371 (c)(1),
(2) Date: Nov. 18, 2019

(87) PCT Pub. No.: WO2018/213848
PCT Pub. Date: Nov. 22, 2018

(65) Prior Publication Data
US 2020/0255519 A1 Aug. 13, 2020

Related U.S. Application Data
(60) Provisional application No. 62/508,809, filed on May 19, 2017.

(51) Int. Cl.
| | | |
|---|---|---|
| *C07K 16/28* | (2006.01) | |
| *A61K 35/17* | (2015.01) | |
| *A61K 39/00* | (2006.01) | |
| *A61K 39/395* | (2006.01) | |

(52) U.S. Cl.
CPC .......... *C07K 16/2809* (2013.01); *A61K 35/17* (2013.01); *A61K 39/3955* (2013.01); *A61K 2039/5156* (2013.01); *C07K 2317/24* (2013.01); *C07K 2317/92* (2013.01); *C07K 2319/02* (2013.01); *C07K 2319/03* (2013.01); *C07K 2319/033* (2013.01); *C07K 2319/30* (2013.01)

(58) Field of Classification Search
CPC ............ C07K 16/2809; C07K 2317/92; C07K 2319/03; C07K 2319/30; A61K 35/17; A61K 39/3955; A61K 2039/5156
See application file for complete search history.

(56) References Cited

U.S. PATENT DOCUMENTS

| 7,964,565 | B2 * | 6/2011 | Harlan | A61P 31/04 514/18.7 |
|---|---|---|---|---|
| 2011/0286980 | A1 | 11/2011 | Brenner | |
| 2012/0014957 | A1 * | 1/2012 | Ghayur | A61P 17/02 424/136.1 |
| 2013/0071397 | A1 | 3/2013 | Schlessinger et al. | |
| 2016/0046730 | A1 | 2/2016 | Ghayur et al. | |
| 2016/0082056 | A1 * | 3/2016 | Marchini | A61K 31/635 424/93.6 |
| 2016/0326249 | A1 * | 11/2016 | Ng | C07K 16/2809 |
| 2018/0237533 | A1 * | 8/2018 | Juillerat | C07K 16/2803 |

FOREIGN PATENT DOCUMENTS

| EP | 2 759 551 A1 | 7/2014 |
|---|---|---|
| EP | 2 759 551 B1 | 7/2014 |
| WO | WO-97/031898 A1 | 9/1997 |
| WO | WO-2011/146862 A1 | 11/2011 |
| WO | WO-2014/151960 A2 | 9/2014 |
| WO | WO-2014/151960 A3 | 9/2014 |
| WO | WO-2015/017214 A1 | 2/2015 |

(Continued)

OTHER PUBLICATIONS

Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*

(Continued)

*Primary Examiner* — Meera Natarajan
*Assistant Examiner* — Cheom-Gil Cheong
(74) *Attorney, Agent, or Firm* — Mintz, Levin, Cohn, Ferris, Glovsky and Popeo, P.C.

(57) ABSTRACT

Chemically induced dimerizers (AbCIDs) have emerged as one of the most powerful tools to artificially regulate signaling pathways in cells; however, no facile method to identify or design these systems currently exists. The present invention provides a methodology to rapidly generate antibody-based chemically induced dimerizers (AbCIDs) from known small-molecule-protein complexes by selecting for synthetic antibodies that recognize the chemical epitope created by the bound small molecule. Success of this strategy is demonstrated by generating ten chemically-inducible antibodies against the BCL-xL/ABT-737 complex. Three of the antibodies are highly selective for the BCL-xL/ABT-737 complex over BCL-xL alone. Two exemplary important cellular applications of AbCIDs are demonstrated by applying them intracellularly to induce CRISPRa-mediated gene expression and extracellularly to regulate CAR T-cell activation with the small molecule, ABT-737. ABT-737 is not toxic at the concentrations used to activate AbCIDs in cells. AbCIDs provided by this invention are new and orthogonal AbCIDs, expanding the limited toolbox of available CIDs.

11 Claims, 42 Drawing Sheets

Specification includes a Sequence Listing.

(56) References Cited

FOREIGN PATENT DOCUMENTS

| WO | WO-2016/168769 | A1 | 10/2016 | | |
|---|---|---|---|---|---|
| WO | WO-2016/168773 | A2 | 10/2016 | | |
| WO | WO-2016/168773 | A3 | 10/2016 | | |
| WO | WO-2017/070554 | A1 | 4/2017 | | |
| WO | WO-2017070554 | A1 | * | 4/2017 | ............. C07K 16/44 |

OTHER PUBLICATIONS

Klimka et al., British Journal of Cancer, 2000, 83:252-260. (Year: 2000).*
Ward et al., Nature, 1989, 341:544-546. (Year: 1989).*
Cartellieri, M. et al. (Aug. 12, 2016). "Switching CAR T cells on and off: a novel modular platform for retargeting of T cells to AML blasts," *Blood Cancer* 6(8):e458.
Extended European Search Report dated Feb. 5, 2021, for EP Patent Application No. 18802749.4, 10 pages.
Gayda, S. et al. (Jun. 17, 2014, e-published Jun. 5, 2014). "Water channel in the binding site of a high affinity anti-methotrexate antibody," *Biochemistry* 53(23):3719-3726.
Hill, Z.B. et al. (Feb. 2018, e-published Dec. 4, 2017). "Human antibody-based chemically induced dimerizers for cell therapeutic applications," *Nature Chemical Biology* 14(2):112-117.
International Search Report dated Oct. 18, 2018, for PCT Application No. PCT/US2018/033750, filed May 21, 2018, 5 pages.
Kim, M.S. et al. (Mar. 4, 2015, e-published Feb. 24, 2015). "Redirection of genetically engineered CAR-T cells using bifunctional small molecules," *Journal of the American Chemical Society* 137(8):2832-2835.
Lee, E.F. et al. (Sep. 2007, e-published Jun. 15, 2007). "Crystal structure of ABT-737 complexed with Bcl-XL: implications for selectivity of antagonists of the Bcl-2 family," *Cell Death & Differentiation* 14(9):1711-1713.
MacCorkle, R.A. et al. (Mar. 31, 1998). "Synthetic activation of caspases: artificial death switches," *PNAS USA* 95(7):3655-3660.
Rodgers, D.T. et al. (Jan. 26, 2016, e-published Jan. 12, 2016). "Switch-mediated activation and retargeting of CAR-T cells for B-cell malignancies," *PNAS USA* 113(4):E459-E468.
Voβ, S et al. (Oct. 2015, e-published Sep. 29, 2015). "Chemically induced dimerization: reversible and spatiotemporal control of protein function in cells," *Curr Opin Chem Biol* 28:194-201.
Written Opinion dated Oct. 18, 2018, for PCT Application No. PCT/US2018/033750, filed May 21, 2018, 9 pages.
Di Stasi, A. et al. (Nov. 3, 2011). "Inducible apoptosis as a safety switch for adoptive cell therapy," *N Engl J Med* 365(18):1673-1683.
Straathof, K.C. et al. (Jun. 1, 2005, e-published Feb. 22, 2005). "An inducible caspase 9 safety switch for T-cell therapy," *Blood* 105(11):4247-4254.

\* cited by examiner

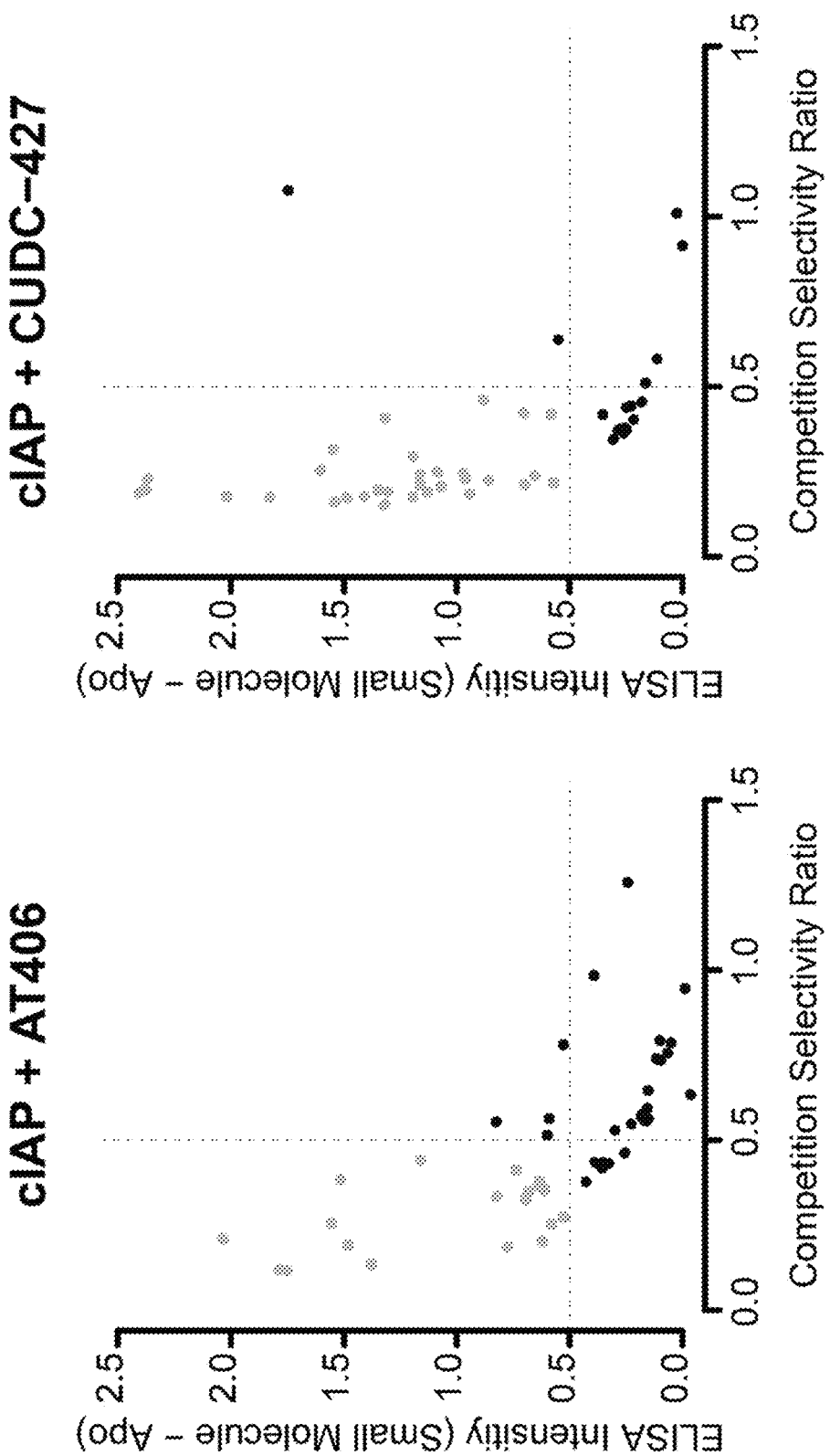

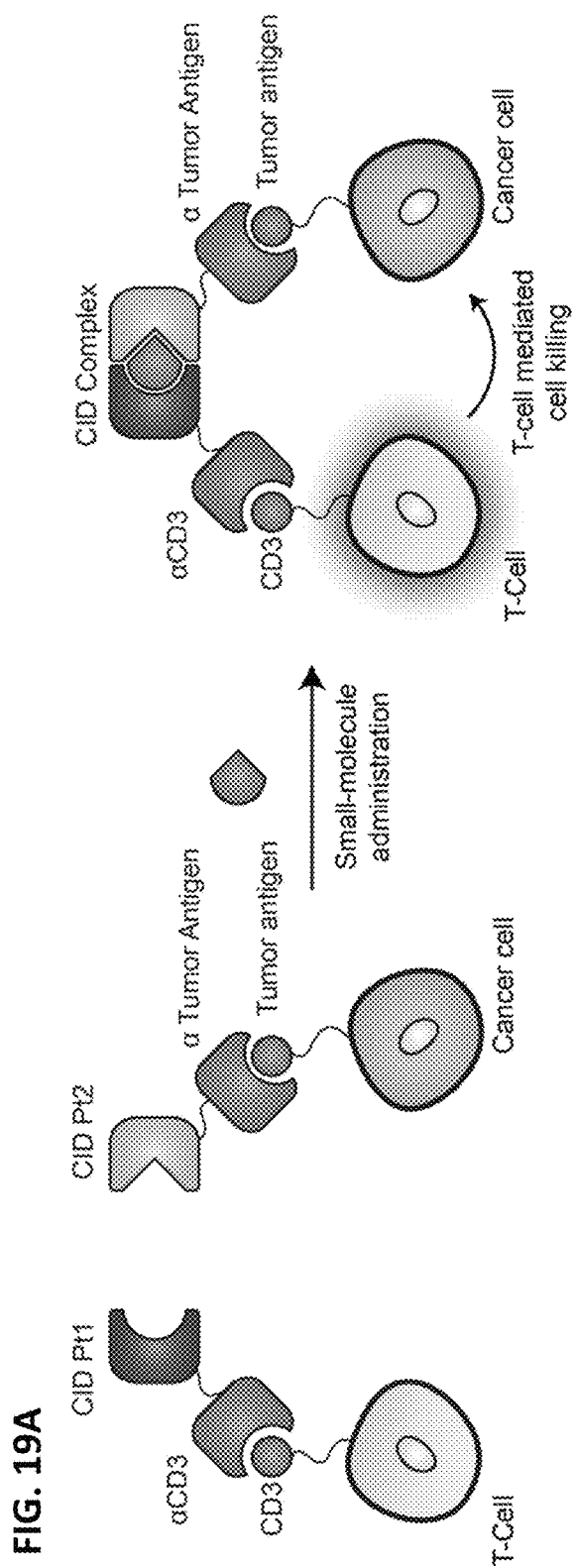
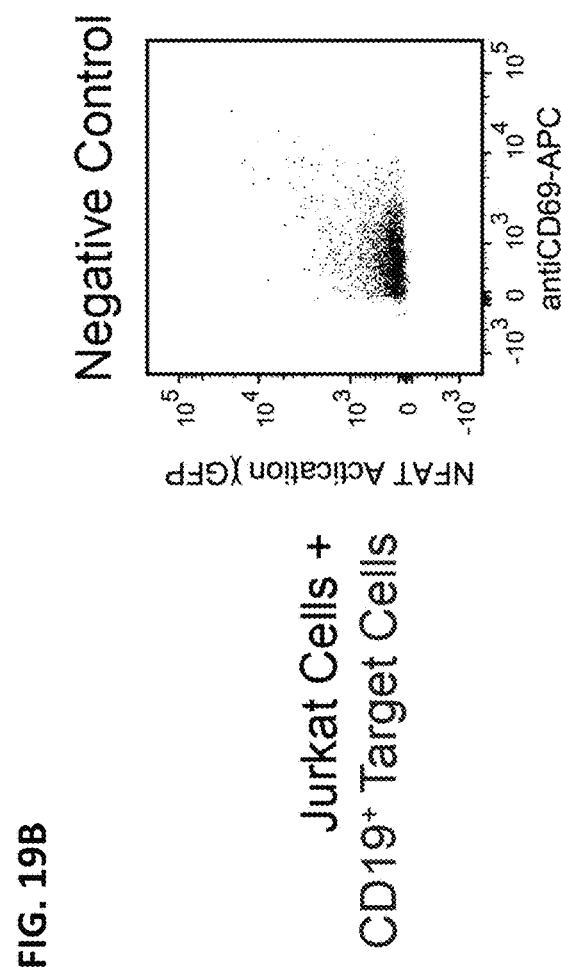
FIG. 19A
FIG. 19B

ANTIBODY CHEMICALLY INDUCED DIMERIZER (AbCID) AS MOLECULAR SWITCHES FOR REGULATING CELLULAR THERAPIES

CROSS REFERENCE TO RELATED APPLICATION

This application claims the benefit of priority to U.S. Provisional Patent Application No. 62/508,809 filed May 19, 2017, the entire contents of which are incorporated by reference herein and for all purposes.

STATEMENT AS TO RIGHTS TO INVENTIONS MADE UNDER FEDERALLY SPONSORED RESEARCH OR DEVELOPMENT

This invention was made with government support under grant nos. R01 CA191018 and R01 GM097316 awarded by the National Institutes of Health. The government has certain rights in the invention.

FIELD

The present disclosure relates to compositions and methods for regulating cellular therapies. In particular, the compositions include a general architecture for generating physiologically functional synthetic antibody chemically induced dimerizer (AbCID) complexes that function as molecular switches. Further provided are methods of using such compositions, such as for the treatment of various diseases and conditions.

BACKGROUND OF THE INVENTION

Chemically induced dimerizers (CIDs) are powerful tools for dose and temporal control over protein-protein interactions (Spencer, et al., *Science*, 262:1019-1024 (1993); Clackson, T., *Chemical Biology*, pgs. 227-249 (2008); Fegan, et al., *Chem. Rev.*, 110:33153336 (2010); Putyrski, et al., *FEBS Lett.*, 586:2097-2105 (2012)). CIDs have been applied to the development of artificial cellular circuits (Lienert, et al., *Nat. Rev. Mol. Cell Biol.*, 15:95107 (2014)), activating split-enzyme activity (Shekhawat, et al., *Curr. Opin. Chem. Biol.*, 15:789-797 (2011); Nguyen, et al., *Nat. Commun.*, 7:12009 (2016); Zetsche, et al., *Nat. Biotechnol.*, 33:139-142 (2015); Pelletier, et al., *Proc. Natl. Acad. Sci. USA*, 95:12141-12146 (1998)), and more recently used in the clinic as safety switches for next-generation T-cell therapies (Straathof, et al., *Blood*, 105:4247-4254 (2005); Di Stasi, et al., *N. Engl. J. Med.*, 365:1673-1683 (2011)). A number of homo- and hetero-CIDs have been developed but the vast majority are limited to pieces of natural proteins known to bind the small molecule inducers, such as the prototypical rapamycin-FKBP12-FRB system (Spencer, et al., *Science*, 262:1019-1024 (1993); Ho, et al., *Nature*, 382:822-826 (1996); Belshaw, et al., *Proc. Natl. Acad. Sci. USA*, 93:4604-4607 (1996); Rivera, et al., *Nat. Med.*, 2:1028-1032 (1996); Farrar, et al., *Nature*, 383:178-181 (1996); Miyamoto, et al., *Nat. Chem. Biol.*, 8:465-470 (2012); Erhart, et al., *Chem. Biol.*, 20:549-557 (2013); Kopytek, et al., *Chem. Biol.*, 7:313-321 (2000); Liang, et al., *Sci. Signal.*, 4, rs2 (2011); Czlapinski, et al., *J. Am. Chem. Soc.*, 130:13186-13187 (2008)). Currently, no general method to design or identify these tools exists. However, the expanded use of and interest in CIDs for multiplexed control of biological events in cells and animals necessitates invention of many more small-molecule-inducible systems. Moreover, CIDs have promise in human therapy but there is no systematic means of generating CID based on human derived parts to reduce or eliminate the risk of immunogenicity.

Previous workers have shown it is possible to use phage display to generate antibodies that could specifically bind to protein conformations "trapped" by binding of small molecules (Gao, et al., *Proc. Natl. Acad. Sci. USA*, 106:3071-3076 (2009); Rizk, et al., *Nat. Struct. Mol. Biol.*, 18:437-442 (2011); Staus, et al., *Nature*, 535:448-452 (2016); Thomsen, et al., *Proc. Natl. Acad. Sci. USA*, 110:8477-8482 (2013)). In these cases, the antibody shows an increased affinity for the small-molecule-bound form of the protein, similar to a CID. However, the antibody is often able to bind the protein in the trapped conformation, independent of the small molecule. For this reason, the selectivity of conformation-selective antibodies for the bound form over the apo form is limited, reducing their utility as selective CIDs. Thus, there is a need in the art for improved CIDs. Moreover, the application of CID technology for human therapy to regulate engineered proteins or cells is highly dependent on using human-derived protein scaffolds to reduce immunogenicity. To date the only CID system that contains fully human parts is the FKBP-FRB CID and the small molecules used to activate it are toxic either or lacking in drug-like properties in their own right. Thus, there is a need to expand the development of CIDs with human derived proteins or antibodies.

SUMMARY

Several aspects described herein relate to compositions and methods including an antibody chemically induced dimerizer (AbCID).

In one aspect, provided herein is a system comprising: (a) a first chemically-induced dimer (CID) component comprising (i) a first binding moiety capable of interacting with a small molecule to form a complex between the first CID component and the small molecule; and (ii) a first adapter moiety linked to the first binding moiety, or a first nucleic acid encoding polypeptide components of the first CID component; and (b) a second CID component comprising (i) a second binding moiety that specifically binds to the complex between the small molecule and the first CID component; and (ii) a second adapter moiety linked to the second binding moiety, or a second nucleic acid encoding polypeptide components of the second CID component, wherein the second binding moiety specifically binds to a site of the complex comprising at least a portion of the small molecule and a portion of the first binding moiety. In some embodiments, the system further comprises the small molecule, wherein the second CID component is bound to a complex between the small molecule and the first CID component at a site of the complex comprising at least a portion of the small molecule and a portion of the first binding moiety. In some embodiments, the site of the complex comprising at least a portion of the small molecule and a portion of the first binding moiety is an interface between the small molecule and a binding site of the first binding moiety for the small molecule, comprising at least one atom of the small molecule and one atom of the first binding moiety.

In some embodiments, according to any of the systems described above, the first binding moiety is a first antibody moiety that specifically binds to the small molecule. In some embodiments, the small molecule is methotrexate.

In some embodiments, according to any of the systems described above, the first binding moiety is derived from a naturally occurring binding partner of the small molecule, or a small molecule-binding variant thereof. In some embodiments, the naturally occurring binding partner is Bcl-2, Bcl-xL, FK506 binding protein (FKBP), or cellular inhibitor of apoptosis protein 1 (cIAP1). In some embodiments, the naturally occurring binding partner is Bcl-2 and the small molecule is ABT-199, ABT-263 or an analog thereof. In some embodiments, the naturally occurring binding partner is Bcl-xL and the small molecule is ABT-737 or an analog thereof. In some embodiments, the naturally occurring binding partner is FKBP and the small molecule is a synthetic ligand of rapamycin (SLF) having the structure of Formula (I) or an analog thereof. In some embodiments, the naturally occurring binding partner is cIAP1 and the small molecule is GDC-0152, LCL161, AT406, CUDC-427, Birinapant, or an analog thereof.

In some embodiments, according to any of the systems described above, the second binding moiety is an antibody moiety that specifically binds to a chemical-epitope comprising at least a portion of the small molecule and a portion of the first binding moiety.

In some embodiments, according to any of the systems described above, the second CID component binds to the complex of the first CID component and the small molecule with a dissociation constant ($K_d$) no more than about 1/500 times its $K_d$ for binding to each of the free first CID component and the free small molecule.

In another aspect, provided herein is a system comprising: (a) a first CID component comprising an ABT-737-binding domain of Bcl-xL, or a first nucleotide encoding polypeptide components of the first CID component; and (b) a second CID component comprising an antibody moiety capable of specifically binding to a complex between ABT-737 and the first CID component, or a second nucleic acid encoding polypeptide components of the second CID component, wherein the antibody moiety of the second CID component comprises heavy chain and light chain complementarity determining regions (CDRs) according to Table 1. In some embodiments, the ABT-737-binding domain comprises the amino acid sequence of SEQ ID NO: 314.

In another aspect, provided herein is a system comprising: (a) a first CID component comprising an ABT-199-binding domain of Bcl-2, or a first nucleotide encoding polypeptide components of the first CID component; and (b) a second CID component comprising an antibody moiety capable of specifically binding to a complex between ABT-199 and the first CID component, or a second nucleic acid encoding polypeptide components of the second CID component, wherein the antibody moiety of the second CID component comprises heavy chain and light chain complementarity determining regions (CDRs) according to Table 2. In some embodiments, the ABT-199-binding domain comprises the amino acid sequence of SEQ ID NO: 315.

In another aspect, provided herein is a system comprising: (a) a first CID component comprising an ABT-263-binding domain of Bcl-2, or a first nucleotide encoding polypeptide components of the first CID component; and (b) a second CID component comprising an antibody moiety capable of specifically binding to a complex between ABT-263 and the first CID component, or a second nucleic acid encoding polypeptide components of the second CID component, wherein the antibody moiety of the second CID component comprises heavy chain and light chain complementarity determining regions (CDRs) according to Table 3. In some embodiments, the ABT-263-binding domain comprises the amino acid sequence of SEQ ID NO: 315.

In another aspect, provided herein is a system comprising: (a) a first CID component comprising a synthetic ligand of rapamycin (SLF)-binding domain of FKBP, or a first nucleotide encoding polypeptide components of the first CID component, wherein the SLF has the structure of Formula (I); and (b) a second CID component comprising an antibody moiety capable of specifically binding to a complex between the SLF and the first CID component, or a second nucleic acid encoding polypeptide components of the second CID component, wherein the antibody moiety of the second CID component comprises heavy chain and light chain complementarity determining regions (CDRs) according to Table 4. In some embodiments, the SLF-binding domain comprises the amino acid sequence of SEQ ID NO: 316.

In another aspect, provided herein is a system comprising: (a) a first CID component comprising a GDC-0152-binding domain of cIAP1, or a first nucleotide encoding polypeptide components of the first CID component; and (b) a second CID component comprising an antibody moiety capable of specifically binding to a complex between GDC-0152 and the first CID component, or a second nucleic acid encoding polypeptide components of the second CID component, wherein the antibody moiety of the second CID component comprises heavy chain and light chain complementarity determining regions (CDRs) according to Table 5. In some embodiments, the GDC-0152-binding domain comprises the amino acid sequence of SEQ ID NO: 317.

In another aspect, provided herein is a system comprising: (a) a first CID component comprising a LCL161-binding domain of cIAP1, or a first nucleotide encoding polypeptide components of the first CID component; and (b) a second CID component comprising an antibody moiety capable of specifically binding to a complex between LCL161 and the first CID component, or a second nucleic acid encoding polypeptide components of the second CID component, wherein the antibody moiety of the second CID component comprises heavy chain and light chain complementarity determining regions (CDRs) according to Table 6. In some embodiments, the LCL161-binding domain comprises the amino acid sequence of SEQ ID NO: 317.

In another embodiments, provided herein is a system comprising: (a) a first CID component comprising a AT406-binding domain of cIAP1, or a first nucleotide encoding polypeptide components of the first CID component; and (b) a second CID component comprising an antibody moiety capable of specifically binding to a complex between AT406 and the first CID component, or a second nucleic acid encoding polypeptide components of the second CID component, wherein the antibody moiety of the second CID component comprises heavy chain and light chain complementarity determining regions (CDRs) according to Table 7. In some embodiments, the AT406-binding domain comprises the amino acid sequence of SEQ ID NO: 317.

In another embodiment, provided herein is a system comprising: (a) a first CID component comprising a CUDC-427-binding domain of cIAP1, or a first nucleotide encoding polypeptide components of the first CID component; and (b) a second CID component comprising an antibody moiety capable of specifically binding to a complex between CUDC-427 and the first CID component, or a second nucleic acid encoding polypeptide components of the second CID component, wherein the antibody moiety of the second CID component comprises heavy chain and light chain complementarity determining regions (CDRs) according to Table 8.

In some embodiments, the CUDC-427-binding domain comprises the amino acid sequence of SEQ ID NO: 317.

In another aspect, provided herein is a system comprising: (a) a first CID component comprising a methotrexate-binding Fab, or a first nucleotide encoding polypeptide components of the first CID component, wherein the methotrexate-binding Fab HC-CDR1, HC-CDR2, HC-CDR3, LC-CDR1, LC-CDR2, and LC-CDR3 comprise the amino acid sequences of SEQ ID NOs: 318, 319, 320, 321, 322, and 323, respectively; and (b) a second CID component comprising an antibody moiety capable of specifically binding to a complex between methotrexate and the first CID component, or a second nucleic acid encoding polypeptide components of the second CID component, wherein the antibody moiety of the second CID component comprises heavy chain and light chain complementarity determining regions (CDRs) according to Table 9.

In some embodiments, according to any of the systems described above, (a) the first adapter moiety comprises a DNA binding domain and the second adapter moiety comprises a transcriptional regulatory domain; or (b) the second adapter moiety comprises a DNA binding domain and the first adapter moiety comprises a transcriptional regulatory domain, wherein the first CID component and the second CID component are configured such that when dimerized in the presence of the small molecule to form the CID, the CID is capable of regulating transcription of a target gene. In some embodiments, (a) the transcriptional regulatory domain is a transcriptional activation domain, and the CID is capable of upregulating transcription of the target gene; or (b) the transcriptional regulatory domain is a transcriptional repressor domain, and the CID is capable of downregulating transcription of the target gene. In some embodiments, the DNA binding domain is derived from a naturally occurring transcriptional regulator. In some embodiments, the DNA binding domain is derived from an RNA-guided endonuclease or a DNA-guided endonuclease. In some embodiments, the RNA-guided endonuclease or DNA-guided endonuclease is catalytically dead. In some embodiments, the DNA binding domain is derived from a catalytically dead Cas9 (dCas9).

In some embodiments, according to any of the systems described above, the first CID component and the second CID component are configured such that when dimerized in the presence of the small molecule to form a CID associated with a target cell, the CID is capable of inducing target cell death. In some embodiments, the first adapter moiety and the second adapter moiety are together capable of inducing apoptosis in the target cell. In some embodiments, the first adapter moiety and/or the second adapter moiety are derived from a caspase protein. In some embodiments, the first adapter moiety and the second adapter moiety are derived from caspase-9. In some embodiments, the target cell is an engineered cell adoptively transferred to an individual. In some embodiments, the target cell is a T cell expressing a chimeric antigen receptor (CAR).

In some embodiments, according to any of the systems described above, the first CID component and the second CID component are configured such that when dimerized in the presence of the small molecule to form a CID associated with a T cell, the CID is a heterodimeric CAR capable of activating the T cell upon binding a target antigen. In some embodiments, (a) the first adapter moiety comprises (i) a transmembrane domain; (ii) a cytoplasmic co-stimulatory domain; and (iii) a cytoplasmic signaling domain; and the second adapter moiety comprises an extracellular antigen-binding moiety; or (b) the second adapter moiety comprises (i) a transmembrane domain; (ii) a cytoplasmic co-stimulatory domain; and (iii) a cytoplasmic signaling domain; and the first adapter moiety comprises an extracellular antigen-binding moiety; wherein the extracellular antigen-binding moiety specifically binds to the target antigen. In some embodiments, the CID component comprising the extracellular antigen-binding moiety further comprises a secretory signal peptide. In some embodiments, (a) the first adapter moiety comprises (i) a cytoplasmic co-stimulatory domain or a cytoplasmic signaling domain; (ii) a transmembrane domain; and (iii) an extracellular antigen-binding moiety; and the second adapter moiety comprises a cytoplasmic co-stimulatory domain or a cytoplasmic signaling domain; or (b) the second adapter moiety comprises (i) a cytoplasmic co-stimulatory domain or a cytoplasmic signaling domain; (ii) a transmembrane domain; and (iii) an extracellular antigen-binding moiety; and the first adapter moiety comprises a cytoplasmic co-stimulatory domain or a cytoplasmic signaling domain; wherein the extracellular antigen-binding moiety specifically binds to the target antigen. In some embodiments, the first adapter moiety comprises (i) a cytoplasmic co-stimulatory domain or a cytoplasmic signaling domain; and (ii) a transmembrane domain; and the second adapter moiety comprises (i) a cytoplasmic co-stimulatory domain or a cytoplasmic signaling domain; and (ii) a transmembrane domain; wherein the first or second CID component further comprises an extracellular antigen-binding moiety linked to its binding moiety; and wherein the extracellular antigen-binding moiety specifically binds to the target antigen. In some embodiments, the first and second CID components together comprise a cytoplasmic co-stimulatory domain and a cytoplasmic signaling domain.

In some embodiments, according to any of the systems described above, the first CID component and the second CID component are configured such that when dimerized in the presence of the small molecule to form a CID, the CID is a heterodimeric bispecific T cell engager capable of redirecting a T cell to a target cell. In some embodiments, (a) the first adapter moiety comprises a T cell antigen-binding moiety and the second adapter moiety comprises a target cell antigen-binding moiety; or (b) the second adapter moiety comprises a T cell antigen-binding moiety and the first adapter moiety comprises a target cell antigen-binding moiety. In some embodiments, the T cell antigen-binding moiety is an antibody moiety that specifically binds to CD3. In some embodiments, the target cell antigen-binding moiety is an antibody moiety that specifically binds to a cell surface antigen associated with a diseased cell. In some embodiments, the diseased cell is a cancer cell. In some embodiments, the target cell antigen-binding moiety is an antibody moiety that specifically binds to CD19.

In some embodiments, according to any of the systems described above, the first CID component and the second CID component are configured such that when dimerized in the presence of the small molecule to form a CID associated with an immune cell, the CID is a heterodimeric signaling molecule capable of modulating activation of the immune cell. In some embodiments, the first adapter moiety comprises (i) a transmembrane domain; and (ii) a cytoplasmic co-stimulatory domain; and the second adapter moiety comprises (i) a transmembrane domain; and (ii) a cytoplasmic co-stimulatory domain. In some embodiments, the first adapter moiety further comprises a cytoplasmic signaling domain and/or the second adapter moiety further comprises a cytoplasmic signaling domain. In some embodiments, the immune cell is a T cell. In some embodiments, the T cell is a CAR T cell.

In another aspect, provided herein is a method of selecting binding moieties from a binding molecule library, wherein the binding moieties specifically bind to a complex between a small molecule and a cognate binding moiety, comprising: (a) screening an input set of binding moieties for binding moieties that do not bind to the cognate binding moiety in the absence of the small molecule, thereby generating a set of counter selected binding moieties; and (b) screening an input set of binding moieties for binding moieties that bind to the complex of the small molecule and the cognate binding moiety, thereby generating a set of positively selected binding moieties; and (c) conducting one or more rounds of screening, wherein each round of screening comprises the screening of step (a) and the screening of step (b), such that a set of binding moieties that specifically bind to the complex between the small molecule and the cognate binding moiety is generated. In some embodiments, the method comprises two or more rounds of screening, and wherein (1) the input set of binding moieties of step (a) for the first round of screening is the binding molecule library, (2) the input set of binding moieties of step (b) for each round of screening is the set of counter selected binding moieties of step (a) from the given round of screening, (3) the input set of binding moieties of step (a) for each round of screening following the first round of screening is the set of positively selected binding moieties of step (b) from the previous round of screening, and (4) the set of binding moieties that specifically bind to the complex between the small molecule and the cognate binding moiety is the set of positively selected binding moieties of step (b) for the last round of screening. In some embodiments, the method comprises at least 2 rounds of selection.

In some embodiments, according to any of the methods of selecting binding moieties described above, at least one of the binding moieties in the set of binding moieties that specifically bind to the complex between the small molecule and the cognate binding moiety binds to the complex with a dissociation constant ($K_d$) no more than about 1/500 times its $K_d$ for binding to each of the free small molecule and the free cognate binding moiety. In some embodiments, each of the binding moieties in the set of binding moieties that specifically bind to the complex between the small molecule and the cognate binding moiety binds to the complex with a dissociation constant ($K_d$) no more than about 1/500 times its $K_d$ for binding to each of the free small molecule and the free cognate binding moiety.

In some embodiments, according to any of the methods of selecting binding moieties described above, the binding molecule library is an antibody library, a DARPin library, a nanobody library, or an aptamer library. In some embodiments, the binding molecule library is an antibody library. In some embodiments, the antibody library is a phage-displayed Fab library.

In another aspect, provided herein is a construct comprising an antibody moiety that specifically binds to a complex between a small molecule and a binding moiety prepared by a process comprising the steps of: (A) selecting antibody moieties from an antibody library according to any of the methods of selecting binding moieties described above; and (B) providing a construct comprising one of the antibodies moieties of (A).

In some embodiments, according to any of the systems described above, the second binding moiety is an antibody moiety selected by a process comprising the steps of: (A) selecting antibody moieties from an antibody library according to any of the methods of selecting binding moieties described above; and (B) selecting the second binding moiety to be one of the antibodies moieties of (A).

In another aspect, provided herein is a method of modulating the expression of a target gene in a cell, comprising expressing the first and second CID components of any of the systems described above comprising components of a CID capable of regulating transcription of a target gene in the cell and modifying the amount of the small molecule in the cell to modulate the expression of the target gene.

In another aspect, provided herein is a method of treating a disease in an individual, comprising: (A) expressing the first and second CID components of any of the systems described above comprising components of a CID capable of regulating transcription of a target gene in target cells in an individual, wherein the expression level of the target gene in the target cells is associated with the disease; and (B) administering to the individual the small molecule in a regimen effective to treat the disease.

In another aspect, provided herein is nucleic acid encoding the first and second CID components of any of the systems described above comprising components of a CID capable of regulating transcription of a target gene.

In another aspect, provided herein is a cell comprising the first and second CID components of any of the systems described above comprising components of a CID capable of regulating transcription of a target gene.

In another aspect, provided herein is a method of controlling the survival of target cells in an individual, comprising: (A) expressing the first and second CID components of any of the systems described above comprising components of a CID capable of inducing target cell death in the target cells; and (B) administering to the individual the small molecule in a regimen effective to (I) kill a predetermined amount of the target cells; or (II) maintain a predetermined amount of the target cells. In some embodiments, the target cells are part of an adoptive cell therapy in the individual. In some embodiments, the target cells are CAR T cells.

In another aspect, provided herein is a method of treating a disease in an individual, comprising: (A) administering to the individual an adoptive cell therapy for the disease comprising modified cells, wherein the modified cells express the first and second CID components of any of the systems described above comprising components of a CID capable of inducing target cell death; and (B) administering to the individual the small molecule in a regimen effective to (I) kill a predetermined amount of the adoptively transferred cells; or (II) maintain a predetermined amount of the adoptively transferred cells. In some embodiments, the adoptive cell therapy is a CAR T cell therapy.

In another aspect, provided herein is nucleic acid encoding the first and second CID components of any of the systems described above comprising components of a CID capable of inducing target cell death.

In another aspect, provided herein is a cell comprising the first and second CID components of any of the systems described above comprising components of a CID capable of inducing target cell death. In some embodiments, the cell is part of an adoptive cell therapy. In some embodiments, the cell is a CAR T cell.

In another aspect, provided herein is a method of modulating an immune response to a target cell in an individual, comprising: (A) administering to the individual modified T cells expressing the first and second CID components of any of the systems described above comprising components of a CID that forms a heterodimeric CAR, wherein the target antigen is expressed on the surface of the target cell; and (B)

administering to the individual the small molecule in a regimen effective to modulate an immune response to the target cell.

In another aspect, provided herein is a method of modulating an immune response to a target cell in an individual, comprising: (A) administering to the individual modified T cells expressing the CID component of any of the systems described above comprising components of a CID that forms a heterodimeric CAR comprising the cytoplasmic signaling domain; (B) administering to the individual the CID component of the CID comprising the extracellular antigen-binding moiety, wherein the target antigen is expressed on the surface of the target cell; and (C) administering to the individual the small molecule in a regimen effective to modulate an immune response to the target cell.

In some embodiments, according to any of the methods of modulating an immune response to a target cell described above, the regimen is effective to maintain an immune response to the target cell with fewer adverse effects in the individual as compared to a corresponding method comprising administration of CAR T cells expressing a conventional CAR comprising the corresponding CAR domains of the CID.

In another aspect, provided herein is a method of treating a disease characterized by a target cell in an individual, comprising: (A) administering to the individual modified T cells expressing the first and second CID components of any of the systems described above comprising components of a CID that forms a heterodimeric CAR, wherein the target antigen is expressed on the surface of the target cell; and (B) administering to the individual the small molecule in a regimen effective to treat the disease.

In another aspect, provided herein is a method of treating a disease characterized by a target cell in an individual, comprising: (A) administering to the individual modified T cells expressing the CID component of any of the systems described above comprising components of a CID that forms a heterodimeric CAR comprising the cytoplasmic signaling domain; (B) administering to the individual the CID component of the CID comprising the extracellular antigen-binding moiety, wherein the target antigen is expressed on the surface of the target cell; and (C) administering to the individual the small molecule in a regimen effective to treat the disease.

In some embodiments, according to any of the methods of treating a disease characterized by a target cell described above, the regimen is effective to treat the disease with fewer adverse effects in the individual as compared to a corresponding method comprising administration of CAR T cells expressing a conventional CAR comprising the corresponding CAR domains of the CID.

In another aspect, provided herein is nucleic acid encoding the first and second CID components of any of the systems described above comprising components of a CID that forms a heterodimeric CAR.

In another aspect, provided herein is a T cell comprising the first and second CID components of any of the systems described above comprising components of a CID that forms a heterodimeric CAR.

In another aspect, provided herein is a T cell comprising the CID component of any of the systems described above comprising components of a CID that forms a heterodimeric CAR comprising the cytoplasmic signaling domain.

In another aspect, provided herein is a method of modulating an immune response to a target cell in an individual, comprising: (A) administering to the individual the first and second CID components of any of the systems described above comprising components of a CID that forms a heterodimeric bispecific T cell engager; and (B) administering to the individual the small molecule in a regimen effective to modulate an immune response to the target cell. In some embodiments, the regimen is effective to maintain an immune response to the target cell with fewer adverse effects in the individual as compared to a corresponding method comprising administration of a conventional bispecific T cell engager comprising the corresponding bispecific T cell engager domains of the CID.

In another aspect, provided herein is a method of treating a disease characterized by a target cell in an individual, comprising: (A) administering to the individual the first and second CID components of any of the systems described above comprising components of a CID that forms a heterodimeric bispecific T cell engager; and (B) administering to the individual the small molecule in a regimen effective to treat the disease. In some embodiments, the regimen is effective to treat the disease with fewer adverse effects in the individual as compared to a corresponding method comprising administration of a conventional bispecific T cell engager comprising the corresponding bispecific T cell engager domains of the CID.

In another aspect, provided herein is nucleic acid encoding the first and second CID components of any of the systems described above comprising components of a CID that forms a heterodimeric bispecific T cell engager.

In another aspect, provided herein is a method of modulating an immune response mediated by T cells in an individual, comprising: (A) expressing the first and second CID components of any of the systems described above comprising components of a CID that forms a heterodimeric signaling molecule in the T cells; and (B) administering to the individual the small molecule in a regimen effective to modulate an immune response mediated by the T cells. In some embodiments, the regimen is effective to maintain an immune response mediated by the T cells with fewer adverse effects in the individual as compared to a corresponding method comprising expression of a monomeric signaling molecule comprising the corresponding signaling domains of the CID in the T cells.

In another aspect, provided here is a method of treating a disease characterized by a target cell in an individual, comprising: (A) expressing the first and second CID components of any of the systems described above comprising components of a CID that forms a heterodimeric signaling molecule in T cells in the individual capable of recognizing and killing the target cell; and (B) administering to the individual the small molecule in a regimen effective to treat the disease. In some embodiments, the regimen is effective to treat the disease with fewer adverse effects in the individual as compared to a corresponding method comprising expression of a monomeric signaling molecule comprising the corresponding signaling domains of the CID in the T cells.

In some embodiments, according to any of the methods employing a CID that forms a heterodimeric signaling molecule described above, the T cells are CAR T cells.

In another aspect, provided herein is nucleic acid encoding the first and second CID components of any of the systems described above comprising components of a CID that forms a heterodimeric signaling molecule.

In another aspect, provided herein is a T cell comprising the first and second CID components of any of the systems described above comprising components of a CID that forms a heterodimeric signaling molecule. In some embodiments, the T cell is a CAR T cell.

BRIEF DESCRIPTION OF THE DRAWINGS

FIG. 2A shows chemical structures and amino acid sequence of the binding ligands: ABT-737, ABT-263, and Bak peptide.

FIG. 2B shows the crystal structures of ABT-737, ABT-263, and Bak peptide bound to BCL-xL (Protein Data Bank Accession Code: 2YXJ, 4QNQ, and 5FMK), demonstrating that each ligand binds a nearly identical conformation of BCL-xL.

FIG. 2C shows biolayer interferometry showing Fabs AZ1-AZ3 bind potently to BCL-xL in the presence of ABT-737, with greatly reduced potency in the presence of ABT-263, and weakly or undetectably in the presence of Bak peptide. The data shows the Fabs can readily discriminate between subtle structural differences in the small molecules, and supports that Fabs AZ1, AZ2, and AZ3 are chemical-epitope selective. The isotype control is a Fab selected against CD55, with an identical scaffold to AZ1, AZ2, and AZ3 but differing CDR sequences.

FIG. 3A shows a schematic of the AbCID regulated gene activation system. Inducible recruitment of the VPR transcriptional activation domain to dCas9 results in the expression of a luciferase reporter.

FIG. 3B shows quantitation of luciferase activity 48 hours after addition of ABT-737 (20 nM) to the AbCID-gated system compared to the addition of rapamycin (100 nM) to the conventional CID. Values are normalized to a positive control, which is dCas9 genetically fused to VPR, and background subtracted with a negative control, which is dCas9-VPR with a negative sgRNA. Each data point represents the mean of 4 independent experiments±s.d.

FIG. 3C shows dose response after 48-hour induction by addition of ABT-737 to the AbCID-gated system. Each data point represents the mean of 3 independent experiments±s.d.

FIG. 4 shows extracellular AbCIDs used to regulate CAR T-cell activation.

FIG. 9A shows Fab AZ1 showing potent and reversible binding to BCL-xL in the presence of ABT-737 (left) and no significant binding in the absence of ABT-737 (right).

FIG. 9B shows Fab AZ3 showing potent binding to BCL-xL in the presence of ABT-737 (left) and negligible binding in the absence of ABT-737 (right).

FIG. 9C shows Fab AZ4 bound less potently to BCL-xL than Fabs AZ1 and AZ3 in the presence of ABT-737 (left) and also showed less selectivity for the ABT-737-bound form over DMSO only (right). Kinetic data for AZ4 could not be accurately fit and as such, no global-fit data is reported.

FIG. 12A shows quantification of CD69 expression, as measured by immunofluorescence flow cytometry, 20 hours after initiation of co-culture with either CD19$^+$ or CD19$^-$ K562 target cells and addition of antibody (5 nM) and varying concentrations of small molecule. Addition of ABT-737 in the presence of CD19$^+$ K562 cells and bispecific antibody resulted in dose-dependent expression of CD69, but no expression was observed in the absence of ABT-737 or when co-cultured with CD19$^-$ K562 cells. The defective AbCID CAR, which lacks the CD19-binding scFv portion of the antibody, showed no expression of CD69 under all conditions. Each data point represents the mean of 3 independent experiments±s.d.

FIG. 12B shows quantification of IL-2 secretion, as measured by ELISA, 20 hours after initiation of co-culture with either CD19$^+$ or CD19$^-$ K562 target cells and addition of antibody (5 nM) and varying concentrations of small molecule. Addition of ABT-737 in the presence of CD19$^+$ K562 cells and bispecific antibody resulted in dose-dependent secretion of IL-2, but no secretion was observed in the absence of ABT-737 or when co-cultured with CD19$^-$ K562 cells. The defective AbCID CAR, which lacks the CD19-binding scFv portion of the antibody, showed no secretion of IL-2 under all conditions. Each data point represents the mean of 3 independent experiments±s.d.

FIG. 19A shows a schematic an AbCID-regulated inducible bispecific T cell engager, where the AbCID components are linked to an antibody recognizing CD3 and an antibody specifically binding to a tumor specific antigen. Administration of the small molecule dimerizer allows generation of the CID complex, resulting in recruitment of the T-cell to the cancer cells expressing the tumor specific antigen.

DETAILED DESCRIPTION

Figure 1A:
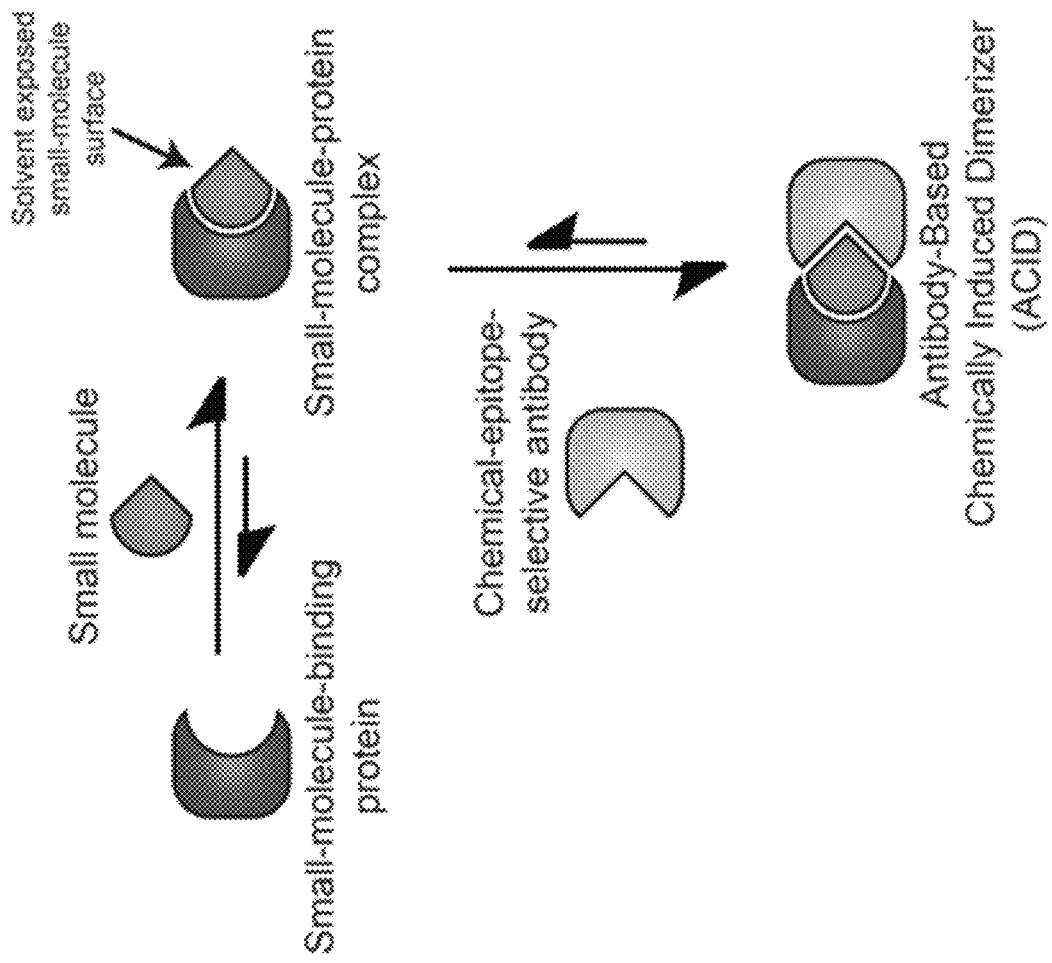
FIG. 1A shows a graphic summary of the design, production and characterization of exemplary antibody-based chemically-induced dimerizers (AbCIDs).

Temporal control over protein-protein interaction is of great importance for biological signaling. In various embodiments, the present invention provides a chemically induced dimerizer facilitating heteromeric Protein$^a$-Protein$^b$ interaction via a small-molecule (SM) chemically induced dimerizer. In the exemplary systems described herein, Protein$^a$ of the two-part Protein$^a$-Protein$^b$ dimer comprises an antibody or antibody fragment (Ab) and Protein$^b$ is chosen based on its ability to bind potently to a small-molecule (SM) ligand. As will be appreciated by those of skill in the art, the antibody can be replaced in the compositions and methods of the invention with any protein specifically binding the SM.

The Abs are generated by any practical method, however, in an exemplary embodiment, Abs are generated from Ab-phage libraries selected against the SM bound form of Protein$^b$ and counter-selected against the unbound form of Protein$^b$. In this way it can be ensured the selected Ab binds more strongly to or only to the SM-Protein$^b$ complex. In a further embodiment, Abs are extensively characterized, and selected for those Abs utilizing the SM ligand as part of its binding interface.

Thus, in an exemplary embodiment, the present invention further provides an antibody specifically binding a Protein$^b$-SM complex. An exemplary species of these antibodies is one in which the specific binding encompasses at least a portion of both the SM and Protein$^b$. In a further exemplary embodiment, the portion of the SM and portion of Protein$^b$ are those portions involved in the specific binding of Protein$^b$ to SM. Protein$^b$-SM-Protein$^a$ dimers with these properties are also provided.

Exemplary Abs bind selectively to the ABT-737 (SM) bound form of the protein BCL-XL (Protein$^b$) by making contact with both BCL-XL and ABT-737.

In an exemplary embodiment, the amount of an AbCID or one of its components necessary to activate a biological system of interest is below the toxic threshold in such system of the AbCID. Thus, when the AbCID of the invention are utilized as therapeutic agents, they have an acceptable therapeutic index. Similarly, when the AbCIDs are used in diagnostic or experimental systems, the AbCIDs are not significantly toxic in the systems in which they are utilized.

The invention is exemplified herein by reference to a novel method to rapidly generate chemically induced dimerizers using known small-molecule-protein complexes and synthetic antibody libraries. This method is exemplified by generating AbCIDs from the BCL-xL/ABT-737 complex. These AbCIDs can be applied to regulate a diverse range of biological processes in living cells, including CRISPRa mediated gene expression and CAR T-cell activation. Finally, we showed that the concentration range of ABT-737 used to activate AbCIDs was far below the concentration at which toxicity was observed in cells.

The present invention provides methods with the ability to rapidly generate new CIDS, e.g., AbCIDs, from different small-molecule-protein pairs in which a significant portion of the small-molecule is solvent accessible. The strategy underlying various embodiments of the invention and the AbCIDs generated thereby represent a novel and promising approach to develop next-generation CID tools for cell biology, synthetic biology, and therapeutic applications.

Definitions

Unless defined otherwise, all technical and scientific terms used herein have the same meaning as commonly understood by one of ordinary skill in the art to which the disclosure pertains. All patents, applications, published applications and other publications referenced herein are expressly incorporated by reference in their entireties unless stated otherwise. In the event that there are a plurality of definitions for a term herein, those in this section prevail unless stated otherwise.

As used herein, "a" or "an" may mean one or more than one.

"About" has its plain and ordinary meaning when read in light of the specification, and may be used, for example, when referring to a measurable value and may be meant to encompass variations of ±20% or +10%, more preferably +5%, even more preferably ±1%, and still more preferably ±0.1% from the specified value.

"Antibody chemically induced dimerizer", or "AbCID" refers to a complex formed between a small organic or organometallic compound ("SM") having at least a first SM binding motif recognized by a complementary binding motif on a first protein (Protein$^b$), and a second SM binding motif recognizing a complementary binding motif on a second protein (Protein$^b$), which is an antibody. When the first and second proteins are brought together in the AbCID, the first and second protein dimerize through their binding to the SM through the respective binding domains. In an exemplary embodiment, the first protein, the second protein or both proteins specifically bind to the SM through the first SM binding motif and the second SM binding motif, respectively. The SM can bind two molecules of the same protein through different binding motifs (i.e., first and second proteins are the same protein) or it can bind different proteins through its different binding motifs (i.e., first and second proteins are different proteins). In those embodiments in which the first protein and/or the second protein is an antibody, the SM is alternatively referred to herein as an "antigen" or "epitope", and the antibody sequence or region binding to the SM as the "paratope".

The present invention utilizes a wide array of small molecules as components of chemically induced dimerizers. Exemplary SMs include ABT-263, ABT-199 and ABT-737. See, for example, Spencer, D. M., Wandless, T. J., Schreiber, S. L. & Crabtree, G. R. Controlling signal transduction with synthetic ligands. *Science* 262, 1019-1024 (1993); Ho, S. N., Biggar, S. R., Spencer, D. M., Schreiber, S. L. & Crabtree, G. R. Dimeric ligands define a role for transcriptional activation domains in reinitiation. *Nature* 382, 822-826 (1996); Belshaw, P. J., Ho, S. N., Crabtree, G. R. & Schreiber, S. L. Controlling protein association and subcellular localization with a synthetic ligandc that induces heterodimerization of proteins. *Proc. Natl. Acad Sci. USA* 93, 4604-4607 (1996); Rivera, V. M. et al. A humanized system for pharmacologic control of gene expression. *Nat. Med* 2, 1028-1032 (1996); Farrar, M. A., Alberol-11a, J. & Perlmutter, R. M. Activation of the Raf-1 kinase cascade by coumermycin-induced dimerization. *Nature* 383, 178-181 (1996); Miyamoto, T. et al. Rapid and orthogonal logic gating with a gibberellin-induced dimerization system. *Nat. Chem. Biol.* 8, 465-470 (2012); Erhart, D. et al. Chemical development of intracellular protein heterodimerizers. *Chem. Biol.* 20, 549-557 (2013); Kopytek, S. J., Standaert, R. F., Dyer, J. C. & Hu, J. C. Chemically induced dimerization of dihydrofolate reductase by a homobifunctional dimer of methotrexate. *Chem. Biol.* 7, 313-321 (2000); Liang, F. S., Ho, W. Q. & Crabtree, G. R. Engineering the ABA plant stress pathway for regulation of induced proximity. *Sci. Signal.* 4, rs2 (2011); and Czlapinski, J. L. et al. Conditional glycosylation in eukaryotic cells using a biocompatible chemical inducer of dimerization. *J. Am. Chem. Soc.* 130, 13186-13187 (2008).

Figure 2A:
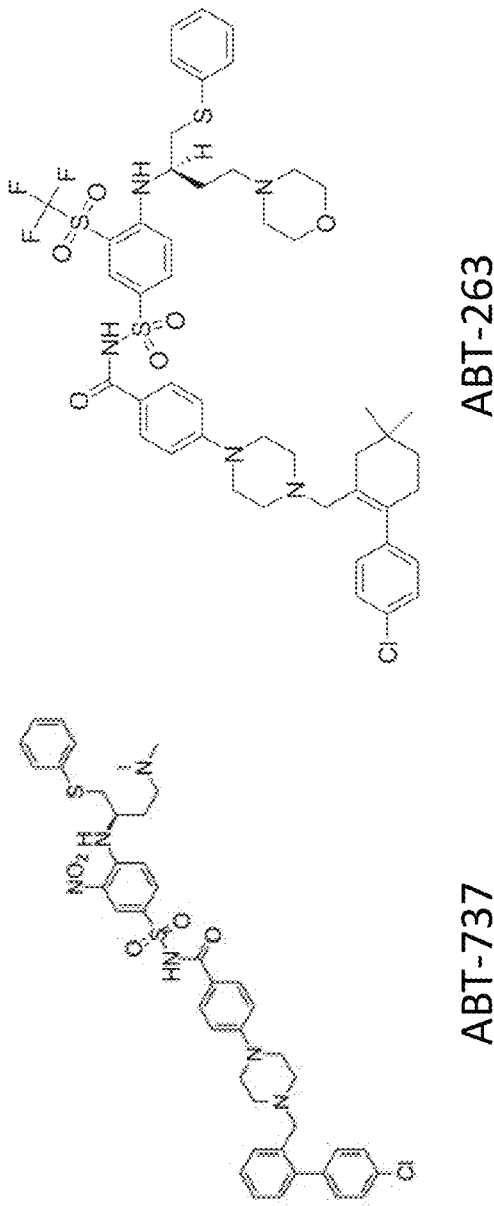
FIGS. 2A-2C show a demonstration of chemical-epitope selectivity for Fabs AZ1, AZ2, and AZ3.
Figure 2B:
Figure 2B:
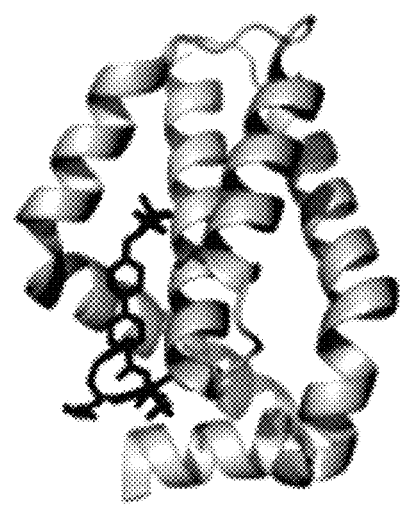
Figure 2B:
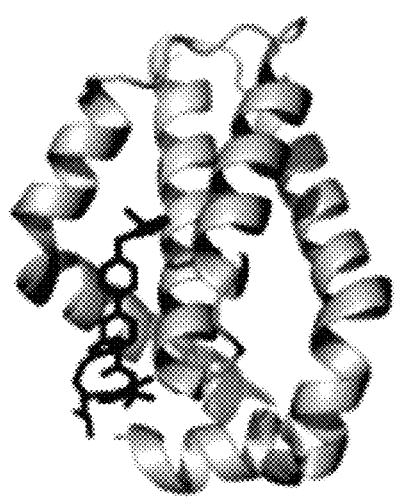

A "small molecule" refers to an organic compound, including an organometallic compound, of a molecular weight less than about 2 kDa. In an exemplary embodiment, the small molecule is not a member of the group consisting of naturally occurring polynucleotides, polypeptides, polysaccharides, and synthetic polymers composed of a plurality of repeating units. An exemplary small molecule comprises one or more substituted or unsubstituted aryl, substituted or unsubstituted heteroaryl or substituted or unsubstituted heterocycloalkyl moieties linked together directly, fused or linked through a substituted or unsubstituted alkyl or substituted or unsubstituted heteroalkyl linker. Exemplary SM components of AbCIDs are members of the ABT family and methotrexate and derivatives and analogs. In various embodiments, the small molecule has significant binding to a cell surface protein (e.g., a cell surface receptor) associated with a disease state and/or disease progression. An exemplary disease is a proliferative disorder, e.g., cancer. Exemplary target cell protein binding compounds include, without limitation, compounds that have significant binding to EGFR, Bcl-2, Bcl-xL, Bcl-w and MCL1. Exemplary small molecule AbCID components are shown in FIG. 2A. Other exemplary small molecules include BH3 mimetics. Billard, *Mol. Cancer Ther.*, 2013: 12(9); 1691-7163.

By "amino acid" and "amino acid identity", as used herein, is meant one of the 20 naturally occurring amino acids or any non-natural analogues that may be present at a specific, defined position. By "protein" herein is meant at least two covalently attached amino acids, which includes proteins, polypeptides, oligopeptides and peptides. The protein may be made up of naturally occurring amino acids and peptide bonds, or synthetic peptidomimetic structures, i.e. "analogs", such as peptoids (see Simon et al., PNAS USA 89(20):9367 (1992)) particularly when peptides are to be administered to a patient. Thus "amino acid", or "peptide residue", as used herein means both naturally occurring and synthetic amino acids. For example, homophenylalanine, citrulline and norleucine are considered amino acids for the purposes of the invention. "Amino acid" also includes imino acid residues such as proline and hydroxyproline. The side chain may be in either the (R) or the (S) configuration. In the preferred embodiment, the amino acids are in the (S) or L-configuration. If non-naturally occurring side chains are used, non-amino acid substituents may be used, for example to prevent or retard in vivo degradation.

By "amino acid modification", as used herein, is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g., the 20 amino acids that have codons in DNA and RNA. The preferred amino acid modification herein is a substitution.

By "amino acid substitution" or "substitution", as used herein, is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E272Y refers to a variant polypeptide, in this case an Fc variant, in which the glutamic acid at position 272 is replaced with tyrosine, wherein numbering is according to the EU system as in Kabat. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion", as used herein, is meant the addition of an amino acid sequence at a particular position in a parent polypeptide sequence. For example, –233E or 233E designates an insertion of glutamic acid after position 233 and before position 234. Additionally, –233ADE or A233ADE designates an insertion of AlaAspGlu after position 233 and before position 234.

By "amino acid deletion" or "deletion", as used herein, is meant the removal of an amino acid sequence at a particular position in a parent polypeptide sequence. For example, E233- or E233#, E2330 or E233del designates a deletion of glutamic acid at position 233. Additionally, EDA233- or EDA233# designates a deletion of the sequence GluAspAla that begins at position 233.

As used herein, "polypeptide", refers to at least two covalently attached amino acids, which includes proteins, polypeptides, oligopeptides and peptides. The peptidyl group may comprise naturally occurring amino acids and peptide bonds, or synthetic peptidomimetic structures, i.e., "analogs", such as peptoids (see Simon et al., PNAS USA 89(20):9367 (1992), entirely incorporated by reference). The amino acids may either be naturally occurring or synthetic (e.g., not an amino acid that is coded for by DNA); as will be appreciated by those in the art. For example, homophenylalanine, citrulline, ornithine and norleucine are considered synthetic amino acids for the purposes of the invention, and both D- and L- (R or S) configured amino acids may be utilized. The variants of the present invention may comprise modifications that include the use of synthetic amino acids incorporated using, for example, the technologies developed by Schultz and colleagues, including but not limited to methods described by Cropp & Shultz, 2004, Trends Genet. 20(12):625-30, Anderson et al., 2004, Proc Natl Acad Sci USA 101 (2):7566-71, Zhang et al., 2003, 303(5656):371-3, and Chin et al., 2003, Science 301(5635): 964-7, all entirely incorporated by reference. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

Exemplary polypeptides of the invention specifically bind to a protein displayed on the surface of a target cell, as outlined herein. By "specifically bind" herein is meant that the polypeptides have a binding constant in the range of at least $10^{-4}$-$10^{-6}$ $M^{-1}$, with a preferred range being $10^{-7}$-$10^{-9}$ $M^+$.

Specifically included within the definition of "polypeptides" are aglycosylated polypeptides. By "aglycosylated polypeptide", as used herein, is meant a polypeptide that lacks carbohydrate attached at position 297 of the Fc region, wherein numbering is according to the EU system as in Kabat. The aglycosylated polypeptide may be a deglycosylated polypeptide, that is an antibody or an antibody fragment from which the Fc carbohydrate has been removed, for example chemically or enzymatically. Alternatively, the aglycosylated polypeptide may be a nonglycosylated or unglycosylated antibody or fragment thereof expressed without Fc carbohydrate, for example by mutation of one or residues that encode the glycosylation pattern or by expression in an organism that does not attach carbohydrates to proteins, for example bacteria.

By "parent polypeptide" or "precursor polypeptide" (including Fc parent or precursors), as used herein, is meant a polypeptide that is subsequently modified to generate a variant. Said parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent Fc polypeptide", as used herein, is meant an unmodified Fc polypeptide that is modified to generate a variant, and by "parent antibody" as used herein is meant an unmodified antibody that is modified to generate a variant antibody.

By "position", as used herein, is meant a location in the sequence of a protein. Positions may be numbered sequentially, or according to an established format, for example the EU index for antibody numbering.

By "ADCC" or "antibody dependent cell-mediated cytotoxicity", as used herein, is meant the cell-mediated reaction wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity.

By "ADCP" or antibody dependent cell-mediated phagocytosis, as used herein, is meant the cell-mediated reaction wherein nonspecific cytotoxic cells that express FcγRs recognize bound antibody on a target cell and subsequently cause phagocytosis of the target cell.

Another mode of cytotoxicity displayed by AbCIDs of the invention is T-cell-mediated cytotoxicity, e.g., CAR T-cell-mediated cytotoxicity.

In various embodiments, one or both of these mechanisms is a basis for the therapeutic efficacy of CIDs, e.g., AbCIDs of the invention.

By "target antigen" as used herein is meant the molecule that is bound specifically by the variable region of a given antibody. A target antigen may be a protein, carbohydrate, lipid, or other chemical compound. A range of suitable exemplary target antigens are described herein.

By "target cell" as used herein is meant a cell that expresses a target antigen.

"Abs" refers to antibodies. By "antibody", as used herein, herein is meant a protein consisting of one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (μ), delta (δ), gamma (γ), sigma (ζ), and alpha (α) which encode the IgM, IgD, IgG, IgE, and IgA isotypes respectively. Antibody herein is meant to include full length antibodies and antibody fragments, and may refer to a natural antibody from any organism, an engineered antibody, or an antibody generated recombinantly for experimental, therapeutic, or other purposes as further defined below. Thus, "antibody" includes both polyclonal and monoclonal antibody (mAb). Methods of preparation and purification of monoclonal and polyclonal antibodies are known in the art and e.g., are described in Harlow and Lane, Antibodies: A Laboratory Manual (New York: Cold Spring Harbor Laboratory Press, 1988). As outlined herein, "antibody" specifically includes Fc variants described herein, "full length" antibodies including the Fc variant fragments described herein, and Fc variant fusions to other proteins as described herein.

The term "antibody" includes antibody fragments, as are known in the art, such as Fab, Fab', F(ab')2, Fcs or other antigen-binding subsequences of antibodies, such as, single chain antibodies (scFab and scFv for example), chimeric antibodies, etc., either produced by the modification of whole antibodies or those synthesized de novo using recombinant DNA technologies. The term "antibody" further comprises polyclonal antibodies and mAbs which can be agonist or antagonist antibodies.

Specifically included within the definition of "antibody" are full-length antibodies that contain an Fc variant portion.

By "full length antibody" herein is meant the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In some mammals, for example in camels and llamas, IgG antibodies may consist of only two heavy chains, each heavy chain comprising a variable domain attached to the Fc region. By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3.

In a preferred embodiment, the antibodies of the invention are humanized. Using current monoclonal antibody technology one can produce a humanized antibody to virtually any target antigen that can be identified [Stein, Trends Biotechnol. 15:88-90 (1997)]. Humanized forms of non-human (e.g., murine) antibodies are chimeric molecules of immunoglobulins, immunoglobulin chains or fragments thereof (such as Fv, Fc, Fab, Fab', F(ab')2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature 321:522-525 (1986); Riechmann et al., Nature 332:323-329 (1988); and Presta, Curr. Op. Struct. Biol. 2:593-596 (1992)]. Methods for humanizing non-human antibodies are well known in the art.

Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., supra; Riechmann et al., supra; and Verhoeyen et al., Science, 239:1534-1536 (1988)], by substituting rodent CDRs or CDR sequences for the corresponding sequences of a human antibody. Additional examples of humanized murine monoclonal antibodies are also known in the art, e.g., antibodies binding human protein C [O'Connor et al., Protein Eng. 11:321-8 (1998)], interleukin 2 receptor [Queen et al., Proc. Natl. Acad. Sci., U.S.A. 86:10029-33 (1989)], and human epidermal growth factor receptor 2 [Carter et al., Proc. Natl. Acad. Sci. U.S.A. 89:4285-9

(1992)]. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In a preferred embodiment, the antibodies of the invention are based on human sequences, and thus human sequences are used as the "base" sequences, against which other sequences, such as rat, mouse and monkey sequences are compared. In order to establish homology to primary sequence or structure, the amino acid sequence of a precursor or parent antibody or scFv is directly compared to the corresponding human sequence. After aligning the sequences, using one or more of the homology alignment programs described herein (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the human polypeptide are defined. Alignment of conserved residues preferably should conserve 100% of such residues. However, alignment of greater than 75% or as little as 50% of conserved residues is also adequate to define equivalent residues (sometimes referred to herein as "corresponding residues").

By "residue" as used herein is meant a position in a protein and its associated amino acid identity wherein numbering is according to the EU system as in Kabat. For example, Asparagine 297 (also referred to as Asn297 or N297) is a residue at position 297 in the human antibody IgG1.

Equivalent residues may also be defined by determining homology at the level of tertiary structure for an scFv fragment whose tertiary structure has been determined by x-ray crystallography. Equivalent residues are defined as those for which the atomic coordinates of two or more of the main chain atoms of a particular amino acid residue of the parent or precursor (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the scFv variant fragment.

By "Fv" or "Fv fragment" or "Fv region" as used herein is meant a polypeptide that comprises the VL and VH domains of a single antibody. As will be appreciated by those in the art, these generally are made up of two chains, or can be combined (generally with a linker as discussed herein) to form a scFv.

By "single chain Fv" or "scFv" herein is meant a variable heavy (VH) domain covalently attached to a variable light (VL) domain, generally using a scFv linker as discussed herein, to form a scFv or scFv domain. A scFv domain can be in either orientation from N- to C-terminus (VH-linker-VL or VL-linker-VH).

By "single chain Fab" or "scFab" as used herein is meant a variable heavy (VH) domain covalently attached to a constant heavy (CH) domain, which is in turn attached to a constant light (CL) domain attached to a variable light (VL) domain, generally using a scFab linker as discussed herein, to form a scFab or scFab domain.

By "variable region", as used herein, is meant the region of an immunoglobulin that comprises one or more Ig domains substantially encoded by any of the Vκ, Vλ, VL and/or VH genes that make up the kappa, lambda, and heavy and light chain immunoglobulin genetic loci respectively.

"CD-x" refers to a cluster of differentiation (CD) protein. In exemplary embodiments, CD-x is selected from those CD proteins having a role in the recruitment or activation of T-cells in a subject to whom a polypeptide construct of the invention has been administered. In an exemplary embodiment, CD-x is selected from CD-19 and CD-3. In an exemplary embodiment, CD-x is a target for a CAR T-cell.

By "antigen binding domain" or "ABD" herein is meant a set of six Complementary Determining Regions (CDRs) that, when present as part of a polypeptide sequence, specifically binds a target antigen as discussed herein. Thus, a "checkpoint antigen binding domain" binds a target checkpoint antigen as outlined herein. As is known in the art, these CDRs are generally present as a first set of variable heavy CDRs (vhCDRs or VHCDRs) and a second set of variable light CDRs (vlCDRs or VLCDRs), each comprising three CDRs: vhCDR1, vhCDR2, vhCDR3 for the heavy chain and vlCDR1, vlCDR2 and vlCDR3 for the light. The CDRs are present in the variable heavy and variable light domains, respectively, and together form an Fv region. Thus, in some cases, the six CDRs of the antigen binding domain are contributed by a variable heavy and variable light chain. In a "Fab" format, the set of 6 CDRs are contributed by two different polypeptide sequences, the variable heavy domain (vh or VH; containing the vhCDR1, vhCDR2 and vhCDR3) and the variable light domain (vl or VL; containing the vlCDR1, vlCDR2 and vlCDR3), with the C-terminus of the vh domain being attached to the N-terminus of the CH1 domain of the heavy chain and the C-terminus of the vl domain being attached to the N-terminus of the constant light domain (and thus forming the light chain). In a scFv or scFab format, the vh and vl domains are covalently attached, generally through the use of a linker as outlined herein, into a single polypeptide sequence, which can be either (starting from the N-terminus) vh-linker-vl or vl-linker-vh, with the former being generally preferred (including optional domain linkers on each side, depending on the format used. An exemplary antigen binding domain recognizes and specifically binds to the Protein$^b$-SM complex. Exemplary CDRs of exemplary Protein$^b$ molecules of the invention are provided in Tables 1-9, and exemplary heavy chain and light chain variable domain scaffolds are provided in SEQ ID NOs: 312 and 313, respectively.

By "Fc", "Fc region", "FC polypeptide", etc. as used herein is meant an antibody as defined herein that includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ2. Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an antibody, antibody fragment, or Fc fusion. An Fc may be an antibody, Fc fusion, or a protein or protein domain that comprises Fc. Particularly preferred are Fc variants, which are non-naturally occurring variants of an Fc.

By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. By "immunoglobulin (Ig) domain" herein is meant a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains. By "immunoglobulin (Ig) domain" herein is meant a region of an immunoglobulin that exists as a distinct structural entity as ascertained by one skilled in the art of protein structure. Ig domains typically have a characteristic-sandwich folding topology. The known Ig domains in the IgG class of antibodies are VH, Cγ1, Cγ2, Cγ3, VL, and CL.

By "wild type or WT" herein is meant an amino acid sequence or a nucleotide sequence that is found in nature, including allelic variations. A WT protein has an amino acid sequence or a nucleotide sequence that has not been intentionally modified.

By "variant polypeptide" as used herein is meant a polypeptide sequence that differs from that of a parent polypeptide sequence by virtue of at least one amino acid modification. Modifications can include substitutions, deletions, and additions. Variant polypeptide may refer to the polypeptide itself, a composition comprising the polypeptide, or the amino sequence that encodes it. Preferably, the variant polypeptide has at least one amino acid modification compared to the parent polypeptide, e.g. from about one to about ten amino acid modifications, and preferably from about one to about five amino acid modifications compared to the parent. The variant polypeptide sequence herein will preferably possess at least about 80% homology with a parent polypeptide sequence, and most preferably at least about 90% homology, more preferably at least about 95% homology. Accordingly, by "Fc variant" as used herein is meant an Fc sequence that differs from that of a parent Fc sequence by virtue of at least one amino acid modification. Similarly, an exemplary "inactive VL domain" or "inactive VH domain" is a variant of a parent VL or VH polypeptide.

In some embodiments, the AbCIDs and/or the polypeptide components of the invention are "isolated" or "substantially pure" polypeptides. "Isolated" or "substantially pure", when used to describe the polypeptides disclosed herein, means a polypeptide that has been identified, separated and/or recovered from a component of its production environment. Preferably, the polypeptide is free or substantially free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. The desired polypeptide in the production medium may constitute at least about 5%, at least about 25% or at least about 50% by weight of the total polypeptide the medium.

Exemplary isolated polypeptides and AbCIDs including the polypeptides of the invention are substantially or essentially free from components, which are used to produce the material. For peptides of the invention, the term "isolated" refers to material that is substantially or essentially free from components, which normally accompany the material in the mixture used to prepare the peptide. "Isolated" and "pure" are used interchangeably. Typically, isolated polypeptides of the invention have a level of purity preferably expressed as a range. The lower end of the range of purity for the polypeptide constructs is about 60%, about 70% or about 80% and the upper end of the range of purity is about 70%, about 80%, about 90% or more than about 90%.

When the polypeptides are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

In various embodiments, Protein$^b$ binds to SM through one or more binding domains. According to the present invention, binding domains are components of one or more polypeptides. Such polypeptides may include proteinaceous parts and non-proteinaceous parts (e.g. chemical linkers or chemical cross-linking agents such as glutaraldehyde). Polypeptides (including fragments thereof, preferably biologically active fragments, and peptides, usually having more than 30 amino acids) comprise two or more amino acids coupled to each other via a covalent peptide bond (resulting in a chain of amino acids).

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^-$ M, at least about $10^{-5}$ M, at least about $10^-$ M, at least about $10^{-7}$ M, at least about $10^{-8}$ M, at least about $10^{-9}$ M, alternatively at least about $10^{-1}$ at least about $10^{-11}$ M, at least about $10^{-12}$ M, M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a association constant or $K_d$ for an antigen or epitope of at least 20-, 50-, 100-, 500-, 1000-, 5,000-, 10,000- or more times greater for the epitope relative to a control, where association constant or $K_d$ refers to an association rate of a particular antibody-antigen interaction. Binding affinity is generally measured using a Biacore® assay.

The terms "essentially does not specifically bind", "does not substantially specifically bind" or "is not capable of specifically binding" are used interchangeably and mean that a binding domain of the present invention does not bind a protein or antigen other than the target antigen, i.e., does not show reactivity of more than 30%, preferably not more than 20%, more preferably not more than 10%, particularly preferably not more than 9%, 8%, 7%, 6% or 5% with proteins or antigens other than the target antigen. This term is relevant to antibodies of the invention with respect to their lack of interaction with Protein$^b$ and SM when they are not bound in the Protein$^b$-SM complex.

The term "bispecific" as used herein refers to an antibody which is "at least bispecific", i.e., it comprises at least a first binding domain (e.g., target antigen, e.g., Bcl-xL, EGFR) and a second binding domain (e.g., CD-x, e.g., CD-19 or CD-3), wherein the first binding domain binds to one antigen or target, and the second binding domain binds to another antigen or target. Accordingly, polypeptide constructs according to the invention comprise specificities for at least two different antigens or targets. The term "bispecific polypeptide construct" of the invention also encompasses multispecific polypeptide constructs such as trispecific polypeptide constructs, the latter ones including three binding domains, or constructs having more than three (e.g., four, five . . . ) specificities.

Exemplary embodiments of the invention utilize antibodies which are bispecific, they do not occur naturally and they are markedly different from naturally occurring products. A "bispecific" antibody is hence an artificial hybrid polypeptide having at least two distinct binding sites with different specificities. Bispecific polypeptide constructs can be produced by a variety of method. See, e.g., Songsivilai & Lachmann, Clin. Exp. Immunol. 79:315-321 (1990).

When the antibodies of the invention are scFv or scFab antibodies, these antibodies may or may not comprise peptide linkers (spacer peptides). The term "peptide linker" comprises in accordance with the present invention an amino acid sequence by which the amino acid sequences of one (variable and/or binding) domain and another (variable and/or binding) domain of the antibody construct of the invention are linked with each other. An essential technical feature of such peptide linker is that it does not comprise any polymerization activity. Among the suitable peptide linkers are those described in U.S. Pat. Nos. 4,751,180 and 4,935,233 or WO 88/09344. The peptide linkers can also be used to attach other domains or modules or regions (such as half-life extending domains) to the antibody construct of the invention.

In those embodiments in which a linker is used, this linker is preferably of a length and sequence sufficient to ensure that each of the target antigen and CD-3 binding domains can, independently from one another, retain their differential binding specificities. For peptide linkers which connect the at least two binding domains (or two variable domains) in the antibody construct of the invention, those peptide linkers are preferred which comprise an optimized number of amino acid residues. For scFv antibody constructs exemplary linkers are, e.g. 12 amino acid residues or less. Thus, peptide linkers of 12, 11, 10, 9, 8, 7, 6 or 5 amino acid residues are of use. For scFab antibody constructs of the invention, exemplary linkers include up to about 80 amino acids, e.g., up to about 70, 60, 50, 40, 30, 20 amino acids.

An envisaged peptide linker with less than 5 amino acids comprises 4, 3, 2 or one amino acid(s), wherein Gly-rich linkers are preferred. A particularly preferred "single" amino acid in the context of said "peptide linker" is Gly. Accordingly, said peptide linker may consist of the single amino acid Gly. Another preferred embodiment of a peptide linker is characterized by the amino acid sequence Gly-Gly-Gly-Gly-Ser, i.e. Gly4Ser (SEQ ID NO: 325), or polymers thereof, i.e. (Gly4Ser)$_x$, where x is an integer of 1 or greater (e.g. 2 or 3). The characteristics of said peptide linker, which comprise the absence of the promotion of secondary structures, are known in the art and are described e.g. in Dall'Acqua et al. (Biochem. (1998) 37, 9266-9273), Cheadle et al. (Mol Immunol (1992) 29, 21-30) and Raag and Whitlow (FASEB (1995) 9(1), 73-80). Peptide linkers which furthermore do not promote any secondary structures are also of use. The linkage of said domains to each other can be provided, e.g., by genetic engineering, as described in the examples. Methods for preparing fused and operatively linked bispecific single chain constructs and expressing them in mammalian cells or bacteria are well-known in the art (e.g. WO 99/54440 or Sambrook et al., Molecular Cloning: A Laboratory Manual, Cold Spring Harbor Laboratory Press, Cold Spring Harbor, N.Y., 2001).

Exemplary embodiments of the invention comprise at least one scFv domain, which, while not naturally occurring, generally includes a variable heavy domain and a variable light domain, linked together by a scFv linker. As outlined herein, while the scFv domain is generally from N- to C-terminus oriented as VH-scFv linker-VL, this can be reversed for any of the scFv domains (or those constructed using VH and VL sequences from Fabs), to VL-scFv linker-VH, with optional linkers at one or both ends depending on the format. Also included are embodiments in which an scFab is a component.

As shown herein, there are a number of suitable scFab and scFv linkers that can be used, including traditional peptide bonds, generated by recombinant techniques. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 80 amino acids in length, preferably about 1 to 50 amino acids in length. In one embodiment, linkers of 1 to 20 amino acids in length may be used, with from about 5 to about 10 amino acids finding use in some embodiments. Useful linkers include glycine-serine polymers, including for example (GS)n, (GSGGS)n, (GGGGS)n, and (GGGS)n, where n is an integer of at least one (and generally from 3 to 4), glycine-alanine polymers, alanine-serine polymers, and other flexible linkers. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use as linkers.

Other linker sequences may include any sequence of any length of CL/CH1 domain but not all residues of CL/CH1 domain; for example the first 5-12 amino acid residues of the CL/CH1 domains. Linkers can be derived from immunoglobulin light chain, for example Cκ or Cλ. Linkers can be derived from immunoglobulin heavy chains of any isotype, including for example Cγ1, Cγ2, Cγ3, Cγ4, Cα1, Cα2, Cδ, Cε, and Cμ. Linker sequences may also be derived from other proteins such as Ig-like proteins (e.g. TCR, FcR, KIR), hinge region-derived sequences, and other natural sequences from other proteins.

In some embodiments, the linker is a "domain linker", used to link together any two domains as outlined herein. While any suitable linker can be used, many embodiments utilize a glycine-serine polymer, including for example (GS)n, (GSGGS)n, (GGGGS)n, and (GGGS)n, where n is an integer of at least one (and generally from 3 to 4 to 5) as well as any peptide sequence that allows for attachment of the two domains with sufficient length and flexibility to allow each domain to retain its biological function.

By "computational screening method" herein is meant any method for designing one or more polypeptide construct of the invention, including mutations in a component (e.g., VH, VL) of the construct, wherein said method utilizes a computer to evaluate the energies of the interactions of potential amino acid side chain substitutions with each other and/or with the rest of the protein. As will be appreciated by those skilled in the art, evaluation of energies, referred to as energy calculation, refers to some method of scoring one or more amino acid modifications. Said method may involve a physical or chemical energy term, or may involve knowledge-, statistical-, sequence-based energy terms, and the like. The calculations that compose a computational screening method are herein referred to as "computational screening calculations".

As used herein, the term "tumor" refers to all neoplastic cell growth and proliferation, whether malignant or benign, and all cancerous and pre-cancerous cells and tissues.

"Invasive angiogenesis" refers to the formation of blood vessels for the support of pathological conditions, including malignant and non-malignant tumors as well as the abnormal formation of new blood vessels in macular degeneration.

The terms, "cancer" and "cancerous" refer to or describe the physiological condition in mammals that is typically characterized by unregulated cell growth. Examples of cancer include but are not limited to carcinomas, lymphomas and leukemias.

As used herein, the terms "treat" or "treatment" refer to both therapeutic treatment and prophylactic or preventative measures, wherein the object is to prevent or slow down (lessen) an undesired physiological change or disorder, such as the progression of multiple sclerosis, arthritis, or cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

"AZx" (e.g., AZ1, AZ2, AZ3, refers to an antibody of the invention specifically binding ABT-737 complexed with BCL-xL, BCL-2, or BCL-W, and conjugates thereof.)

The terms "targeting moiety" and "targeting agent", as used herein, refer to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is linked to a carrier, e.g., multivalent agents. Therapeutic moiety also includes peptides, and constructs that include peptides. "Therapeutic moiety" thus means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is linked to a carrier, e.g., multivalent agents.

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, interferons and radioactive agents. Also encompassed within the scope of the term "anti-tumor drug," are conjugates of peptides with anti-tumor activity, e.g. TNF-□. Conjugates include, but are not limited to those formed between a therapeutic protein and a glycoprotein of the invention. A representative conjugate is that formed between PSGL-1 and TNF-□.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin and analogs or homologs thereof. Other toxins include, for example, ricin, CC-1065 and analogues, the duocarmycins. Still other toxins include diphtheria toxin, and snake venom (e.g., cobra venom).

As used herein, "a radioactive agent" includes any radioisotope that is effective in diagnosing or destroying a tumor. Examples include, but are not limited to, indium-111, cobalt-60 and technetium. Additionally, naturally occurring radioactive elements such as uranium, radium, and thorium, which typically represent mixtures of radioisotopes, are suitable examples of a radioactive agent. The metal ions are typically chelated with an organic chelating moiety.

As used herein, "pharmaceutically acceptable carrier" includes any material, which when combined with the conjugate retains the activity of the conjugate activity and is non-reactive with the subject's immune system. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods.

The term "half-life" or "t½", as used herein in the context of administering a SM or a SM-protein complex to a patient, is defined as the time required for plasma concentration of the substance administered to a patient to be reduced by one half. There may be more than one half-life associated with the administered species depending on multiple clearance mechanisms, redistribution, and other mechanisms well known in the art. Usually, alpha and beta half-lives are defined such that the alpha phase is associated with redistribution, and the beta phase is associated with clearance. However, with protein drugs that are, for the most part, confined to the bloodstream, there can be at least two clearance half-lives. For some glycosylated peptides, rapid beta phase clearance may be mediated via receptors on macrophages, or endothelial cells that recognize terminal galactose, N-acetylgalactosamine, N-acetylglucosamine, mannose, or fucose. Slower beta phase clearance may occur via renal glomerular filtration for molecules with an effective radius <2 nm (approximately 68 kD) and/or specific or non-specific uptake and metabolism in tissues. PEGylation may cap terminal sugars (e.g. galactose or N-acetylgalactosamine) and thereby block rapid alpha phase clearance via receptors that recognize these sugars. It may also confer a larger effective radius and thereby decrease the volume of distribution and tissue uptake, thereby prolonging the late beta phase. Thus, the precise impact of PEGylation on alpha phase and beta phase half-lives will vary depending upon the size, state of glycosylation, and other parameters, as is well known in the art. Further explanation of "half-life" is found in Pharmaceutical Biotechnology (1997, DFA Crommelin and R D Sindelar, eds., Harwood Publishers, Amsterdam, pp 101-120).

The term "alkyl," by itself or as part of another substituent, means, unless otherwise stated, a straight or branched chain, or cyclic hydrocarbon radical, or combination thereof, which may be fully saturated, mono- or polyunsaturated and can include mono-, di- and multivalent radicals, having the number of carbon atoms designated (i.e., $C_1$-$C_{10}$ means one to ten carbons). Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, includes "alkylene" and, optionally, those derivatives of alkyl defined in more detail below, such as "heteroalkyl."

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, P and S, and wherein the nitrogen and sulfur atoms may optionally be oxidized and the nitrogen heteroatom may optionally be quaternized. The heteroatom(s) O, N, S, P and Si may be placed at any interior position of the heteroalkyl group or at the position at which the alkyl group is attached to the remainder of the molecule. Examples include, but are not limited to, —CH2-CH2-O—CH3, —CH2-CH2-NH—CH3, —CH2-CH2-N(CH3)-CH3, —CH2-S—CH2-CH3, —CH2-CH2, —S(O)—CH3, —CH2-CH2-S(O)2-CH3, —CH=CH—O—CH3, —Si(CH3)3, —CH2-CH=N—OCH3, and —CH=CH—N(CH3)-CH3. Up to two heteroatoms may be consecutive, such as, for example, —CH2-NH—OCH3 and —CH2-O—Si(CH3)3. Similarly, the term "heteroalkylene" by itself or as part of another substituent means a divalent radical derived from heteroalkyl, as exemplified, but not limited by, —CH2-CH2-S—CH2-CH2- and —CH2-S—CH2-CH2-NH—CH2-. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)2R'— represents both —C(O)2R'— and —R'C(O)2-.

The terms "cycloalkyl" and "heterocycloalkyl", by themselves or in combination with other terms, represent, unless otherwise stated, cyclic versions of "alkyl" and "heteroalkyl", respectively. Also included are di- and multi-valent species such as "cycloalkylene." Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C1-C4)alkyl" is meant to include, but not be limited to, species such as trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Also included are di- and multi-valent linker species, such as "arylene." Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO2R', —CONR'R", —OC(O)NR'R", —NR"C(O)R', SO3R', —NR'—C(O)NR"R'", —NR"C(O)2R', —NR—C (NR'R"R'")=NR"", —NR—C(NR'R")=NR'", —S(O)R', —S(O)2R', —S(O)2NR'R", —NRSO2R', —CN and NO2 in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. Accordingly, from the above discussion of substituents, one of skill in the art will understand that the terms "substituted alkyl" and "heteroalkyl" are meant to include groups that have carbon atoms bound to groups other than hydrogen atoms, such as haloalkyl (e.g., —CF3 and —CH2CF3) and acyl (e.g., —C(O)CH3, —C(O)CF3, —C(O)CH2OCH3, and the like).

The substituents set forth in the paragraph above are referred to herein as "alkyl group substituents."

Similar to the substituents described for the alkyl radical, substituents for the aryl and heteroaryl groups are varied and are selected from, for example: halogen, —OR', =O, =NR', =N—OR', —NR'R", —SR', -halogen, —OC(O)R', —C(O)R', —CO2R', —CONR'R", —OC(O)NR'R", —NR"C(O)R', —NR'C(O)NR"R'", —NR"C(O)2R', —NR—C(NR'R")=NR'", —S(O)R', —S(O)2R', —SO3R', —S(O)2NR'R", —NRSO2R', —CN and —NO2, —R', —N3, —CH(Ph)2, fluoro(C1-C4)alkoxy, and fluoro(C1-C4) alkyl, in a number ranging from zero to the total number of open valences on the aromatic ring system; and where R', R", R'" and R"" are preferably independently selected from hydrogen, (C1-C8)alkyl and heteroalkyl, unsubstituted aryl and heteroaryl, (unsubstituted aryl)-(C1-C4)alkyl, and (unsubstituted aryl)oxy-(C1-C4)alkyl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH2)$_r$—B—, wherein A and B are independently —CRR'—, —O—, —NR—, —S—, —S(O)—, —S(O)2-, —S(O)2NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")d-, where s and d are independently integers of from 0 to 3, and X is —O—, —NR'—, —S—, —S(O)—, —S(O)2-, or —S(O)2NR'—. The substituents R, R', R" and R'" are preferably independently selected from hydrogen or substituted or unsubstituted (C1-C6)alkyl.

The substituents set forth in the two paragraphs above are referred to herein as "aryl group substituents."

In forming conjugates of Protein$^a$ and/or Protein$^b$ of the invention, the protein precursor components of these conjugates of the invention include one or more "reactive functional group". Exemplary species include a reactive functional group attached directly to the protein or to a linker attached to the protein. An exemplary reactive functional group is attached to an alkyl or heteroalkyl linker on the protein. When the reactive group is attached to a substituted or unsubstituted alkyl or substituted or unsubstituted heteroalkyl linker moiety, the reactive group is preferably located at a terminal position of the alkyl or heteroalkyl chain. Reactive groups and classes of reactions useful in practicing the present invention are generally those that are well known in the art of bioconjugate chemistry. Currently favored classes of reactions available with the protein conjugates of the invention are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). The conditions are sufficiently mild that the protein precursor and the desired protein conjugate do not undergo significant degradation under the reaction conditions used to deploy the reactive functional group in a conjugation reaction. Useful reactions are discussed in, for example, March, Advance Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982.

Useful reactive functional groups include, for example: (a) carboxyl groups and derivatives thereof including, but not limited to activated esters, e.g., N-hydroxysuccinimide esters, N-hydroxyphthalimide, N-hydroxybenztriazole esters, p-nitrophenyl esters; acid halides; acyl imidazoles; thioesters; alkyl, alkenyl, alkynyl and aromatic esters; and activating groups used in peptide synthesis; (b) hydroxyl groups and hydroxylamines, which can be converted to esters, sulfonates, phosphoramidates, ethers, aldehydes, etc. (c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups, which are capable of participating in Diels-Alder reactions such as, for example, maleimido groups; (e) aldehyde or ketone groups, allowing derivatization via formation of carbonyl derivatives, e.g., imines, hydrazones, semicarbazones or oximes, or via such mechanisms as Grignard addition or alkyllithium addition; (f) sulfonyl halide groups for reaction with amines, for example, to form sulfonamides; (g) thiol groups, which can be converted to disulfides or reacted with acyl halides, for example; (h) amine, hydrazine or sulfhydryl groups, which can be, for example, acylated, alkylated or oxidized; (i) alkenes, which can undergo, for example, cycloadditions, acylation, Michael addition, etc; (j) epoxides, which can react with, for example, amines and hydroxyl compounds; and (k) phosphoramidites and other standard functional groups useful in nucleic acid synthesis.

In various embodiments, the reactive functional group is a member selected from:

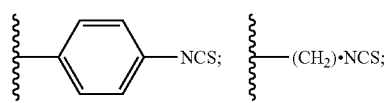

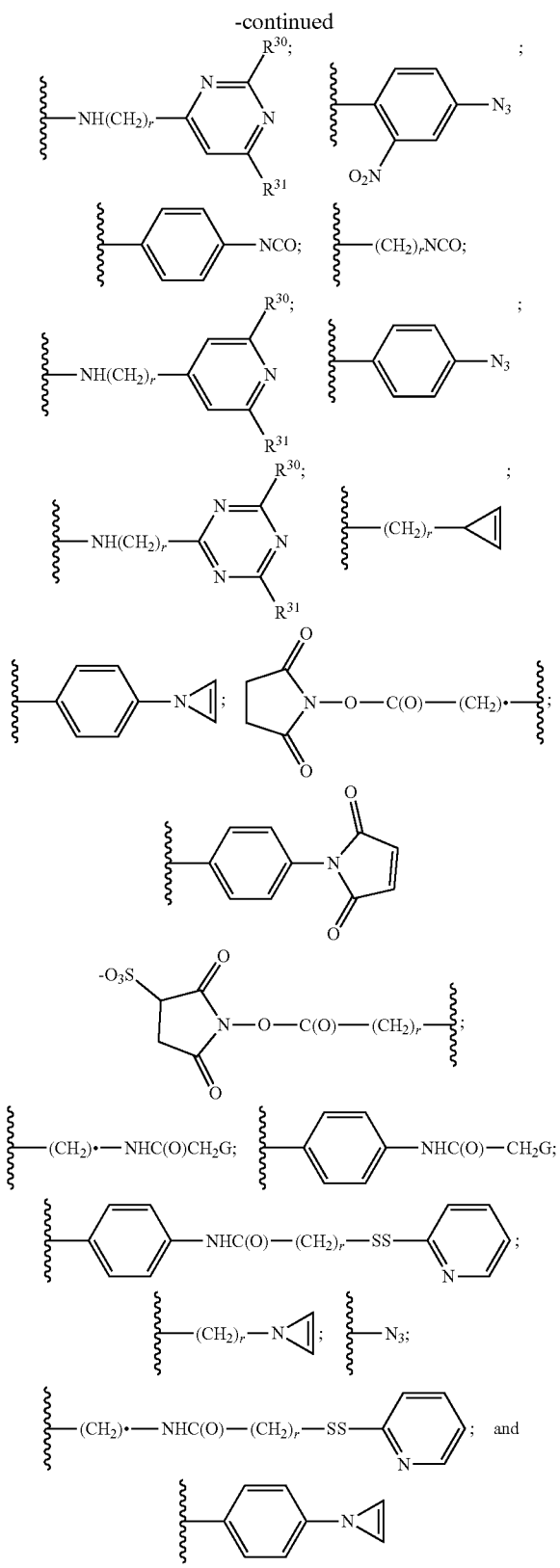

in which each r is independently selected from the integers from 1 to 10; G is a halogen; and R30 and $R^{31}$ are members independently selected from H and halogen and at least one of R30 and $R^{31}$ is halogen.

The reactive functional groups can be chosen such that they do not participate in, or interfere with, the reactions necessary to assemble or utilize the polypeptide conjugate. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

"Analyte", "target", "substance to be assayed", and "target species," as utilized herein refer to the species of interest in an assay mixture. The terms refer to a substance, which is detected qualitatively or quantitatively using a material, process or device of the present invention. Examples of such substances include cells and portions thereof, enzymes, "Analyte", "target", "substance to be assayed", and "target species," as utilized herein refer to the species of interest in an assay mixture. The terms refer to a substance, which is detected qualitatively or quantitatively using a material, process or device of the present invention. Examples of such substances include cells and portions thereof, enzymes, "CRISPR" refers to Clustered Regularly Interspaced Short Palindromic Repeats are prokaryotic immune systems first discovered by Ishino in *E. coli*. (Ishino, et al., Journal of Bacteriology 169(12): 5429-5433 (1987)). These system provide immunity in bacteria and archaea against viruses and plasmids by targeting the nucleic acids of the viruses and plasmids in a sequence-specific manner.

There are two main stages involved in these immune systems; the first is acquisition and the second is interference. The first stage involves cutting the genome of invading viruses and plasmids and integrating segments of this into the CRISPR locus of the bacteria and archaea. The segments to be integrated into the genome are known as protospacers and help in protecting the organism from subsequent attack by the same virus or plasmid. The second stage involves attacking an invading virus or plasmid. This stage relies upon the integrated sequences, called spacers, being transcribed to RNA and following some processing this RNA then hybridizes with a complementary sequence in the DNA or RNA of an invading polynucleotide (e.g., a virus or a plasmid) while also associating with a protein, or protein complex, that effectively binds and/or cleaves the DNA or RNA.

There are several different CRISPR-Cas systems and the nomenclature and classification of these has changed as the systems are further characterized. In Class 2 Type II systems there are two strands of RNA that are part of the CRISPR-Cas system: a CRISPR RNA (crRNA) and a transactivating CRISPR RNA (tracrRNA). The tracrRNA hybridizes to a complementary region of pre-crRNA facilitating maturation of the pre-crRNA to crRNA by an RNase III enzyme. The duplex formed by the tracrRNA and crRNA is recognized by, and associates with a protein, Cas9, which is directed to a target nucleic acid by a sequence of the crRNA that is complementary to, and hybridizes with, a sequence in the target nucleic acid. It has been demonstrated that these minimal components of the RNA-based immune system can be reprogrammed to target DNA in a site-specific manner by using a single protein and two RNA guide sequences or a single RNA molecule.

AbCIDs

In various embodiments, the present invention provides access to compounds and methods to achieve temporal SM control over the formation of a Protein$^a$-Protein$^b$ dimer. In exemplary embodiments, these AbCID-induced interactions serve as molecular switches, which lead to the transmissions of cellular signals. These signals can be programmed to be pro-survival or pro-death depending on the therapeutic need and application. An exemplary signal activates T cells.

The present invention can be applied to a number of applications, e.g., engineered T-Cell therapy and control of gene expression, e.g., using CRISPR.

Chimeric antigen receptor (CAR) T-Cell therapy is showing great promise in treating a number of cancers. Unfortunately, overly activated T-Cells often have negative side effects, limiting the use of this therapy. The present invention is exemplified by application to CAR T-Cells in two ways: For example, one of the key problems with CAR-T-cells is that they have a long half-life in the body. Thus there is an interest in removing them once they have had the therapeutic effect. The present invention is of use to build a SM-induced death switch so CAR T-cells can be eliminated from a subject being treated with same when desired. For example, the invention can be utilized to incorporate a chemically inducible death switch into a CAR T system so that if the T-Cells become toxic to the patient, a SM can be administered that will selectively trip the switch and kill the engineered T-Cells.

The instant invention also provides an activator and antigen recruiter for CAR T-Cells. In an exemplary embodiment, the scFv portion of a CAR is replaced with BCL-XL (Protein$^b$), and Protein$^a$ (Ab) is part of a bispecfic antibody which also targeted cancer-specific antigens on the tumors surface Addition of ABT-737 dimerizes Protein$^b$ and Protein$^b$, which leads to activation of the T-cell, while simultaneously recruiting the T-Cells to their cancer target (FIG. 2). As the small molecule is titratable and reversible, this allows for the modulation of the T-Cells' activation and the duration of their effect, greatly improving the therapeutic index and thus safety of this therapeutic approach.

One aspect of the present disclosure provides a dimer formed through a AbCID, which incorporates a RNA-guided endonucleases comprising at least one nuclear localization signal, which permits entry of the endonuclease into the nuclei of eukaryotic cells and embryos such as, for example, non-human one cell embryos. RNA-guided endonucleases also comprise at least one nuclease domain and at least one domain that interacts with a guide RNA. An RNA-guided endonuclease is directed to a specific nucleic acid sequence (or target site) by a guide RNA. The guide RNA interacts with the RNA-guided endonuclease as well as the target site such that, once directed to the target site, the RNA-guided endonuclease is able to introduce a double-stranded break into the target site nucleic acid sequence. Since the guide RNA provides the specificity for the targeted cleavage, the endonuclease of the RNA-guided endonuclease is universal and can be used with different guide RNAs to cleave different target nucleic acid sequences. Provided herein are isolated RNA-guided endonucleases, isolated nucleic acids (i.e., RNA or DNA) encoding the RNA-guided endonucleases, vectors comprising nucleic acids encoding the RNA-guided endonucleases, and protein-RNA complexes comprising the RNA-guided endonuclease plus a guide RNA. Also of use in methods of the invention are catalytically inactive variants of Cas-9.

The RNA-guided endonuclease can be derived from a clustered regularly interspersed short palindromic repeats (CRISPR)/CRISPR-associated (Cas) system. The CRISPR/Cas system can be a type I, a type II, or a type III system. Non-limiting examples of suitable CRISPR/Cas proteins include Cas3, Cas4, Cas5, Cas5e (or CasD), Cash, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14charged, Csx10, Csx16, CsaX, Csx3, Csz1, Csx15, Csf1, Csf2, Csf3, Csf4, and Cu1966.

In one embodiment, the RNA-guided endonuclease is derived from a type II CRISPR/Cas system. In specific embodiments, the RNA-guided endonuclease is derived from a Cas9 protein. The Cas9 protein can be from *Streptococcus pyogenes, Streptococcus thermophilus, Streptococcus* sp., *Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderi ales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum the rmopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina*.

In general, CRISPR/Cas proteins comprise at least one RNA recognition and/or RNA binding domain. RNA recognition and/or RNA binding domains interact with guide RNAs. CRISPR/Cas proteins can also comprise nuclease domains (i.e., DNase or RNase domains), DNA binding domains, helicase domains, RNAse domains, protein-protein interaction domains, dimerization domains, as well as other domains.

The CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzymatic activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the function of the fusion protein. The CRISPR/Cas-like protein can also be truncated or modified to optimize the activity of the effector domain of the fusion protein. As will be appreciated by those of skill in the art, either Protein$^a$ or Protein$^b$ can be fused to other DNA-binding proteins besides Cas9, e.g., Zinc-finger proteins.

In some embodiments, the CRISPR/Cas-like protein can be derived from a wild type Cas9 protein or fragment thereof. In other embodiments, the CRISPR/Cas-like protein can be derived from modified Cas9 protein. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein.

In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-stranded break in DNA. (Jinek et al., Science, 2012, 337: 816-821). In some embodiments, the Cas9-derived protein can be modified to contain only one functional nuclease domain (either a RuvC-like or a HNH-like nuclease domain). For example, the Cas9-derived protein can be modified such that one of the nuclease domains is deleted or mutated such that it is no longer functional (i.e., the nuclease activity is absent). In some embodiments in which one of the nuclease domains is inactive, the Cas9-derived protein is able to introduce a nick into a double-stranded nucleic acid (such protein is termed a "nickase"), but not cleave the double-stranded DNA. For example, an aspartate to alanine (D10A) conversion in a RuvC-like domain converts the Cas9-derived protein into a nickase. Likewise, a histidine to alanine (H840A or H839A) conversion in a HNH domain converts the Cas9-derived protein into a nickase. Each nuclease domain can be modified using well-known methods, such as site-directed mutagenesis, PCR-mediated mutagenesis, and total gene synthesis, as well as other methods known in the art. The compounds and methods of the present invention can also be applied to regulate genetic circuits using proteins other than CRISPR-derived proteins, e.g., TALEN, Zinc Finger Proteins, etc.

In an exemplary embodiment, the AbCID forms a dimer having an in vivo half-life, which is longer than any subset of its components when administered to a subject.

In various embodiments, the AbCID forms a dimer between a first protein conjugate comprising a member selected from a first therapeutic moiety, a first targeting moiety, a first detectable moiety and a first combination thereof; and a second protein conjugate comprising a second therapeutic moiety, a second targeting moiety, a second detectable moiety and a second combination thereof. In an exemplary embodiment, this dimer is formed in vivo following administration of the SM or the Protein-SM complex to a patient in need of therapeutic intervention by such administration.

Exemplary embodiments of the invention utilize antibodies as one or both of Protein$^a$ and Protein$^b$. As is discussed herein, the term "antibody" is used in its most general sense. Antibodies finding use in the present invention can be of a number of formats as described herein, including traditional full antibodies as well as antibody derivatives, fragments and mimetics, as described herein, depicted in the figures and generally described in the art.

Figure 6:
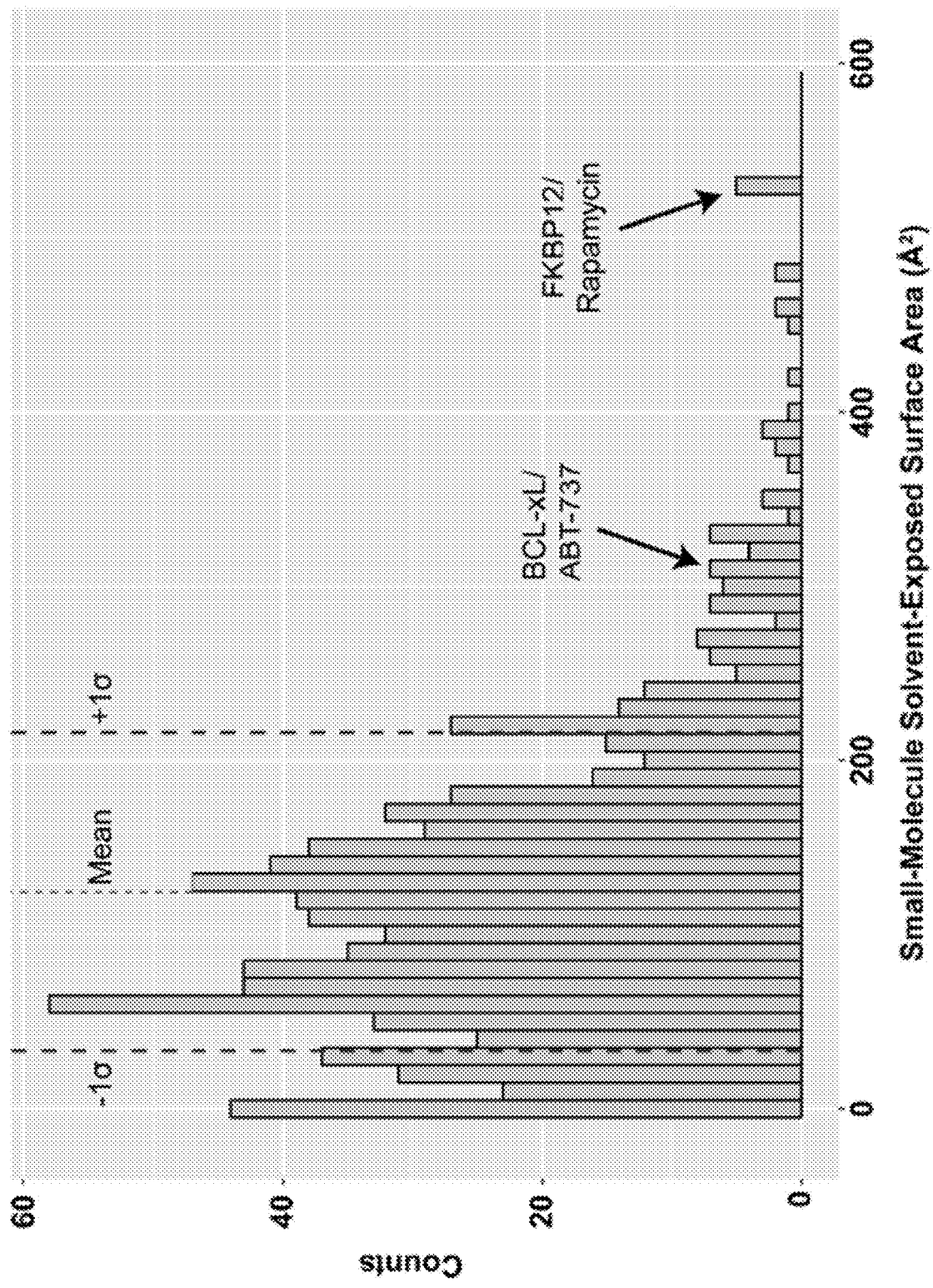
FIG. 6 shows analysis of the solvent accessibility of the small molecule in 866 small-molecule-protein complex crystal structures from the Protein Data Bank. We hypothesized that the large amount of solvent-exposed surface area of ABT-737 when in complex with BCL-xL (308 Å$^2$) would provide a chemical epitope for direct recognition by an antibody. The FKBP12/rapamycin complex (528 Å$^2$), which is part of a naturally occurring CID, is a stark outlier in this analysis, supporting our hypothesis.

Thus, in an exemplary embodiment, the invention provides an antibody capable of specifically binding to a complex formed between Protein$^b$ and its cognate SM binding partner. In various embodiments, the antibody specifically binds to at least a portion of the complexed SM. In various embodiments, the antibody binds to at least a portion of Protein$^b$ complexed with SM. In an exemplary embodiment, the antibody binds simultaneously to both at least a portion of the complexed SM and at least a portion of Protein$^b$ bound to SM. In various embodiments, one or both of these binding modalities is a component of the specific binding of the antibody to the Protein$^b$-SM complex. In an exemplary embodiment, Protein$^a$ binds to the Protein$^b$-SM complex at a position or surface having substantial solvent access. There are several approaches useful to define surface accessibility of the SM in the Protein$^b$-SM complex. For example, a crystal structure of the Protein$^b$-SM complex can be used to calculate the solvent accessibility of the SM in the complex. FIG. 6 provides an exemplification, showing calculation of surface accessibility for various SMs when bound to Protein$^b$ based on known structures of the complex. Other methods of inferring solvent accessibility of the bound SM include NMR methods to either determine their structure, or solvent interactions with the SM. Another measure of surface accessibility is the amount of surface area of the Protein$^b$-SM complex exposed to solvent. Exemplary ranges for a solvent exposed surface area are less than about 1000 $Å^2$, e.g., less than about 500 $Å^2$, less than about 100 $Å^2$, less than about 50 $Å^2$. In exemplary embodiments, the solvent accessible surface is from about 1 to about 20 $Å^2$, e.g., from about 1 to about 10 $Å^2$, or from about 10-20 $Å^2$.

Traditional full antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention provides dimers incorporating bispecific antibodies that generally are based on the IgG class, which has several subclasses, including, but not limited to IgG1, IgG2, IgG3, and IgG4. In general, IgG1, IgG2 and IgG4 are used more frequently than IgG3. It should be noted that IgG1 has different allotypes with polymorphisms at 356 (D or E) and 358 (L or M). In an exemplary embodiment, Protein$^a$, and/or Protein$^b$ is a humanized Ab generated, when made part of a bi-specifc antibody, would allow for SM-induced formation of Ab-mediated cell-cell interactions, such as T-Cells engineered to express BCL-XL on their surface and cancer cells with tumor specific antigens.

"Isotype" as used herein is meant any of the subclasses of immunoglobulins defined by the chemical and antigenic characteristics of their constant regions. It should be understood that therapeutic antibodies can also comprise hybrids of isotypes and/or subclasses. For example, as shown in US Publication 2009/0163699, incorporated by reference, the present invention covers pI engineering of IgG1/G2 hybrids.

The amino-terminal portion of each chain includes a variable region of about 100 to 110 or more amino acids primarily responsible for antigen recognition, generally referred to in the art and herein as the "Fv domain" or "Fv region". In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

As will be appreciated by those in the art, the exact numbering and placement of the CDRs can be different among different numbering systems. However, it should be understood that the disclosure of a variable heavy and/or variable light sequence includes the disclosure of the associated (inherent) CDRs. Accordingly, the disclosure of each variable heavy region is a disclosure of the vhCDRs (e.g. vhCDR1, vhCDR2 and vhCDR3) and the disclosure of each variable light region is a disclosure of the vlCDRs (e.g. vlCDR1, vlCDR2 and vlCDR3).

Throughout the present specification, the Kabat numbering system is generally used when referring to a residue in the variable domain (approximately, residues 1-107 of the light chain variable region and residues 1-113 of the heavy chain variable region) and the EU numbering system for Fc regions (e.g, Kabat et al., supra (1991)).

The present invention provides a large number of different CDR sets. In this case, a "full CDR set" comprises the three variable light and three variable heavy CDRs, e.g. a vlCDR1, vlCDR2, vlCDR3, vhCDR1, vhCDR2 and vhCDR3. These can be part of a larger variable light or variable heavy domain, respectfully. In addition, as more fully outlined herein, the variable heavy and variable light domains can be on separate polypeptide chains, when a heavy and light chain is used (for example when Fabs are used), or on a single polypeptide chain in the case of scFv sequences.

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope. An exemplary epitope is that which is formed by the complex formed by the binding of the SM to Protein[b]. In an exemplary embodiment employing ABT-737 as a part of the epitope, it has been demonstrated that a related analogue, ABT-263, does not result in the formation of a dimer, thereby demonstrating that at least a portion of the SM is a component of the binding site for Protein[b].

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide. Exemplary epitopes of use in the compounds and methods of the invention include those structures formed by the binding of SM by Protein[b].

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and non-conformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning." As outlined below, the invention not only includes the enumerated antigen binding domains and antibodies herein, but those that compete for binding with the epitopes bound by the enumerated antigen binding domains.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al., entirely incorporated by reference).

Exemplary AbCIDs

In some embodiments, according to any of the AbCIDs described herein, the AbCID comprises (a) a first CID component comprising an ABT-737-binding domain of Bcl-xL and (b) a second CID component comprising an antibody moiety capable of specifically binding to a complex between ABT-737 and the first CID component, wherein the antibody moiety of the second CID component comprises a heavy chain variable domain and a light chain variable domain comprising HC-CDRs and LC-CDRs as shown in Table 1, or variants thereof having at least 85% homology. In some embodiments, the ABT-737-binding domain comprises the amino acid sequence of SEQ ID NO: 314 or a variant thereof having at least 85% homology to the amino acid sequence of SEQ ID NO: 314.

TABLE 1

| | Bcl-xL + ABT-737 | | | |
| --- | --- | --- | --- | --- |
| Clone | HC-CDR1 (SEQ ID NO) | HC-CDR2 (SEQ ID NO) | HC-CDR3 (SEQ ID NO) | LC-CDR3 (SEQ ID NO) |
| FAB-AZ1 | 1 | 53 | 113 | 214 |
| FAB-AZ2 | 2 | 54 | 114 | 215 |
| FAB-AZ3 | 3 | 53 | 115 | 216 |
| FAB-AZ4 | 4 | 55 | 116 | 217 |
| FAB-AZ5 | 5 | 56 | 117 | 218 |
| FAB-AZ6 | 6 | 57 | 118 | 219 |
| FAB-AZ7 | 7 | 58 | 119 | 219 |
| FAB-AZ8 | 8 | 59 | 120 | 220 |
| FAB-AZ9 | 9 | 60 | 120 | 221 |
| FAB-AZ10 | 10 | 61 | 120 | 222 |

For all clones: LC-CDR1-SEQ ID NO: 310, LC-CDR2-SEQ ID NO: 311

In some embodiments, according to any of the AbCIDs described herein, the AbCID comprises (a) a first CID component comprising an ABT-199-binding domain of Bcl-2 and (b) a second CID component comprising an antibody moiety capable of specifically binding to a complex between ABT-199 and the first CID component, wherein the antibody moiety of the second CID component comprises a heavy chain variable domain and a light chain variable domain comprising HC-CDRs and LC-CDRs as shown in Table 2, or variants thereof having at least 85% homology. In some embodiments, the ABT-199-binding domain comprises the amino acid sequence of SEQ ID NO: 315 or a variant thereof having at least 85% homology to the amino acid sequence of SEQ ID NO: 315.

TABLE 2

Bcl-2 + ABT-199

| Clone | HC-CDR1 (SEQ ID NO) | HC-CDR2 (SEQ ID NO) | HC-CDR3 (SEQ ID NO) | LC-CDR3 (SEQ ID NO) |
|---|---|---|---|---|
| FAB-AZ11 | 11 | 62 | 120 | 223 |
| FAB-AZ12 | 9 | 63 | 121 | 224 |
| FAB-AZ13 | 12 | 64 | 122 | 225 |
| FAB-AZ14 | 13 | 65 | 123 | 226 |
| FAB-AZ15 | 14 | 66 | 120 | 227 |
| FAB-AZ16 | 15 | 67 | 124 | 228 |
| FAB-AZ17 | 16 | 68 | 125 | 229 |
| FAB-AZ18 | 17 | 69 | 126 | 230 |
| FAB-AZ19 | 18 | 70 | 127 | 231 |
| FAB-AZ20 | 19 | 71 | 128 | 232 |
| FAB-AZ21 | 1 | 72 | 129 | 233 |
| FAB-AZ22 | 19 | 73 | 130 | 234 |
| FAB-AZ23 | 20 | 74 | 131 | 235 |
| FAB-AZ24 | 14 | 55 | 120 | 236 |
| FAB-AZ25 | 14 | 66 | 132 | 237 |
| FAB-AZ26 | 21 | 56 | 133 | 238 |
| FAB-AZ27 | 15 | 67 | 134 | 228 |
| FAB-AZ28 | 14 | 56 | 135 | 239 |
| FAB-AZ29 | 22 | 55 | 136 | 240 |
| FAB-AZ30 | 19 | 66 | 120 | 241 |
| FAB-AZ31 | 23 | 75 | 137 | 242 |
| FAB-AZ32 | 19 | 66 | 120 | 243 |
| FAB-AZ33 | 14 | 55 | 120 | 244 |
| FAB-AZ34 | 23 | 75 | 137 | 242 |
| FAB-AZ35 | 9 | 76 | 138 | 245 |
| FAB-AZ36 | 24 | 77 | 139 | 246 |
| FAB-AZ37 | 25 | 78 | 140 | 247 |
| FAB-AZ38 | 8 | 79 | 141 | 248 |
| FAB-AZ39 | 11 | 55 | 120 | 249 |
| FAB-AZ40 | 26 | 69 | 142 | 250 |
| FAB-AZ41 | 27 | 80 | 143 | 251 |
| FAB-AZ42 | 28 | 81 | 144 | 252 |
| FAB-AZ43 | 29 | 82 | 145 | 253 |

For all clones: LC-CDR1-SEQ ID NO: 310, LC-CDR2-SEQ ID NO: 311

In some embodiments, according to any of the AbCIDs described herein, the AbCID comprises (a) a first CID component comprising an ABT-263-binding domain of Bcl-2 and (b) a second CID component comprising an antibody moiety capable of specifically binding to a complex between ABT-263 and the first CID component, wherein the antibody moiety of the second CID component comprises a heavy chain variable domain and a light chain variable domain comprising HC-CDRs and LC-CDRs as shown in Table 3, or variants thereof having at least 85% homology. In some embodiments, the ABT-263-binding domain comprises the amino acid sequence of SEQ ID NO: 315 or a variant thereof having at least 85% homology to the amino acid sequence of SEQ ID NO: 315.

TABLE 3

Bcl-2 + ABT-263

| Clone | HC-CDR1 (SEQ ID NO) | HC-CDR2 (SEQ ID NO) | HC-CDR3 (SEQ ID NO) | LC-CDR3 (SEQ ID NO) |
|---|---|---|---|---|
| FAB-AZ44 | 30 | 83 | 146 | 254 |
| FAB-AZ45 | 31 | 84 | 147 | 255 |
| FAB-AZ46 | 32 | 58 | 148 | 256 |
| FAB-AZ47 | 33 | 85 | 149 | 257 |
| FAB-AZ48 | 32 | 58 | 148 | 256 |
| FAB-AZ49 | 34 | 86 | 150 | 258 |

TABLE 3-continued

Bcl-2 + ABT-263

| Clone | HC-CDR1 (SEQ ID NO) | HC-CDR2 (SEQ ID NO) | HC-CDR3 (SEQ ID NO) | LC-CDR3 (SEQ ID NO) |
|---|---|---|---|---|
| FAB-AZ50 | 35 | 87 | 151 | 259 |
| FAB-AZ51 | 30 | 83 | 152 | 260 |
| FAB-AZ52 | 36 | 81 | 153 | 261 |
| FAB-AZ53 | 30 | 83 | 154 | 262 |
| FAB-AZ54 | 37 | 58 | 155 | 263 |
| FAB-AZ55 | 30 | 88 | 156 | 264 |
| FAB-AZ56 | 31 | 89 | 157 | 265 |
| FAB-AZ57 | 13 | 81 | 158 | 266 |
| FAB-AZ58 | 27 | 88 | 159 | 267 |

For all clones: LC-CDR1-SEQ ID NO: 310, LC-CDR2-SEQ ID NO: 311

In some embodiments, according to any of the AbCIDs described herein, the AbCID comprises (a) a first CID component comprising an LCL161-binding domain of cIAP1 and (b) a second CID component comprising an antibody moiety capable of specifically binding to a complex between LCL161 and the first CID component, wherein the antibody moiety of the second CID component comprises a heavy chain variable domain and a light chain variable domain comprising HC-CDRs and LC-CDRs as shown in Table 4, or variants thereof having at least 85% homology. In some embodiments, the LCL161-binding domain comprises the amino acid sequence of SEQ ID NO: 317 or a variant thereof having at least 85% homology to the amino acid sequence of SEQ ID NO: 317.

TABLE 4 cIAP1 + LCL161

| Clone | HC-CDR1 (SEQ ID NO) | HC-CDR2 (SEQ ID NO) | HC-CDR3 (SEQ ID NO) | LC-CDR3 (SEQ ID NO) |
|---|---|---|---|---|
| FAB-AZ59 | 38 | 56 | 160 | 268 |
| FAB-AZ60 | 39 | 90 | 161 | 269 |
| FAB-AZ61 | 33 | 91 | 162 | 270 |
| FAB-AZ62 | 40 | 92 | 163 | 271 |
| FAB-AZ63 | 36 | 93 | 164 | 272 |

For all clones: LC-CDR1-SEQ ID NO: 310, LC-CDR2-SEQ ID NO: 311

In some embodiments, according to any of the AbCIDs described herein, the AbCID comprises (a) a first CID component comprising an GDC-0152-binding domain of cIAP1 and (b) a second CID component comprising an antibody moiety capable of specifically binding to a complex between GDC-0152 and the first CID component, wherein the antibody moiety of the second CID component comprises a heavy chain variable domain and a light chain variable domain comprising HC-CDRs and LC-CDRs as shown in Table 5, or variants thereof having at least 85% homology. In some embodiments, the GDC-0152-binding domain comprises the amino acid sequence of SEQ ID NO: 317 or a variant thereof having at least 85% homology to the amino acid sequence of SEQ ID NO: 317.

TABLE 5 cIAP1 + GDC-0152

| Clone | HC-CDR1 (SEQ ID NO) | HC-CDR2 (SEQ ID NO) | HC-CDR3 (SEQ ID NO) | LC-CDR3 (SEQ ID NO) |
|---|---|---|---|---|
| FAB-AZ65 | 9 | 56 | 165 | 273 |
| FAB-AZ66 | 35 | 94 | 166 | 274 |
| FAB-AZ67 | 38 | 95 | 167 | 275 |

TABLE 5-continued

| | cIAP1 + GDC-0152 | | | |
|---|---|---|---|---|
| Clone | HC-CDR1 (SEQ ID NO) | HC-CDR2 (SEQ ID NO) | HC-CDR3 (SEQ ID NO) | LC-CDR3 (SEQ ID NO) |
| FAB-AZ68 | 41 | 96 | 168 | 276 |
| FAB-AZ69 | 33 | 64 | 169 | 277 |
| FAB-AZ70 | 38 | 65 | 170 | 278 |
| FAB-AZ71 | 26 | 88 | 171 | 279 |
| FAB-AZ72 | 40 | 97 | 172 | 253 |
| FAB-AZ73 | 42 | 98 | 173 | 280 |
| FAB-AZ74 | 38 | 88 | 174 | 253 |
| FAB-AZ75 | 43 | 99 | 175 | 281 |
| FAB-AZ76 | 40 | 100 | 176 | 282 |
| FAB-AZ77 | 44 | 101 | 177 | 283 |
| FAB-AZ78 | 30 | 102 | 178 | 284 |
| FAB-AZ79 | 45 | 96 | 179 | 285 |
| FAB-AZ80 | 44 | 81 | 180 | 286 |

For all clones: LC-CDR1-SEQ ID NO: 310, LC-CDR2-SEQ ID NO: 311

In some embodiments, according to any of the AbCIDs described herein, the AbCID comprises (a) a first CID component comprising an AT406-binding domain of cIAP1 and (b) a second CID component comprising an antibody moiety capable of specifically binding to a complex between AT406 and the first CID component, wherein the antibody moiety of the second CID component comprises a heavy chain variable domain and a light chain variable domain comprising HC-CDRs and LC-CDRs as shown in Table 6, or variants thereof having at least 85% homology. In some embodiments, the AT406-binding domain comprises the amino acid sequence of SEQ ID NO: 317 or a variant thereof having at least 85% homology to the amino acid sequence of SEQ ID NO: 317

TABLE 6

| | cIAP1 + AT406 | | | |
|---|---|---|---|---|
| Clone | HC-CDR1 (SEQ ID NO) | HC-CDR2 (SEQ ID NO) | HC-CDR3 (SEQ ID NO) | LC-CDR3 (SEQ ID NO) |
| FAB-AZ81 | 38 | 73 | 181 | 287 |
| FAB-AZ82 | 31 | 103 | 182 | 288 |
| FAB-AZ83 | 31 | 104 | 183 | 289 |
| FAB-AZ84 | 33 | 63 | 184 | 290 |
| FAB-AZ85 | 46 | 82 | 185 | 291 |
| FAB-AZ86 | 13 | 82 | 186 | 253 |
| FAB-AZ87 | 26 | 93 | 187 | 253 |
| FAB-AZ88 | 13 | 82 | 188 | 253 |
| FAB-AZ89 | 13 | 94 | 189 | 253 |
| FAB-AZ90 | 20 | 71 | 190 | 292 |
| FAB-AZ91 | 47 | 81 | 191 | 293 |

For all clones: LC-CDR1-SEQ ID NO: 310, LC-CDR2-SEQ ID NO: 311

In some embodiments, according to any of the AbCIDs described herein, the AbCID comprises (a) a first CID component comprising an CUDC-427-binding domain of cIAP1 and (b) a second CID component comprising an antibody moiety capable of specifically binding to a complex between CUDC-427 and the first CID component, wherein the antibody moiety of the second CID component comprises a heavy chain variable domain and a light chain variable domain comprising HC-CDRs and LC-CDRs as shown in Table 7, or variants thereof having at least 85% homology. In some embodiments, the CUDC-427-binding domain comprises the amino acid sequence of SEQ ID NO: 317 or a variant thereof having at least 85% homology to the amino acid sequence of SEQ ID NO: 317.

TABLE 7

| | cIAP1 + CUDC-427 | | | |
|---|---|---|---|---|
| Clone | HC-CDR1 (SEQ ID NO) | HC-CDR2 (SEQ ID NO) | HC-CDR3 (SEQ ID NO) | LC-CDR3 (SEQ ID NO) |
| FAB-AZ92 | 48 | 105 | 192 | 253 |
| FAB-AZ93 | 38 | 106 | 193 | 294 |
| FAB-AZ94 | 13 | 94 | 194 | 253 |
| FAB-AZ95 | 38 | 82 | 195 | 253 |
| FAB-AZ96 | 42 | 107 | 196 | 295 |
| FAB-AZ97 | 49 | 108 | 197 | 296 |
| FAB-AZ98 | 36 | 109 | 198 | 297 |
| FAB-AZ99 | 45 | 107 | 199 | 298 |
| FAB-AZ100 | 13 | 82 | 200 | 299 |
| FAB-AZ101 | 49 | 110 | 201 | 300 |
| FAB-AZ102 | 50 | 82 | 202 | 253 |
| FAB-AZ103 | 26 | 83 | 203 | 301 |
| FAB-AZ104 | 51 | 90 | 204 | 302 |
| FAB-AZ105 | 33 | 94 | 205 | 303 |
| FAB-AZ106 | 13 | 82 | 206 | 253 |

For all clones: LC-CDR1-SEQ ID NO: 310, LC-CDR2-SEQ ID NO: 311

In some embodiments, according to any of the AbCIDs described herein, the AbCID comprises (a) a first CID component comprising a synthetic ligand of rapamycin (SLF)-binding domain of FKBP, wherein the SLF has the structure of Formula (I):

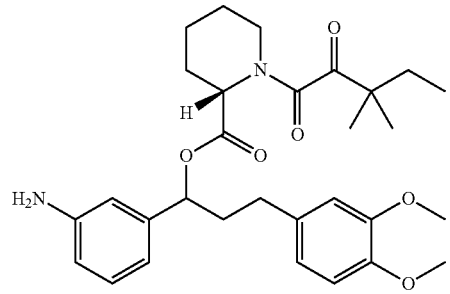 [SMILES: CCC(C)(C)C(=O)C(=O)N1CCCC[C@H]1C(=O)OC(CCc1ccc(OC)c(OC)c1)c1cccc(N)c1]

and (b) a second CID component comprising an antibody moiety capable of specifically binding to a complex between the SLF and the first CID component, wherein the antibody moiety of the second CID component comprises a heavy chain variable domain and a light chain variable domain comprising HC-CDRs and LC-CDRs as shown in Table 8, or variants thereof having at least 85% homology. In some embodiments, the SLF-binding domain comprises the amino acid sequence of SEQ ID NO: 316 or a variant thereof having at least 85% homology to the amino acid sequence of SEQ ID NO: 316.

TABLE 8

| | FKBP + SLF | | | |
|---|---|---|---|---|
| Clone | HC-CDR1 (SEQ ID NO) | HC-CDR2 (SEQ ID NO) | HC-CDR3 (SEQ ID NO) | LC-CDR3 (SEQ ID NO) |
| FAB-AZ107 | 37 | 89 | 207 | 304 |
| FAB-AZ108 | 31 | 73 | 208 | 305 |
| FAB-AZ109 | 26 | 111 | 209 | 306 |
| FAB-AZ110 | 13 | 82 | 210 | 253 |
| FAB-AZ111 | 43 | 83 | 211 | 307 |
| FAB-AZ112 | 35 | 112 | 212 | 308 |

For all clones: LC-CDR1-SEQ ID NO: 310, LC-CDR2-SEQ ID NO: 311

In some embodiments, according to any of the AbCIDs described herein, the AbCID comprises (a) a first CID component comprising a methotrexate-binding Fab, wherein the methotrexate-binding Fab HC-CDR1, HC-CDR2, HC-CDR3, LC-CDR1, LC-CDR2, and LC-CDR3 comprise the amino acid sequences of SEQ ID NOs: 318, 319, 320, 321, 322, and 323, respectively, or variants thereof having at least 85% homology and (b) a second CID component comprising an antibody moiety capable of specifically binding to a complex between methotrexate and the first CID component, wherein the antibody moiety of the second CID component comprises a heavy chain variable domain and a light chain variable domain comprising HC-CDRs and LC-CDRs as shown in Table 9, or variants thereof having at least 85% homology. In some embodiments, the methotrexate-binding Fab is a methotrexate-binding Fab as described in Gayda et al. Biochemistry 2014 53 (23), 3719-3726.

TABLE 9

Fab + methotrexate

| Clone | HC-CDR1 (SEQ ID NO) | HC-CDR2 (SEQ ID NO) | HC-CDR3 (SEQ ID NO) | LC-CDR3 (SEQ ID NO) |
|---|---|---|---|---|
| FAB-AZ118 | 52 | 100 | 213 | 309 |

LC-CDR1-SEQ ID NO: 310, LC-CDR2-SEQ ID NO: 311

Systems

In some embodiments, provided herein is a system comprising (a) a first chemically-induced dimer (CID) component comprising (i) a first binding moiety capable of interacting with a small molecule to form a complex between the first CID component and the small molecule (such a first binding moiety also referred to herein as Protein$^b$); and (ii) a first adapter moiety linked to the first binding moiety, or a first nucleic acid encoding polypeptide components of the first CID component; and (b) a second CID component comprising (i) a second binding moiety that specifically binds to the complex between the small molecule and the first CID component (such a second binding moiety also referred to herein as Protein$^a$); and (ii) a second adapter moiety linked to the second binding moiety, or a second nucleic acid encoding polypeptide components of the second CID component, wherein the second binding moiety specifically binds to a site of the complex comprising at least a portion of the small molecule and a portion of the first binding moiety. In some embodiments, the system further comprises the small molecule, wherein the second CID component is bound to a complex between the small molecule and the first CID component at a site of the complex comprising at least a portion of the small molecule and a portion of the first binding moiety. In some embodiments, the site of the complex comprising at least a portion of the small molecule and a portion of the first binding moiety is an interface between the small molecule and a binding site of the first binding moiety for the small molecule, comprising at least one atom of the small molecule and one atom of the first binding moiety.

In some embodiments, according to any of the systems described herein wherein the second binding moiety specifically binds to a site of the complex comprising at least a portion of the small molecule and a portion of the first binding moiety, the first binding moiety is a first antibody moiety that specifically binds to the small molecule. In some embodiments, the small molecule is methotrexate. In some embodiments, the first antibody moiety that specifically binds to methotrexate is a methotrexate-binding Fab. For example, in some embodiments, the first antibody moiety is a methotrexate-binding Fab as described in Gayda et al. Biochemistry 2014 53 (23), 3719-3726. In some embodiments, the first antibody moiety is a methotrexate-binding Fab comprising one or more CDRs from the methotrexate-binding Fab described in Gayda et al. In some embodiments, the first antibody moiety is a methotrexate-binding Fab comprising each of the CDRs from the methotrexate-binding Fab described in Gayda et al. In some embodiments, the methotrexate-binding Fab comprises HC-CDR1, HC-CDR2, HC-CDR3, LC-CDR1, LC-CDR2, and LC-CDR3 comprising the amino acid sequences of SEQ ID NOs: 318, 319, 320, 321, 322, and 323, respectively, or variants thereof having at least 85% homology.

In some embodiments, according to any of the systems described herein wherein the second binding moiety specifically binds to a site of the complex comprising at least a portion of the small molecule and a portion of the first binding moiety, the first binding moiety is derived from a naturally occurring binding partner of the small molecule, or a small molecule-binding variant thereof. In some embodiments, the naturally occurring binding partner is Bcl-2, Bcl-xL, FK506 binding protein (FKBP), or cellular inhibitor of apoptosis protein 1 (cIAP1). In some embodiments, the naturally occurring binding partner is Bcl-2 and the small molecule is ABT-199, ABT-263 or an analog thereof. In some embodiments, the naturally occurring binding partner is Bcl-xL and the small molecule is ABT-737 or an analog thereof. In some embodiments, the naturally occurring binding partner is FKBP and the small molecule is a synthetic ligand of rapamycin (SLF) having the structure of Formula (I) or an analog thereof. In some embodiments, the naturally occurring binding partner is cIAP1 and the small molecule is GDC-0152, LCL161, AT406, CUDC-427, Birinapant, or an analog thereof.

In some embodiments, according to any of the systems described herein wherein the second binding moiety specifically binds to a site of the complex comprising at least a portion of the small molecule and a portion of the first binding moiety, the second binding moiety is an antibody moiety that specifically binds to a chemical-epitope comprising at least a portion of the small molecule and a portion of the first binding moiety. In some embodiments, the site of the complex comprising at least a portion of the small molecule and a portion of the first binding moiety is an interface between the small molecule and a binding site of the first binding moiety for the small molecule, comprising at least one atom of the small molecule and one atom of the first binding moiety.

In some embodiments, according to any of the systems described herein, the second CID component binds to the complex of the first CID component and the small molecule with a dissociation constant ($K_d$) no more than about $1/250$ times (such as no more than about any of $1/300$, $1/350$, $1/400$, $1/450$, $1/500$, $1/600$, $1/700$, $1/800$, $1/900$, $1/1000$, $1/1100$, $1/1200$, $1/1300$, $1/1400$, or $1/1500$ times, or less) its $K_d$ for binding to each of the free first CID component and the free small molecule.

In some embodiments, provided herein is a system comprising (a) a first CID component comprising (i) an ABT-737-binding domain of Bcl-xL and (ii) a first adapter moiety, or a first nucleotide encoding polypeptide components of the first CID component; and (b) a second CID component comprising (i) an antibody moiety capable of specifically binding to a complex between ABT-737 and the first CID component and (ii) a second adapter moiety, or a second nucleic acid encoding polypeptide components of the second CID component, wherein the antibody moiety of the second CID component comprises heavy chain and light chain complementarity determining regions (CDRs) according to Table 1, or variants thereof having at least 85% homology. In some embodiments, the ABT-737-binding domain comprises the amino acid sequence of SEQ ID NO: 314 or a variant thereof having at least 85% homology to the amino acid sequence of SEQ ID NO: 314.

In some embodiments, provided herein is a system comprising (a) a first CID component comprising (i) an ABT-199-binding domain of Bcl-2 and (ii) a first adapter moiety, or a first nucleotide encoding polypeptide components of the first CID component; and (b) a second CID component comprising (i) an antibody moiety capable of specifically binding to a complex between ABT-199 and the first CID component and (ii) a second adapter moiety, or a second nucleic acid encoding polypeptide components of the second CID component, wherein the antibody moiety of the second CID component comprises heavy chain and light chain complementarity determining regions (CDRs) according to Table 2, or variants thereof having at least 85% homology. In some embodiments, the ABT-199-binding domain comprises the amino acid sequence of SEQ ID NO: 315 or a variant thereof having at least 85% homology to the amino acid sequence of SEQ ID NO: 315.

In some embodiments, provided herein is a system comprising (a) a first CID component comprising (i) an ABT-263-binding domain of Bcl-2 and (ii) a first adapter moiety, or a first nucleotide encoding polypeptide components of the first CID component; and (b) a second CID component comprising (i) an antibody moiety capable of specifically binding to a complex between ABT-263 and the first CID component and (ii) a second adapter moiety, or a second nucleic acid encoding polypeptide components of the second CID component, wherein the antibody moiety of the second CID component comprises heavy chain and light chain complementarity determining regions (CDRs) according to Table 3, or variants thereof having at least 85% homology. In some embodiments, the ABT-263-binding domain comprises the amino acid sequence of SEQ ID NO: 315 or a variant thereof having at least 85% homology to the amino acid sequence of SEQ ID NO: 315.

In some embodiments, provided herein is a system comprising (a) a first CID component comprising (i) a synthetic ligand of rapamycin (SLF)-binding domain of FKBP and (ii) a first adapter moiety, or a first nucleotide encoding polypeptide components of the first CID component, wherein the SLF has the structure of Formula (I); and (b) a second CID component comprising (i) an antibody moiety capable of specifically binding to a complex between the SLF and the first CID component and (ii) a second adapter moiety, or a second nucleic acid encoding polypeptide components of the second CID component, wherein the antibody moiety of the second CID component comprises heavy chain and light chain complementarity determining regions (CDRs) according to Table 4, or variants thereof having at least 85% homology. In some embodiments, the SLF-binding domain comprises the amino acid sequence of SEQ ID NO: 316 or a variant thereof having at least 85% homology to the amino acid sequence of SEQ ID NO: 316.

In some embodiments, provided herein is a system comprising (a) a first CID component comprising (i) a GDC-0152-binding domain of cIAP1 and (ii) a first adapter moiety, or a first nucleotide encoding polypeptide components of the first OD component; and (b) a second CID component comprising (i) an antibody moiety capable of specifically binding to a complex between GDC-0152 and the first CID component and (ii) a second adapter moiety, or a second nucleic acid encoding polypeptide components of the second CID component, wherein the antibody moiety of the second CID component comprises heavy chain and light chain complementarity determining regions (CDRs) according to Table 5, or variants thereof having at least 85% homology. In some embodiments, the GDC-0152-binding domain comprises the amino acid sequence of SEQ ID NO: 317 or a variant thereof having at least 85% homology to the amino acid sequence of SEQ ID NO: 317.

In some embodiments, provided herein is a system comprising (a) a first CID component comprising (i) a LCL161-binding domain of cIAP1 and (ii) a first adapter moiety, or a first nucleotide encoding polypeptide components of the first CID component; and (b) a second CID component comprising (i) an antibody moiety capable of specifically binding to a complex between LCL161 and the first CID component and (ii) a second adapter moiety, or a second nucleic acid encoding polypeptide components of the second CID component, wherein the antibody moiety of the second CID component comprises heavy chain and light chain complementarity determining regions (CDRs) according to Table 6, or variants thereof having at least 85% homology. In some embodiments, the LCL161-binding domain comprises the amino acid sequence of SEQ ID NO: 317 or a variant thereof having at least 85% homology to the amino acid sequence of SEQ ID NO: 317.

In some embodiments, provided herein is a system comprising (a) a first CID component comprising (i) a AT406-binding domain of cIAP1 and (ii) a first adapter moiety, or a first nucleotide encoding polypeptide components of the first CID component; and (b) a second CID component comprising (i) an antibody moiety capable of specifically binding to a complex between AT406 and the first CID component and (ii) a second adapter moiety, or a second nucleic acid encoding polypeptide components of the second CID component, wherein the antibody moiety of the second CID component comprises heavy chain and light chain complementarity determining regions (CDRs) according to Table 7, or variants thereof having at least 85% homology. In some embodiments, the AT406-binding domain comprises the amino acid sequence of SEQ ID NO: 317 or a variant thereof having at least 85% homology to the amino acid sequence of SEQ ID NO: 317.

In some embodiments, provided herein is a system comprising (a) a first OD component comprising (i) a CUDC-427-binding domain of cIAP1 and (ii) a first adapter moiety, or a first nucleotide encoding polypeptide components of the first CID component; and (b) a second CID component comprising (i) an antibody moiety capable of specifically binding to a complex between CUDC-427 and the first CID component and (ii) a second adapter moiety, or a second nucleic acid encoding polypeptide components of the second CID component, wherein the antibody moiety of the second CID component comprises heavy chain and light chain complementarity determining regions (CDRs) according to Table 8, or variants thereof having at least 85% homology. In some embodiments, the CUDC-427-binding domain comprises the amino acid sequence of SEQ ID NO: 317 or a variant thereof having at least 85% homology to the amino acid sequence of SEQ ID NO: 317.

In some embodiments, provided herein is a system comprising (a) a first CID component comprising (i) a methotrexate-binding Fab and (ii) a first adapter moiety, or a first nucleotide encoding polypeptide components of the first CID component; and (b) a second CID component comprising (i) an antibody moiety capable of specifically binding to a complex between methotrexate and the first CID component and (ii) a second adapter moiety, or a second nucleic acid encoding polypeptide components of the second CID component, wherein the antibody moiety of the second CID component comprises heavy chain and light chain complementarity determining regions (CDRs) according to Table 9, or variants thereof having at least 85% homology. In some embodiments, the methotrexate-binding Fab HC-CDR1, HC-CDR2, HC-CDR3, LC-CDR1, LC-CDR2, and LC-CDR3 comprise the amino acid sequences of SEQ ID NOs: 318, 319, 320, 321, 322, and 323, respectively. In some embodiments, the methotrexate-binding Fab is a methotrexate-binding Fab as described in Gayda et al. Biochemistry 2014 53 (23), 3719-3726.

Transcriptional Regulator

In some embodiments, according to any of the systems described herein, (a) the first adapter moiety comprises a DNA binding domain and the second adapter moiety comprises a transcriptional regulatory domain; or (b) the second adapter moiety comprises a DNA binding domain and the first adapter moiety comprises a transcriptional regulatory domain, wherein the first CID component and the second CID component are configured such that when dimerized in the presence of the small molecule to form the CID, the CID is capable of regulating transcription of a target gene. In some embodiments, the first CID component further comprises a nuclear localization signal and the second CID component further comprises a nuclear localization signal. In some embodiments, (i) the transcriptional regulatory domain is a transcriptional activation domain, and the CID is capable of upregulating transcription of the target gene; or (ii) the transcriptional regulatory domain is a transcriptional repressor domain, and the CID is capable of downregulating transcription of the target gene. In some embodiments, the transcriptional regulatory domain is a VPR transcriptional activation domain (see, for example, Chavez, et al., *Nat. Methods,* 12:326-328 (2015)). In some embodiments, the DNA binding domain is derived from a naturally occurring transcriptional regulator. In some embodiments, the DNA binding domain is derived from an RNA-guided endonuclease or a DNA-guided endonuclease. In some embodiments, the RNA-guided endonuclease or DNA-guided endonuclease is catalytically dead. In some embodiments, the DNA binding domain is derived from a catalytically dead Cas9 (dCas9). Examples of adapter moieties, such as dCas9, that can be used in CIDs capable of regulating gene transcription can be found, for example, in U.S. Pat. No. 8,993,233.

In some embodiments, according to any of the systems described herein, (a) the first adapter moiety comprises a DNA binding domain and the second adapter moiety comprises a transcriptional regulatory domain; or (b) the second adapter moiety comprises a DNA binding domain and the first adapter moiety comprises a transcriptional regulatory domain, wherein the first CID component and the second CID component are configured such that when dimerized in the presence of the small molecule to form the CID, the CID is capable of regulating transcription of a target gene, wherein the transcriptional regulatory domain is a VPR transcriptional activation domain and the DNA binding domain is derived from dCas9.

Kill Switch

In some embodiments, according to any of the systems described herein, the first CID component and the second CID component are configured such that when dimerized in the presence of the small molecule to form a CID associated with a target cell, the CID is capable of inducing target cell death. In some embodiments, the first adapter moiety and the second adapter moiety are together capable of inducing apoptosis in the target cell. In some embodiments, the first adapter moiety and/or the second adapter moiety are derived from a caspase protein. In some embodiments, the target cell is an engineered cell adoptively transferred to an individual. In some embodiments, the target cell is a T cell expressing a chimeric antigen receptor (CAR). Examples of adapter moieties that can be used in CIDs capable of inducing cell death can be found, for example, in U.S. Patent Publication Nos. US20160175359 and US20160166613.

Control of apoptosis by dimerization of proapoptotic proteins with widely available small molecules should permit an experimenter or clinician to tightly and rapidly control the viability of a cell-based implant that displays unwanted effects. Examples of these effects include, but are not limited to, Graft versus Host (GvH) immune responses against off-target tissue or excessive, uncontrolled growth or metastasis of an implant, or CAR T cell-mediated cytokine release syndrome. Rapid induction of apoptosis will severely attenuate the unwanted cell's function and permit the natural clearance of the dead cells by phagocytic cells, such as macrophages, without undue inflammation. Apoptosis is tightly regulated and naturally uses scaffolds, such as Apaf-1, CRADD/RAIDD, or FADD/Mortl, to oligomerize and activate the caspases that can ultimately kill the cell. Apaf-1 can assemble the apoptotic protease Caspase-9 into a latent complex that then forms an active oligomeric apoptosome upon recruitment of cytochrome C to the scaffold. The key event is oligomerization of the scaffold units causing dimerization and activation of the caspase. Similar adapters, such as CRADD, can oligomerize Caspase-2, leading to apoptosis. The compositions and methods provided herein use, for example, AbCIDs that permit the spontaneous dimerization and activation of caspase units present as adapter moieties upon recruitment with a small molecule.

Using certain of the compositions and methods provided herein, caspase activation occurs only when a small molecule is present to allow dimerization of caspase-fused CID components of an AbCID. In these methods, the two AbCID components must be present as a dimeric unit, not as monomers, to drive caspase dimerization (e.g., caspase-9). The CID components may be localized within the cytosol as soluble entities or present in specific subcellular locales, such as the plasma membrane through targeting signals. The components used to activate apoptosis and the downstream components that degrade the cell are shared by all cells and across species. With regard to Caspase-9 activation, these methods can be broadly utilized in cell lines, in normal primary cells, such as, for example, but not limited to, T cells, or in cell implants. The Caspase-9 polypeptide may be full length or truncated.

Caspase polypeptides other than Caspase-9 that may be used as adapter moieties of the AbCIDs described herein include, for example, Caspase-1, Caspase-3, and Caspase-8. Discussions of these Caspase polypeptides may be found in, for example, MacCorkle, R. A., et al., Proc. Natl. Acad. Sci. U.S.A. (1998) 95:3655-3660; and Fan, L., et al. (1999) Human Gene Therapy 10:2273-2285).

Chimeric Antigen Receptor (CAR)

In some embodiments, according to any of the systems described herein, the first CID component and the second CID component are configured such that when dimerized in the presence of the small molecule to form a CID associated with a T cell, the CID is a heterodimeric CAR capable of activating the T cell upon binding a target antigen.

In some embodiments, according to any of the systems described herein, (a) the first adapter moiety comprises (i) a transmembrane domain; (ii) a cytoplasmic co-stimulatory domain; and (iii) a cytoplasmic signaling domain; and the second adapter moiety comprises an extracellular antigen-binding moiety; or (b) the second adapter moiety comprises (i) a transmembrane domain; (ii) a cytoplasmic co-stimulatory domain; and (iii) a cytoplasmic signaling domain; and the first adapter moiety comprises an extracellular antigen-binding moiety; wherein the extracellular antigen-binding moiety specifically binds to a target antigen. See, for example, FIG. 4A. In some embodiments, the CID component comprising the extracellular antigen-binding moiety further comprises a secretory signal peptide.

In some embodiments, according to any of the systems described herein, (a) the first adapter moiety comprises (i) a cytoplasmic co-stimulatory domain or a cytoplasmic signaling domain; (ii) a transmembrane domain; and (iii) an extracellular antigen-binding moiety; and the second adapter moiety comprises a cytoplasmic co-stimulatory domain or a cytoplasmic signaling domain; or (b) the second adapter moiety comprises (i) a cytoplasmic co-stimulatory domain or a cytoplasmic signaling domain; (ii) a transmembrane domain; and (iii) an extracellular antigen-binding moiety; and the first adapter moiety comprises a cytoplasmic co-stimulatory domain or a cytoplasmic signaling domain; wherein the extracellular antigen-binding moiety specifically binds to a target antigen. See, for example, FIG. 4B. In some embodiments, the first and second CID components together comprise a cytoplasmic co-stimulatory domain and a cytoplasmic signaling domain.

In some embodiments, according to any of the systems described herein, the first adapter moiety comprises (i) a cytoplasmic co-stimulatory domain or a cytoplasmic signaling domain; and (ii) a transmembrane domain; and the second adapter moiety comprises (i) a cytoplasmic co-stimulatory domain or a cytoplasmic signaling domain; and (ii) a transmembrane domain; wherein the first or second CID component further comprises an extracellular antigen-binding moiety linked to its binding moiety; and wherein the extracellular antigen-binding moiety specifically binds to a target antigen. See, for example, FIG. 4C. In some embodiments, first and second CID components together comprise a cytoplasmic co-stimulatory domain and a cytoplasmic signaling domain.

Examples of adapter moieties that can be used in CIDs to form heterodimeric CARs can be found, for example, in U.S. Pat. No. 9,587,020.

In some embodiments, an AbCID described herein can be present in the plasma membrane of a eukaryotic cell, e.g., a mammalian cell, where suitable mammalian cells include, but are not limited to, a cytotoxic cell, a T lymphocyte, a stem cell, a progeny of a stem cell, a progenitor cell, a progeny of a progenitor cell, and an NK cell. When present in the plasma membrane of a eukaryotic cell, the AbCID is active in the presence of: 1) the small molecule that allows for dimerization of the first and second CID components; and 2) a factor that binds the extracellular antigen-binding moiety. The factor that binds the extracellular antigen-binding domain can be a soluble (e.g., not bound to a cell) factor; a factor present on the surface of a cell such as a target cell; a factor presented on a solid surface; a factor present in a lipid bilayer; and the like.

In some embodiments, an AbCID of the present disclosure, when present in the plasma membrane of a eukaryotic cell, and when activated by a small molecule, results in cytotoxic activity by the cell toward a target cell that expresses on its cell surface an antigen to which the extracellular antigen-binding domain binds. For example, where the eukaryotic cell is a cytotoxic cell (e.g., an NK cell or a cytotoxic T lymphocyte), an AbCID of the present disclosure, when present in the plasma membrane of the cell, and when activated by a small molecule, increases cytotoxic activity of the cell toward a target cell that expresses on its cell surface an antigen to which the extracellular antigen-binding domain binds. For example, where the eukaryotic cell is an NK cell or a T lymphocyte, an AbCID of the present disclosure, when present in the plasma membrane of the cell, and when activated by a small molecule, increases cytotoxic activity of the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cell in the absence of the small molecule.

In some embodiments, an AbCID of the present disclosure, when present in the plasma membrane of a eukaryotic cell, and when activated by an antigen that binds the extracellular antigen-binding domain and a small molecule, can result in other CAR activation related events such as proliferation, expansion, intracellular signaling modulation, cellular differentiation, or cell death.

An extracellular antigen-binding domain suitable for use in an AbCID of the present disclosure can be any antigen-binding polypeptide, a wide variety of which are known in the art. In some instances, the extracellular antigen-binding domain is a single chain FY (scFv). Other antibody based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use. In some instances, T-cell receptor (TCR) based recognition domains such as single chain TCR (scTv, single chain two-domain TCR containing VαVβ) are also suitable for use.

An extracellular antigen-binding domain suitable for use in an AbCID of the present disclosure can have a variety of antigen-binding specificities. In some cases, the extracellular antigen-binding domain is specific for an epitope present in an antigen that is expressed by (synthesized by) a cancer cell, i.e., a cancer cell associated antigen. The cancer cell associated antigen can be an antigen associated with, e.g., a breast cancer cell, a B cell lymphoma, a Hodgkin lymphoma cell, an ovarian cancer cell, a prostate cancer cell, a mesothelioma, a lung cancer cell (e.g., a small cell lung cancer cell), a non-Hodgkin B-cell lymphoma (B-NHL) cell, an ovarian cancer cell, a prostate cancer cell, a mesothelioma cell, a lung cancer cell (e.g., a small cell lung cancer cell), a melanoma cell, a chronic lymphocytic leukemia cell, an acute lymphocytic leukemia cell, a neuroblastoma cell, a glioma, a glioblastoma, a medulloblastoma, a colorectal cancer cell, etc. A cancer cell associated antigen may also be expressed by a non-cancerous cell.

Bispecific T Cell Engager

In some embodiments, according to any of the systems described herein, the first CID component and the second CID component are configured such that when dimerized in the presence of the small molecule to form a CID, the CID is a heterodimeric bispecific T cell engager capable of redirecting a T cell to a target cell. In some embodiments, (a) the first adapter moiety comprises a T cell antigen-binding moiety and the second adapter moiety comprises a target cell antigen-binding moiety; or (b) the second adapter moiety comprises a T cell antigen-binding moiety and the first adapter moiety comprises a target cell antigen-binding moiety. In some embodiments, the T cell antigen-binding moiety is an antibody moiety that specifically binds to CD3. In some embodiments, the target cell antigen-binding moiety is an antibody moiety that specifically binds to a cell surface antigen associated with a diseased cell. In some embodiments, the diseased cell is a cancer cell. In some embodiments, the target cell antigen-binding moiety is an antibody moiety that specifically binds to CD19. Examples of adapter moieties that can be used in CIDs to form heterodimeric bispecific T cell engagers can be found, for example, in U.S. Patent Publication No. US20140050660.

T Cell Modulation

In some embodiments, according to any of the systems described herein, the first CID component and the second CID component are configured such that when dimerized in the presence of the small molecule to form a CID associated with an immune cell, the CID is a heterodimeric signaling molecule capable of modulating activation of the immune cell. In some embodiments, the first adapter moiety comprises (i) a transmembrane domain; and (ii) a cytoplasmic co-stimulatory domain; and the second adapter moiety comprises (i) a transmembrane domain; and (ii) a cytoplasmic co-stimulatory domain. In some embodiments, the immune cell is a T cell. In some embodiments, the T cell is a CAR T cell. Examples of adapter moieties that can be used in CIDs to form heterodimeric signaling molecules capable of modulating activation of an immune cell can be found, for example, in U.S. Patent Publication No. 20140286987.

In some embodiments, the adapter moieties of an AbCID described herein comprise one or more co-stimulatory polypeptides, such as, for example, CD28 and 4-1BB, with and without the CD3 zeta chain, to enable AbCID-dependent proliferation and co-stimulation. The AbCID may be used alone to provide co-stimulation, and increase a T cell immune response. Using such AbCIDs, a population of T cells, for example a population with non-specific targets, may be transfected or transformed with DNA encoding an AbCID, then administered to a subject to enhance a general immune response. These AbCIDs may also be expressed in a cell along with a CAR. In such methods, an inducible AbCID is used in combination with a CAR, thereby segregating CAR signaling into two separate functions. This second function, provided by the CAR, provides antigen-specific cytotoxicity to the engineered T cells.

Co-stimulatory polypeptide molecules are capable of amplifying the cell-mediated immune response through activation of signaling pathways involved in cell survival and proliferation. Co-stimulatory proteins that are contemplated include, for example, the members of tumor necrosis factor receptor (TNFR) family (i.e., CD40, RANK/TRANCE-R, OX40, and 4-1BB) and CD28 family members (CD28, ICOS). Co-stimulatory proteins may include, for example, CD28, 4-1BB, and OX40. Stimulatory proteins may include, for example, the CD3 zeta chain. More than one co-stimulatory polypeptide, or co-stimulatory polypeptide cytoplasmic region may be used in the inducible AbCIDs described herein. For example, the AbCID may comprise a CD28 cytoplasmic polypeptide and a 4-1BB cytoplasmic polypeptide. Or, for example, the AbCID may comprise a CD28 cytoplasmic polypeptide and an OX40 cytoplasmic polypeptide. Or, for example, the AbCID may further comprise a CD3 zeta domain polypeptide.

Methods of Producing an AbCID

In some embodiments, provided herein is a method of selecting binding moieties from a binding molecule library, wherein the binding moieties specifically bind to a complex between a small molecule and a cognate binding moiety, comprising: (a) screening an input set of binding moieties for binding moieties that do not bind to the cognate binding moiety in the absence of the small molecule, thereby generating a set of counter selected binding moieties; and (b) screening an input set of binding moieties for binding moieties that bind to the complex of the small molecule and the cognate binding moiety, thereby generating a set of positively selected binding moieties; and (c) conducting one or more rounds of screening, wherein each round of screening comprises the screening of step (a) and the screening of step (b), such that a set of binding moieties that specifically bind to the complex between the small molecule and the cognate binding moiety is generated. In some embodiments, the method comprises two or more rounds of screening, wherein (1) the input set of binding moieties of step (a) for the first round of screening is the binding molecule library, (2) the input set of binding moieties of step (b) for each round of screening is the set of counter selected binding moieties of step (a) from the given round of screening, (3) the input set of binding moieties of step (a) for each round of screening following the first round of screening is the set of positively selected binding moieties of step (b) from the previous round of screening, and (4) the set of binding moieties that specifically bind to the complex between the small molecule and the cognate binding moiety is the set of positively selected binding moieties of step (b) for the last round of screening. In some embodiments, the method comprises at least 2 (such as at least any of 2, 3, 4, 5, 6, or more) rounds of selection. In some embodiments, at least one of the binding moieties in the set of binding moieties that specifically bind to the complex between the small molecule and the cognate binding moiety binds to the complex with a dissociation constant ($K_d$) no more than about $1/250$ times (such as no more than about any of $1/300$, $1/350$, $1/400$, $1/450$, $1/500$, $1/600$, $1/700$, $1/800$, $1/900$, $1/1000$, $1/1100$, $1/1200$, $1/1300$, $1/1400$, or $1/1500$ times, or less) its $K_d$ for binding to each of the free small molecule and the free cognate binding moiety. In some embodiments, each of the binding moieties in the set of binding moieties that specifically bind to the complex between the small molecule and the cognate binding moiety binds to the complex with a dissociation constant ($K_d$) no more than about $1/250$ times (such as no more than about any of $1/300$, $1/350$, $1/400$, $1/450$, $1/500$, $1/600$, $1/700$, $1/800$, $1/900$, $1/1000$, $1/1100$, $1/1200$, $1/1300$, $1/1400$, or $1/1500$ times, or less) its $K_d$ for binding to each of the free small molecule and the free cognate binding moiety. In some embodiments, the binding molecule library is an antibody library, a DARPin library, a nanobody library, or an aptamer library. In some embodiments, the binding molecule library is an antibody library. In some embodiments, the antibody library is a phage-displayed Fab library.

In some embodiments, provided herein is a construct comprising an antibody moiety that specifically binds to a complex between a small molecule and a binding moiety prepared by a process comprising the steps of: (A) selecting antibody moieties that specifically bind to the complex between the small molecule and the binding moiety from an antibody library according to any of the methods described herein; and (B) providing a construct comprising one of the antibodies moieties of (A). In some embodiments, the construct is a second CID component of an AbCID according to any of the embodiments described herein, and the first CID component of the AbCID comprises the binding moiety. In some embodiments, the antibody moiety specifically binds to a site of the complex comprising at least a portion of the small molecule and a portion of the binding moiety. In some embodiments, the site of the complex comprising at least a portion of the small molecule and a portion of the binding moiety is an interface between the small molecule and a binding site of the binding moiety for the small molecule, comprising at least one atom of the small molecule and one atom of the binding moiety.

In some embodiments, provided herein is a system according to any of the embodiments described herein, wherein the second binding moiety is an antibody moiety selected by a process comprising the steps of: (A) selecting antibody moieties that specifically bind to the complex between the small molecule and the first binding moiety from an antibody library according to any of the methods described herein; and (B) selecting the second binding moiety to be one of the antibodies moieties of (A). In some embodiments, the antibody moiety specifically binds to a site of the complex comprising at least a portion of the small molecule and a portion of the first binding moiety. In some embodiments, the site of the complex comprising at least a portion of the small molecule and a portion of the first binding moiety is an interface between the small molecule and a binding site of the first binding moiety for the small molecule, comprising at least one atom of the small molecule and one atom of the first binding moiety.

Methods of using an AbCID
Transcriptional Regulation

In some embodiments, provided herein is a method of modulating the expression of a target gene in a cell, comprising expressing in the cell the first and second CID components of a system according to any of the embodiments described herein wherein the CID is capable of regulating transcription of a target gene, and modifying the amount of the small molecule in the cell to modulate the expression of the target gene.

In some embodiments, provided herein is a method of modulating the expression of a target gene in a cell, comprising: (A) expressing in the cell (a) a first chemically-induced dimer (CID) component comprising (i) a first binding moiety capable of interacting with a small molecule to form a complex between the first CID component and the small molecule; and (ii) a first adapter moiety linked to the first binding moiety; and (b) a second CID component comprising (i) a second binding moiety that specifically binds to the complex between the small molecule and the first CID component; and (ii) a second adapter moiety linked to the second binding moiety, wherein (1) the first adapter moiety comprises a DNA binding domain and the second adapter moiety comprises a transcriptional regulatory domain; or (2) the second adapter moiety comprises a DNA binding domain and the first adapter moiety comprises a transcriptional regulatory domain, wherein the first CID component and the second CID component are configured such that when dimerized in the presence of the small molecule to form the CID, the CID is capable of regulating transcription of the target gene; and (B) modifying the amount of the small molecule in the cell to modulate the expression of the target gene. In some embodiments, the first CID component further comprises a nuclear localization signal and the second CID component further comprises a nuclear localization signal. In some embodiments, (i) the transcriptional regulatory domain is a transcriptional activation domain, and the CID is capable of upregulating transcription of the target gene; or (ii) the transcriptional regulatory domain is a transcriptional repressor domain, and the CID is capable of downregulating transcription of the target gene. In some embodiments, the transcriptional regulatory domain is a VPR transcriptional activation domain In some embodiments, the DNA binding domain is derived from a naturally occurring transcriptional regulator. In some embodiments, the DNA binding domain is derived from an RNA-guided endonuclease or a DNA-guided endonuclease. In some embodiments, the RNA-guided endonuclease or DNA-guided endonuclease is catalytically dead. In some embodiments, the DNA binding domain is derived from a catalytically dead Cas9 (dCas9).

In some embodiments, according to any of the methods of modulating the expression of a target gene in a cell described herein, the first binding moiety comprises an ABT-737-binding domain of Bcl-xL and the second binding moiety comprises an antibody moiety capable of specifically binding to a complex between ABT-737 and the first binding moiety, wherein the antibody moiety comprises a heavy chain variable domain and a light chain variable domain comprising HC-CDRs and LC-CDRs as shown in Table 1, or variants thereof having at least 85% homology. In some embodiments, the ABT-737-binding domain comprises the amino acid sequence of SEQ ID NO: 314 or a variant thereof having at least 85% homology to the amino acid sequence of SEQ ID NO: 314.

In some embodiments, according to any of the methods of modulating the expression of a target gene in a cell described herein, the first binding moiety comprises an ABT-199-binding domain of Bcl-2 and the second binding moiety comprises an antibody moiety capable of specifically binding to a complex between ABT-199 and the first binding moiety, wherein the antibody moiety comprises a heavy chain variable domain and a light chain variable domain comprising HC-CDRs and LC-CDRs as shown in Table 2, or variants thereof having at least 85% homology. In some embodiments, the ABT-199-binding domain comprises the amino acid sequence of SEQ ID NO: 315 or a variant thereof having at least 85% homology to the amino acid sequence of SEQ ID NO: 315.

In some embodiments, according to any of the methods of modulating the expression of a target gene in a cell described herein, the first binding moiety comprises an ABT-263-binding domain of Bcl-2 and the second binding moiety comprises an antibody moiety capable of specifically binding to a complex between ABT-263 and the first binding moiety, wherein the antibody moiety comprises a heavy chain variable domain and a light chain variable domain comprising HC-CDRs and LC-CDRs as shown in Table 3, or variants thereof having at least 85% homology. In some embodiments, the ABT-263-binding domain comprises the amino acid sequence of SEQ ID NO: 315 or a variant thereof having at least 85% homology to the amino acid sequence of SEQ ID NO: 315.

In some embodiments, according to any of the methods of modulating the expression of a target gene in a cell described herein, the first binding moiety comprises an LCL161-binding domain of cIAP1 and the second binding moiety comprises an antibody moiety capable of specifically binding to a complex between LCL161 and the first binding moiety, wherein the antibody moiety comprises a heavy chain variable domain and a light chain variable domain comprising HC-CDRs and LC-CDRs as shown in Table 4, or variants thereof having at least 85% homology. In some embodiments, the LCL161-binding domain comprises the amino acid sequence of SEQ ID NO: 317 or a variant thereof having at least 85% homology to the amino acid sequence of SEQ ID NO: 317.

In some embodiments, according to any of the methods of modulating the expression of a target gene in a cell described herein, the first binding moiety comprises an GDC-0152-binding domain of cIAP1 and the second binding moiety comprises an antibody moiety capable of specifically binding to a complex between GDC-0152 and the first binding moiety, wherein the antibody moiety comprises a heavy chain variable domain and a light chain variable domain comprising HC-CDRs and LC-CDRs as shown in Table 5, or variants thereof having at least 85% homology. In some embodiments, the GDC-0152-binding domain comprises the amino acid sequence of SEQ ID NO: 317 or a variant thereof having at least 85% homology to the amino acid sequence of SEQ ID NO: 317.

In some embodiments, according to any of the methods of modulating the expression of a target gene in a cell described herein, the first binding moiety comprises an AT406-binding domain of cIAP1 and the second binding moiety comprises an antibody moiety capable of specifically binding to a complex between AT406 and the first binding moiety, wherein the antibody moiety comprises a heavy chain variable domain and a light chain variable domain comprising HC-CDRs and LC-CDRs as shown in Table 6, or variants thereof having at least 85% homology. In some embodiments, the AT406-binding domain comprises the amino acid sequence of SEQ ID NO: 317 or a variant thereof having at least 85% homology to the amino acid sequence of SEQ ID NO: 317.

In some embodiments, according to any of the methods of modulating the expression of a target gene in a cell described herein, the first binding moiety comprises an CUDC-427-binding domain of cIAP1 and the second binding moiety comprises an antibody moiety capable of specifically binding to a complex between CUDC-427 and the first binding moiety, wherein the antibody moiety comprises a heavy chain variable domain and a light chain variable domain comprising HC-CDRs and LC-CDRs as shown in Table 7, or variants thereof having at least 85% homology. In some embodiments, the CUDC-427-binding domain comprises the amino acid sequence of SEQ ID NO: 317 or a variant thereof having at least 85% homology to the amino acid sequence of SEQ ID NO: 317.

In some embodiments, according to any of the methods of modulating the expression of a target gene in a cell described herein, the first binding moiety comprises an SLF-binding domain of FKBP and the second binding moiety comprises an antibody moiety capable of specifically binding to a complex between SLF and the first binding moiety, wherein the antibody moiety comprises a heavy chain variable domain and a light chain variable domain comprising HC-CDRs and LC-CDRs as shown in Table 8, or variants thereof having at least 85% homology. In some embodiments, the SLF-binding domain comprises the amino acid sequence of SEQ ID NO: 316 or a variant thereof having at least 85% homology to the amino acid sequence of SEQ ID NO: 316.

In some embodiments, according to any of the methods of modulating the expression of a target gene in a cell described herein, the first binding moiety comprises a methotrexate-binding Fab, wherein the methotrexate-binding Fab HC-CDR1, HC-CDR2, HC-CDR3, LC-CDR1, LC-CDR2, and LC-CDR3 comprise the amino acid sequences of SEQ ID NOs: 318, 319, 320, 321, 322, and 323, respectively, or variants thereof having at least 85% homology, and the second binding moiety comprises an antibody moiety capable of specifically binding to a complex between methotrexate and the first binding moiety, wherein the antibody moiety comprises a heavy chain variable domain and a light chain variable domain comprising HC-CDRs and LC-CDRs as shown in Table 9, or variants thereof having at least 85% homology. In some embodiments, the methotrexate-binding Fab is a methotrexate-binding Fab as described in Gayda et al. Biochemistry 2014 53 (23), 3719-3726.

Cell Survival

In some embodiments, provided herein is a method of controlling the survival of target cells in an individual, comprising: (A) expressing in the target cells the first and second CID components of a system according to any of the embodiments described herein wherein the CID is capable of inducing target cell death; and (B) administering to the individual the small molecule in a regimen effective to (I) kill a predetermined amount of the target cells; or (II) maintain a predetermined amount of the target cells.

In some embodiments, provided herein is a method of controlling the survival of target cells in an individual, comprising: (A) expressing in the target cells (a) a first chemically-induced dimer (CID) component comprising (i) a first binding moiety capable of interacting with a small molecule to form a complex between the first CID component and the small molecule; and (ii) a first adapter moiety linked to the first binding moiety; and (b) a second CID component comprising (i) a second binding moiety that specifically binds to the complex between the small molecule and the first CID component; and (ii) a second adapter moiety linked to the second binding moiety, wherein the first adapter moiety and the second adapter moiety are together capable of inducing apoptosis in the target cell; and (B) administering to the individual the small molecule in a regimen effective to (I) kill a predetermined amount of the target cells; or (II) maintain a predetermined amount of the target cells. In some embodiments, the first adapter moiety and/or the second adapter moiety are derived from a caspase protein. In some embodiments, the target cells are engineered cells adoptively transferred to the individual. In some embodiments, the target cells are part of an adoptive cell therapy in the individual. In some embodiments, the target cells are T cells expressing a chimeric antigen receptor (CAR).

In some embodiments, according to any of the methods of controlling the survival of target cells in an individual described herein, the first binding moiety comprises an ABT-737-binding domain of Bcl-xL and the second binding moiety comprises an antibody moiety capable of specifically binding to a complex between ABT-737 and the first binding moiety, wherein the antibody moiety comprises a heavy chain variable domain and a light chain variable domain comprising HC-CDRs and LC-CDRs as shown in Table 1, or variants thereof having at least 85% homology. In some embodiments, the ABT-737-binding domain comprises the amino acid sequence of SEQ ID NO: 314 or a variant thereof having at least 85% homology to the amino acid sequence of SEQ ID NO: 314.

In some embodiments, according to any of the methods of controlling the survival of target cells in an individual described herein, the first binding moiety comprises an ABT-199-binding domain of Bcl-2 and the second binding moiety comprises an antibody moiety capable of specifically binding to a complex between ABT-199 and the first binding moiety, wherein the antibody moiety comprises a heavy chain variable domain and a light chain variable domain comprising HC-CDRs and LC-CDRs as shown in Table 2, or variants thereof having at least 85% homology. In some embodiments, the ABT-199-binding domain comprises the amino acid sequence of SEQ ID NO: 315 or a variant thereof having at least 85% homology to the amino acid sequence of SEQ ID NO: 315.

In some embodiments, according to any of the methods of controlling the survival of target cells in an individual described herein, the first binding moiety comprises an ABT-263-binding domain of Bcl-2 and the second binding moiety comprises an antibody moiety capable of specifically binding to a complex between ABT-263 and the first binding moiety, wherein the antibody moiety comprises a heavy chain variable domain and a light chain variable domain comprising HC-CDRs and LC-CDRs as shown in Table 3, or variants thereof having at least 85% homology. In some embodiments, the ABT-263-binding domain comprises the amino acid sequence of SEQ ID NO: 315 or a variant thereof having at least 85% homology to the amino acid sequence of SEQ ID NO: 315.

In some embodiments, according to any of the methods of controlling the survival of target cells in an individual described herein, the first binding moiety comprises an LCL161-binding domain of cIAP1 and the second binding moiety comprises an antibody moiety capable of specifically binding to a complex between LCL161 and the first binding moiety, wherein the antibody moiety comprises a heavy chain variable domain and a light chain variable domain comprising HC-CDRs and LC-CDRs as shown in Table 4, or variants thereof having at least 85% homology. In some embodiments, the LCL161-binding domain comprises the amino acid sequence of SEQ ID NO: 317 or a variant thereof having at least 85% homology to the amino acid sequence of SEQ ID NO: 317.

In some embodiments, according to any of the methods of controlling the survival of target cells in an individual described herein, the first binding moiety comprises an GDC-0152-binding domain of cIAP1 and the second binding moiety comprises an antibody moiety capable of specifically binding to a complex between GDC-0152 and the first binding moiety, wherein the antibody moiety comprises a heavy chain variable domain and a light chain variable domain comprising HC-CDRs and LC-CDRs as shown in Table 5, or variants thereof having at least 85% homology. In some embodiments, the GDC-0152-binding domain comprises the amino acid sequence of SEQ ID NO: 317 or a variant thereof having at least 85% homology to the amino acid sequence of SEQ ID NO: 317.

In some embodiments, according to any of the methods of controlling the survival of target cells in an individual described herein, the first binding moiety comprises an AT406-binding domain of cIAP1 and the second binding moiety comprises an antibody moiety capable of specifically binding to a complex between AT406 and the first binding moiety, wherein the antibody moiety comprises a heavy chain variable domain and a light chain variable domain comprising HC-CDRs and LC-CDRs as shown in Table 6, or variants thereof having at least 85% homology. In some embodiments, the AT406-binding domain comprises the amino acid sequence of SEQ ID NO: 317 or a variant thereof having at least 85% homology to the amino acid sequence of SEQ ID NO: 317.

In some embodiments, according to any of the methods of controlling the survival of target cells in an individual described herein, the first binding moiety comprises an CUDC-427-binding domain of cIAP1 and the second binding moiety comprises an antibody moiety capable of specifically binding to a complex between CUDC-427 and the first binding moiety, wherein the antibody moiety comprises a heavy chain variable domain and a light chain variable domain comprising HC-CDRs and LC-CDRs as shown in Table 7, or variants thereof having at least 85% homology. In some embodiments, the CUDC-427-binding domain comprises the amino acid sequence of SEQ ID NO: 317 or a variant thereof having at least 85% homology to the amino acid sequence of SEQ ID NO: 317.

In some embodiments, according to any of the methods of controlling the survival of target cells in an individual described herein, the first binding moiety comprises an SLF-binding domain of FKBP and the second binding moiety comprises an antibody moiety capable of specifically binding to a complex between SLF and the first binding moiety, wherein the antibody moiety comprises a heavy chain variable domain and a light chain variable domain comprising HC-CDRs and LC-CDRs as shown in Table 8, or variants thereof having at least 85% homology. In some embodiments, the SLF-binding domain comprises the amino acid sequence of SEQ ID NO: 316 or a variant thereof having at least 85% homology to the amino acid sequence of SEQ ID NO: 316.

In some embodiments, according to any of the methods of controlling the survival of target cells in an individual described herein, the first binding moiety comprises a methotrexate-binding Fab, wherein the methotrexate-binding Fab HC-CDR1, HC-CDR2, HC-CDR3, LC-CDR1, LC-CDR2, and LC-CDR3 comprise the amino acid sequences of SEQ ID NOs: 318, 319, 320, 321, 322, and 323, respectively, or variants thereof having at least 85% homology, and the second binding moiety comprises an antibody moiety capable of specifically binding to a complex between methotrexate and the first binding moiety, wherein the antibody moiety comprises a heavy chain variable domain and a light chain variable domain comprising HC-CDRs and LC-CDRs as shown in Table 9, or variants thereof having at least 85% homology. In some embodiments, the methotrexate-binding Fab is a methotrexate-binding Fab as described in Gayda et al. Biochemistry 2014 53 (23), 3719-3726.

Immune Modulation

In some embodiments, provided herein is a method of modulating an immune response to a target cell in an individual, comprising: (A) administering to the individual modified T cells expressing the first and second CID components of a system according to any of the embodiments described herein wherein the CID is a heterodimeric CAR specific for a target antigen, and wherein the target antigen is expressed on the surface of the target cell; and (B) administering to the individual the small molecule in a regimen effective to modulate an immune response to the target cell.

In some embodiments, provided herein is a method of modulating an immune response to a target cell in an individual, comprising: (A) administering to the individual modified T cells expressing (a) a first chemically-induced dimer (CID) component comprising (i) a first binding moiety capable of interacting with a small molecule to form a complex between the first CID component and the small molecule; and (ii) a first adapter moiety linked to the first binding moiety; and (b) a second CID component comprising (i) a second binding moiety that specifically binds to the complex between the small molecule and the first CID component; and (ii) a second adapter moiety linked to the second binding moiety, wherein (1) the first adapter moiety comprises (i) a transmembrane domain; (ii) a cytoplasmic co-stimulatory domain; and (iii) a cytoplasmic signaling domain; and the second adapter moiety comprises an extracellular antigen-binding moiety; or (2) the second adapter moiety comprises (i) a transmembrane domain; (ii) a cytoplasmic co-stimulatory domain; and (iii) a cytoplasmic signaling domain; and the first adapter moiety comprises an extracellular antigen-binding moiety; wherein the extracellular antigen-binding moiety specifically binds to the target antigen; and (B) administering to the individual the small molecule in a regimen effective to modulate an immune response to the target cell. In some embodiments, the CID component comprising the extracellular antigen-binding moiety further comprises a secretory signal peptide. In some embodiments, the regimen is effective to maintain an immune response to the target cell with fewer adverse effects in the individual as compared to a corresponding method comprising administration of CAR T cells expressing a conventional CAR comprising the corresponding CAR domains of the CID.

In some embodiments, provided herein is a method of modulating an immune response to a target cell in an individual, comprising: (A) administering to the individual modified T cells expressing a first chemically-induced dimer (CID) component comprising (i) a first binding moiety capable of interacting with a small molecule to form a complex between the first CID component and the small molecule; and (ii) a first adapter moiety linked to the first binding moiety, wherein the first adapter moiety comprises (i) a transmembrane domain; (ii) a cytoplasmic co-stimulatory domain; and (iii) a cytoplasmic signaling domain; (B) administering to the individual a second CID component comprising (i) a second binding moiety that specifically binds to the complex between the small molecule and the first CID component; and (ii) a second adapter moiety linked to the second binding moiety, wherein the second adapter moiety comprises an extracellular antigen-binding moiety, and wherein the extracellular antigen-binding moiety specifically binds to the target antigen; and (C) administering to the individual the small molecule in a regimen effective to modulate an immune response to the target cell. In some embodiments, the regimen is effective to maintain an immune response to the target cell with fewer adverse effects in the individual as compared to a corresponding method comprising administration of CAR T cells expressing a conventional CAR comprising the corresponding CAR domains of the CID.

In some embodiments, provided herein is a method of modulating an immune response to a target cell in an individual, comprising: (A) administering to the individual a first chemically-induced dimer (CID) component comprising (i) a first binding moiety capable of interacting with a small molecule to form a complex between the first CID component and the small molecule; and (ii) a first adapter moiety linked to the first binding moiety, wherein the first adapter moiety comprises an extracellular antigen-binding moiety, and wherein the extracellular antigen-binding moiety specifically binds to the target antigen; (B) administering to the individual modified T cells expressing a second CID component comprising (i) a second binding moiety that specifically binds to the complex between the small molecule and the first CID component; and (ii) a second adapter moiety linked to the second binding moiety, wherein the second adapter moiety comprises (i) a transmembrane domain; (ii) a cytoplasmic co-stimulatory domain; and (iii) a cytoplasmic signaling domain; and (C) administering to the individual the small molecule in a regimen effective to modulate an immune response to the target cell. In some embodiments, the regimen is effective to maintain an immune response to the target cell with fewer adverse effects in the individual as compared to a corresponding method comprising administration of CAR T cells expressing a conventional CAR comprising the corresponding CAR domains of the CID.

In some embodiments, provided herein is a method of modulating an immune response to a target cell in an individual, comprising: (A) administering to the individual the first and second CID components of a system according to any of the embodiments described herein wherein the CID is a heterodimeric bispecific T cell engager capable of redirecting a T cell to the target cell; and (B) administering to the individual the small molecule in a regimen effective to modulate an immune response to the target cell.

In some embodiments, provided herein is a method of modulating an immune response to a target cell in an individual, comprising: (A) administering to the individual (a) a first chemically-induced dimer (CID) component comprising (i) a first binding moiety capable of interacting with a small molecule to form a complex between the first CID component and the small molecule; and (ii) a first adapter moiety linked to the first binding moiety; and (b) a second CID component comprising (i) a second binding moiety that specifically binds to the complex between the small molecule and the first CID component; and (ii) a second adapter moiety linked to the second binding moiety, wherein (1) the first adapter moiety comprises a T cell antigen-binding moiety and the second adapter moiety comprises a target cell antigen-binding moiety; or (2) the second adapter moiety comprises a T cell antigen-binding moiety and the first adapter moiety comprises a target cell antigen-binding moiety; and (B) administering to the individual the small molecule in a regimen effective to modulate an immune response to the target cell. In some embodiments, the T cell antigen-binding moiety is an antibody moiety that specifically binds to CD3. In some embodiments, the target cell antigen-binding moiety is an antibody moiety that specifically binds to a cell surface antigen associated with a diseased cell. In some embodiments, the diseased cell is a cancer cell. In some embodiments, the target cell antigen-binding moiety is an antibody moiety that specifically binds to CD19. In some embodiments, the regimen is effective to maintain an immune response to the target cell with fewer adverse effects in the individual as compared to a corresponding method comprising administration of a conventional bispecific T cell engager (e.g., BiTE®) comprising the corresponding bispecific T cell engager domains of the CID.

In some embodiments, provided herein is a method of modulating an immune response mediated by T cells in an individual, comprising: (A) expressing in the T cells the first and second CID components of a system according to any of the embodiments described herein wherein the CID is a heterodimeric signaling molecule capable of modulating activation of the immune cell; and (B) administering to the individual the small molecule in a regimen effective to modulate an immune response mediated by the T cells.

In some embodiments, provided herein is a method of modulating an immune response mediated by T cells in an individual, comprising: (A) expressing in the T cells (a) a first chemically-induced dimer (CID) component comprising (i) a first binding moiety capable of interacting with a small molecule to form a complex between the first CID component and the small molecule; and (ii) a first adapter moiety linked to the first binding moiety; and (b) a second CID component comprising (i) a second binding moiety that specifically binds to the complex between the small molecule and the first CID component; and (ii) a second adapter moiety linked to the second binding moiety, wherein the first adapter moiety comprises (i) a transmembrane domain; and (ii) a cytoplasmic co-stimulatory domain; and the second adapter moiety comprises (i) a transmembrane domain; and (ii) a cytoplasmic co-stimulatory domain; and (B) administering to the individual the small molecule in a regimen effective to modulate an immune response mediated by the T cells. In some embodiments, the regimen is effective to maintain an immune response mediated by the T cells with fewer adverse effects in the individual as compared to a corresponding method comprising expression of a monomeric signaling molecule comprising the corresponding signaling domains of the CID in the T cells. In some embodiments, the T cells are CAR T cells.

In some embodiments, according to any of the methods of modulating an immune response in an individual described herein, the first binding moiety comprises an ABT-737-binding domain of Bcl-xL and the second binding moiety comprises an antibody moiety capable of specifically binding to a complex between ABT-737 and the first binding moiety, wherein the antibody moiety comprises a heavy chain variable domain and a light chain variable domain comprising HC-CDRs and LC-CDRs as shown in Table 1, or variants thereof having at least 85% homology. In some embodiments, the ABT-737-binding domain comprises the amino acid sequence of SEQ ID NO: 314 or a variant thereof having at least 85% homology to the amino acid sequence of SEQ ID NO: 314.

In some embodiments, according to any of the methods of modulating an immune response in an individual described herein, the first binding moiety comprises an ABT-199-binding domain of Bcl-2 and the second binding moiety comprises an antibody moiety capable of specifically binding to a complex between ABT-199 and the first binding moiety, wherein the antibody moiety comprises a heavy chain variable domain and a light chain variable domain comprising HC-CDRs and LC-CDRs as shown in Table 2, or variants thereof having at least 85% homology. In some embodiments, the ABT-199-binding domain comprises the amino acid sequence of SEQ ID NO: 315 or a variant thereof having at least 85% homology to the amino acid sequence of SEQ ID NO: 315.

In some embodiments, according to any of the methods of modulating an immune response in an individual described herein, the first binding moiety comprises an ABT-263-binding domain of Bcl-2 and the second binding moiety comprises an antibody moiety capable of specifically binding to a complex between ABT-263 and the first binding moiety, wherein the antibody moiety comprises a heavy chain variable domain and a light chain variable domain comprising HC-CDRs and LC-CDRs as shown in Table 3, or variants thereof having at least 85% homology. In some embodiments, the ABT-263-binding domain comprises the amino acid sequence of SEQ ID NO: 315 or a variant thereof having at least 85% homology to the amino acid sequence of SEQ ID NO: 315.

In some embodiments, according to any of the methods of modulating an immune response in an individual described herein, the first binding moiety comprises an LCL161-binding domain of cIAP1 and the second binding moiety comprises an antibody moiety capable of specifically binding to a complex between LCL161 and the first binding moiety, wherein the antibody moiety comprises a heavy chain variable domain and a light chain variable domain comprising HC-CDRs and LC-CDRs as shown in Table 4, or variants thereof having at least 85% homology. In some embodiments, the LCL161-binding domain comprises the amino acid sequence of SEQ ID NO: 317 or a variant thereof having at least 85% homology to the amino acid sequence of SEQ ID NO: 317.

In some embodiments, according to any of the methods of modulating an immune response in an individual described herein, the first binding moiety comprises an GDC-0152-binding domain of cIAP1 and the second binding moiety comprises an antibody moiety capable of specifically binding to a complex between GDC-0152 and the first binding moiety, wherein the antibody moiety comprises a heavy chain variable domain and a light chain variable domain comprising HC-CDRs and LC-CDRs as shown in Table 5, or variants thereof having at least 85% homology. In some embodiments, the GDC-0152-binding domain comprises the amino acid sequence of SEQ ID NO: 317 or a variant thereof having at least 85% homology to the amino acid sequence of SEQ ID NO: 317.

In some embodiments, according to any of the methods of modulating an immune response in an individual described herein, the first binding moiety comprises an AT406-binding domain of cIAP1 and the second binding moiety comprises an antibody moiety capable of specifically binding to a complex between AT406 and the first binding moiety, wherein the antibody moiety comprises a heavy chain variable domain and a light chain variable domain comprising HC-CDRs and LC-CDRs as shown in Table 6, or variants thereof having at least 85% homology. In some embodiments, the AT406-binding domain comprises the amino acid sequence of SEQ ID NO: 317 or a variant thereof having at least 85% homology to the amino acid sequence of SEQ ID NO: 317.

In some embodiments, according to any of the methods of modulating an immune response in an individual described herein, the first binding moiety comprises an CUDC-427-binding domain of cIAP1 and the second binding moiety comprises an antibody moiety capable of specifically binding to a complex between CUDC-427 and the first binding moiety, wherein the antibody moiety comprises a heavy chain variable domain and a light chain variable domain comprising HC-CDRs and LC-CDRs as shown in Table 7, or variants thereof having at least 85% homology. In some embodiments, the CUDC-427-binding domain comprises the amino acid sequence of SEQ ID NO: 317 or a variant thereof having at least 85% homology to the amino acid sequence of SEQ ID NO: 317.

In some embodiments, according to any of the methods of modulating an immune response in an individual described herein, the first binding moiety comprises an SLF-binding domain of FKBP and the second binding moiety comprises an antibody moiety capable of specifically binding to a complex between SLF and the first binding moiety, wherein the antibody moiety comprises a heavy chain variable domain and a light chain variable domain comprising HC-CDRs and LC-CDRs as shown in Table 8, or variants thereof having at least 85% homology. In some embodiments, the SLF-binding domain comprises the amino acid sequence of SEQ ID NO: 316 or a variant thereof having at least 85% homology to the amino acid sequence of SEQ ID NO: 316.

In some embodiments, according to any of the methods of modulating an immune response in an individual described herein, the first binding moiety comprises a methotrexate-binding Fab, wherein the methotrexate-binding Fab HC-CDR1, HC-CDR2, HC-CDR3, LC-CDR1, LC-CDR2, and LC-CDR3 comprise the amino acid sequences of SEQ ID NOs: 318, 319, 320, 321, 322, and 323, respectively, or variants thereof having at least 85% homology, and the second binding moiety comprises an antibody moiety capable of specifically binding to a complex between methotrexate and the first binding moiety, wherein the antibody moiety comprises a heavy chain variable domain and a light chain variable domain comprising HC-CDRs and LC-CDRs as shown in Table 9, or variants thereof having at least 85% homology. In some embodiments, the methotrexate-binding Fab is a methotrexate-binding Fab as described in Gayda et al. Biochemistry 2014 53 (23), 3719-3726.

Cells

In some aspects, provided herein are engineered cells, such as engineered mammalian cells (e.g., T cells), comprising one or more components of an AbCID as set forth and described herein. In some embodiments, the AbCID comprises a first CID component and a second CID component. In some embodiments, the engineered cells comprises the first CID component and/or nucleic acid encoding the first CID component. In some embodiments, the engineered cells comprises the second CID component and/or nucleic acid encoding the second CID component. In some embodiments, the engineered cells comprises i) the first CID component and/or nucleic acid encoding the first CID component and ii) the second CID component and/or nucleic acid encoding the second CID component. In some embodiments, the engineered cells are engineered T cells. In some embodiments, the engineered T cells are human.

In some embodiments, an engineered cell described herein comprises a first CID component of an AbCID. In some embodiments, the first CID component comprises (i) a first binding moiety capable of interacting with a small molecule to form a complex between the first CID component and the small molecule; and (ii) a first adapter moiety linked to the first binding moiety. In some embodiments, the engineered cell further comprises a second CID component of the AbCID. In some embodiments, the second CID component comprises (i) a second binding moiety that specifically binds to the complex between the small molecule and the first CID component; and (ii) a second adapter moiety linked to the second binding moiety. In some embodiments, the engineered cell does not comprise a second CID component of the AbCID.

In some embodiments, an engineered cell described herein comprises a second CID component of an AbCID. In some embodiments, the second CID component comprises (i) a second binding moiety that specifically binds to the complex between the small molecule and the first CID component; and (ii) a second adapter moiety linked to the second binding moiety. In some embodiments, the engineered cell further comprises a first CID component of the AbCID. In some embodiments, the first CID component comprises (i) a first binding moiety capable of interacting with a small molecule to form a complex between the first CID component and the small molecule; and (ii) a first adapter moiety linked to the first binding moiety. In some embodiments, the engineered cell does not comprise a first CID component of the AbCID.

In some embodiments, an engineered cell described herein comprises nucleic acid encoding a first CID component of an AbCID. In some embodiments, the first CID component comprises (i) a first binding moiety capable of interacting with a small molecule to form a complex between the first CID component and the small molecule; and (ii) a first adapter moiety linked to the first binding moiety. In some embodiments, the engineered cell further comprises the first CID component. In some embodiments, the engineered cell further comprises nucleic acid encoding a second CID component of the AbCID. In some embodiments, the second CID component comprises (i) a second binding moiety that specifically binds to the complex between the small molecule and the first CID component; and (ii) a second adapter moiety linked to the second binding moiety. In some embodiments, the engineered cell further comprises the second CID component. In some embodiments, the engineered cell does not comprise nucleic acid encoding a second CID component of the AbCID.

In some embodiments, an engineered cell described herein comprises nucleic acid encoding a second CID component of an AbCID. In some embodiments, the second CID component comprises (i) a second binding moiety that specifically binds to the complex between the small molecule and the first CID component; and (ii) a second adapter moiety linked to the second binding moiety. In some embodiments, the engineered cell further comprises the second CID component. In some embodiments, the engineered cell further comprises nucleic acid encoding a first CID component of the AbCID. In some embodiments, the first CID component comprises (i) a first binding moiety capable of interacting with a small molecule to form a complex between the first CID component and the small molecule; and (ii) a first adapter moiety linked to the first binding moiety. In some embodiments, the engineered cell further comprises the first CID component. In some embodiments, the engineered cell does not comprise nucleic acid encoding a first CID component of the AbCID.

In some embodiments, the engineered cells are T cells, or precursor cells capable of differentiating into T cells. In some embodiments, the engineered cells are CD3+, CD8+, and/or CD4+T lymphocytes. In some embodiments, the engineered cells are CD8+T cytotoxic lymphocyte cells, which may include naïve CD8+ T cells, central memory CD8+ T cells, effector memory CD8+ T cells, or bulk CD8+ T cells.

The lymphocytes (T lymphocytes) can be collected in accordance with known techniques and enriched or depleted by known techniques such as affinity binding to antibodies such as flow cytometry and/or immunomagnetic selection. After enrichment and/or depletion steps, in vitro expansion of the desired T lymphocytes can be carried out in accordance with known techniques or variations thereof that will be apparent to those skilled in the art. In some embodiments, the T cells are autologous T cells obtained from a patient.

For example, the desired T cell population or subpopulation can be expanded by adding an initial T lymphocyte population to a culture medium in vitro, and then adding to the culture medium feeder cells, such as non-dividing peripheral blood mononuclear cells (PBMC), (e.g., such that the resulting population of cells contains at least 5, 10, 20, or 40 or more PBMC feeder cells for each T lymphocyte in the initial population to be expanded); and incubating the culture (e.g. for a time sufficient to expand the numbers of T cells). The non-dividing feeder cells can comprise gamma-irradiated PBMC feeder cells. In some embodiments, the PBMC are irradiated with gamma rays in the range of 3000 to 3600 rads to prevent cell division. In some embodiments, the PBMC are irradiated with gamma rays of 3000, 3100, 3200, 3300, 3400, 3500 or 3600 rads or any value of rads between any two endpoints of any of the listed values to prevent cell division. The order of addition of the T cells and feeder cells to the culture media can be reversed if desired. The culture can typically be incubated under conditions of temperature and the like that are suitable for the growth of T lymphocytes. For the growth of human T lymphocytes, for example, the temperature will generally be at least 25° C., preferably at least 30° C., more preferably 37° C. In some embodiments, the temperature for the growth of human T lymphocytes is 22, 24, 26, 28, 30, 32, 34, 36, 37° C., or any other temperature between any two endpoints of any of the listed values.

After isolation of T lymphocytes both cytotoxic and helper T lymphocytes can be sorted into naïve, memory, and effector T cell subpopulations either before or after expansion.

CD8+ cells can be obtained by using standard methods. In some embodiments, CD8+ cells are further sorted into naïve, central memory, and effector memory cells by identifying cell surface antigens that are associated with each of those types of CD8+ cells. In some embodiments, memory T cells are present in both CD62L+ and CD62L-subsets of CD8+ peripheral blood lymphocytes. PBMC are sorted into CD62L-CD8+ and CD62L+CD8+ fractions after staining with anti-CD8 and anti-CD62L antibodies. In some embodiments, the expression of phenotypic markers of central memory $T_{CM}$ include CD45RO, CD62L, CCR7, CD28, CD3, and/or CD127 and are negative or low for granzyme B. In some embodiments, central memory T cells are CD45RO+, CD62L+, and/or CD8+ T cells. In some embodiments, effector TE are negative for CD62L, CCR7, CD28, and/or CD127, and positive for granzyme B and/or perforin. In some embodiments, naïve CD8+ T lymphocytes are characterized by the expression of phenotypic markers of naïve T cells comprising CD62L, CCR7, CD28, CD3, CD127, and/or CD45RA.

Chimeric and Humanized Antibodies

In some embodiments, the antibodies of the invention are derived from a mixture from different species, e.g. a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference.

In certain embodiments, the antibodies of the invention comprise a heavy chain variable region from a particular germline heavy chain immunoglobulin gene and/or a light chain variable region from a particular germline light chain immunoglobulin gene. For example, such antibodies may comprise or consist of a human antibody comprising heavy or light chain variable regions that are "the product of" or "derived from" a particular germline sequence. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a humanized antibody typically is at least 90% identical in amino acids sequence to an amino acid sequence encoded by a human germline immunoglobulin gene and contains amino acid residues that identify the antibody as being derived from human sequences when compared to the germline immunoglobulin amino acid sequences of other species (e.g., murine germline sequences). In certain cases, a humanized antibody may be at least 95, 96, 97, 98 or 99%, or even at least 96%, 97%, 98%, or 99% identical in amino acid sequence to the amino acid sequence encoded by the germline immunoglobulin gene. Typically, a humanized antibody derived from a particular human germline sequence will display no more than 10-20 amino acid differences from the amino acid sequence encoded by the human germline immunoglobulin gene (prior to the introduction of any skew, pI and ablation variants herein; that is, the number of variants is generally low, prior to the introduction of the variants of the invention). In certain cases, the humanized antibody may display no more than 5, or even no more than 4, 3, 2, or 1 amino acid difference from the amino acid sequence encoded by the germline immunoglobulin gene (again, prior to the introduction of any skew, pI and ablation variants herein; that is, the number of variants is generally low, prior to the introduction of the variants of the invention).

In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

Methods of Treatment

Exemplary methods of the invention are directed to the use of AbCIDs to treat patients having a disease treatable by a therapeutic agent comprising a dimer between Protein$^b$ and Protein$^b$ formed through an AbCID as discussed herein. Exemplary diseases include, without limitation, cancer, invasive angiogenesis and autoimmune diseases.

The following discussion refers to treatment of various diseases and disorders with AbCIDs of the invention, the methods described herein are also applicable to conjugates. It will be apparent to those of skill in the art that this discussion applies to Protein$^a$, Protein$^b$, antibodies, antigen-binding fragments, variants, and derivatives of the protein components of dimers formed through these AbCIDs.

In one embodiment, treatment of a subject in need thereof includes the application or administration of an AbCID of the invention to an isolated tissue, cells or cell line from a patient, where the patient has a disease, a symptom of a disease, or a predisposition toward a disease, e.g., a T cell or CAR T cell. In another embodiment, treatment is also intended to include the application or administration of a pharmaceutical composition comprising the AbCID of the invention to an isolated tissue, cells or cell line from a patient, who has a disease, a symptom of a disease, or a predisposition toward a disease. Exemplary pharmaceutical compositions include an AbCID or a protein complex thereof in admixture with a pharmaceutically acceptable carrier, excipient, etc.

Exemplary AbCIDs of the present invention are useful for the treatment of various malignant and non-malignant tumors. By "anti-tumor activity" is intended a reduction in the rate of malignant cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. For example, therapy with at least one AbCID causes a physiological response, for example, a reduction in angiogenesis, that is beneficial with respect to treatment of disease states in a human.

In one embodiment, the invention relates to AbCID molecules, e.g., antibodies or binding fragments thereof and conjugates thereof, according to the present invention for use as a medicament, in particular for use in the treatment or prophylaxis of cancer or for use in a precancerous condition or lesion. In certain embodiments, the AbCID of the invention is used for the treatment of lymphoma or leukemia.

Further AbCIDs of the present invention can also be used to inhibit angiogenesis for the treatment of pathological conditions dependent upon the formation of new blood vessels, including tumor development and macular degeneration. Angiogenesis is a complex multistep morphogenetic event during which endothelial cells, stimulated by major determinants of vascular remodeling, dynamically modify their cell-to-cell and cell-to-matrix contacts and move directionally to be reorganized into a mature vascular tree (Bussolino et al., Trends Biochem Sci. 22:251-256 (1997); Risau, Nature 386:671-674 (1997); Jain, Nat. Med. 9:685-693 (2003)). The formation of new blood vessels is a key step during embryo development, but it also occurs in adults in physiologic and in pathologic conditions, such as retinopathy, rheumatoid arthritis, ischemia, and particularly tumor growth and metastasis (Carmeliet, Nat. Med. 9:653-660 (2003)). This pathological formation of new blood vessels is herein referred to as "invasive angiogenesis." Basile et al., PNAS 103(24):9017-9022 (2006)). Angiogenesis is a frequently used strategy by which a wide variety of carcinomas may promote angiogenesis.

In accordance with the methods of the present invention, at least one AbCID, as defined elsewhere herein is used to promote a positive therapeutic response with respect to a malignant human cell. By "positive therapeutic response" with respect to cancer treatment is intended an improvement in the disease in association with the anti-tumor activity of these binding molecules. e.g. antibodies or fragments thereof, and/or an improvement in the symptoms associated with the disease. That is, an anti-proliferative effect, the prevention of further tumor outgrowths, a reduction in tumor size, a decrease in tumor vasculature, a reduction in the number of cancer cells, and/or a decrease in one or more symptoms associated with the disease can be observed. Thus, for example, an improvement in the disease may be characterized as a complete response. By "complete response" is intended an absence of clinically detectable disease with normalization of any previously abnormal radiographic studies, bone marrow, and cerebrospinal fluid (CSF). Such a response must persist for at least one month following treatment according to the methods of the invention. Alternatively, an improvement in the disease may be categorized as being a partial response. By "partial response" is intended at least about a 50% decrease in all measurable tumor burden (i.e., the number of tumor cells present in the subject) in the absence of new lesions and persisting for at least one month. Such a response is applicable to measurable tumors only.

Tumor response can be assessed for changes in tumor morphology (i.e., overall tumor burden, tumor cell count, and the like) using screening techniques such as bioluminescent imaging, for example, luciferase imaging, bone scan imaging, and tumor biopsy sampling including bone marrow aspiration (BMA). In addition to these positive therapeutic responses, the subject undergoing therapy with the anti-CD100 binding molecule, e.g., an antibody or antigen-binding fragment thereof, may experience the beneficial effect of an improvement in the symptoms associated with the disease. For example, the subject may experience a decrease in the so-called B symptoms, e.g. night sweats, fever, weight loss, and/or urticaria.

The AbCIDs described herein may also find use in the treatment of inflammatory diseases and deficiencies or disorders of the immune system. Inflammatory diseases are characterized by inflammation and tissue destruction, or a combination thereof. By "anti-inflammatory activity" is intended a reduction or prevention of inflammation. "Inflammatory disease" includes any inflammatory immune-mediated process where the initiating event or target of the immune response involves non-self antigen(s), including, for example, alloantigens, xenoantigens, viral antigens, bacterial antigens, unknown antigens, or allergens. In one embodiment, the inflammatory disease is an inflammatory disorder of the peripheral or central nervous system. In another embodiment, the inflammatory disease is an inflammatory disorder of the joints.

Further, for purposes of the present invention, the term "inflammatory disease(s)" includes "autoimmune disease(s)." As used herein, the term "autoimmunity" is generally understood to encompass inflammatory immune-mediated processes involving "self" antigens. In autoimmune diseases, self antigen(s) trigger host immune responses. An autoimmune disease can result from an inappropriate immune response directed against a self antigen (an autoantigen), which is a deviation from the normal state of self-tolerance. In general, antibodies (particularly, but not exclusively, IgG antibodies), acting as cytotoxic molecules or as immune complexes, are the principal mediators of various autoimmune diseases, many of which can be debilitating or life-threatening.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the AbCID may experience the beneficial effect of an improvement in the symptoms associated with the disease.

The AbCID can be used in combination with at least one other cancer therapy, including, but not limited to, surgery or surgical procedures (e.g., splenectomy, hepatectomy, lymphadenectomy, leukophoresis, bone marrow transplantation, and the like); radiation therapy; chemotherapy, optionally in combination with autologous bone marrow transplant, or other cancer therapy; where the additional cancer therapy is administered prior to, during, or subsequent to the AbCID molecule, e.g., antibody or antigen binding fragment thereof, therapy. Thus, where the combined therapies comprise administration of an AbCID of the invention in combination with administration of another therapeutic agent, as with chemotherapy, radiation therapy, other anti-cancer antibody therapy, small molecule-based cancer therapy, or vaccine/immunotherapy-based cancer therapy, the methods of the invention encompass co-administration, using separate formulations or a single pharmaceutical formulation, or and consecutive administration in either order.

The AbCID molecules of the invention can be used in combination with any known therapies for cancer, autoimmune and inflammatory diseases, including any agent or combination of agents that are known to be useful, or which have been used or are currently in use, for treatment of autoimmune and inflammatory diseases. Thus, where the combined therapies comprise administration of an AbCID molecule in combination with administration of another therapeutic agent, the methods of the invention encompass co-administration, using separate formulations or a single pharmaceutical formulation, and consecutive administration in either order. In some embodiments of the invention, the AbCIDs described herein are administered in combination with immunosuppressive drugs or anti-inflammatory drugs, wherein the antibody and the therapeutic agent(s) may be administered sequentially, in either order, or simultaneously (i.e., concurrently or within the same time frame).

A further embodiment of the invention is the use of an AbCID for diagnostic monitoring of protein levels in tissue as part of a clinical testing procedure, e.g., to determine the efficacy of a given treatment regimen. For example, detection can be facilitated by coupling the AbCID to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, di chl orotriazinyl amine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

Transcriptional Regulation

In some embodiments, provided herein is a method of treating a disease in an individual, comprising expressing in target cells in the individual the first and second CID components of a system according to any of the embodiments described herein wherein the CID is capable of regulating transcription of a target gene, wherein the expression level of the target gene in the target cells is associated with the disease, and administering to the individual the small molecule in a regimen effective to treat the disease.

In some embodiments, provided herein is a method of treating a disease in an individual, wherein the expression level of a target gene in the target cells is associated with the disease, comprising: (A) expressing in target cells in the individual (a) a first chemically-induced dimer (CID) component comprising (i) a first binding moiety capable of interacting with a small molecule to form a complex between the first CID component and the small molecule; and (ii) a first adapter moiety linked to the first binding moiety; and (b) a second CID component comprising (i) a second binding moiety that specifically binds to the complex between the small molecule and the first CID component; and (ii) a second adapter moiety linked to the second binding moiety, wherein (1) the first adapter moiety comprises a DNA binding domain and the second adapter moiety comprises a transcriptional regulatory domain; or (2) the second adapter moiety comprises a DNA binding domain and the first adapter moiety comprises a transcriptional regulatory domain, wherein the first CID component and the second CID component are configured such that when dimerized in the presence of the small molecule to form the CID, the CID is capable of regulating transcription of the target gene; and (B) administering to the individual the small molecule in a regimen effective to treat the disease. In some embodiments, the first CID component further comprises a nuclear localization signal and the second CID component further comprises a nuclear localization signal. In some embodiments, (i) the transcriptional regulatory domain is a transcriptional activation domain, and the CID is capable of upregulating transcription of the target gene; or (ii) the transcriptional regulatory domain is a transcriptional repressor domain, and the CID is capable of downregulating transcription of the target gene. In some embodiments, the transcriptional regulatory domain is a VPR transcriptional activation domain In some embodiments, the DNA binding domain is derived from a naturally occurring transcriptional regulator. In some embodiments, the DNA binding domain is derived from an RNA-guided endonuclease or a DNA-guided endonuclease. In some embodiments, the RNA-guided endonuclease or DNA-guided endonuclease is catalytically dead. In some embodiments, the DNA binding domain is derived from a catalytically dead Cas9 (dCas9).

Cell Survival

In some embodiments, provided herein is a method of treating a disease in an individual, comprising: (A) administering to the individual an adoptive cell therapy for the disease comprising modified cells, wherein the modified cells express the first and second CID components of a system according to any of the embodiments described herein wherein the CID is capable of inducing target cell death; and (B) administering to the individual the small molecule in a regimen effective to (I) kill a predetermined amount of the adoptively transferred cells; or (II) maintain a predetermined amount of the adoptively transferred cells.

In some embodiments, provided herein is a method of treating a disease in an individual, comprising: (A) administering to the individual an adoptive cell therapy for the disease comprising modified cells, wherein the modified cells express (a) a first chemically-induced dimer (CID) component comprising (i) a first binding moiety capable of interacting with a small molecule to form a complex between the first CID component and the small molecule; and (ii) a first adapter moiety linked to the first binding moiety; and (b) a second CID component comprising (i) a second binding moiety that specifically binds to the complex between the small molecule and the first CID component; and (ii) a second adapter moiety linked to the second binding moiety, wherein the first adapter moiety and the second adapter moiety are together capable of inducing apoptosis in the target cell; and (B) administering to the individual the small molecule in a regimen effective to (I) kill a predetermined amount of the adoptively transferred cells; or (II) maintain a predetermined amount of the adoptively transferred cells. In some embodiments, the first adapter moiety and/or the second adapter moiety are derived from a caspase protein. In some embodiments, the adoptive cell therapy is a CAR T cell therapy.

Immune Modulation

In some embodiments, provided herein is a method of treating a disease characterized by a target cell in an individual, comprising: (A) administering to the individual modified T cells expressing the first and second CID components of a system according to any of the embodiments described herein wherein the CID is a heterodimeric CAR specific for a target antigen, and wherein the target antigen is expressed on the surface of the target cell; and (B) administering to the individual the small molecule in a regimen effective to treat the disease.

In some embodiments, provided herein is a method of treating a disease characterized by a target cell in an individual, comprising: (A) administering to the individual modified T cells expressing (a) a first chemically-induced dimer (CID) component comprising (i) a first binding moiety capable of interacting with a small molecule to form a complex between the first CID component and the small molecule; and (ii) a first adapter moiety linked to the first binding moiety; and (b) a second CID component comprising (i) a second binding moiety that specifically binds to the complex between the small molecule and the first CID component; and (ii) a second adapter moiety linked to the second binding moiety, wherein (1) the first adapter moiety comprises (i) a transmembrane domain; (ii) a cytoplasmic co-stimulatory domain; and (iii) a cytoplasmic signaling domain; and the second adapter moiety comprises an extracellular antigen-binding moiety; or (2) the second adapter moiety comprises (i) a transmembrane domain; (ii) a cytoplasmic co-stimulatory domain; and (iii) a cytoplasmic signaling domain; and the first adapter moiety comprises an extracellular antigen-binding moiety; wherein the extracellular antigen-binding moiety specifically binds to the target antigen; and (B) administering to the individual the small molecule in a regimen effective to treat the disease. In some embodiments, the CID component comprising the extracellular antigen-binding moiety further comprises a secretory signal peptide. In some embodiments, the regimen is effective to treat the disease with fewer adverse effects in the individual as compared to a corresponding method comprising administration of CAR T cells expressing a conventional CAR comprising the corresponding CAR domains of the CID.

In some embodiments, provided herein is a method of treating a disease characterized by a target cell in an individual, comprising: (A) administering to the individual modified T cells expressing a first chemically-induced dimer (CID) component comprising (i) a first binding moiety capable of interacting with a small molecule to form a complex between the first CID component and the small molecule; and (ii) a first adapter moiety linked to the first binding moiety, wherein the first adapter moiety comprises (i) a transmembrane domain; (ii) a cytoplasmic co-stimulatory domain; and (iii) a cytoplasmic signaling domain; (B) administering to the individual a second CID component comprising (i) a second binding moiety that specifically binds to the complex between the small molecule and the first CID component; and (ii) a second adapter moiety linked to the second binding moiety, wherein the second adapter moiety comprises an extracellular antigen-binding moiety, and wherein the extracellular antigen-binding moiety specifically binds to the target antigen; and (C) administering to the individual the small molecule in a regimen effective to treat the disease. In some embodiments, the regimen is effective to treat the disease with fewer adverse effects in the individual as compared to a corresponding method comprising administration of CAR T cells expressing a conventional CAR comprising the corresponding CAR domains of the CID.

In some embodiments, provided herein is a method of treating a disease characterized by a target cell in an individual, comprising: (A) administering to the individual a first chemically-induced dimer (CID) component comprising (i) a first binding moiety capable of interacting with a small molecule to form a complex between the first CID component and the small molecule; and (ii) a first adapter moiety linked to the first binding moiety, wherein the first adapter moiety comprises an extracellular antigen-binding moiety, and wherein the extracellular antigen-binding moiety specifically binds to the target antigen; (B) administering to the individual modified T cells expressing a second CID component comprising (i) a second binding moiety that specifically binds to the complex between the small molecule and the first CID component; and (ii) a second adapter moiety linked to the second binding moiety, wherein the second adapter moiety comprises (i) a transmembrane domain; (ii) a cytoplasmic co-stimulatory domain; and (iii) a cytoplasmic signaling domain; and (C) administering to the individual the small molecule in a regimen effective to treat the disease. In some embodiments, the regimen is effective to treat the disease with fewer adverse effects in the individual as compared to a corresponding method comprising administration of CAR T cells expressing a conventional CAR comprising the corresponding CAR domains of the CID.

In some embodiments, provided herein is a method of treating a disease characterized by a target cell in an individual, comprising: (A) administering to the individual the first and second CID components of a system according to any of the embodiments described herein wherein the CID is a heterodimeric bispecific T cell engager capable of redirecting a T cell to the target cell; and (B) administering to the individual the small molecule in a regimen effective to treat the disease.

In some embodiments, provided herein is a method of treating a disease characterized by a target cell in an individual, comprising: (A) administering to the individual (a) a first chemically-induced dimer (CID) component comprising (i) a first binding moiety capable of interacting with a small molecule to form a complex between the first CID component and the small molecule; and (ii) a first adapter moiety linked to the first binding moiety; and (b) a second CID component comprising (i) a second binding moiety that specifically binds to the complex between the small molecule and the first CID component; and (ii) a second adapter moiety linked to the second binding moiety, wherein (1) the first adapter moiety comprises a T cell antigen-binding moiety and the second adapter moiety comprises a target cell antigen-binding moiety; or (2) the second adapter moiety comprises a T cell antigen-binding moiety and the first adapter moiety comprises a target cell antigen-binding moiety; and (B) administering to the individual the small molecule in a regimen effective to treat the disease. In some embodiments, the T cell antigen-binding moiety is an antibody moiety that specifically binds to CD3. In some embodiments, the target cell antigen-binding moiety is an antibody moiety that specifically binds to a cell surface antigen associated with a diseased cell. In some embodiments, the diseased cell is a cancer cell. In some embodiments, the target cell antigen-binding moiety is an antibody moiety that specifically binds to CD19. In some embodiments, the regimen is effective to treat the disease with fewer adverse effects in the individual as compared to a corresponding method comprising administration of a conventional bispecific T cell engager comprising the corresponding bispecific T cell engager domains of the CID.

In some embodiments, provided herein is a method of treating a disease characterized by a target cell in an individual, comprising: (A) expressing in T cells in the individual capable of recognizing and killing the target cell the first and second CID components of a system according to any of the embodiments described herein wherein the CID is a heterodimeric signaling molecule capable of modulating activation of the T cell; and (B) administering to the individual the small molecule in a regimen effective to treat the disease.

In some embodiments, provided herein is a method of treating a disease characterized by a target cell in an individual, comprising: (A) expressing in T cells in the individual capable of recognizing and killing the target cell (a) a first chemically-induced dimer (CID) component comprising (i) a first binding moiety capable of interacting with a small molecule to form a complex between the first CID component and the small molecule; and (ii) a first adapter moiety linked to the first binding moiety; and (b) a second CID component comprising (i) a second binding moiety that specifically binds to the complex between the small molecule and the first CID component; and (ii) a second adapter moiety linked to the second binding moiety, wherein the first adapter moiety comprises (i) a transmembrane domain; and (ii) a cytoplasmic co-stimulatory domain; and the second adapter moiety comprises (i) a transmembrane domain; and (ii) a cytoplasmic co-stimulatory domain; and (B) administering to the individual the small molecule in a regimen effective to treat the disease. In some embodiments, the T cells are CAR T cells. In some embodiments, the regimen is effective to treat the disease with fewer adverse effects in the individual as compared to a corresponding method comprising expression of a monomeric signaling molecule comprising the corresponding signaling domains of the CID in the T cells.

In some embodiments, according to any of the methods of treating a disease in an individual described herein, the first binding moiety comprises an ABT-737-binding domain of Bcl-xL and the second binding moiety comprises an antibody moiety capable of specifically binding to a complex between ABT-737 and the first binding moiety, wherein the antibody moiety comprises a heavy chain variable domain and a light chain variable domain comprising HC-CDRs and LC-CDRs as shown in Table 1, or variants thereof having at least 85% homology. In some embodiments, the ABT-737-binding domain comprises the amino acid sequence of SEQ ID NO: 314 or a variant thereof having at least 85% homology to the amino acid sequence of SEQ ID NO: 314.

In some embodiments, according to any of the methods of treating a disease in an individual described herein, the first binding moiety comprises an ABT-199-binding domain of Bcl-2 and the second binding moiety comprises an antibody moiety capable of specifically binding to a complex between ABT-199 and the first binding moiety, wherein the antibody moiety comprises a heavy chain variable domain and a light chain variable domain comprising HC-CDRs and LC-CDRs as shown in Table 2, or variants thereof having at least 85% homology. In some embodiments, the ABT-199-binding domain comprises the amino acid sequence of SEQ ID NO: 315 or a variant thereof having at least 85% homology to the amino acid sequence of SEQ ID NO: 315.

In some embodiments, according to any of the methods of treating a disease in an individual described herein, the first binding moiety comprises an ABT-263-binding domain of Bcl-2 and the second binding moiety comprises an antibody moiety capable of specifically binding to a complex between ABT-263 and the first binding moiety, wherein the antibody moiety comprises a heavy chain variable domain and a light chain variable domain comprising HC-CDRs and LC-CDRs as shown in Table 3, or variants thereof having at least 85% homology. In some embodiments, the ABT-263-binding domain comprises the amino acid sequence of SEQ ID NO: 315 or a variant thereof having at least 85% homology to the amino acid sequence of SEQ ID NO: 315.

In some embodiments, according to any of the methods of treating a disease in an individual described herein, the first binding moiety comprises an LCL161-binding domain of cIAP1 and the second binding moiety comprises an antibody moiety capable of specifically binding to a complex between LCL161 and the first binding moiety, wherein the antibody moiety comprises a heavy chain variable domain and a light chain variable domain comprising HC-CDRs and LC-CDRs as shown in Table 4, or variants thereof having at least 85% homology. In some embodiments, the LCL161-binding domain comprises the amino acid sequence of SEQ ID NO: 317 or a variant thereof having at least 85% homology to the amino acid sequence of SEQ ID NO: 317.

In some embodiments, according to any of the methods of treating a disease in an individual described herein, the first binding moiety comprises an GDC-0152-binding domain of cIAP1 and the second binding moiety comprises an antibody moiety capable of specifically binding to a complex between GDC-0152 and the first binding moiety, wherein the antibody moiety comprises a heavy chain variable domain and a light chain variable domain comprising HC-CDRs and LC-CDRs as shown in Table 5, or variants thereof having at least 85% homology. In some embodiments, the GDC-0152-binding domain comprises the amino acid sequence of SEQ ID NO: 317 or a variant thereof having at least 85% homology to the amino acid sequence of SEQ ID NO: 317.

In some embodiments, according to any of the methods of treating a disease in an individual described herein, the first binding moiety comprises an AT406-binding domain of cIAP1 and the second binding moiety comprises an antibody moiety capable of specifically binding to a complex between AT406 and the first binding moiety, wherein the antibody moiety comprises a heavy chain variable domain and a light chain variable domain comprising HC-CDRs and LC-CDRs as shown in Table 6, or variants thereof having at least 85% homology. In some embodiments, the AT406-binding domain comprises the amino acid sequence of SEQ ID NO: 317 or a variant thereof having at least 85% homology to the amino acid sequence of SEQ ID NO: 317.

In some embodiments, according to any of the methods of treating a disease in an individual described herein, the first binding moiety comprises an CUDC-427-binding domain of cIAP1 and the second binding moiety comprises an antibody moiety capable of specifically binding to a complex between CUDC-427 and the first binding moiety, wherein the antibody moiety comprises a heavy chain variable domain and a light chain variable domain comprising HC-CDRs and LC-CDRs as shown in Table 7, or variants thereof having at least 85% homology. In some embodiments, the CUDC-427-binding domain comprises the amino acid sequence of SEQ ID NO: 317 or a variant thereof having at least 85% homology to the amino acid sequence of SEQ ID NO: 317.

In some embodiments, according to any of the methods of treating a disease in an individual described herein, the first binding moiety comprises an SLF-binding domain of FKBP and the second binding moiety comprises an antibody moiety capable of specifically binding to a complex between SLF and the first binding moiety, wherein the antibody moiety comprises a heavy chain variable domain and a light chain variable domain comprising HC-CDRs and LC-CDRs as shown in Table 8, or variants thereof having at least 85% homology. In some embodiments, the SLF-binding domain comprises the amino acid sequence of SEQ ID NO: 316 or a variant thereof having at least 85% homology to the amino acid sequence of SEQ ID NO: 316.

In some embodiments, according to any of the methods of treating a disease in an individual described herein, the first binding moiety comprises a methotrexate-binding Fab, wherein the methotrexate-binding Fab HC-CDR1, HC-CDR2, HC-CDR3, LC-CDR1, LC-CDR2, and LC-CDR3 comprise the amino acid sequences of SEQ ID NOs: 318, 319, 320, 321, 322, and 323, respectively, or variants thereof having at least 85% homology, and the second binding moiety comprises an antibody moiety capable of specifically binding to a complex between methotrexate and the first binding moiety, wherein the antibody moiety comprises a heavy chain variable domain and a light chain variable domain comprising HC-CDRs and LC-CDRs as shown in Table 9, or variants thereof having at least 85% homology. In some embodiments, the methotrexate-binding Fab is a methotrexate-binding Fab as described in Gayda et al. Biochemistry 2014 53 (23), 3719-3726.

Pharmaceutical Compositions and Administration Methods

Methods of preparing and administering the AbCIDs, of the invention to a subject in need thereof are well known to or are readily determined by those skilled in the art. The route of administration of the AbCID may be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the invention, an example of a form for administration would be a solution for injection, in particular for intravenous or intraarterial injection or drip. Usually, a suitable pharmaceutical composition for injection may comprise a buffer (e.g., acetate, phosphate or citrate buffer), a surfactant (e.g., polysorbate), optionally a stabilizer agent (e.g., human albumin), etc. However, in other methods compatible with the teachings herein, a AbCID of the invention can be delivered directly to the site of the adverse cellular population thereby increasing the exposure of the diseased tissue to the therapeutic agent.

As discussed herein, a AbCID of the invention may be administered in a pharmaceutically effective amount for the in vivo treatment of various cell-mediated diseases such as certain types of cancers, autoimmune diseases, inflammatory diseases including central nervous system (CNS) and peripheral nervous system (PNS) inflammatory diseases, and invasive angiogenesis. In this regard, it will be appreciated that the disclosed binding molecules of the invention will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of a AbCID conjugated or unconjugated, shall be held to mean an amount sufficient to achieve effective binding to a target and to achieve a benefit, e.g., to ameliorate symptoms of a disease or disorder or to detect a substance or a cell.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and fat.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject invention, pharmaceutically acceptable carriers include, but are not limited to, 0.01-0.1 M and preferably 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g. glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an AbCID by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in U.S. patent application Ser. No. 09/259,337. Such articles of manufacture will preferably have labels or package inserts indicating that the associated compositions are useful for treating a subject suffering from, or predisposed to a disease or disorder.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of AbCID that may be combined with the carrier materials to produce a single dosage form will vary depending upon the host treated and the particular mode of administration. The composition may be administered as a single dose, multiple doses or over an established period of time in an infusion. Dosage regimens also may be adjusted to provide the optimum desired response (e.g., a therapeutic or prophylactic response).

In keeping with the scope of the present disclosure, AbCIDs of the invention may be administered to a human or other animal in accordance with the aforementioned methods of treatment in an amount sufficient to produce a therapeutic effect. The AbCID of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of AbCID of the invention may prove to be particularly effective.

By "therapeutically effective dose or amount" or "effective amount" is intended an amount of AbCID that when administered brings about a positive therapeutic response with respect to treatment of a patient with a disease to be treated.

Therapeutically effective doses of the compositions of the present invention, for treatment of cell-mediated diseases such as certain types of cancers, e.g., leukemia, lymphoma; autoimmune diseases, e.g., arthritis, multiple sclerosis, inflammatory diseases including central nervous system (CNS) and peripheral nervous system (PNS) inflammatory diseases; and invasive angiogenesis, vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

The amount of at least one AbCID to be administered is readily determined by one of ordinary skill in the art without undue experimentation given the disclosure of the present invention. Factors influencing the mode of administration and the respective amount of at least one AbCID include, but are not limited to, the severity of the disease, the history of the disease, and the age, height, weight, health, and physical condition of the individual undergoing therapy. Similarly, the amount of AbCID to be administered will be dependent upon the mode of administration and whether the subject will undergo a single dose or multiple doses of this agent.

In a further exemplary embodiment, cells of a subject are transfected with nucleic acids encoding $Protein^a$, $Protein^b$, fusions or derivatives thereof or a combination of two or more of these elements, such that the cells produce the protein(s). In various embodiments, the dimers are formed by administering to the subject one or more SM. In this way, the SM dimerizes $Protein^a$, and $Protein^b$, or a fusion or derivative of one or both of these proteins.

Diagnostics

The invention further provides a diagnostic method useful during diagnosis of cell-mediated diseases such as certain types of cancers, autoimmune diseases, inflammatory diseases including, e.g., arthritis, multiple sclerosis, central nervous system (CNS) and peripheral nervous system (PNS) inflammatory diseases, and invasive angiogenesis, which involves measuring the expression level of a disease-associated protein or transcript in tissue or other cells or body fluid from an individual and comparing the measured expression level with a standard expression level in normal tissue or body fluid, whereby an increase in the expression level compared to the standard is indicative of a disorder.

The AbCIDs of the invention, can be used to assay protein levels in a biological sample using classical immunohistological methods known to those of skill in the art (see, e.g., Jalkanen, et al., J. Cell. Biol. 101:976-985 (1985); Jalkanen et al., J. Cell Biol. 105:3087-3096 (1987)). Other antibody-based methods useful for detecting protein expression include immunoassays, such as the enzyme linked immunosorbent assay (ELISA), immunoprecipitation, or Western blotting. Suitable assays are described in more detail elsewhere herein.

By "assaying the expression level of a protein" is intended qualitatively or quantitatively measuring or estimating the level of disease-associated protein in a first biological sample either directly (e.g., by determining or estimating absolute protein level) or relatively (e.g., by comparing to the disease associated polypeptide level in a second biological sample). Preferably, protein expression level in the first biological sample is measured or estimated and compared to a standard protein level, the standard being taken from a second biological sample obtained from an individual not having the disorder or being determined by averaging levels from a population of individuals not having the disorder. As will be appreciated in the art, once the "standard" protein level is known, it can be used repeatedly as a standard for comparison.

By "biological sample" is intended any biological sample obtained from an individual, cell line, tissue culture, or other source of cells potentially expressing a disease-associated protein. Methods for obtaining tissue biopsies and body fluids from mammals are well known in the art.

Immunoassays

AbCIDs of the invention may used in immunoassays, e.g., they may be assayed for immunospecific binding by any method known in the art. The immunoassays that can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl. 0.01 M sodium phosphate at pH 7.2.1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, (1994) Current Protocols in Molecular Biology (John Wiley & Sons, Inc., NY) Vol. 1 at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or .sup.125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, (1994) Current Protocols in Molecular Biology (John Wiley & Sons, Inc., NY) Vol. 1 at 10.8.1.

ELISAs comprise preparing antigen, coating the well of a 96-well microtiter plate with the antigen, adding the antibody of interest conjugated to a detectable compound such as an enzymatic substrate (e.g. horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, (1994) Current Protocols in Molecular Biology (John Wiley & Sons, Inc., NY) Vol. 1 at 11.2.1.

The binding affinity of a Protein$^b$ and its cognate binding partner, e.g., an antibody to an antigen, and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by Scatchard plot analysis. Competition with a second antibody can also be determined using radioimmunoassays. In this case, the antigen is incubated with antibody of interest is conjugated to a labeled compound (e.g., $^3$H or $^{125}$I) in the presence of increasing amounts of an unlabeled second antibody.

AbCIDs, additionally, can be employed histologically, as in immunofluorescence, immunoelectron microscopy or non-immunological assays, for in situ detection of a selected protein. In situ detection may be accomplished by removing a histological specimen from a patient, and applying thereto a labeled AbCID, preferably applied by overlaying the labeled AbCID onto a biological sample. Through the use of such a procedure, it is possible to determine not only the presence of the selected protein, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays using a AbCID will typically comprise incubating a sample, such as a biological fluid, a tissue extract, freshly harvested cells, or lysates of cells which have been incubated in cell culture, in the presence of a detectably labeled AbCID, and detecting the bound antibody by any of a number of techniques well known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled AbCID. The solid phase support may then be washed with the buffer a second time to remove unbound antibody. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of AbCID may be determined according to well known methods. Those skilled in the art will be able to determine operative and optimal assay conditions for each determination by employing routine experimentation.

There are a variety of methods available for measuring the affinity of an antibody-antigen interaction, but relatively few for determining rate constants. Most of the methods rely on either labeling antibody or antigen, which inevitably complicates routine measurements and introduces uncertainties in the measured quantities.

Surface plasmon reasonance (SPR) as performed on BIACORE® offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIAapplications Handbook, version AB (reprinted 1998), BIACORE® code No. BR-1001-86; BIAtechnology Handbook, version AB (reprinted 1998), BIACORE® code No. BR-1001-84. SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIACORE®. measurements monitor interactions directly as they happen. The technique is well suited to determination of kinetic parameters. Comparative affinity ranking is simple to perform, and both kinetic and affinity constants can be derived from the sensorgram data.

When analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction (ka and kd, the rates of complex formation and dissociation, kd/ka=KD). The equilibrium phase provides information on the affinity of the analyte-ligand interaction (KD).

BIAevaluation software provides comprehensive facilities for curve fitting using both numerical integration and global fitting algorithms. With suitable analysis of the data, separate rate and affinity constants for interaction can be obtained from simple BIACORE® investigations. The range of affinities measurable by this technique is very broad ranging from mM to pM.

Epitope specificity is an important characteristic of a monoclonal antibody. Epitope mapping with BIACORE®, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two Abs to bind simultaneously to the same antigen. Abs directed against separate epitopes will bind independently, whereas MAbs directed against identical or closely related epitopes will interfere with each other's binding. These binding experiments with BIACORE® are straightforward to carry out.

In various embodiments BioLayer Interferometry (BLI) is utilized to assess binding, e.g., octet BLI.

Peptide inhibition is another technique used for epitope mapping. This method can complement pair-wise antibody binding studies, and can relate functional epitopes to structural features when the primary sequence of the antigen is known. Peptides or antigen fragments are tested for inhibition of binding of different Abs to immobilized antigen. Peptides which interfere with binding of a given Ab are assumed to be structurally related to the epitope defined by that Ab.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise. Methods In Enzymology (Academic Press, Inc., N.Y.); Miller and Cabs eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor. N.Y., (1986); and in Ausubel et al. (1989) Current Protocols in Molecular Biology (John Wiley and Sons. Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

Nucleic Acid Delivery

In some embodiments, any nucleic acid molecules used in the methods provided herein, e.g. a nucleic acid encoding an AbCID, are packaged into or on the surface of delivery vehicles for delivery to cells. Delivery vehicles contemplated include, but are not limited to, nanospheres, liposomes, quantum dots, nanoparticles, polyethylene glycol particles, hydrogels, and micelles. As described in the art, a variety of targeting moieties can be used to enhance the preferential interaction of such vehicles with desired cell types or locations.

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Exemplary delivery methods and reagents are described in WO2018002719.

Exemplary Embodiments

Embodiment 1. A system comprising: (a) a first chemically-induced dimer (CID) component comprising (i) a first binding moiety capable of interacting with a small molecule to form a complex between the first CID component and the small molecule; and (ii) a first adapter moiety linked to the first binding moiety, or a first nucleic acid encoding polypeptide components of the first CID component; and (b) a second CID component comprising (i) a second binding moiety that specifically binds to the complex between the small molecule and the first OD component; and (ii) a second adapter moiety linked to the second binding moiety, or a second nucleic acid encoding polypeptide components of the second CID component, wherein the second binding moiety specifically binds to a site of the complex comprising at least a portion of the small molecule and a portion of the first binding moiety.

Embodiment 2. The system of embodiment 1, further comprising the small molecule, wherein the second CID component is bound to a complex between the small molecule and the first CID component at a site of the complex comprising at least a portion of the small molecule and a portion of the first binding moiety.

Embodiment 3. The system of embodiment 1 or 2, wherein the site of the complex comprising at least a portion of the small molecule and a portion of the first binding moiety is an interface between the small molecule and a binding site of the first binding moiety for the small molecule, comprising at least one atom of the small molecule and one atom of the first binding moiety.

Embodiment 4. The system of any one of embodiments 1-3, wherein the first binding moiety is a first antibody moiety that specifically binds to the small molecule.

Embodiment 5. The system of embodiment 4, wherein the small molecule is methotrexate.

Embodiment 6. The system of any one of embodiments 1-5, wherein the first binding moiety is derived from a naturally occurring binding partner of the small molecule, or a small molecule-binding variant thereof.

Embodiment 7. The system of embodiment 6, wherein the naturally occurring binding partner is Bcl-2, Bcl-xL, FK506 binding protein (FKBP), or cellular inhibitor of apoptosis protein 1 (cIAP1).

Embodiment 8. The system of embodiment 7, wherein the naturally occurring binding partner is Bcl-2 and the small molecule is ABT-199, ABT-263 or an analog thereof.

Embodiment 9. The system of embodiment 7, wherein the naturally occurring binding partner is Bcl-xL and the small molecule is ABT-737 or an analog thereof.

Embodiment 10. The system of embodiment 7, wherein the naturally occurring binding partner is FKBP and the small molecule is a synthetic ligand of rapamycin (SLF) having the structure of Formula (I) or an analog thereof.

Embodiment 11. The system of embodiment 7, wherein the naturally occurring binding partner is cIAP1 and the small molecule is GDC-0152, LCL161, AT406, CUDC-427, Birinapant, or an analog thereof.

Embodiment 12. The system of any one of embodiments 1-11, wherein the second binding moiety is an antibody moiety that specifically binds to a chemical-epitope comprising at least a portion of the small molecule and a portion of the first binding moiety.

Embodiment 13. The system of any one of embodiments 1-12, wherein the second CID component binds to the complex of the first CID component and the small molecule with a dissociation constant ($K_d$) no more than about 1/500 times its $K_d$ for binding to each of the free first CID component and the free small molecule.

Embodiment 14. A system comprising: (a) a first CID component comprising an ABT-737-binding domain of Bcl-xL, or a first nucleotide encoding polypeptide components of the first CID component; and (b) a second CID component comprising an antibody moiety capable of specifically binding to a complex between ABT-737 and the first CID component, or a second nucleic acid encoding polypeptide components of the second CID component, wherein the antibody moiety of the second CID component comprises heavy chain and light chain complementarity determining regions (CDRs) according to Table 1.

Embodiment 15. The system of embodiment 14, wherein the ABT-737-binding domain comprises the amino acid sequence of SEQ ID NO: 314.

Embodiment 16. A system comprising: (a) a first CID component comprising an ABT-199-binding domain of Bcl-2, or a first nucleotide encoding polypeptide components of the first CID component; and (b) a second CID component comprising an antibody moiety capable of specifically binding to a complex between ABT-199 and the first CID component, or a second nucleic acid encoding polypeptide components of the second CID component, wherein the antibody moiety of the second CID component comprises heavy chain and light chain complementarity determining regions (CDRs) according to Table 2.

Embodiment 17. The system of embodiment 16, wherein the ABT-199-binding domain comprises the amino acid sequence of SEQ ID NO: 315.

Embodiment 18. A system comprising: (a) a first CID component comprising an ABT-263-binding domain of Bcl-2, or a first nucleotide encoding polypeptide components of the first CID component; and (b) a second CID component comprising an antibody moiety capable of specifically binding to a complex between ABT-263 and the first CID component, or a second nucleic acid encoding polypeptide components of the second CID component, wherein the antibody moiety of the second CID component comprises heavy chain and light chain complementarity determining regions (CDRs) according to Table 3.

Embodiment 19. The system of embodiment 18, wherein the ABT-263-binding domain comprises the amino acid sequence of SEQ ID NO: 315.

Embodiment 20. A system comprising: (a) a first CID component comprising a synthetic ligand of rapamycin (SLF)-binding domain of FKBP, or a first nucleotide encoding polypeptide components of the first CID component, wherein the SLF has the structure of Formula (I); and (b) a second CID component comprising an antibody moiety capable of specifically binding to a complex between the SLF and the first CID component, or a second nucleic acid encoding polypeptide components of the second CID component, wherein the antibody moiety of the second CID component comprises heavy chain and light chain complementarity determining regions (CDRs) according to Table 4.

Embodiment 21. The system of embodiment 20, wherein the SLF-binding domain comprises the amino acid sequence of SEQ ID NO: 316.

Embodiment 22. A system comprising: (a) a first CID component comprising a GDC-0152-binding domain of cIAP1, or a first nucleotide encoding polypeptide components of the first CID component; and (b) a second CID component comprising an antibody moiety capable of specifically binding to a complex between GDC-0152 and the first CID component, or a second nucleic acid encoding polypeptide components of the second CID component, wherein the antibody moiety of the second CID component comprises heavy chain and light chain complementarity determining regions (CDRs) according to Table 5.

Embodiment 23. The system of embodiment 22, wherein the GDC-0152-binding domain comprises the amino acid sequence of SEQ ID NO: 317.

Embodiment 24. A system comprising: (a) a first CID component comprising a LCL161-binding domain of cIAP1, or a first nucleotide encoding polypeptide components of the first CID component; and (b) a second CID component comprising an antibody moiety capable of specifically binding to a complex between LCL161 and the first CID component, or a second nucleic acid encoding polypeptide components of the second CID component, wherein the antibody moiety of the second CID component comprises heavy chain and light chain complementarity determining regions (CDRs) according to Table 6.

Embodiment 25. The system of embodiment 24, wherein the LCL161-binding domain comprises the amino acid sequence of SEQ ID NO: 317.

Embodiment 26. A system comprising: (a) a first CID component comprising a AT406-binding domain of cIAP1, or a first nucleotide encoding polypeptide components of the first CID component; and (b) a second CID component comprising an antibody moiety capable of specifically binding to a complex between AT406 and the first CID component, or a second nucleic acid encoding polypeptide components of the second CID component, wherein the antibody moiety of the second CID component comprises heavy chain and light chain complementarity determining regions (CDRs) according to Table 7.

Embodiment 27. The system of embodiment 26, wherein the AT406-binding domain comprises the amino acid sequence of SEQ ID NO: 317.

Embodiment 28. A system comprising: (a) a first CID component comprising a CUDC-427-binding domain of cIAP1, or a first nucleotide encoding polypeptide components of the first CID component; and (b) a second CID component comprising an antibody moiety capable of specifically binding to a complex between CUDC-427 and the first CID component, or a second nucleic acid encoding polypeptide components of the second CID component, wherein the antibody moiety of the second CID component comprises heavy chain and light chain complementarity determining regions (CDRs) according to Table 8.

Embodiment 29. The system of embodiment 28, wherein the CUDC-427-binding domain comprises the amino acid sequence of SEQ ID NO: 317.

Embodiment 30. A system comprising: (a) a first CID component comprising a methotrexate-binding Fab, or a first nucleotide encoding polypeptide components of the first CID component, wherein the methotrexate-binding Fab HC-CDR1, HC-CDR2, HC-CDR3, LC-CDR1, LC-CDR2, and LC-CDR3 comprise the amino acid sequences of SEQ ID NOs: 318, 319, 320, 321, 322, and 323, respectively; and (b) a second CID component comprising an antibody moiety capable of specifically binding to a complex between methotrexate and the first CID component, or a second nucleic acid encoding polypeptide components of the second CID component, wherein the antibody moiety of the second CID component comprises heavy chain and light chain complementarity determining regions (CDRs) according to Table 9.

Embodiment 31. The system of any one of embodiments 1-30, wherein (a) the first adapter moiety comprises a DNA binding domain and the second adapter moiety comprises a transcriptional regulatory domain; or (b) the second adapter moiety comprises a DNA binding domain and the first adapter moiety comprises a transcriptional regulatory domain, wherein the first CID component and the second CID component are configured such that when dimerized in the presence of the small molecule to form the CID, the CID is capable of regulating transcription of a target gene.

Embodiment 32. The system of embodiment 31, wherein (a) the transcriptional regulatory domain is a transcriptional activation domain, and the CID is capable of upregulating transcription of the target gene; or (b) the transcriptional regulatory domain is a transcriptional repressor domain, and the CID is capable of downregulating transcription of the target gene.

Embodiment 33. The system of embodiment 31 or 32, wherein the DNA binding domain is derived from a naturally occurring transcriptional regulator.

Embodiment 34. The system of embodiment 31 or 32, wherein the DNA binding domain is derived from an RNA-guided endonuclease or a DNA-guided endonuclease.

Embodiment 35. The system of embodiment 34, wherein the RNA-guided endonuclease or DNA-guided endonuclease is catalytically dead.

Embodiment 36. The system of embodiment 35, wherein the DNA binding domain is derived from a catalytically dead Cas9 (dCas9).

Embodiment 37. The system of any one of embodiments 1-30, wherein the first CID component and the second CID component are configured such that when dimerized in the presence of the small molecule to form a CID associated with a target cell, the CID is capable of inducing target cell death.

Embodiment 38. The system of embodiment 37, wherein the first adapter moiety and the second adapter moiety are together capable of inducing apoptosis in the target cell.

Embodiment 39. The system of embodiment 38, wherein the first adapter moiety and/or the second adapter moiety are derived from a caspase protein.

Embodiment 40. The system of embodiment 39, wherein the first adapter moiety and the second adapter moiety are derived from caspase-9.

Embodiment 41. The system of any one of embodiments 37-40, wherein the target cell is an engineered cell adoptively transferred to an individual.

Embodiment 42. The system of embodiment 41, wherein the target cell is a T cell expressing a chimeric antigen receptor (CAR).

Embodiment 43. The system of any one of embodiments 1-30, wherein the first CID component and the second CID component are configured such that when dimerized in the presence of the small molecule to form a CID associated with a T cell, the CID is a heterodimeric CAR capable of activating the T cell upon binding a target antigen.

Embodiment 44. The system of embodiment 43, wherein (a) the first adapter moiety comprises (i) a transmembrane domain; (ii) a cytoplasmic co-stimulatory domain; and (iii) a cytoplasmic signaling domain; and the second adapter moiety comprises an extracellular antigen-binding moiety; or (b) the second adapter moiety comprises (i) a transmembrane domain; (ii) a cytoplasmic co-stimulatory domain; and (iii) a cytoplasmic signaling domain; and the first adapter moiety comprises an extracellular antigen-binding moiety; wherein the extracellular antigen-binding moiety specifically binds to the target antigen.

Embodiment 45. The system of embodiment 44, wherein the CID component comprising the extracellular antigen-binding moiety further comprises a secretory signal peptide.

Embodiment 46. The system of embodiment 43, wherein (a) the first adapter moiety comprises (i) a cytoplasmic co-stimulatory domain or a cytoplasmic signaling domain; (ii) a transmembrane domain; and (iii) an extracellular antigen-binding moiety; and the second adapter moiety comprises a cytoplasmic co-stimulatory domain or a cytoplasmic signaling domain; or (b) the second adapter moiety comprises (i) a cytoplasmic co-stimulatory domain or a cytoplasmic signaling domain; (ii) a transmembrane domain; and (iii) an extracellular antigen-binding moiety; and the first adapter moiety comprises a cytoplasmic co-stimulatory domain or a cytoplasmic signaling domain; wherein the extracellular antigen-binding moiety specifically binds to the target antigen.

Embodiment 47. The system of embodiment 43, wherein the first adapter moiety comprises (i) a cytoplasmic co-stimulatory domain or a cytoplasmic signaling domain; and (ii) a transmembrane domain; and the second adapter moiety comprises (i) a cytoplasmic co-stimulatory domain or a cytoplasmic signaling domain; and (ii) a transmembrane domain; wherein the first or second CID component further comprises an extracellular antigen-binding moiety linked to its binding moiety; and wherein the extracellular antigen-binding moiety specifically binds to the target antigen.

Embodiment 48. The system of embodiment 46 or 47, wherein the first and second CID components together comprise a cytoplasmic co-stimulatory domain and a cytoplasmic signaling domain.

Embodiment 49. The system of any one of embodiments 1-30, wherein the first CID component and the second CID component are configured such that when dimerized in the presence of the small molecule to form a CID, the CID is a heterodimeric bispecific T cell engager capable of redirecting a T cell to a target cell.

Embodiment 50. The system of embodiment 49, wherein (a) the first adapter moiety comprises a T cell antigen-binding moiety and the second adapter moiety comprises a target cell antigen-binding moiety; or (b) the second adapter moiety comprises a T cell antigen-binding moiety and the first adapter moiety comprises a target cell antigen-binding moiety.

Embodiment 51. The system of embodiment 50, wherein the T cell antigen-binding moiety is an antibody moiety that specifically binds to CD3.

Embodiment 52. The system of embodiment 50 or 51, wherein the target cell antigen-binding moiety is an antibody moiety that specifically binds to a cell surface antigen associated with a diseased cell.

Embodiment 53. The system of embodiment 52, wherein the diseased cell is a cancer cell.

Embodiment 54. The system of embodiment 52 or 53, wherein the target cell antigen-binding moiety is an antibody moiety that specifically binds to CD19.

Embodiment 55. The system of any one of embodiments 1-30, wherein the first CID component and the second CID component are configured such that when dimerized in the presence of the small molecule to form a CID associated with an immune cell, the CID is a heterodimeric signaling molecule capable of modulating activation of the immune cell.

Embodiment 56. The system of embodiment 55, wherein the first adapter moiety comprises (i) a transmembrane domain; and (ii) a cytoplasmic co-stimulatory domain; and the second adapter moiety comprises (i) a transmembrane domain; and (ii) a cytoplasmic co-stimulatory domain.

Embodiment 57. The system of embodiment 56, wherein the first adapter moiety further comprises a cytoplasmic signaling domain and/or the second adapter moiety further comprises a cytoplasmic signaling domain.

Embodiment 58. The system of any one of embodiments 55-57, wherein the immune cell is a T cell.

Embodiment 59. The system of embodiment 58, wherein the T cell is a CAR T cell.

Embodiment 60. A method of selecting binding moieties from a binding molecule library, wherein the binding moieties specifically bind to a complex between a small molecule and a cognate binding moiety, comprising: (a) screening an input set of binding moieties for binding moieties that do not bind to the cognate binding moiety in the absence of the small molecule, thereby generating a set of counter selected binding moieties; and (b) screening an input set of binding moieties for binding moieties that bind to the complex of the small molecule and the cognate binding moiety, thereby generating a set of positively selected binding moieties; and (c) conducting one or more rounds of screening, wherein each round of screening comprises the screening of step (a) and the screening of step (b), such that a set of binding moieties that specifically bind to the complex between the small molecule and the cognate binding moiety is generated.

Embodiment 61. The method of embodiment 60, wherein the method comprises two or more rounds of screening, and wherein (1) the input set of binding moieties of step (a) for the first round of screening is the binding molecule library, (2) the input set of binding moieties of step (b) for each round of screening is the set of counter selected binding moieties of step (a) from the given round of screening, (3) the input set of binding moieties of step (a) for each round of screening following the first round of screening is the set of positively selected binding moieties of step (b) from the previous round of screening, and (4) the set of binding moieties that specifically bind to the complex between the small molecule and the cognate binding moiety is the set of positively selected binding moieties of step (b) for the last round of screening.

Embodiment 62. The method of embodiment 61, comprising at least 2 rounds of selection.

Embodiment 63. The method of any one of embodiments 60-62, wherein at least one of the binding moieties in the set of binding moieties that specifically bind to the complex between the small molecule and the cognate binding moiety binds to the complex with a dissociation constant ($K_d$) no more than about 1/500 times its $K_d$ for binding to each of the free small molecule and the free cognate binding moiety.

Embodiment 64. The method of embodiment 63, wherein each of the binding moieties in the set of binding moieties that specifically bind to the complex between the small molecule and the cognate binding moiety binds to the complex with a dissociation constant ($K_d$) no more than about 1/500 times its $K_d$ for binding to each of the free small molecule and the free cognate binding moiety.

Embodiment 65. The method of any one of embodiments 60-64, wherein the binding molecule library is an antibody library, a DARPin library, a nanobody library, or an aptamer library.

Embodiment 66. The method of embodiment 65, wherein the binding molecule library is an antibody library.

Embodiment 67. The method of embodiment 66, wherein the antibody library is a phage-displayed Fab library.

Embodiment 68. A construct comprising an antibody moiety that specifically binds to a complex between a small molecule and a binding moiety prepared by a process comprising the steps of: (A) selecting antibody moieties from an antibody library according to the method of any one of embodiments 60-67; and (B) providing a construct comprising one of the antibodies moieties of (A).

Embodiment 69. The system of any one of embodiments 1-59, wherein the second binding moiety is an antibody moiety selected by a process comprising the steps of: (A) selecting antibody moieties from an antibody library according to the method of any one of embodiments 60-67; and (B) selecting the second binding moiety to be one of the antibodies moieties of (A).

Embodiment 70. A method of modulating the expression of a target gene in a cell, comprising expressing the first and second CID components of the system of any one of embodiments 31-36 in the cell and modifying the amount of the small molecule in the cell to modulate the expression of the target gene.

Embodiment 71. A method of treating a disease in an individual, comprising: (A) expressing the first and second CID components of the system of any one of embodiments 31-36 in target cells in an individual, wherein the expression level of the target gene in the target cells is associated with the disease; and (B) administering to the individual the small molecule in a regimen effective to treat the disease.

Embodiment 72. Nucleic acid encoding the first and second CID components of the system of any one of embodiments 31-36.

Embodiment 73. A cell comprising the first and second CID components of the system of any one of embodiments 31-36.

Embodiment 74. A method of controlling the survival of target cells in an individual, comprising: (A) expressing the first and second CID components of the system of any one of embodiments 37-42 in the target cells; and (B) administering to the individual the small molecule in a regimen effective to (I) kill a predetermined amount of the target cells; or (II) maintain a predetermined amount of the target cells.

Embodiment 75. The method of embodiment 74, wherein the target cells are part of an adoptive cell therapy in the individual.

Embodiment 76. The method of embodiment 75, wherein the target cells are CAR T cells.

Embodiment 77. A method of treating a disease in an individual, comprising: (A) administering to the individual an adoptive cell therapy for the disease comprising modified cells, wherein the modified cells express the first and second CID components of the system of any one of embodiments 37-42; and (B) administering to the individual the small molecule in a regimen effective to (I) kill a predetermined amount of the adoptively transferred cells; or (II) maintain a predetermined amount of the adoptively transferred cells.

Embodiment 78. The method of embodiment 77, wherein the adoptive cell therapy is a CAR T cell therapy.

Embodiment 79. Nucleic acid encoding the first and second CID components of the system of any one of embodiments 37-42.

Embodiment 80. A cell comprising the first and second CID components of the system of any one of embodiments 37-42.

Embodiment 81. The cell of embodiment 80, wherein the cell is part of an adoptive cell therapy.

Embodiment 82. The cell of embodiment 81, wherein the cell is a CAR T cell.

Embodiment 83. A method of modulating an immune response to a target cell in an individual, comprising: (A) administering to the individual modified T cells expressing the first and second CID components of the system of any one of embodiments 43-48, wherein the target antigen is expressed on the surface of the target cell; and (B) administering to the individual the small molecule in a regimen effective to modulate an immune response to the target cell.

Embodiment 84. A method of modulating an immune response to a target cell in an individual, comprising: (A) administering to the individual modified T cells expressing the CID component of the system of embodiment 44 comprising the cytoplasmic signaling domain; (B) administering to the individual the CID component of the system of embodiment 44 comprising the extracellular antigen-binding moiety, wherein the target antigen is expressed on the surface of the target cell; and (C) administering to the individual the small molecule in a regimen effective to modulate an immune response to the target cell.

Embodiment 85. The method of embodiment 83 or 84, wherein the regimen is effective to maintain an immune response to the target cell with fewer adverse effects in the individual as compared to a corresponding method comprising administration of CAR T cells expressing a conventional CAR comprising the corresponding CAR domains of the CID.

Embodiment 86. A method of treating a disease characterized by a target cell in an individual, comprising: (A) administering to the individual modified T cells expressing the first and second CID components of the system of any one of embodiments 43-48, wherein the target antigen is expressed on the surface of the target cell; and (B) administering to the individual the small molecule in a regimen effective to treat the disease.

Embodiment 87. A method of treating a disease characterized by a target cell in an individual, comprising: (A) administering to the individual modified T cells expressing the CID component of the system of embodiment 44 comprising the cytoplasmic signaling domain; (B) administering to the individual the CID component of the system of embodiment 44 comprising the extracellular antigen-binding moiety, wherein the target antigen is expressed on the surface of the target cell; and (C) administering to the individual the small molecule in a regimen effective to treat the disease.

Embodiment 88. The method of embodiment 86 or 87, wherein the regimen is effective to treat the disease with fewer adverse effects in the individual as compared to a corresponding method comprising administration of CAR T cells expressing a conventional CAR comprising the corresponding CAR domains of the CID.

Embodiment 89. Nucleic acid encoding the first and second CID components of the system of any one of embodiments 43-48.

Embodiment 90. A T cell comprising the first and second CID components of the system of any one of embodiments 43-48.

Embodiment 91. A T cell comprising the CID component of the system of embodiment 44 comprising the cytoplasmic signaling domain Embodiment 92. A method of modulating an immune response to a target cell in an individual, comprising: (A) administering to the individual the first and second CID components of the system of any one of embodiments 49-54; and (B) administering to the individual the small molecule in a regimen effective to modulate an immune response to the target cell.

Embodiment 93. The method of embodiment 92, wherein the regimen is effective to maintain an immune response to the target cell with fewer adverse effects in the individual as compared to a corresponding method comprising administration of a conventional bispecific T cell engager comprising the corresponding bispecific T cell engager domains of the CID.

Embodiment 94. A method of treating a disease characterized by a target cell in an individual, comprising: (A) administering to the individual the first and second CID components of the system of any one of embodiments 49-54; and (B) administering to the individual the small molecule in a regimen effective to treat the disease.

Embodiment 95. The method of embodiment 94, wherein the regimen is effective to treat the disease with fewer adverse effects in the individual as compared to a corresponding method comprising administration of a conventional bispecific T cell engager comprising the corresponding bispecific T cell engager domains of the CID.

Embodiment 96. Nucleic acid encoding the first and second CID components of the system of any one of embodiments 49-54.

Embodiment 97. A method of modulating an immune response mediated by T cells in an individual, comprising: (A) expressing the first and second CID components of the system of any one of embodiments 55-59 in the T cells; and (B) administering to the individual the small molecule in a regimen effective to modulate an immune response mediated by the T cells.

Embodiment 98. The method of embodiment 97, wherein the regimen is effective to maintain an immune response mediated by the T cells with fewer adverse effects in the individual as compared to a corresponding method comprising expression of a monomeric signaling molecule comprising the corresponding signaling domains of the CID in the T cells.

Embodiment 99. A method of treating a disease characterized by a target cell in an individual, comprising: (A) expressing the first and second CID components of the system of any one of embodiments 55-59 in T cells in the individual capable of recognizing and killing the target cell; and (B) administering to the individual the small molecule in a regimen effective to treat the disease.

Embodiment 100. The method of embodiment 99, wherein the regimen is effective to treat the disease with fewer adverse effects in the individual as compared to a corresponding method comprising expression of a monomeric signaling molecule comprising the corresponding signaling domains of the CID in the T cells.

Embodiment 101. The method of any one of embodiments 97-100, wherein the T cells are CAR T cells.

Embodiment 102. Nucleic acid encoding the first and second CID components of the system of any one of embodiments 55-59.

Embodiment 103. A T cell comprising the first and second CID components of the system of any one of embodiments 55-59.

Embodiment 104. The T cell of embodiment 103, wherein the T cell is a CAR T cell.

The present disclosure has been described above with reference to specific alternatives. However, other alternatives than the above described are equally possible within the scope of the disclosure. Different method steps than those described above, may be provided within the scope of the disclosure. The different features and steps described herein may be combined in other combinations than those described.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those of skill within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

In addition, where features or aspects of the disclosure are described in terms of Markush groups, those skilled in the art will recognize that the disclosure is also thereby described in terms of any individual member or subgroup of members of the Markush group.

Any of the features of an alternative of the first through eleventh aspects is applicable to all aspects and alternatives identified herein. Moreover, any of the features of an alternative of the first through eleventh aspects is independently combinable, partly or wholly with other alternatives described herein in any way, e.g., one, two, or three or more alternatives may be combinable in whole or in part. Further, any of the features of an alternative of the first through eleventh aspects may be made optional to other aspects or alternatives. Although described above in terms of various example alternatives and implementations, it should be understood that the various features, aspects and functionality described in one or more of the individual alternatives are not limited in their applicability to the particular alternative with which they are described, but instead may be applied, alone or in various combinations, to one or more of the other alternatives of the present application, whether or not such alternatives are described and whether or not such features are presented as being a part of a described alternative. Thus, the breadth and scope of the present application should not be limited by any of the above-described example alternatives.

All references cited herein are incorporated herein by reference in their entirety. To the extent publications and patents or patent applications incorporated by reference contradict the disclosure contained in the specification, the specification is intended to supersede and/or take precedence over any such contradictory material. To the extent publications and patents or patent applications incorporated by reference herein contradict the disclosure contained in the specification, the specification is intended to supersede and/or take precedence over any such contradictory material.

The details of one or more embodiments of the disclosure are set forth in the accompanying description below. Any materials and methods similar or equivalent to those described herein can be used in the practice or testing of the present disclosure. Other features, objects and advantages of the disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present description will control.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Some embodiments of the disclosures provided herewith are further illustrated by the following non-limiting examples.

EXAMPLES

Materials and Methods

Small Molecule and Peptide Reagents

ABT-737 (ChemieTek CT-A737), ABT-263 (Selleckchem S1001), ABT-199 (LC-Laboratories V-3579), methotrexate (Sigma-Aldrich A6770), and Bak peptide (Anaspec AS-61616) were used without further purification. For use, ABT-737, ABT-263, ABT-199, and methotrexate and Bak peptide (SEQ ID NO: 324) were each dissolved in DMSO as 10 mM stocks. Stocks were stored at −80° C., until used.

Analysis of Ligand Solvent Exposure

Small-molecule-protein complexes were identified in the Protein Data Bank (rcsb.org/pdb/home/home.do) using their in-house advanced search feature. Search parameters used were: Molecular Weight Search: Min Molecular Weight=100.0 Max Molecular Weight=50000.0 and Binding Affinity: Binding affinity min is 0.001 and Binding affinity max is 1000 and Affinity Type is Ki and TAXONOMY is just *Homo sapiens* (human) and TAXONOMY is only just *Homo sapiens* (human). The list generated was then curated by hand so as to remove complexes in which the ligand was not an organic small molecule, resulting in a final list of 866 structures. Solvent accessible surface area for bound ligands was calculated using Naccess V2.1.1 with default parameters and hydrogen and heteroatoms considered in the calculation. The plot of solvent exposed surface area was generated using the ggplot2 package in R-studio.

Expression and Biotinylation of BCL-xL

The gene encoding C-terminally truncated BCL-xL (residues 2-215) with an N-terminal AviTag was purchased as a gBlock™ (IDT). The gene was cloned into the pMCSG7 vector (Kong, et al., *Biomol. Ther.*, 21:423434 (2013)) using Gibson cloning. A Tabaco Etch Virus (TEV) cut site was then introduced between the AviTag and BCL-xL domain using sight directed mutagenesis. The sequence of the final construct was confirmed by sequencing of the entire gene. The plasmid was transformed into BL21(DE3) *E. coli* cells and a single colony was used to inoculate 1.5 L of 2×YT media containing carbenicillin (100 µg/mL). The culture was grown at 37° C. to an OD600 of 1-1.2, cooled to 18° C. for 1 h and then induced at 18° C. overnight with 0.5 mM IPTG. Cells were harvested by centrifugation and the pellet were stored at −80° C.

For protein purification, the pellet was thawed at 0° C. and then re-suspended in 10 mL of lysis buffer (50 mM Tris, pH 8.0, 200 mM NaCl, 20 mM imidazole) supplemented with PMSF (100 μg/mL). The cells were lysed using a microfludizer and the lysate was cleared by centrifugation at 4° C. The cleared lysate was added to 400 μL of Ni-NTA Superflow resin (Qiagen) and rotated at 4° C. for 1 h. The resin was washed (3×) with lysis buffer and then transferred to a spin column. The purified protein was eluted with elution buffer (50 mM Tris, pH 8.0, 200 mM NaCl, 600 mM imidazole). Fractions were analyzed by SDS-PAGE and those that were found to be >95% pure were pooled, exchanged into storage buffer (25 mM Tris, pH 8.0, 150 mM NaCl, 1 mM DTT) and concentrated.

The purified BCL-xL protein was biotinylated on its AviTag using the standard protocol provided by Avidity. Biotinylation was monitored by intact protein mass spectrometry on a Xevo G2-XS Mass Spectrometer (Waters) and found to be quantitative. The biotinylated BCL-xL was then purified on Ni-NTA as described above, separated into aliquots, snap-frozen and stored at −80° C. for later use.

Phage Display Selections and Phage Tittering

All phage selections were done according to previously established protocols (Seiler, et al., *Nucleic Acids Res.,* 42:D12531260 (2014). Briefly, selections with antibody phage library F were performed using biotinylated BCL-xL captured with streptavidin-coated magnetic beads (Promega). Prior to each selection, the phage pool was incubated with 1 μM of BCL-xL immobilized on streptavidin beads in the absence of ABT-737 in order to deplete the library of any binders to the apo form of BCL-xL. Subsequently, the beads were removed and ABT-737 was added to the phage pool at a concentration of 1 μM. In total, four rounds of selection were performed with decreasing amounts of BCL-xL antigen (100 nM, 50 nM, 10 nM and 10 nM). To reduce the deleterious effects of nonspecific binding phage, we employed a "catch and release" strategy, where specific BCL-xL binding Fab-phage were selectively eluted from the magnetic beads by the addition of 2 μg/mL TEV protease. Individual phage clones from the fourth round of selection were analyzed for sequencing.

Phage titers were performed according to standard protocols. Briefly, TEV eluted phage were used to infect log-phase XL1-Blue *E. coli* cells (Stratagene). Infected cells were incubated at room temperature for 20 minutes on an orbital shaker. Cells were then serially diluted and spotted on LB agar-plates with carbenicillin (50 m/mL) and incubated overnight at 37° C. Phage titers were measured for each round of selections against both the BCL-xL/ABT-737 complex and against apo BCL-xL.

Expression of Fabs

Fabs were expressed according to a previously described protocol (Seiler, et al., *Nucleic Acids Res.,* 42:D1253-1260 (2014)). Briefly, C43 (DE3) Pro+ *E. coli* containing expression plasmids were grown in 2×YT at 37° C. to an OD600 of 0.6-0.8 and then Fab expression was induced by the addition of 1 mM IPTG. Incubation temperature was subsequently reduced to 30° C. and the cultures were allowed to shake for 16-18 h. Cells were harvested by centrifugation and Fabs were purified by Protein A affinity chromatography. Fab purity and integrity was assessed by SDS-PAGE and intact protein mass spectrometry using a Xevo G2-XS Mass Spectrometer (Waters).

Fab ELISAs

ELISAs were performed according to standard protocols. Briefly, 96-well Maxisorp plates were coated with NeutrAvidin (10 μg/ml) overnight at 4° C. and subsequently blocked with BSA (2% w/v) for 1 h at 20° C. 20 nM of biotinylated BCL-xL was captured on the NeutrAvidin-coated wells for 30 minutes followed by the addition of various concentrations of Fab with either 1 μM ABT-737 or 0.05% DMSO for 30 minutes. The bound Fabs were then detected using a horseradish peroxidase (HRP)-conjugated anti-Fab monoclonal antibody (Jackson ImmunoResearch 109-036-097).

Binding Kinetics Analysis

Biolayer interferometery data were measured using an Octet RED384 instrument (ForteBio). Biotinylated BCL-xL was immobilized on a Streptavidin (SA) biosensor using a 200 nM solution. Serial dilutions of Fabs in kinetics buffer (PBS, pH 7.4, 0.05% Tween-20, 0.2% BSA, 10 μM biotin) with small molecule (1 μM), peptide (5 μM), or vehicle (0.05% DMSO) were used as analyte. Affinity (KD) and kinetic parameters (kon and koff) were calculated from a global fit (1:1) of the data using the Octet RED384 software.

Vector Generation for Cellular Assays

Fab AZ1 was converted into a previously described single-chain Fab construct using Gibson cloning (Hornsby, et al., *Mol. Cell. Proteomics,* 14:2833-2847 (2015)).

A gene encoding the Conventional CAR construct (CD8 Signal Sequence-Myc Tag-αCD19scFv-CD8 Hinge Domain-CD8 Transmembrane Domain-4IBB Co-stimulatory Region-CD3ξ Domain) was purchased as a gBlock™ (IDT). The gene was amplified by PCR and cloned into the pLX302 vector (Addgene plasmid #25896) using Gibson cloning. The sequence of the final construct was confirmed by sequencing of the entire gene. The AbCID CAR construct was generated by replacing the aCD19scFv portion of the Conventional CAR vector with the BCL-xL gene (residues 2-215) by Gibson cloning, followed by conversion of BCL-xL to BCL-xL(M159P) by site directed mutagenesis. The M159P mutation has previously been shown to prevent BCL-xL from forming a domain-swapped dimer (Koerber, et al., *J. Mol. Biol.,* 427:576-586 (2015)). We feared that the two-dimensional confinement of the AbCID CAR on the cell membrane would promote dimer formation in BCL-xL (WT), and lead to antigen-independent activation of the CAR T-cells. The M159P mutation did not affect ABT-737 or AZ1 binding (data not shown). The sequence of the final construct was confirmed by sequencing of the entire gene.

The gene for CD19 was obtained from the ORFeome (Raj an, et al., *Sci. Rep.,* 5:10609 (2015)) and fused to a P2A-mCherry gene by overlap extension PCR. The gene was cloned into the pLX302 vector using Gibson cloning. The sequence of the final construct was confirmed by sequencing of the entire gene.

Culturing of Cell Lines

The NFAT reporter Jurkat cells utilized were a generous gift from Arthur Weiss. The K562 and HEK293T cells utilized were from frozen stocks maintained by the Wells lab. The cell lines were not authenticated before use. No test for mycoplasma contamination was performed. Unless otherwise noted all Jurkat and K562 cells lines were cultured in RPMI supplemented with 10% FBS and 1×Pen/Strep. All Jurkat NFAT reporter cells were maintained in G418 (2 mg/mL). All CAR containing Jurkat cell lines were maintained in puromycin (2 μg/mL) in addition to G418. CD19+ K562 cells were maintained in puromycin (2 μg/mL). HEK293 T cells containing the Gal4-UAS-Fluc operon were maintained in High Glucose DMEM supplemented with 10% FBS, 1× Pen/Strep, and puromycin (2 µg/mL). All cell lines were cultured at 37° C. under 5% CO2.

Immunoblotting

HEK293T cells were plated at approximately $0.5 \times 10^6$ cells/well in a 6-well plate and cultured overnight at 37° C. under 5% CO2 before transfection. The cells were transfected with a plasmid encoding scAZ1-avitag using TransIT-293 (Mirus Bio) following the manufacturer's procedure. The cells were further incubated at 37° C. for 48 h. The cells were washed with PBS and lysed with M-PER mammalian protein extraction reagent (Thermo Scientific) supplemented with Complete™ protease inhibitor cocktail (Roche) at 4° C. for 10 minutes. Immunoblotting was performed using an anti-AviTag antibody (GenScript mouse mAb, A01738).

CRISPRa-Mediated Luciferase Assay

For CRISPRa-mediated transcriptional activation, the reporter HEK293T cell line containing the Gal4-UAS-Fluc operon (Collaboration, O. R, Nat. Methods, 13:191-192 (2016)) was seeded at $\sim 0.5 \times 10^6$ cells/well in 6-well plates and cultured under 5% CO2 at 37° C. overnight. The cells were transfected with a plasmid encoding scAZ1-VPR and another plasmid encoding dCas9-BCL-xL and Gal4 sgRNA at a 1:1 ratio. The transfected cells were trypsinized and resuspended in fresh DMEM supplemented with 10% FBS 24 h after transfection. Cells were then aliquoted into a 96-well poly-D-lysine coated plate (Corning) and allowed to adhere for 24 h before 20 nM ABT-737 was added to induce CRISPRa activity. Cells were then further incubated for 48 h before evaluation of luciferase gene expression. To determine luciferase activity, cells were lysed with Bright-Glo Luciferase Assay substrate (Promega) and analyzed using an Infinite M200 PRO plate reader (Tecan). The luciferase activities were background-subtracted with a negative control (cells expressing full-length dCas9-VPR and PHOX2B negative-sgRNA), and normalized against a positive control (cells expressing full-length dCas9-VPR and Gal4 sgRNA). For investigation of cellular dose response, different concentrations of ABT-737 (0.014 nM, 0.041 nM, 0.12 nM, 0.37 nM, 1.1 nM, 3.3 nM, 10 nM, 30 nM, 90 nM, 270 nM) were added to the cells after cells were transfected and aliquoted to a 96-well plate.

Expression of Bispecific Antibody

Expi293 (Life Technologies) cells were transiently co-transfected with two pFUSE (InvivoGen) vectors harboring the AZ1 heavy chain and the AZ1 light chain genetically fused to the aCD19 scFv at a ratio of 1:1. The Expi-Fectamine 293 transfection kit (Life Technologies) was used for transfections as per manufacturer's instructions. Cells were incubated for 7 days at 37° C. in a 5% CO2 environment before the supernatants were harvested by centrifugation. Protein was purified by Protein A affinity chromatography and assessed for quality and integrity by SDS-PAGE.

Generation of Cell Lines

All CAR containing Jurkat cells and CD19+ K562 cells generated for the T-cell activation experiments were generated by lentiviral transduction. To produce virus, HEK293T cells were transfected with a mixture of second-generation lentiviral packaging plasmids at ~80% confluence. FuGene HD (Promega) was used for transfection of the plasmids using 3 jig DNA (1.35 jig pCMV delta8.91, 0.15 jig pMD2-G, 1.5 jig pLX302) and 7.5 jiL of FuGene HD per well of a six-well plate. Media was changed to complete DMEM after 6 h of incubation with transfection mixture. The supernatant was harvested and cleared by passing through a 0.2 jim filter 72 h post transfection. Cleared supernatant was added to target Jurkat NFAT reporter cells and K562 cells (~1 million cells per mL) with 8 jig/mL polybrene and cells were centrifuged at 1000 g at 33° C. for 2 h. Cells were then incubated with viral supernatant mixture overnight before the media was changed to fresh complete RPMI. Cells were expanded for a minimum of 48 h before they were grown in drug selection media. Drug selection for stable cell lines was started by the addition of 2 jig/mL puromycin. Following at least 72 h of incubation in puromycin containing media, cells were analyzed by flow cytometry for expression of the CAR or CD19. High expressing populations of CD19+ K562 cells were enriched by flow cytometry by gating for expression of an intracellular mCherry marker genetically linked to CD19 by a P2A sequence. Jurkat cells displaying high levels of CARs were enriched by flow cytometry by gating for Myc tag antibody staining using a Myc-Tag Mouse mAb Alexa Fluor647 conjugate (Cell Signaling 2233S). All flow cytometry cell sorting was performed using an Arian (BD Biosciences).

Quantification of CAR-T Cell Activation

Jurkat cells expressing CARs were mixed with antigen positive (CD19+) or antigen negative (CD19−) K562 target cells at a ratio of 1:2. Bispecifc antibody (AZ1-αCD19) or Fab (AZ1) and ABT-737 or DMSO was diluted in media and added to cell mixtures. After overnight incubation at 37° C., cells were pelleted by centrifugation. NFAT-dependent GFP reporter expression was quantified by flow cytometry using a FACSCanto II (BD Biosciences). CD69 expression was quantified by immunofluorescence flow cytometry using a FACSCanto II (BD Biosciences) using an APC anti-human CD69 Antibody (Biolegend 310910). IL-2 secretion was quantified by collection of supernatants and analysis by ELISA using the BD Human IL-2 ELISA set as per manufacturer's protocol. All flow cytometry data analysis was performed using FlowJo software and all plots were generated using Prism software (GraphPad).

Assaying Cellular Toxicity of ABT-737

W T Jurkat, AbCID CAR Jurkat, Conventional CAR Jurkat, WT K562, CD19+ K562, and HEK293T cells were plated in 96-well plates at ~5000 cells per well. Each cell line was incubated with varying concentrations of ABT-737 (10 µM initial, 3-fold serial-dilutions, 8 times) or DMSO alone (0.1%). After 24 h, cell viability was measured using a CellTiter-Glo® Luminescent Cell Viability Assay (Promega) and the manufacturer's standard protocol. The percent viability relative to DMSO treatment was plotted and analyzed for each cell line using Prism software (GraphPad).

Example 1: Identification of the BCL-xL/ABT-737 Complex for Generation of an AbCID We reasoned that the ideal complexes to generate selective antibodies against would be those in which a large portion of the small molecule remains solvent exposed when bound. Nature has employed a similar principle in the rapamycin-FKBP12-FRB AbCID system, where rapamycin first binds FKBP12, generating a new binding surface that is then recognized by FRB. Several other natural products use a similar approach for artificial protein recruitment (Fegan, et al., Chem. Rev., 110:3315-3336 (2010)). Additional design principles included that the target protein be a small monomeric domain and that the small molecule inducer be commercially available with desirable pharmacokinetic properties and low toxicity, making it potentially useful for animal model applications.

After a survey of small-molecule-bound structures in the Protein Data Bank (rcsb.org/pdb/home/home.do) we turned our attention to the human BCL-xL/ABT-737 complex (PDB: 2YXJ)(Lee, et al., Cell Death Differ., 14:1711-1713

(2007)). BCL-xL is a member of the anti-apoptotic BCL-2 family of proteins (Czabotar, et at., Nat. Rev. Mol. Cell Biol., 15:49-63 (2014)). This small monomeric protein (.about.26 kDa) is located on the outer membrane of the mitochondria where it sequesters pro-apoptotic members of the BCL-2 family. Because of its anti-apoptotic role, a number of animal and clinically active small-molecule inhibitors have been developed against BCL-xL for the treatment of cancers (Besbes, et al., Oncotarget 6:12862-12871 (2015)). The crystal structure of our candidate ligand, ABT-737 (Oltersdorf, et al., Nature, 435:677-681 (2005)), bound to BCL-xL shows that a large portion of ABT-737 is exposed to solvent (308 A.sup.2) providing a potential chemical epitope for antibody binding. In comparison, an analysis of 866 small-molecule-bound structures in the PDB (FIG. 6) revealed a mean solvent exposed surface area of 125.ANG..sup.2, with rapamycin bound to FKBP12 being an outlier at 528.ANG..sup.2 (PDB:1FKB) (Van Duyne, et al., J. Mol. Biol., 229:105-124 (1993)). Thus, we felt that the BCL-xL/ABT-737 complex would be an ideal first target for the development of an AbCID.

Example 2: Selection of Chemical-Epitope-Selective Antibodies

Figure 1B:
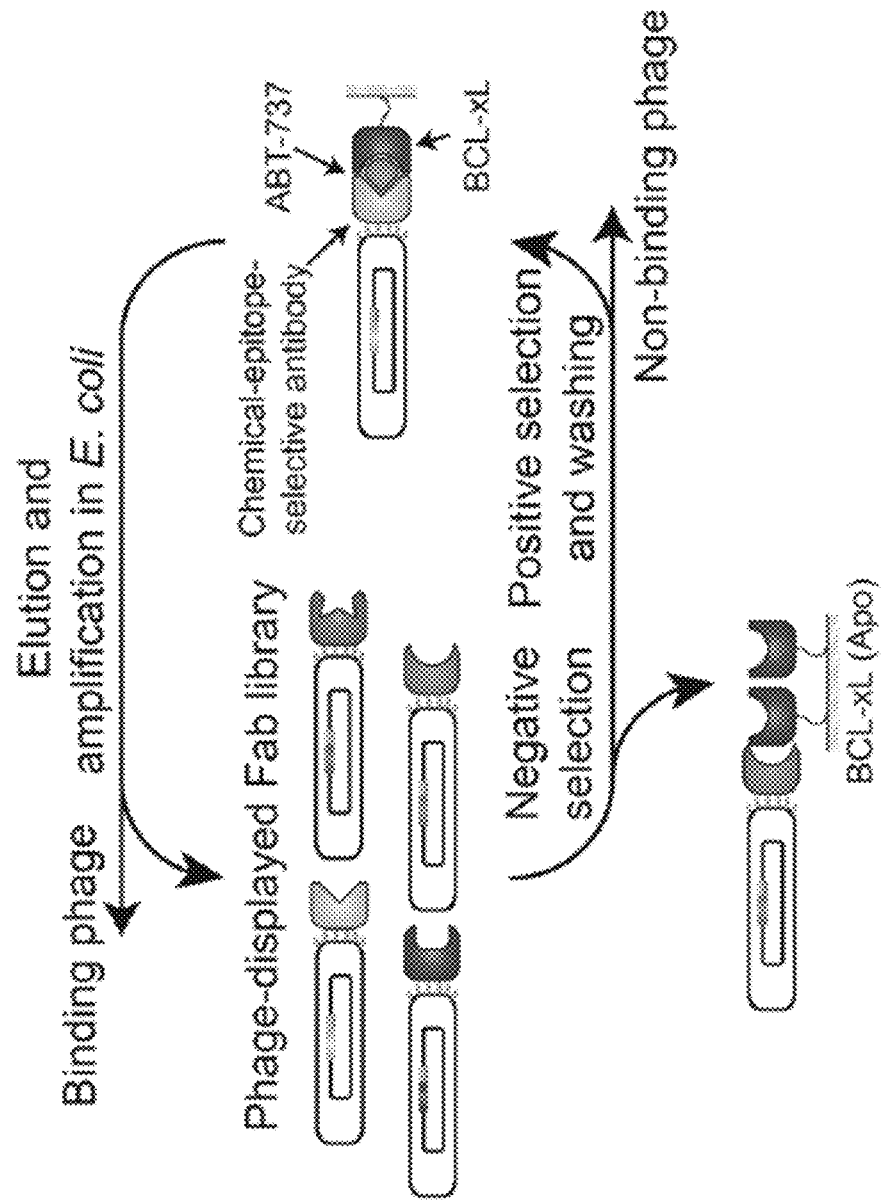
FIG. 1B shows a diagram of the phage selection strategy used to select ABT-737-inducible Fab binders of BCL-xL.
Figure 7:
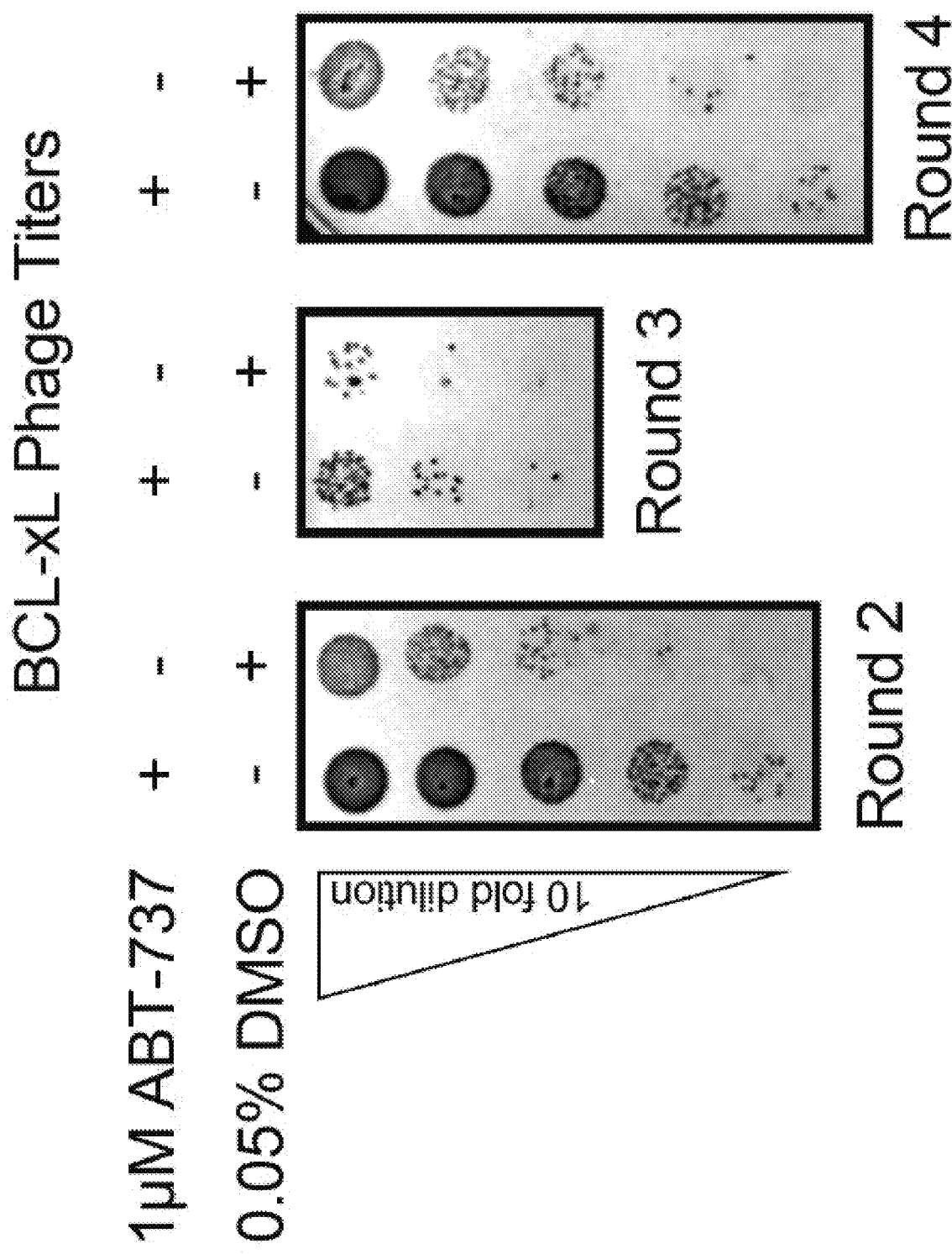
FIG. 7 shows representative titers of phage libraries from Rounds 2 through 4 of Fab-phage selections against BCL-xL bound to ABT-737. Greater than ten-fold enrichment of phage was observed for binding of BCL-xL in the presence of 1 µM ABT-737 compared to DMSO as determined by quantification of recovered colony forming units.

To identify unique chemical-epitope-selective antibodies we utilized a C-terminally truncated form of BCL-xL (residues 2-215) that lacks the mitochondrial-transmembrane domain. Biotinylated BCL-xL was immobilized on streptavidin resin and used for phage selections with a previously developed synthetic antibody-fragment library and selection stategy (Hornsby, et al., Mol. Cell. Proteornics, 14:2833-2847 (2015)). During each round of selection, the phage library was first subjected to stringent counter selection against BCL-xL in the absence of small molecule, thereby removing any Fab-phage that was not selective for the ABT-737-bound form. Positive selections were then performed in the presence of saturating amounts of ABT-737 (1 μM), ensuring that the majority of BCL-xL was bound to ABT-737 (FIG. 1B). A total of four rounds of selection were performed. Encouragingly, we observed significant enrichment of phage titers for selections against BCL-xL in the presence of ABT-737 (FIG. 7). After round four, individual Fab-phage clones were isolated and sequenced. A total of ten Fab-phage with unique sequences in the complementarity-determining regions (CDRs) of the Fab were identified (Table 1).

Figure 1C:
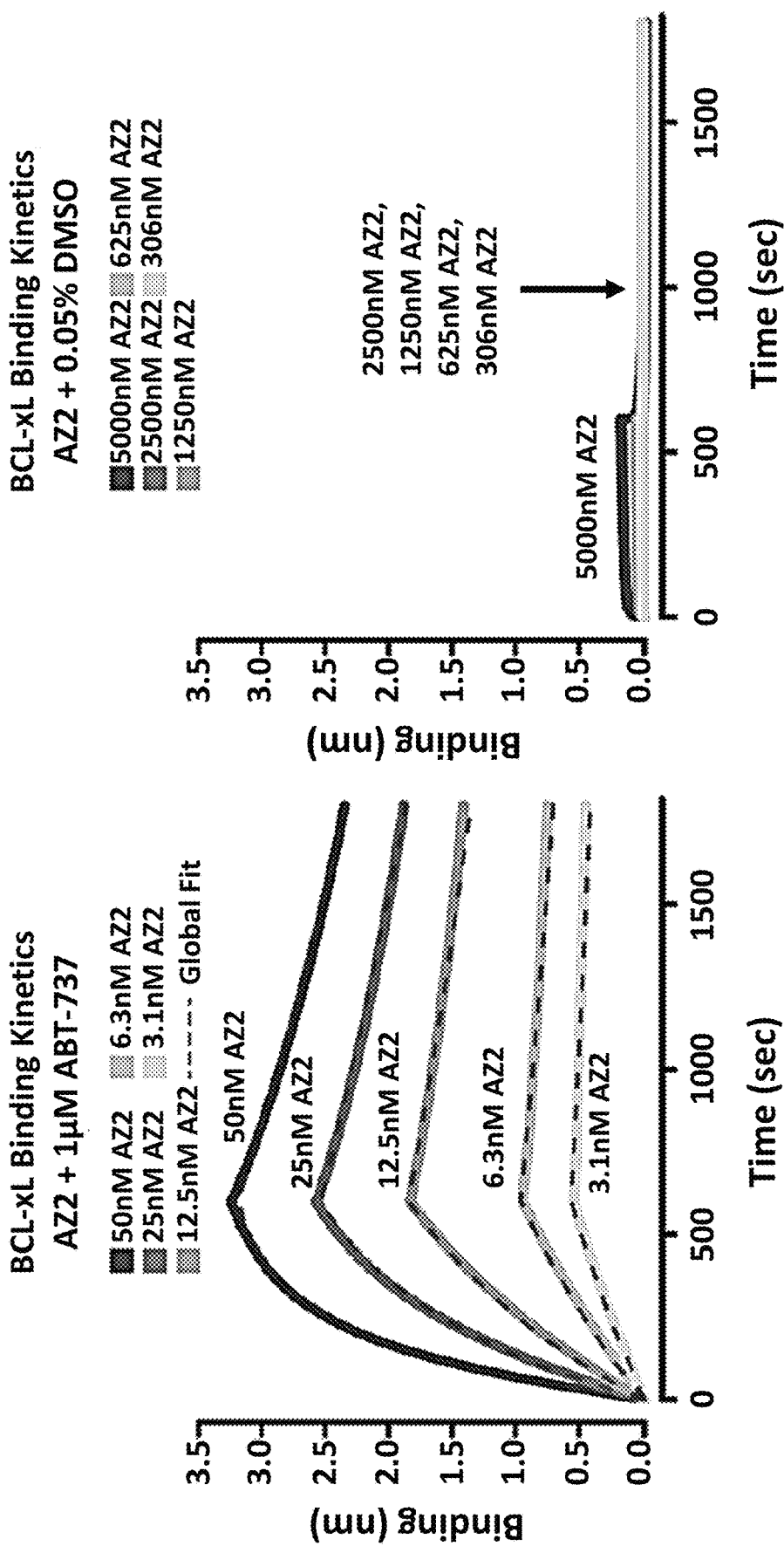
FIG. 1C shows biolayer interferometry showing potent and reversible binding of Fab AZ2 to BCL-xL in the presence of ABT-737 (left) but no significant binding in the absence of ABT-737 (right). Blue curves represent measured data points and dashed red lines represent the global-fit lines used for analysis.
Figure 8:
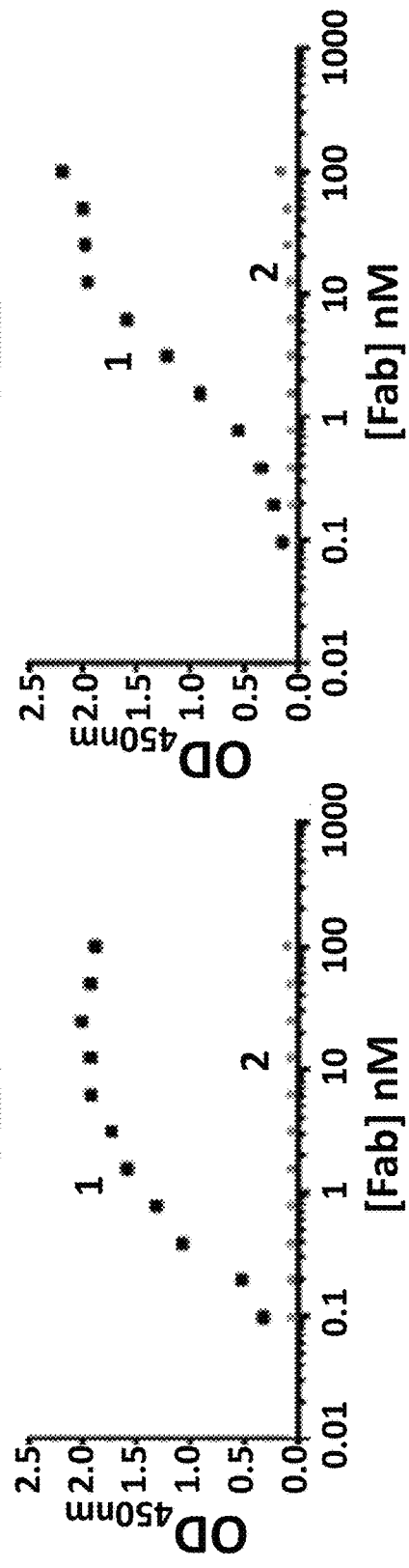
FIG. 8 shows ELISA of purified sequence-unique Fabs derived from ABT-737-bound BCL-xL selections. All Fabs showed enhanced binding in the presence of ABT-737. Four out of the ten Fabs tested (AZ 1-4) exhibited high potency and dose-dependent binding to BCL-xL in the presence of ABT-737 with virtually no appreciable binding in the absence of ABT-737. Each data point represents a single measurement.
Figure 8:
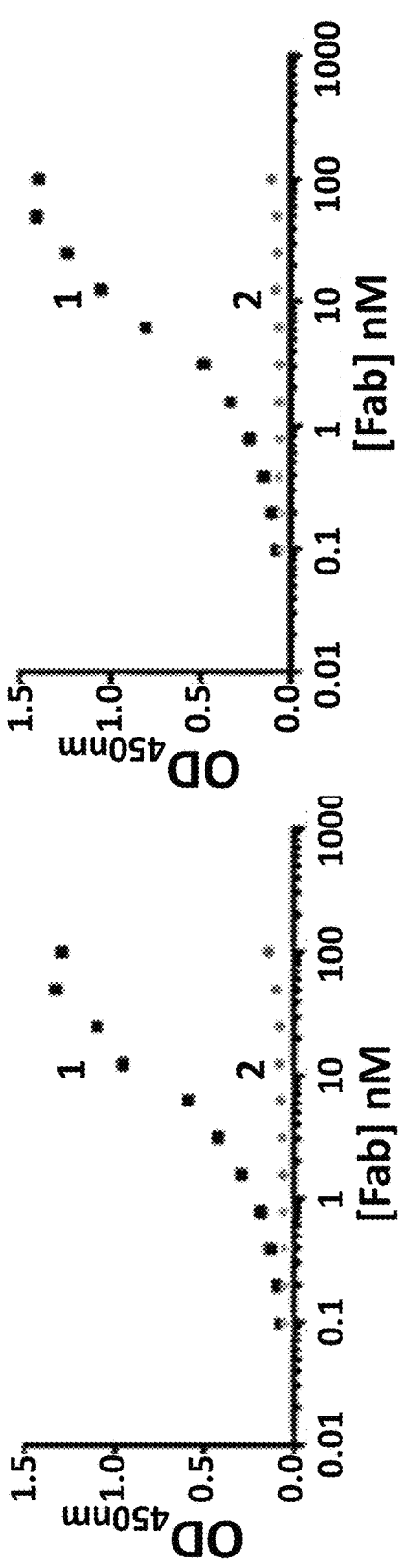
Figure 8:
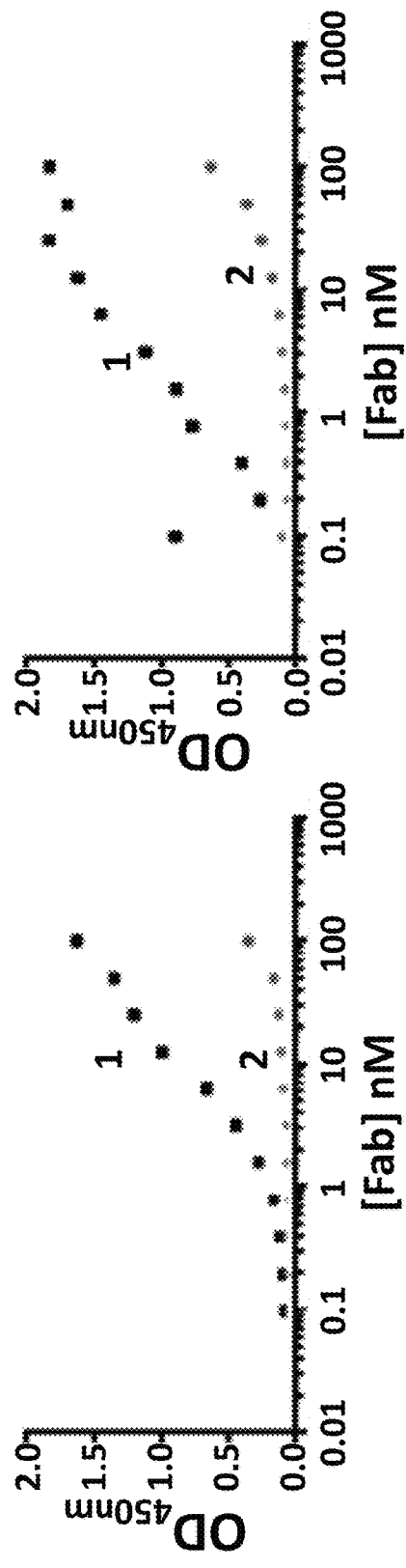
Figure 8:
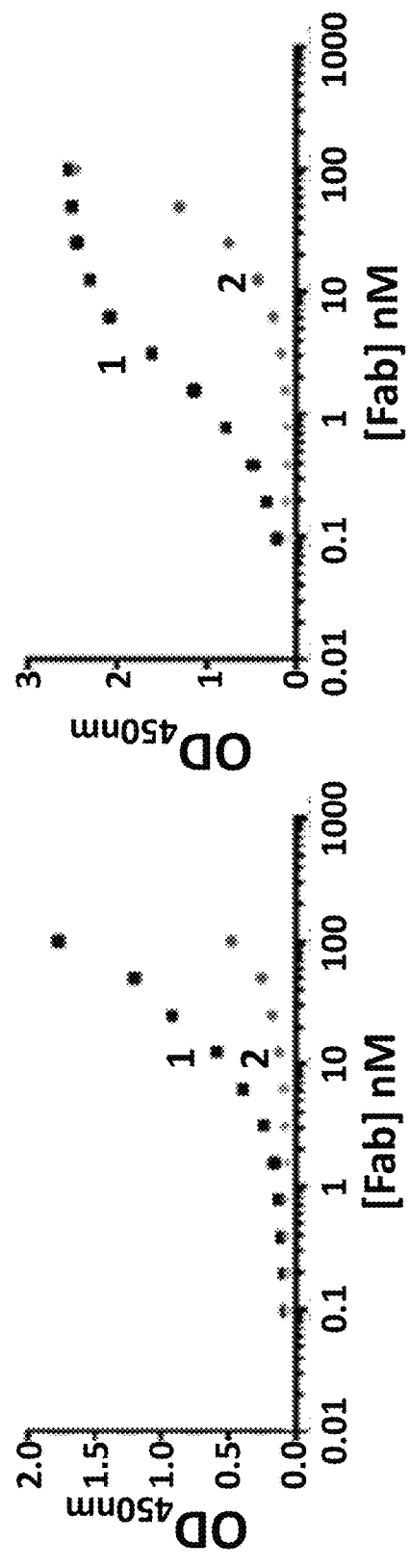
Figure 8:
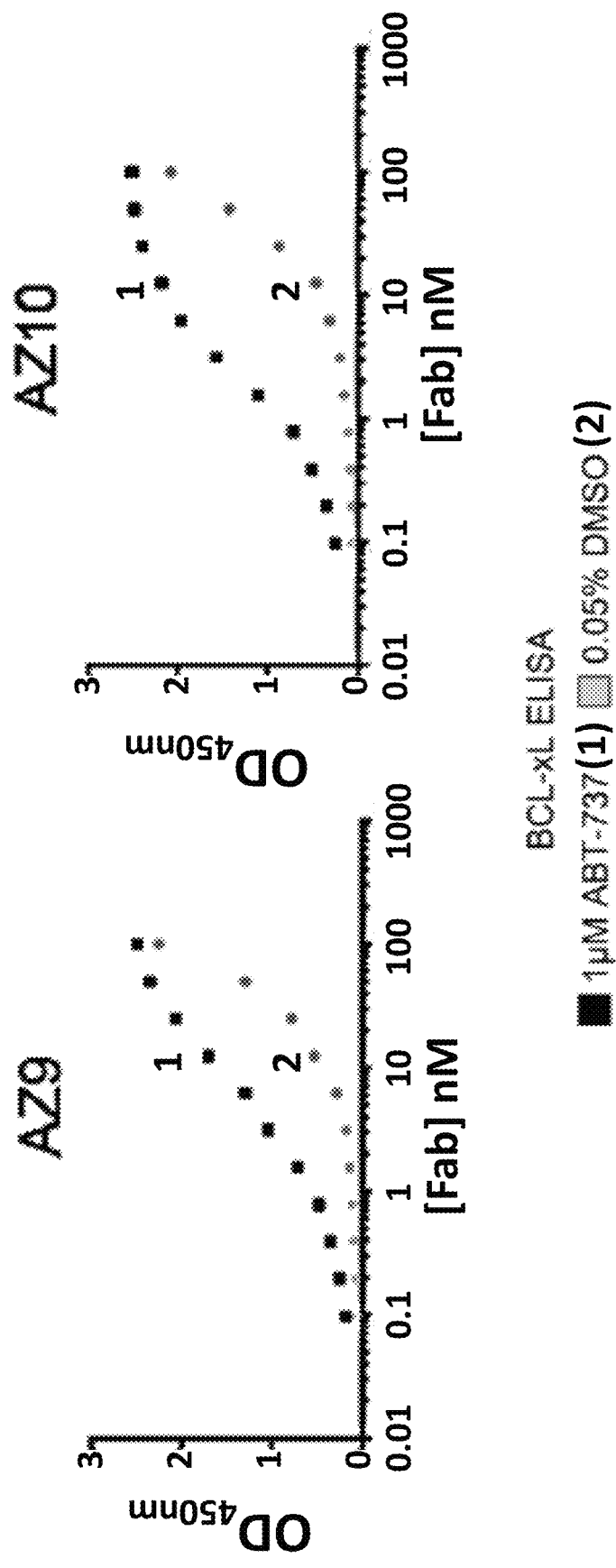
Figure 9A:
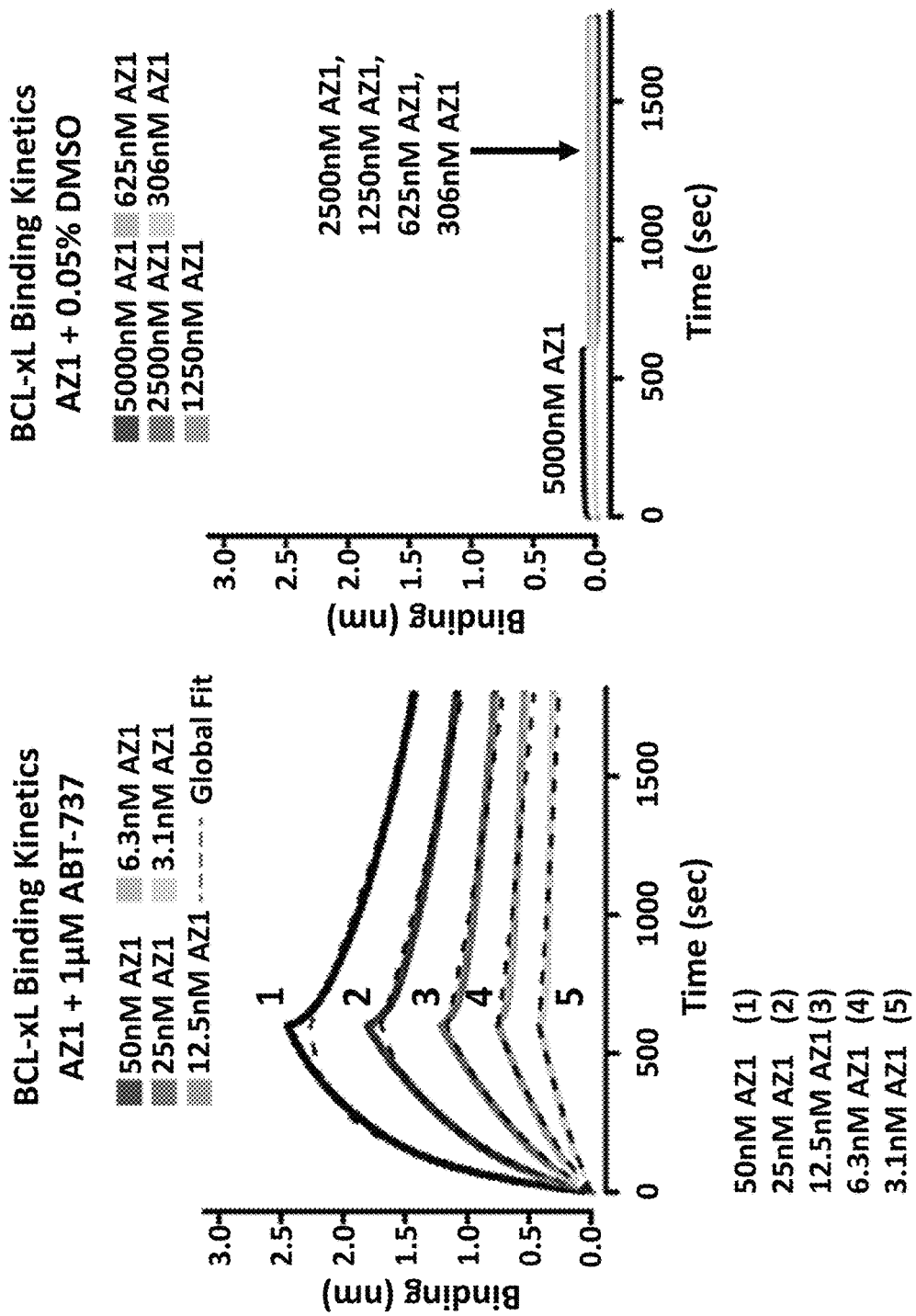
FIGS. 9A-9C show biolayer interferometry of Fabs AZ1, AZ3, and AZ4. Solid curves represent measured data points and dashed lines represent the global-fit lines used for analysis.
Figure 9B:
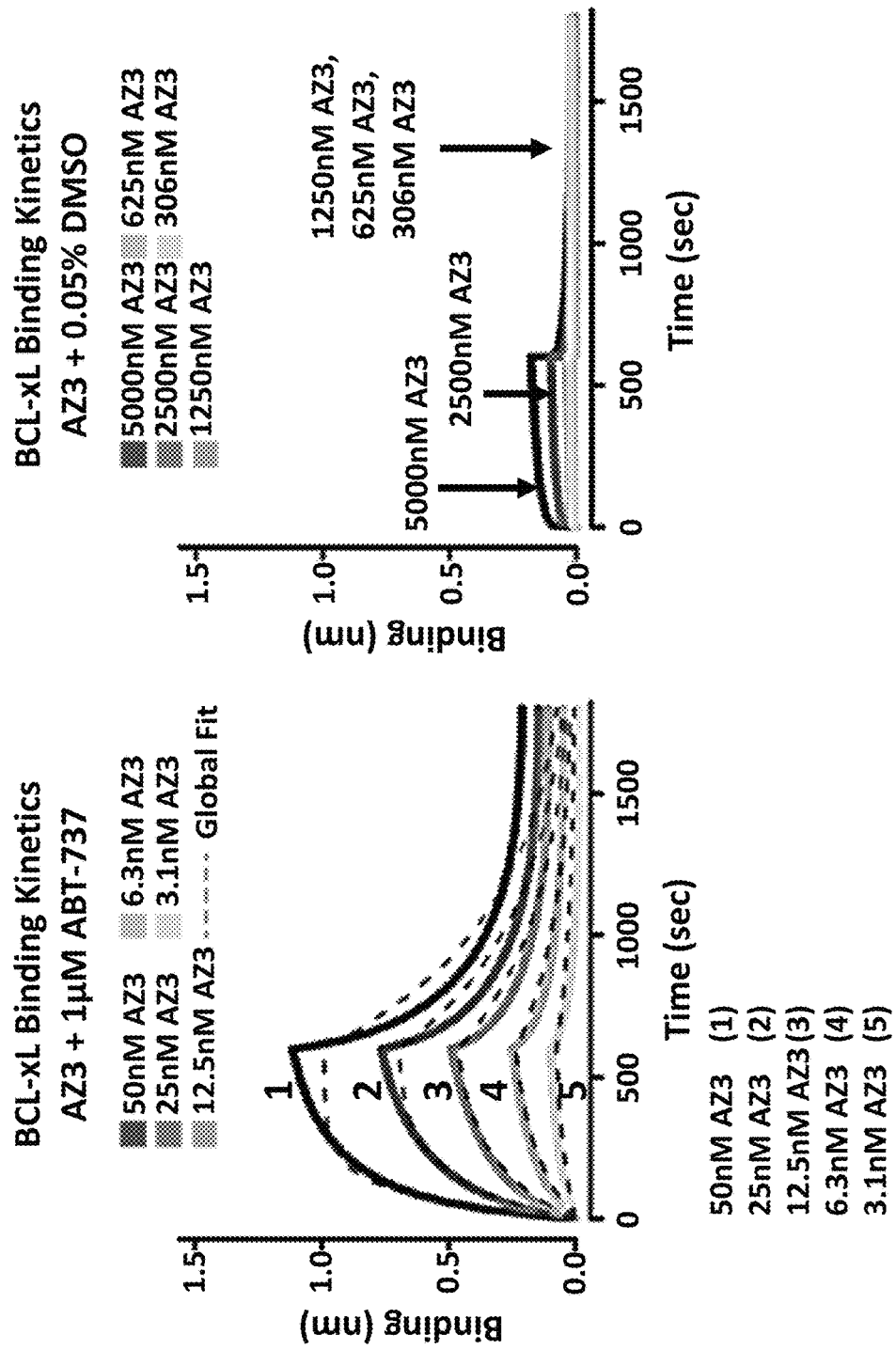
Figure 9C:
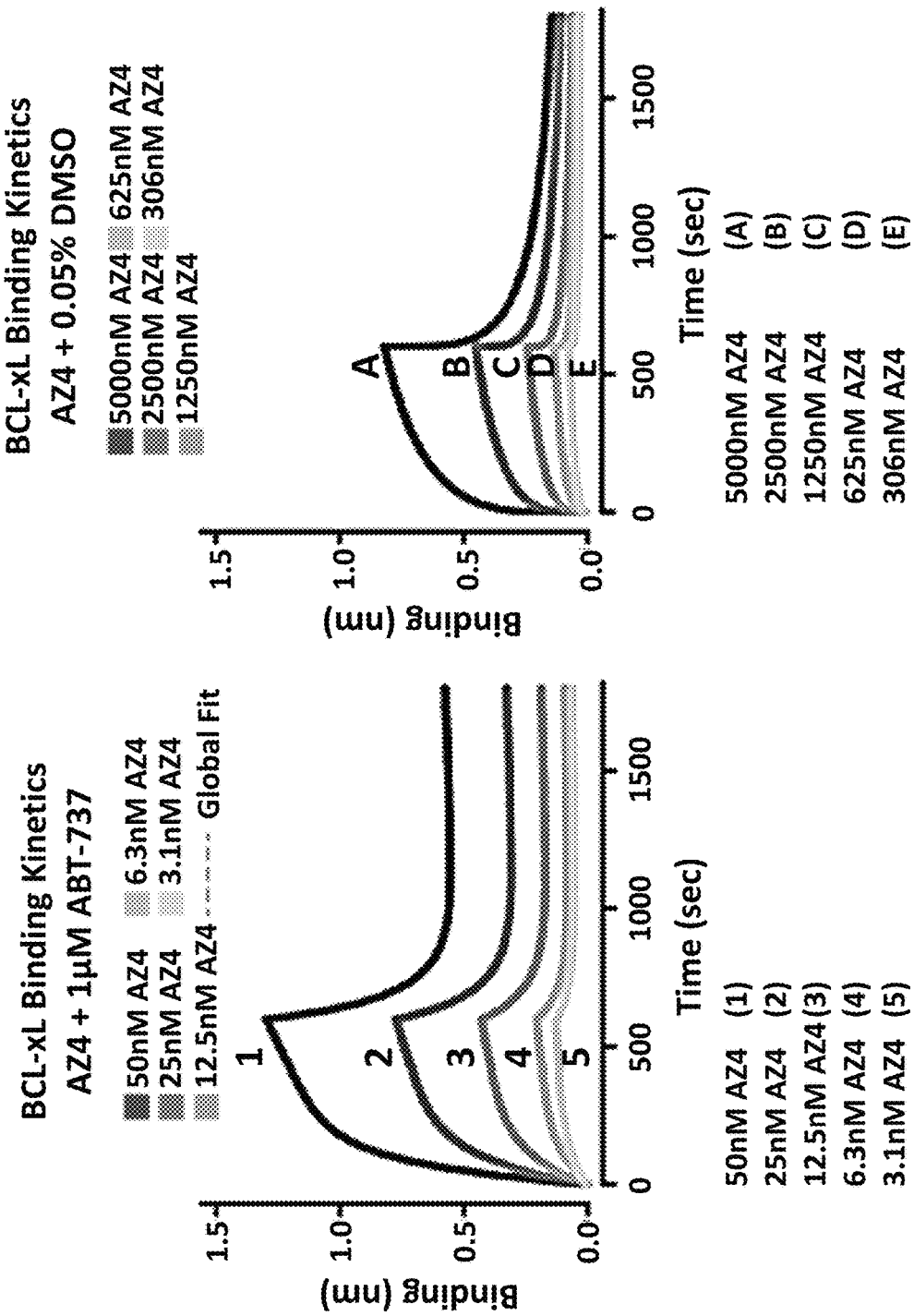

Example 3: Engineered Antibodies are Highly Specific for the ABT-737-Bound Form of BCL-xL The unique Fabs were sub-cloned into a bacterial expression vector, expressed, and purified (Hornsby, et al., Mol. Cell. Proteomics, 14:2833-2847 (2015)). Gratifyingly, enzyme-linked immunosorbent assays (ELISA) with BCL-xL in the presence or absence of ABT-737 showed that all ten Fabs had enhanced binding in the presence of drug. Four Fabs showed excellent potency and extremely strong selectivity for binding in the presence of ABT-737 (FIG. 8). To further profile the four Fabs, we characterized the kinetics of BCL-xL binding in the presence or absence of ABT-737 by bio-layer interferometry (FIG. 1C and FIG. 9) (Shah, et al., J Vis. Exp., e51383 (2014)). Three of the four Fabs (AZ1, AZ2 and AZ3) were very potent binders of BCL-xL in the presence of ABT-737 (KD<10 nM) and showed no detectable binding in the absence of ABT-737 at concentrations up to 5000 nM of Fab (Table 10). Our best Fab (AZ2) showed >2000 fold selectivity for the ABT-737-bound form of BCL-xL over the apo form.

TABLE 10

Binding and kinetic constants measured for binding of Fabs AZ1, AZ2, and AZ3 to BCL-xL in the presence or absence of ABT-737.

| Fab ID | ABT-737 1 μM | $K_D$ ($10^{-9}$ μM) | $K_{ON}$ ($10^5$ M$^{-1}$s$^{-1}$) | $K_{OFF}$ ($10^{-4}$ s$^{-1}$) |
|---|---|---|---|---|
| AZ1 | + | 3.0 | 1.3 | 4.0 |
|  | − | >5000 | N.D. | N.D. |
| AZ2 | + | 2.4 | 1.1 | 2.6 |
|  | − | >5000 | N.D. | N.D. |
| AZ3 | + | 9.5 | 2.2 | 20.9 |
|  | − | >5000 | N.D. | N.D. |

N.D. indicates the values could not be determined due to absence of detectable binding

Example 4: Chemical-Epitope-Selectivity Suggests Direct Contact of the Antibodies with ABT-737

Figure 2C:
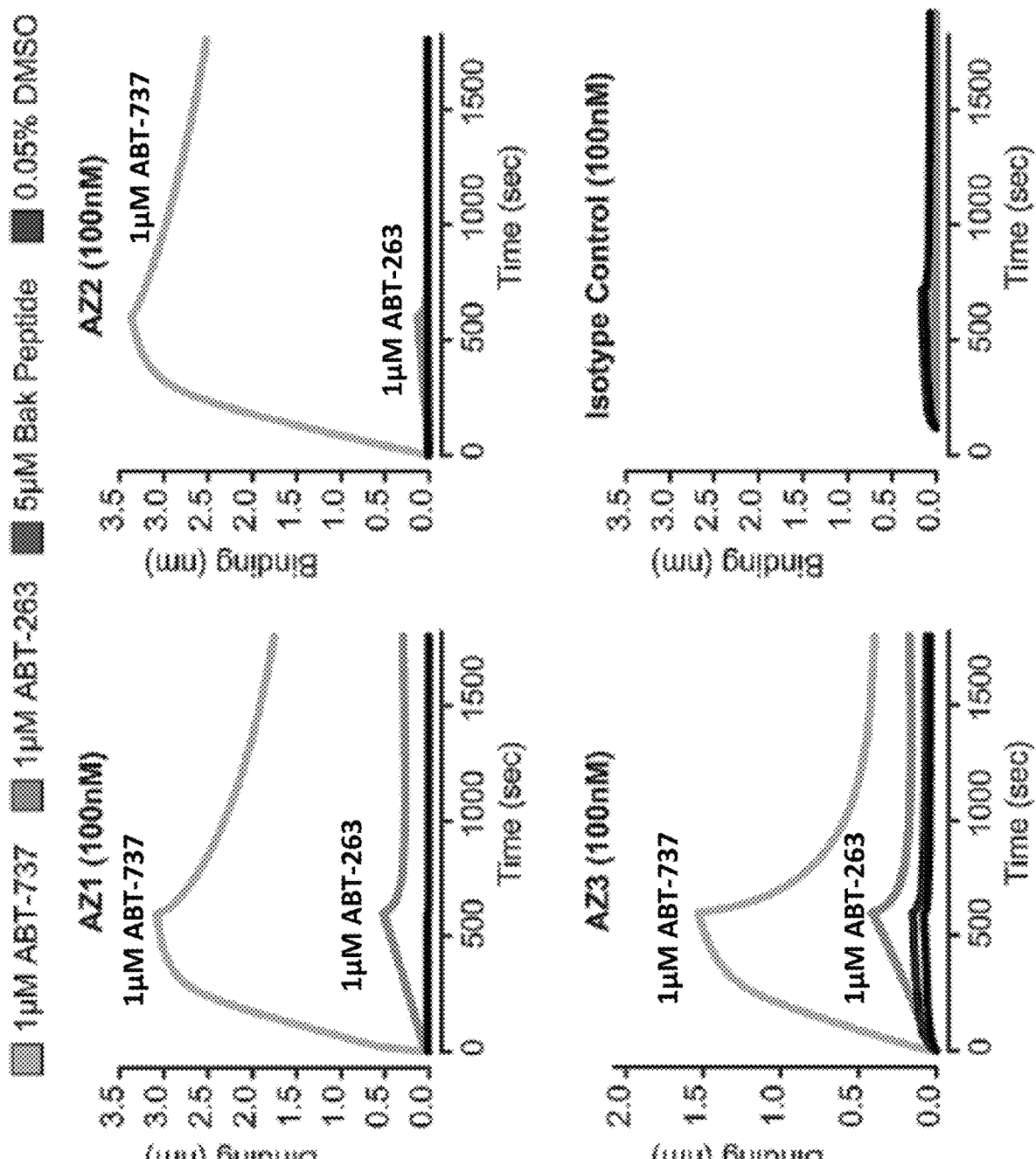

We hypothesized that the exquisite selectivity of our Fabs was the result of direct interactions of the Fab CDRs with parts of ABT-737. We reasoned that if this were the case, the Fab would bind less potently to other BCL-xL-ligand complexes. ABT-263 is an analog that binds with similar potency to the same conformation of BCL-xL as ABT-737 (RMSD=0.8) (FIG. 2A and FIG. 2B) (Tse, et al., Cancer Res., 68, 3421-3428 (2008)). To test our hypothesis, we measured the ability of AZ1, AZ2, and AZ3 to discriminate between ABT-737, ABT-263, and the native-ligand-derived Bak-peptide (Sattler, et al., Science, 275: 983986 (1997)) bound BCL-xL (FIG. 2C). As predicted, we observed dramatically weaker binding of the Fabs to the BCL-xL/ABT-263 complex and no detectable binding of Fabs to the Bak-peptide complex. Although we do not have a crystal structure of the AbCID complex, these data strongly suggest these three antibodies bind near if not over the small-molecule binding site.

Figure 3A:
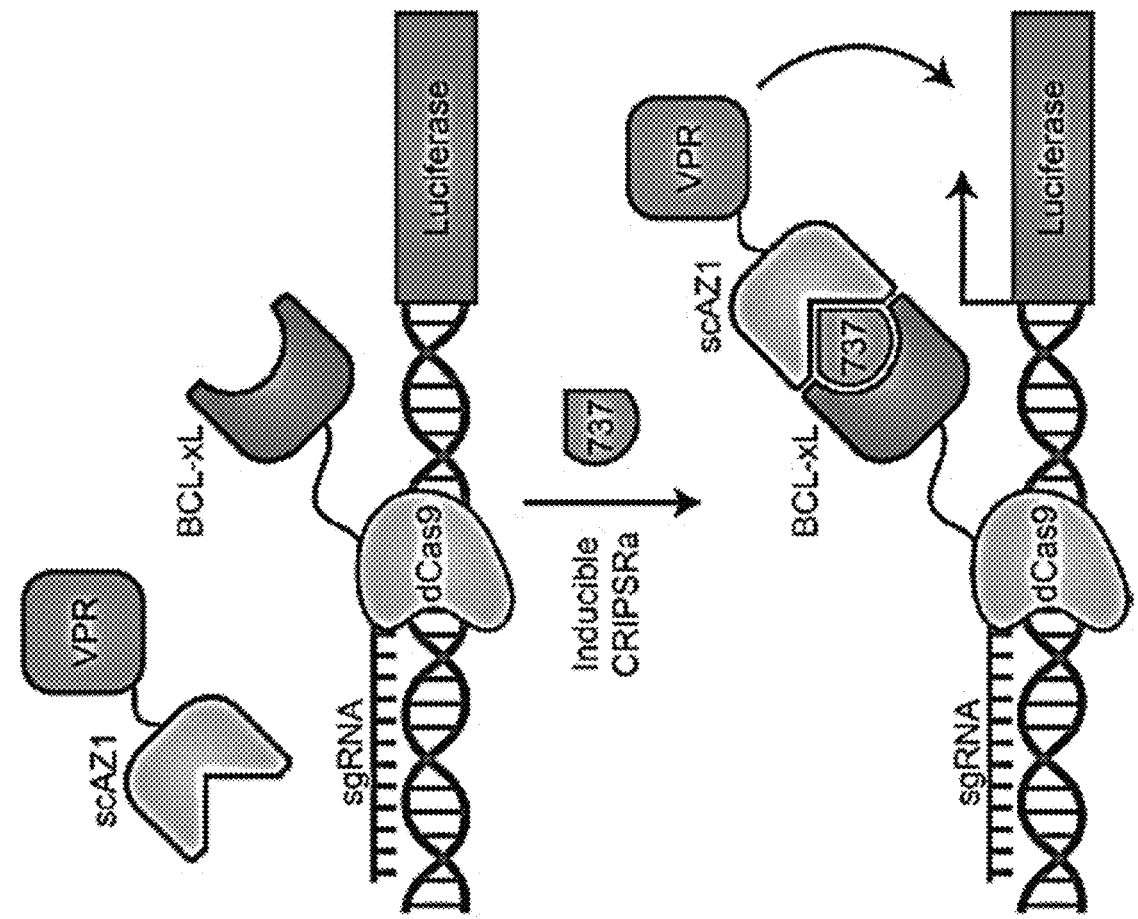
FIGS. 3A-3C show a single-chain Fab version of AZ1 utilized as an intracellular AbCID to regulate CRISPRa-mediated gene activation.
Figure 3B:
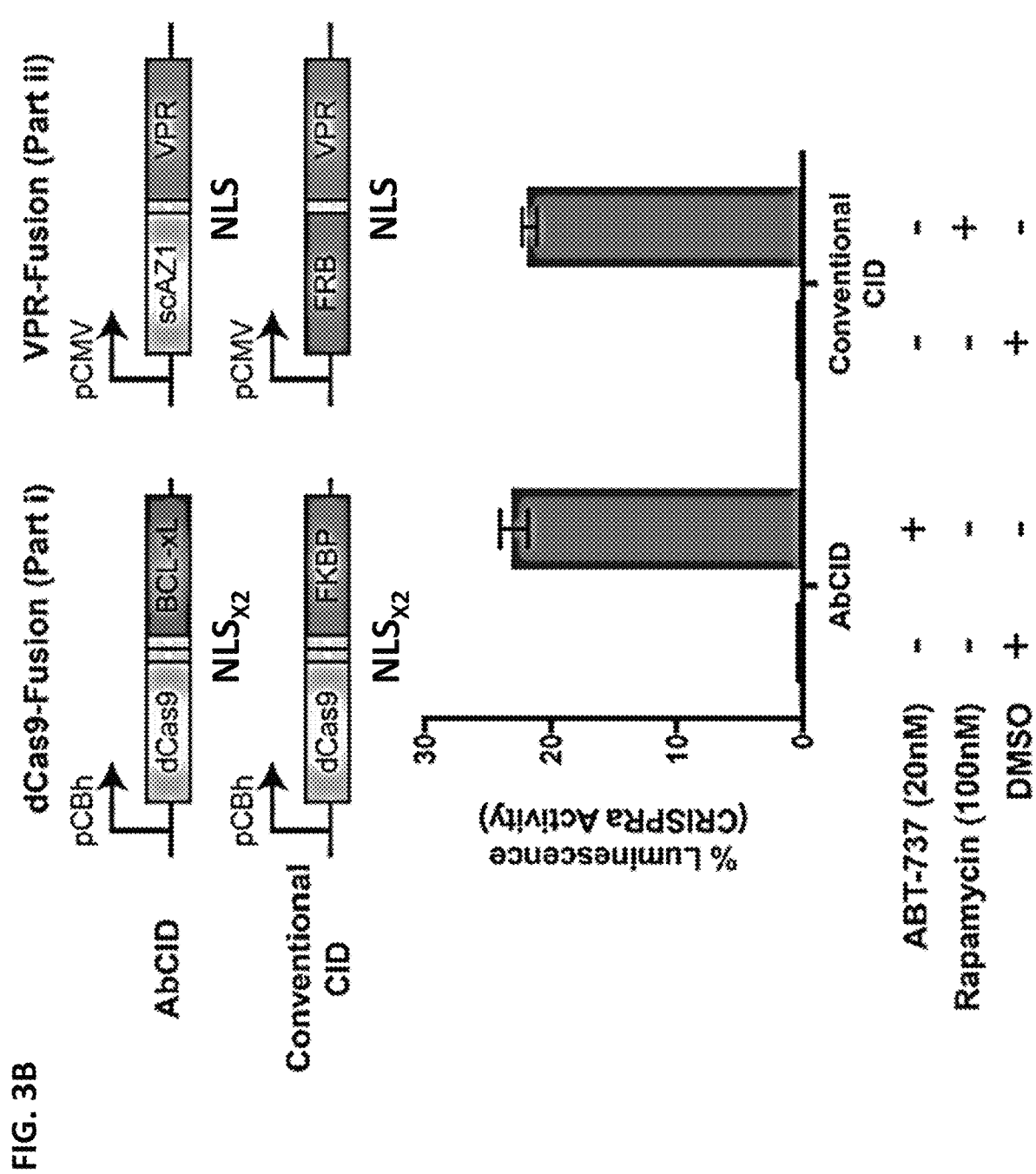
Figure 3C:
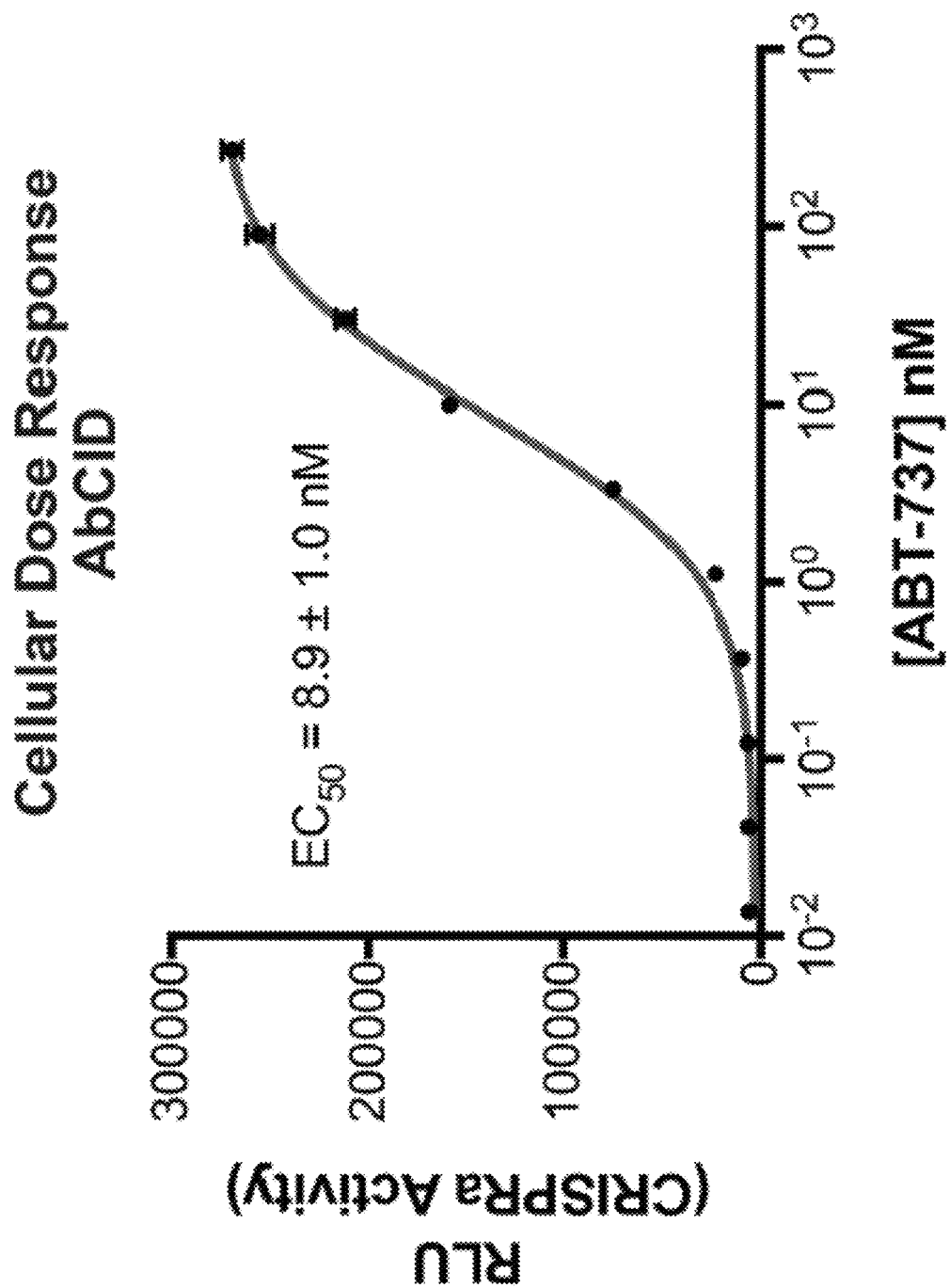
Figure 10:
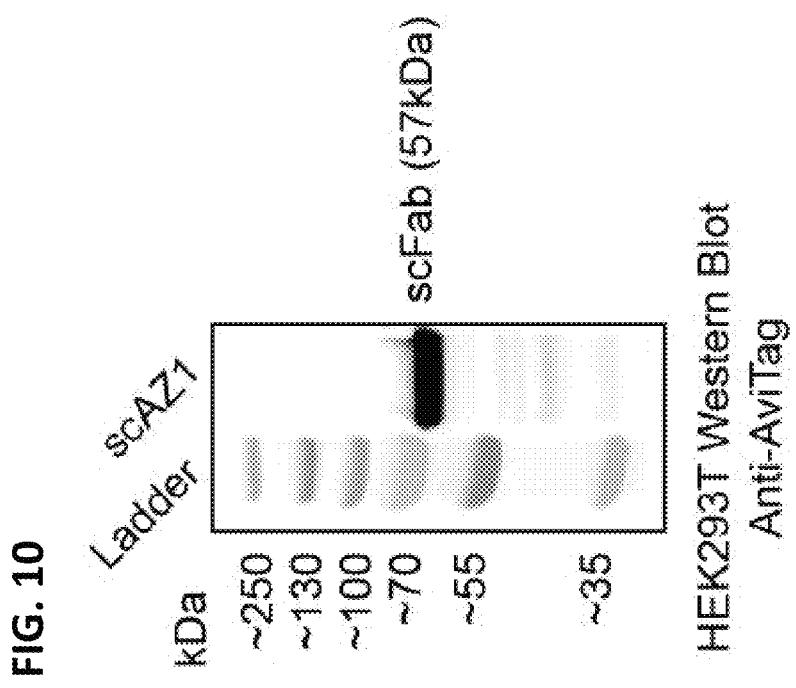
FIG. 10 shows anti-AviTag immunoblotting of HEK293 cell lysate from cells transfected with C-terminal Avi-tagged scAZ1.
Figure 11:
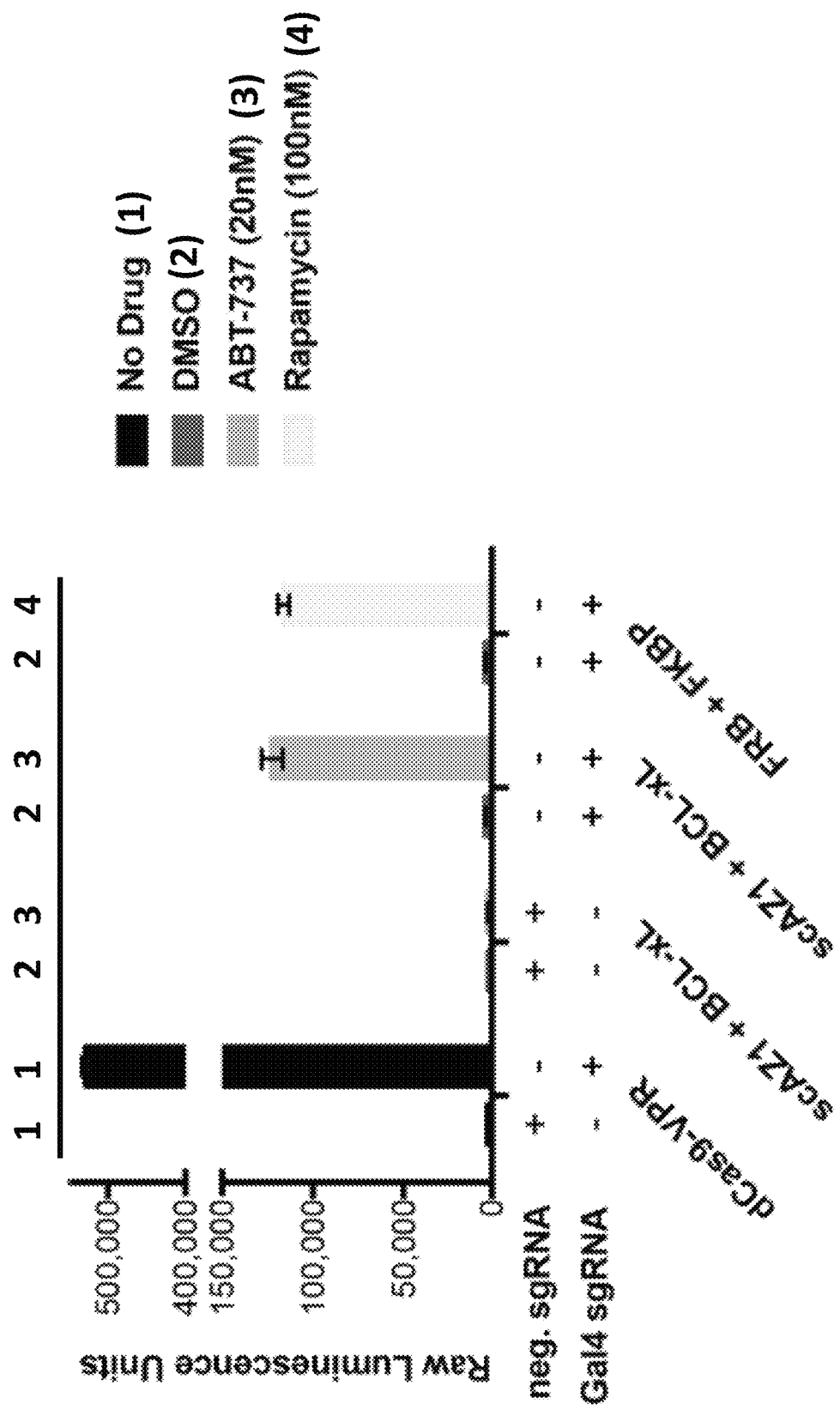
FIG. 11 shows quantitation of luciferase activity 48 hours after addition of ABT-737 (20 nM) to the scAZ1 AbCID gene circuit or rapamycin (100 nM) to the conventional FKBP-FRB CID gene circuit. This raw data was used for normalization and generation of FIG. 3B. Each data point represents the mean of 4 independent experiments±s.d.

Example 5: AZ1 AbCID Induces CRISPRa Mediated Gene Expression in Living Cells Current AbCID technologies are often used for controlling intracellular signaling pathways (Clackson, T., Chemical Biology, pgs. 227-249 (2008); Fegan, et al., Chem. Rev., 110:3315-3336 (2010); Putyrski, et al., FEBS Lett., 586: 2097-2105 (2012)). Due to the disulfide bond linking the heavy and light chains of Fabs and the reducing environment inside the cell, it is generally believed that intracellular expression of Fabs in mammalian cells would lead to an inactive species. Recently, we reported a single-chain Fab (scFab) construct in which the light and heavy chains are genetically fused as a single polypeptide (Koerber, et al., J. Mol. Biol., 427:576-586 (2015)). The scFab scaffold has a very high melting temperature (Tm=~81° C.) so that once formed it is very stable (Koerber, et al., J. Mol. Biol., 427:576-586 (2015)). We hypothesized that conversion of our ABT-737-inducible Fabs into a scFab format may allow for their use in living cells. Indeed, transfection of the AZ1 gene in scFab format (scAZ1) into HEK293T cells resulted in robust expression as measured by immunoblotting (FIG. 10). To test if scAZ1 was active in living cells, we constructed a genetic circuit in which scAZ1 is fused to the VPR transcriptional activation domain (Chavez, et al., Nat. Methods, 12:326-328 (2015)) and BCL-xL is fused to dCas9 (Qi, et al., *Cell*, 152:1173-1183 (2013)) (FIG. 3A). Both constructs contain a nuclear localization sequence, which reduces the possibility of interaction with endogenous BCL-xL while simultaneously priming the system for activation in the nucleus. The dCas9-BCL-xL fusion can be targeted by addition of a specific sgRNA to a promoter that drives a luciferase reporter. If the AbCID functions in cells, addition of ABT-737 should lead to localization of AZ1-VPR to the luciferase reporter, promoting expression of luciferase, which can be readily detected. For comparison, we generated an identical circuit, but utilizing a conventional AbCID based on the rapamycin-FKBP12-FRB system (Rivera, et al., *Nat. Med.*, 2:1028-1032 (1996)), as recently reported by Qi and colleagues (Gao, et al., *Nat. Methods*, 13:1043-1049 (2016)). Indeed, addition of ABT-737 to our engineered cells resulted in robust expression of luciferase, supporting that AZ1 and BCL-xL functioned as an ABT-737-inducible AbCID in living cells (FIG. 3B). The level of activation observed using the AbCID was comparable to that observed by the conventional AbCID. The induction of luciferase expression was dose dependent, with an EC50 of 8.9±1.0 nM (FIG. 3C). Importantly, addition of ABT-737 to an AbCID-gated system with a negative sgRNA resulted in no increase in luciferase expression (FIG. 11). Together, these results support that our AbCID can be used for tunable control of biological systems in living cells.

Example 6: AZ1 AbCID Induces Dose-Dependent Activation of CAR T-Cells

The use of engineered T-cells for the treatment of malignancies has recently become an important paradigm in cancer therapeutics (Fesnak, et al., *Nat. Rev. Cancer*, 16:566-581 (2016)). One such approach, known as chimeric antigen receptor T-cells (CAR T-cells), involves the genetic engineering of a T-cell such that it expresses a surface exposed scFv antibody fragment linked to an intracellular T-cell activation domain. The scFv is specific for a tumor antigen, and results in recruitment of the T-cell to the tumor and antigen-dependent activation of the T-cell. This technique has shown great responses in treating leukemia by targeting the CD19 antigen. However, hyperactivation of CAR T-cells has resulted in off-target cytotoxic effects and in some cases death, limiting utility of this promising modality (Fesnak, et al., *Nat. Rev. Cancer*, 16:566-581 (2016); Brudno, et al., *Blood*, 127:3321-3330 (2016)). For this reason, there has been great interest in developing remote control over the activity of these cells, so as to tune the level of activation or end it should untoward toxicity develop (Wu, et al., *Science*, 350, aab4077 (2015); Cao, et al., *Angew. Chem. Int. Ed*, 55:7520-7524 (2016); Rodgers, et al., *Proc. Natl. Acad. Sci. USA*, 113:E459-468 (2016); Ma, et al., *Proc. Natl. Acad. Sci. USA*, 113:E450-458 (2016)).

Figure 4A:
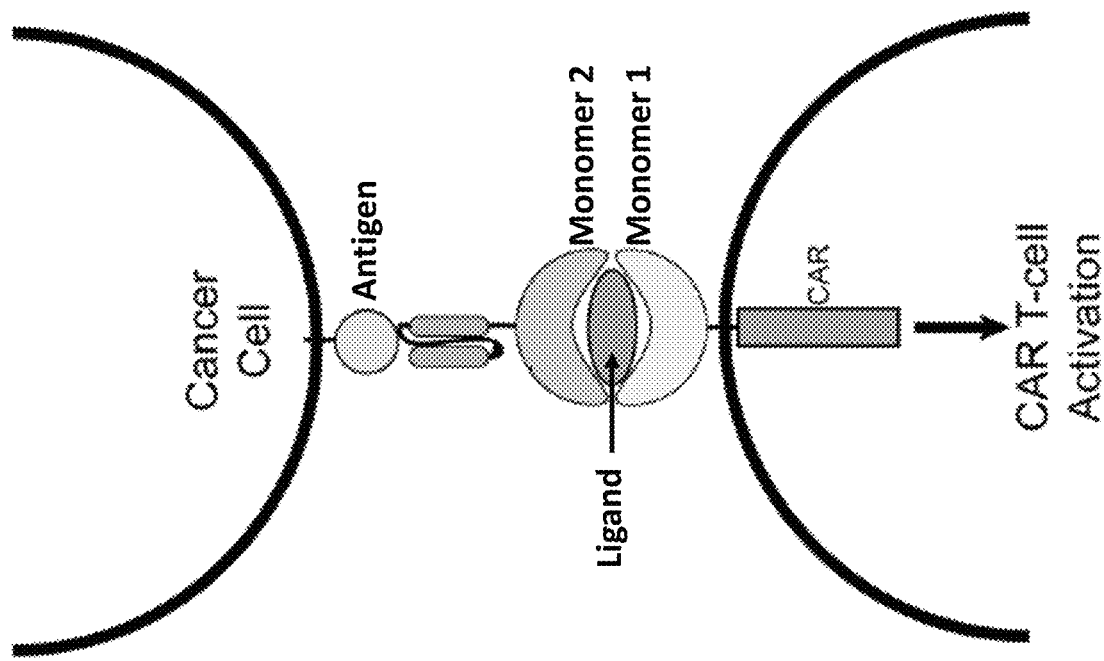
FIG. 4A shows a scheme where the scFv that typically serves as the external portion of a CAR construct is replaced by Monomer 1 of the inducible dimer. Monomer 2 of the dimer is now fused to the scFv to generate a bifunctional protein that will recognize the cancer cell as well as dimerize in the presence of ligand. When ligand is added, the CAR T-cell is recruited to the cancer cell and activated.
Figure 4B:
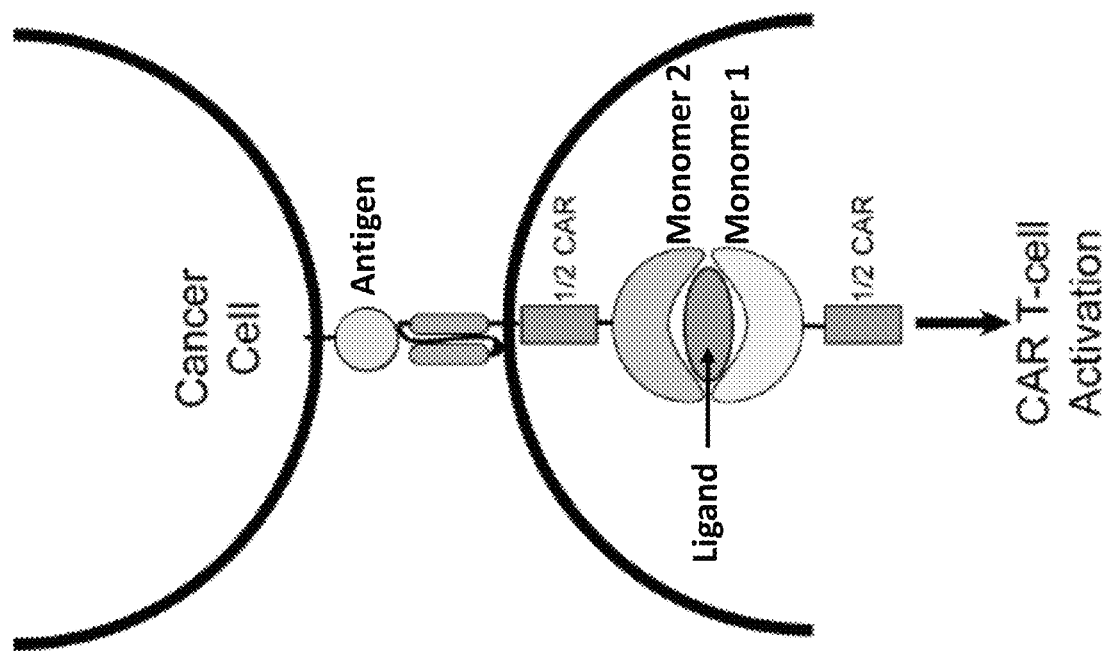
FIG. 4B shows a scheme where the stimulatory and co-stimulatory domains typically found on the internal portion of a CAR construct are split and fused to either Monomer 1 or 2 of the inducible dimer. When ligand is added, the internal portions of the CAR construct are brought together and the CAR T-cell is activated.
Figure 4C:
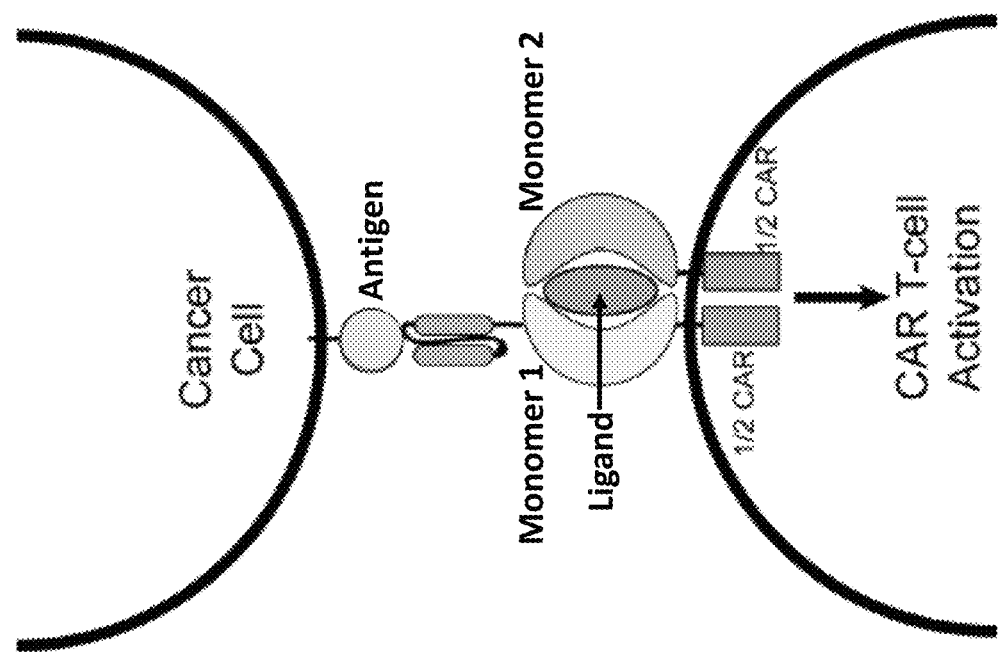
FIG. 4C shows a scheme where the stimulatory and co-stimulatory domains typically found on the internal portion of a CAR construct are split and fused to either Monomer 1 or 2 of the inducible dimer through transmembrane domains, such that the dimerization domains remain extracellular. When ligand is added, the internal portions of the CAR construct are brought together and the CAR T-cell is activated.
Figure 4D:
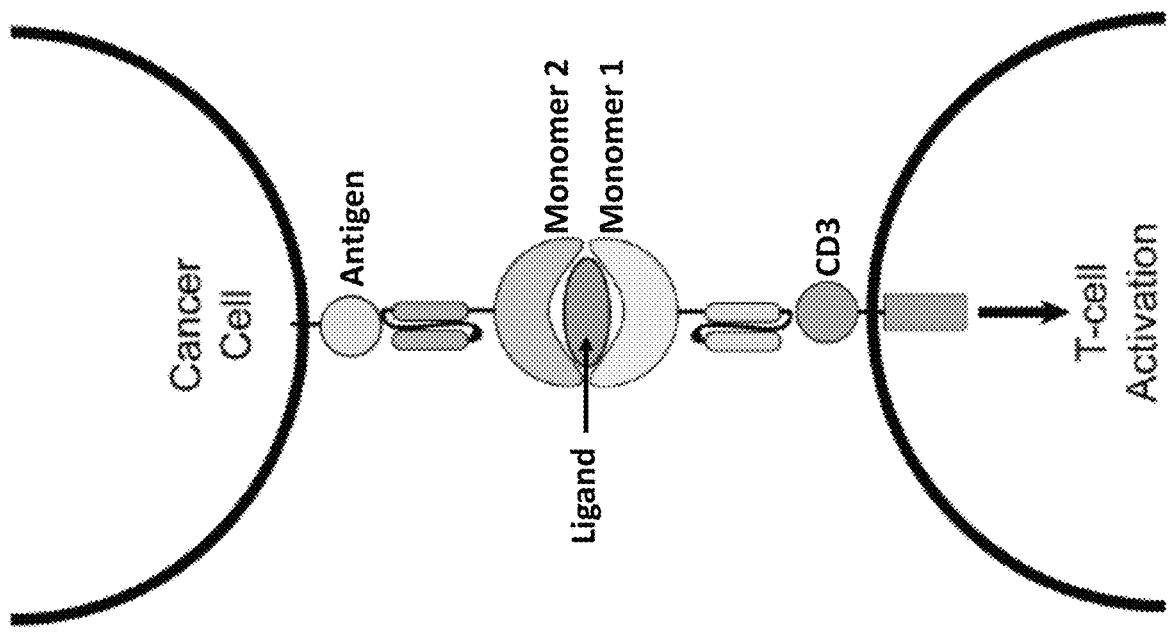
FIG. 4D shows a scheme where an antibody recognizing the CD3 portion of the T-Cell receptor complex is fused to Monomer 1 of the inducible dimer and an antigen-recognizing antibody is then fused to Monomer 2. When ligand is added, the CAR T-cell is recruited to the cancer cell and activated. In essence the system is acting as an inducible bispecific T-cell engaging antibody.
Figure 4E:
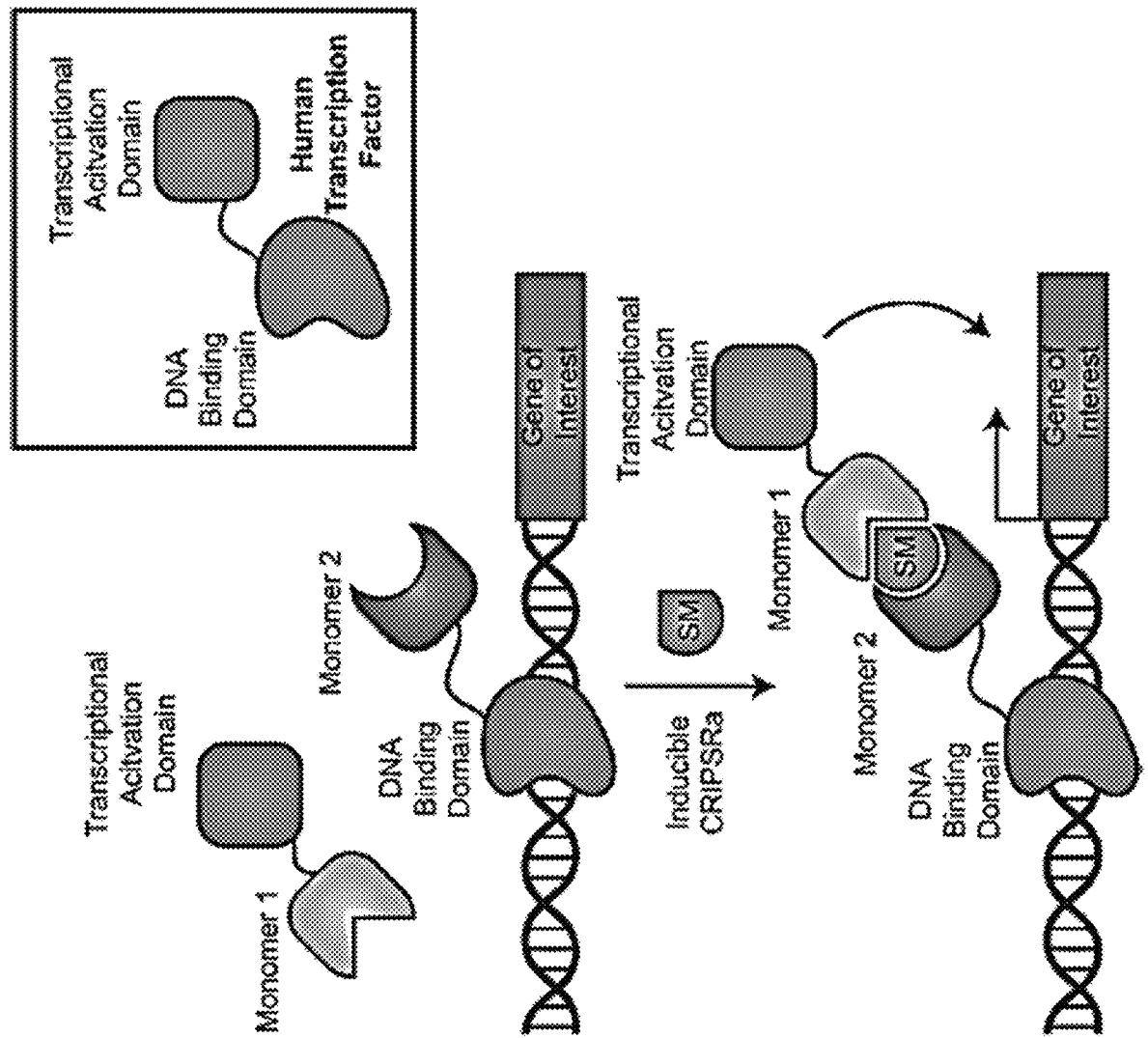
FIG. 4E shows a scheme where the transcriptional activation domain of a split human transcription factor is fused to Monomer 1 of the inducible dimer and the DNA binding domain of a split human transcription factor is then fused to Monomer 2. When ligand is added, the transcriptional activation domain is recruited to the site of the DNA binding domain and transcription of the gene of interest is activated. In essence the system is acting as an inducible gene expression circuit. This can be used to inducibly express the CAR in a CAR T-cell or alternatively to inducibly express and produce a biologic therapeutic.
Figure 4F:
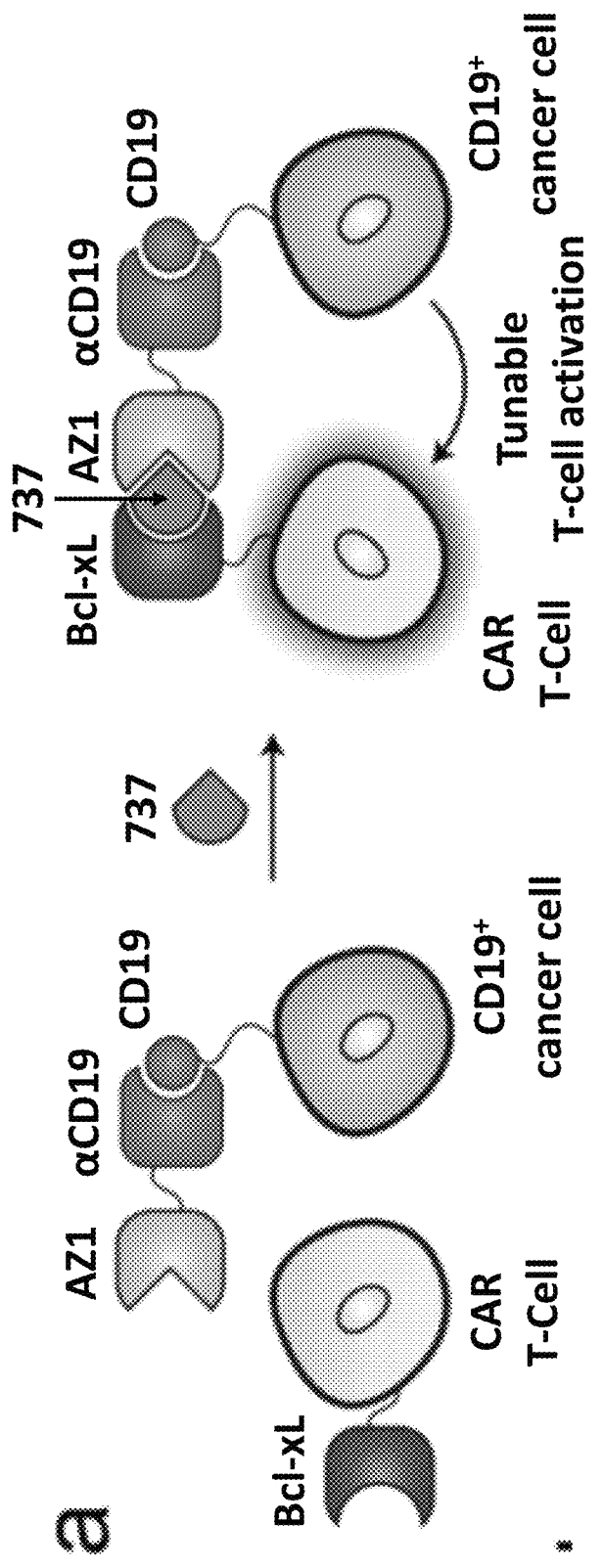
FIG. 4F shows a schematic of AbCID regulated CAR T-cell activation where the CAR contains an extracellular BCL-xL domain in place of the typical scFv. Addition of an AZ1-αCD19 bispecific antibody and various concentrations of ABT-737 results in recruitment to CD19⁺ cancer cells and tunable activation of the CAR T-cells.
Figure 4G:
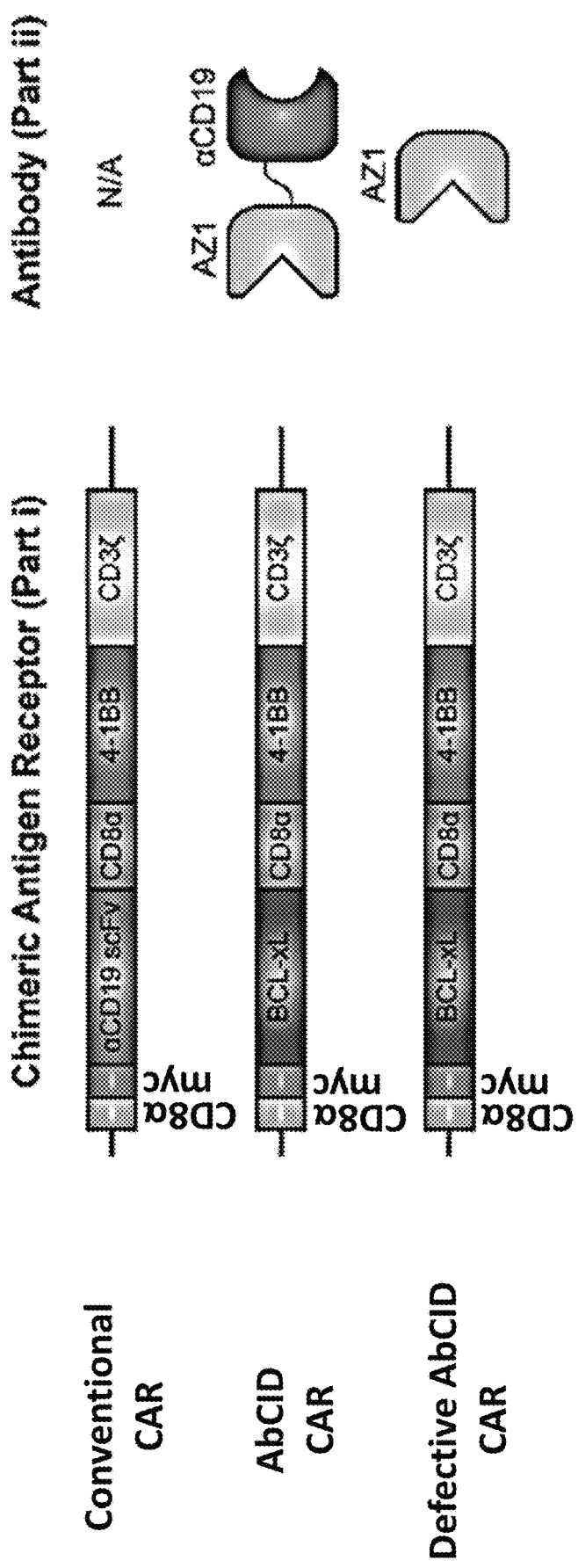
FIG. 4G shows linear diagrams of gene constructs used to produce the CARs and schematics of corresponding antibodies for this study.
Figure 4H:
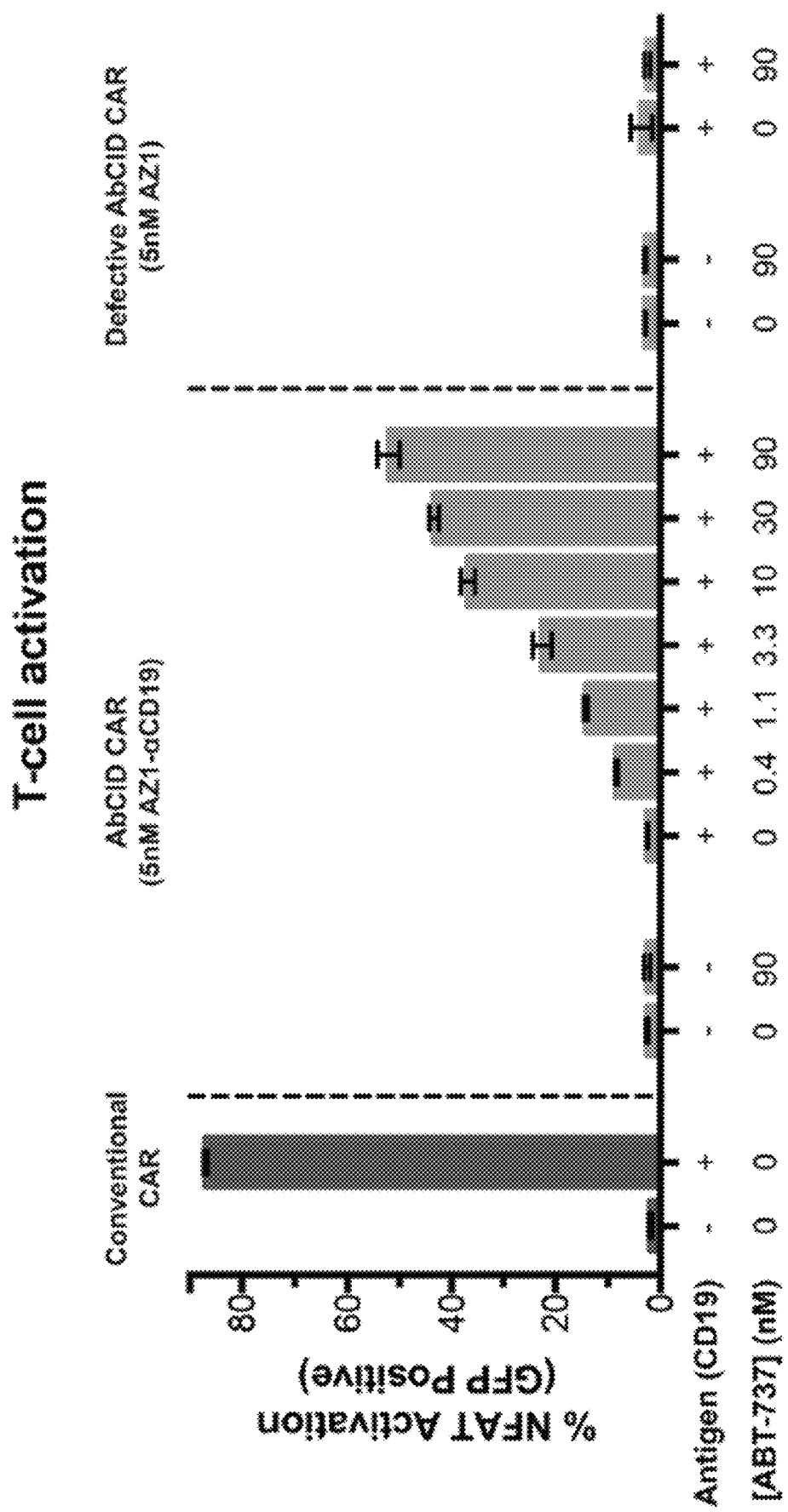
FIG. 4H shows quantification of NFAT-dependent GFP reporter expression 20 hours after initiation of co-culture with either CD19⁺ or CD19⁻ K562 target cells and addition of antibody (5 nM) and varying concentrations of small molecule. Addition of ABT-737 in the presence of CD19⁺ K562 cells and bispecific antibody resulted in dose-dependent activation of the NFAT pathway, but no activation was observed in the absence of ABT-737 or when co-cultured with CD19⁻ K562 cells. The defective AbCID CAR, which lacks the CD19-binding scFv portion of the antibody, was not activated under all conditions. Each data point represents the mean of 3 independent experiments±s.d.
Figure 12A:
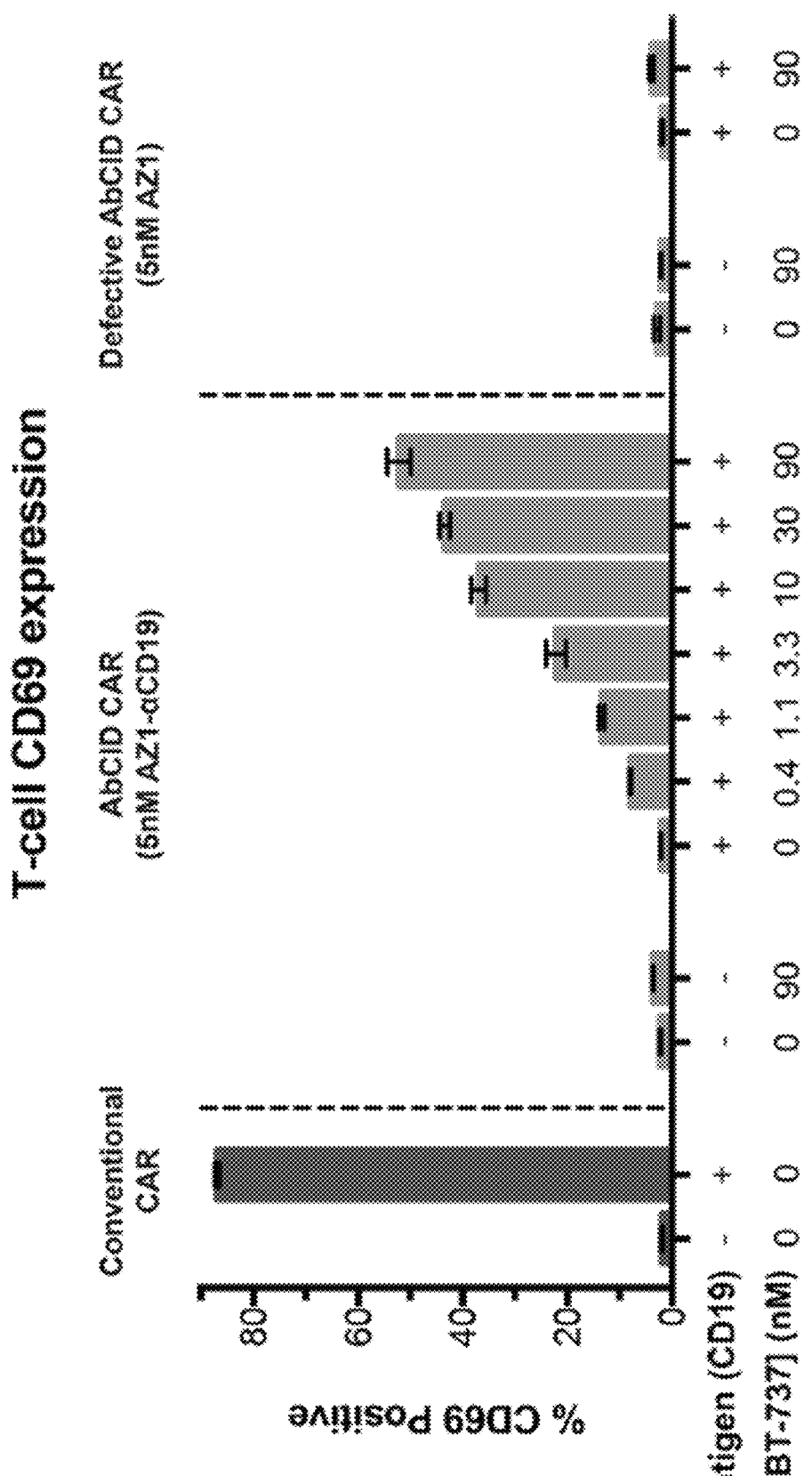
FIGS. 12A and 12B show independent confirmation of CAR T-cell activation by the canonical markers CD69 and secretion of IL-2 upon dose dependent AbCID activation.
Figure 12B:
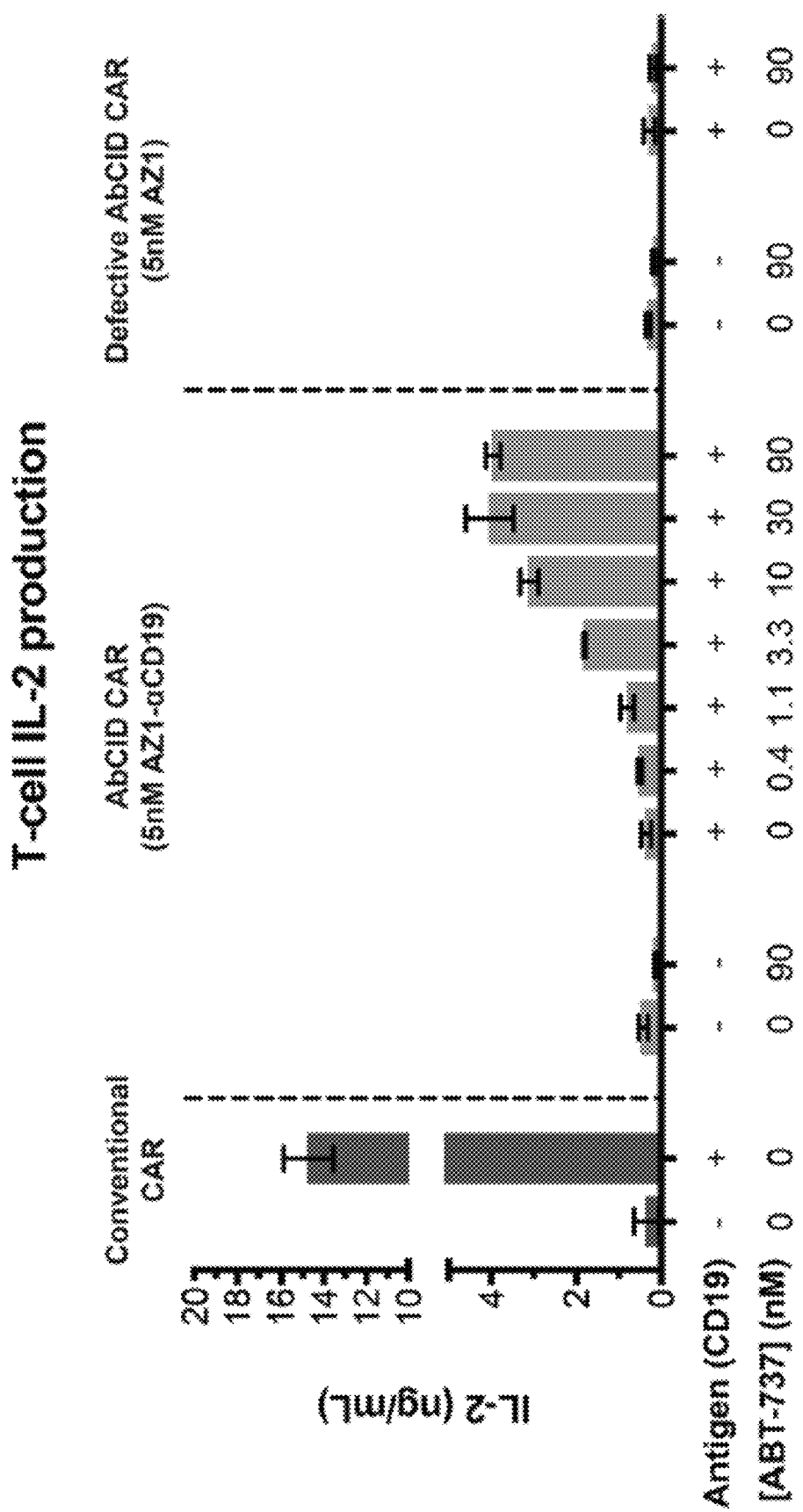

We hypothesized that our AbCID technology could be applied as a unique way to regulate CAR T-cell activity using a small molecule. To test this, we engineered Jurkat T-cells to express a CAR in which the scFv portion of the CAR is replaced by BCL-xL (FIG. 4A and FIG. 4B). This creates a T-cell that contains the machinery required for activation, but no longer binds to the antigen-presenting cells. In parallel, we generated a bispecific antibody by linking a clinically utilized aCD19 scFv (June, et al., *Use of chimeric antigen receptor-modified T cells to treat cancer*. (2012)) to Fab AZ1. Upon addition of ABT-737 the bispecific antibody will be recruited to the CAR T-cell while simultaneously engaging the CD19$^+$ cells. Such a design allows for both inducible and antigen-dependent CAR T-cell activation. To facilitate rapid quantitation of T-cell activation, we utilized a Jurkat T-cell line that had been engineered to express GFP upon activation of the NFAT pathway (Wei, et al., *Nature*, 488:384-388 (2012)). In the presence of CD19$^+$ K562 cells and our bispecific antibody (AZ1-αCD19), addition of ABT-737 resulted in a dose-dependent activation of the CAR T-cells as measured by expression of GFP (FIG. 4C). Activation of the T-cells was further confirmed by expression of the canonical T-cell activation markers, CD69 and secreted Interleukin-2 (FIG. 12) (Ziegler, et al., *Stem Cells*, 12:456-465 (1994); Smith-Garvin, et al., *Annu. Rev. Immunol.*, 27:591-619 (2009)). Importantly, activation of the T-cells was not observed with K562 cells lacking CD19 or if an AbCID was used that did not contain the αCD19 scFv (FIG. 4C). In addition, ABT-737 was not able to induce T-cell activation on its own. While our T-cell system showed ~65% the activation level of the conventional CAR control, the reduced activity may actually be of benefit due to the hyperactivation and toxicity observed with conventional CARs. These data demonstrate that AbCIDs can be used for extracellular regulation of cellular signaling pathways and represent a novel paradigm for small-molecule control of CAR T-cell activation.

ABT-737 Dimerizes AbCIDs in a Non-Toxic Concentration Regime

Figure 5:
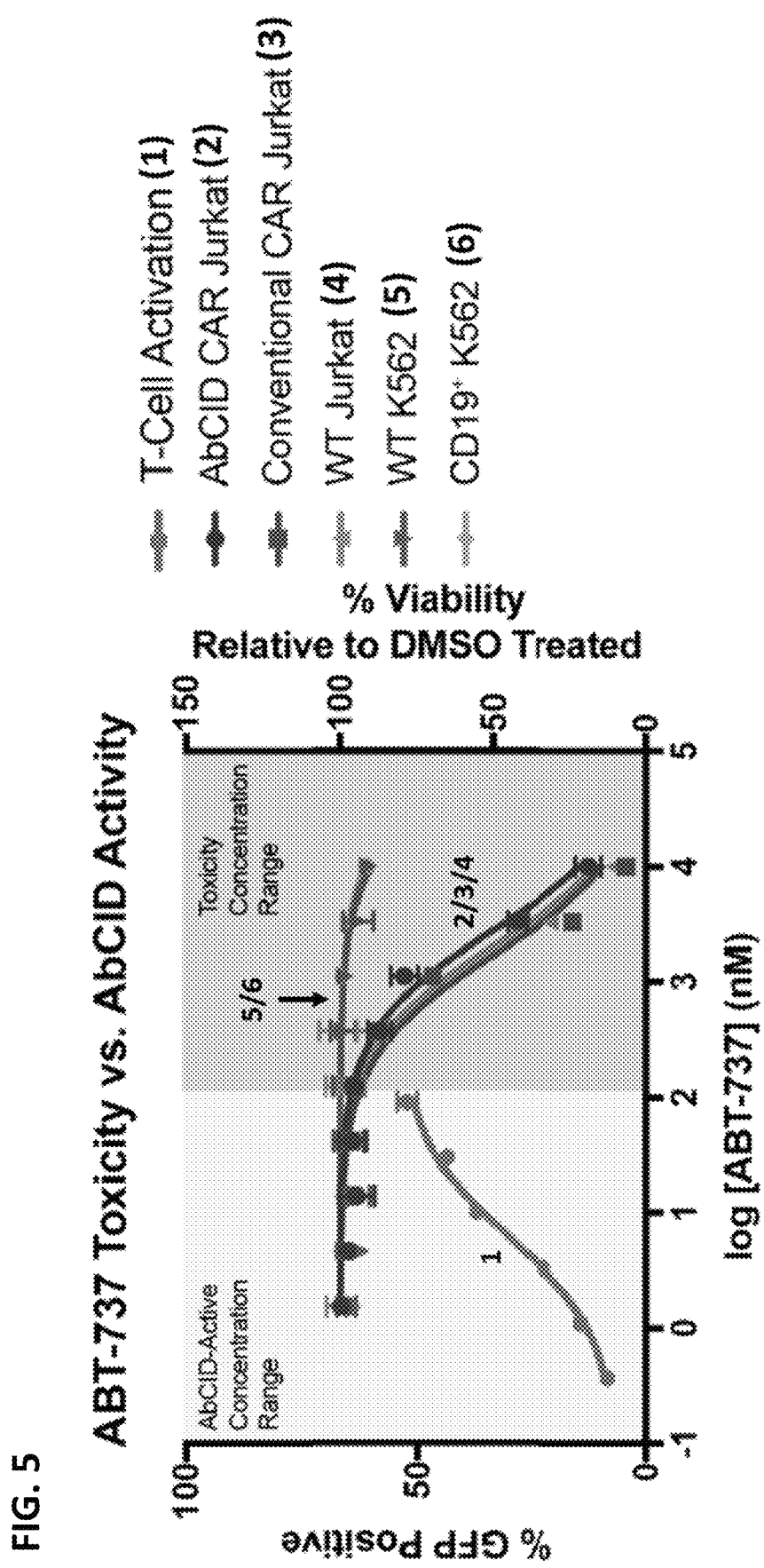
FIG. 5 shows the ABT-737 concentration range necessary for AbCID activation falls below that necessary for cell killing. A CellTiter-Glo assay after 24 hours of ABT-737 treatment was used to measure the viability of Jurkat and K562 cells relative to DMSO treatment alone (right axis). Data is juxtaposed with CAR T-cell activation data from FIG. 4H (left axis). The measured AbCID-activation concentration range was lower and exclusive from the toxicity concentration range. Each data point represents the mean of 3 independent experiments±s.d.
Figure 13:
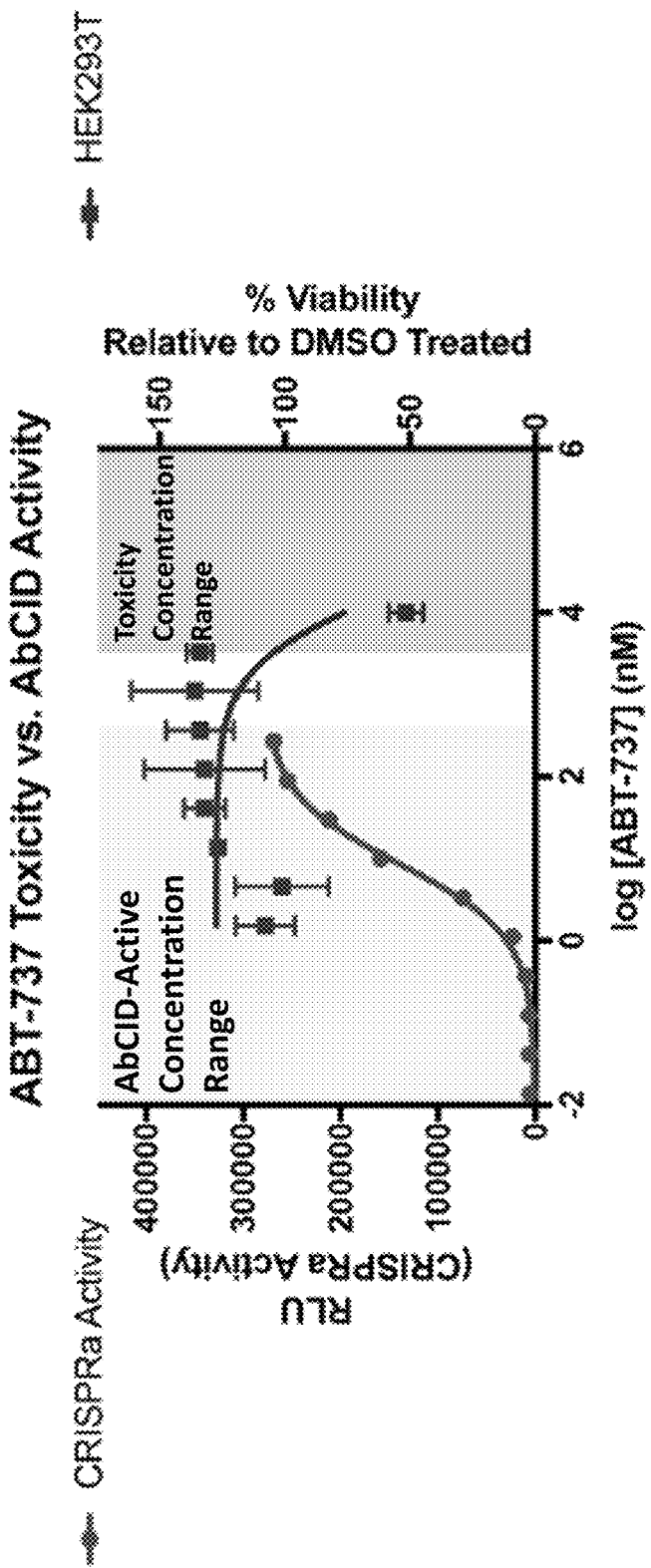
FIG. 13 shows the ABT-737 concentration range necessary for AbCID activation falls below that necessary for cell killing. A CellTiter-Glo assay after 24 hours of ABT-737 treatment was used to measure the viability of HEK293T cells relative to DMSO treatment alone (right axis). Data is juxtaposed with luciferase activity data from FIG. 3C (left axis). The measured AbCID-activation concentration range was lower and exclusive from the toxicity concentration range. Each data point represents the mean of 3 independent experiments±s.d.
Figure 14:
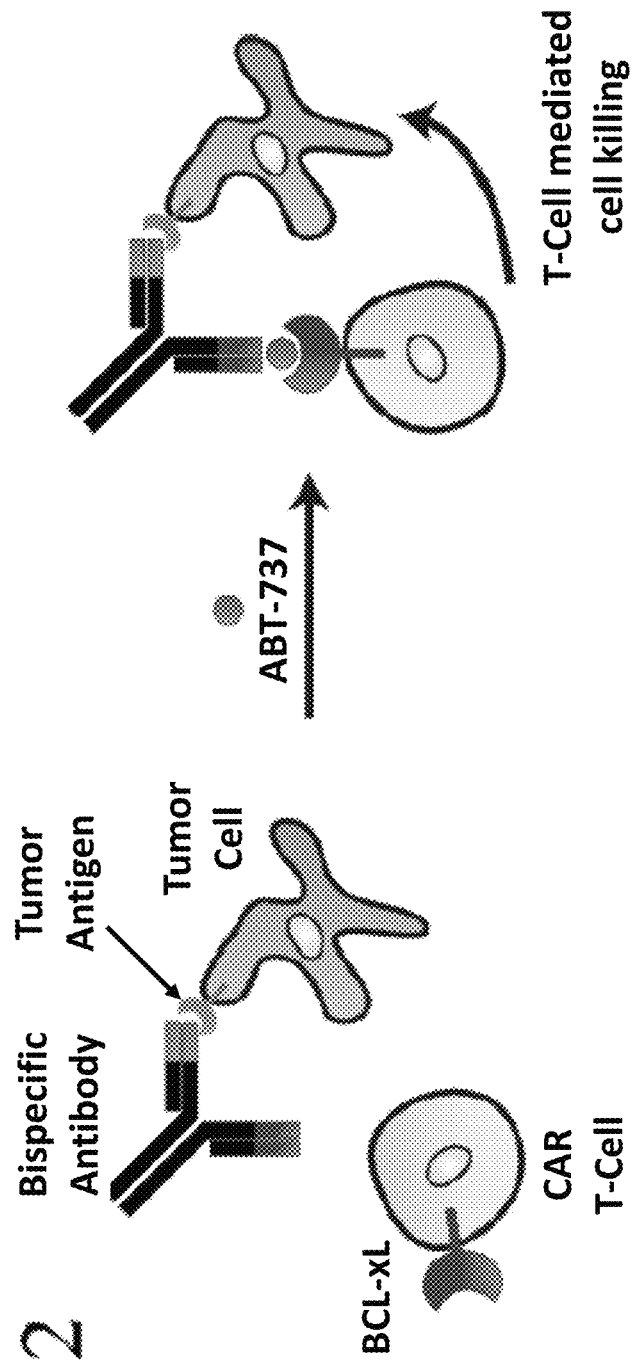
FIG. 14 shows an illustration of the dimerization of a CAR T-cell and a tumor labeled with a bispecific antibody specifically binding to an exemplary small molecule dimerizer binding to both the antibody and the CAR T-cell.

ABT-737 is a soluble, cell-permeable, bioavailable, potent, and commercially available compound, making it an excellent molecule for use in a AbCID, both in cells and potentially in animals. However, it is known that ABT-737 induces apoptosis in some cells types, particularly hematopoietic cells that have high expression levels of BCL-2 family members (Oltersdorf, et al., *Nature*, 435:677-681 (2005)). We thus tested the concentration of ABT-737 necessary to induce apoptosis in Jurkat, K562, and HEK293T cells. Importantly, the concentration ranges used to induce AbCID CAR (<100 nM) and CRISPRa (<270 nM) activity were below the concentrations at which cell death was observed (Jurkat IC50-2 µM, K562 IC50>10 µM, and HEK293T IC50–10 µM) (FIG. 5 and FIG. 13). ABT-737 has been used extensively in mouse cancer models and is generally well tolerated by mice, except for platelet toxicity (Oltersdorf, et al., *Nature*, 435:677-681 (2005)). However, the concentrations used to activate AbCIDs in our cellular assays (<100 nM) are far below the concentration observed to be toxic to platelets (low µM) (Zhang, et al., *Cell Death Differ.*, 14:943-951 (2007)). Additionally, others have also shown that ABT-737 can be applied to activate engineered proteins in live-cell experiments with little observed cytotoxicity (Goreshnik, et al., *J. Am. Chem. Soc.*, 132:938-940 (2010)). Collectively these data support the feasibility of using ABT-737 activated AbCIDs in cellular and animal applications with minimal effect on the viability of these model organisms. Moreover, while ABT-737's lack of bioorthogonality may be a caveat for research applications, it may actually be of benefit from a therapeutic perspective if the AbCID CAR approach described here were to be applied to the treatment of ABT-737-sensitive B-cell malignancies.

Example 7: Methotrexate-Binding Fab/Methotrexate Fab Dimers

Figure 16:
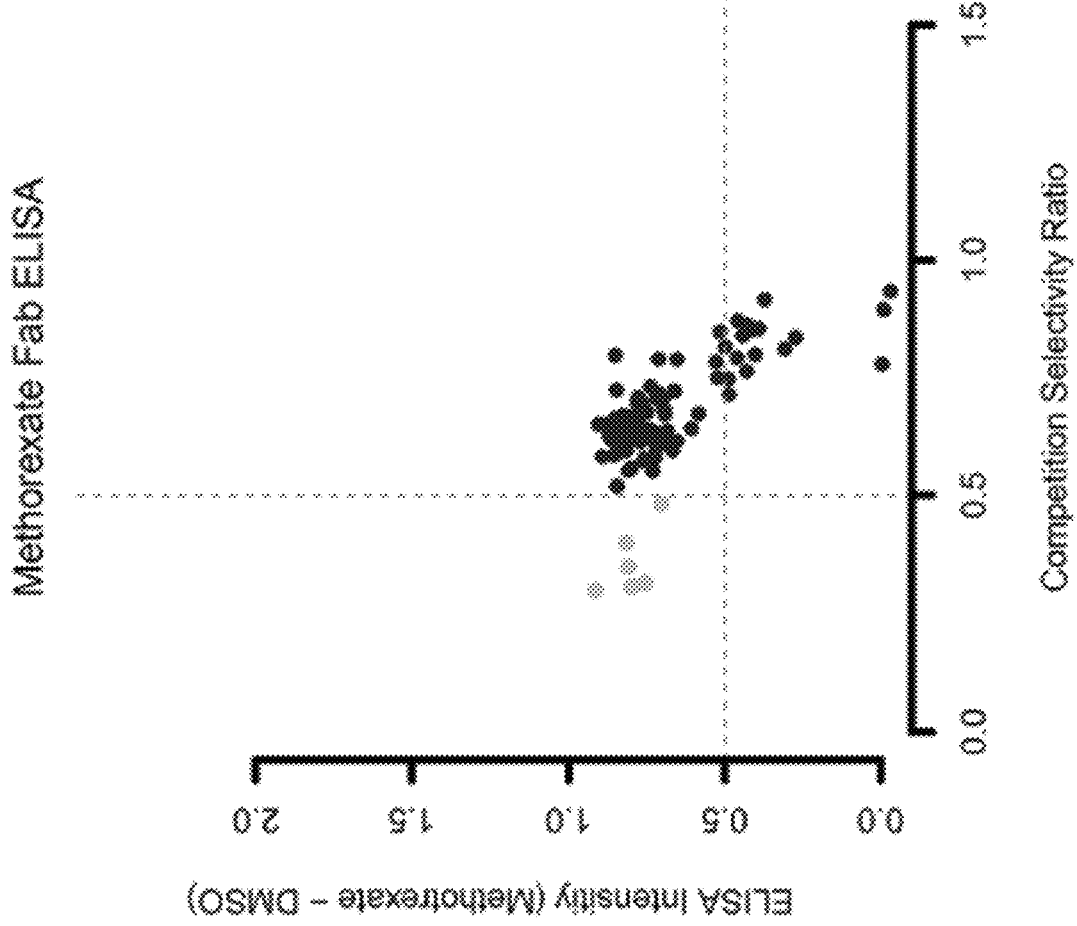
FIG. 16 shows competition ELISA of Fab-phage selected against Methotrexate-binding-Fab/Methotrexate. The top hits (light grey) were sequenced to identify clones with unique sequences.

In addition to the BCL-2 family member Fab dimers, we have generated dimers utilizing a methotrexate-binding Fab (Gayda et al. Biochemistry 2014 53 (23), 3719-3726) and methotrexate. After selections, we performed phage competition ELISA using the isolated Fab-phage from our selections in the presence or absence of Methotrexate (FIG. 16) to identify Fabs that selectively bound to the methotrexate-binding Fab in the presence of methotrexate. The best hits (light grey) were sequenced to identify clones with unique sequences.

Example 8: Bcl-2/ABT-199 Fab Dimers

Figure 15:
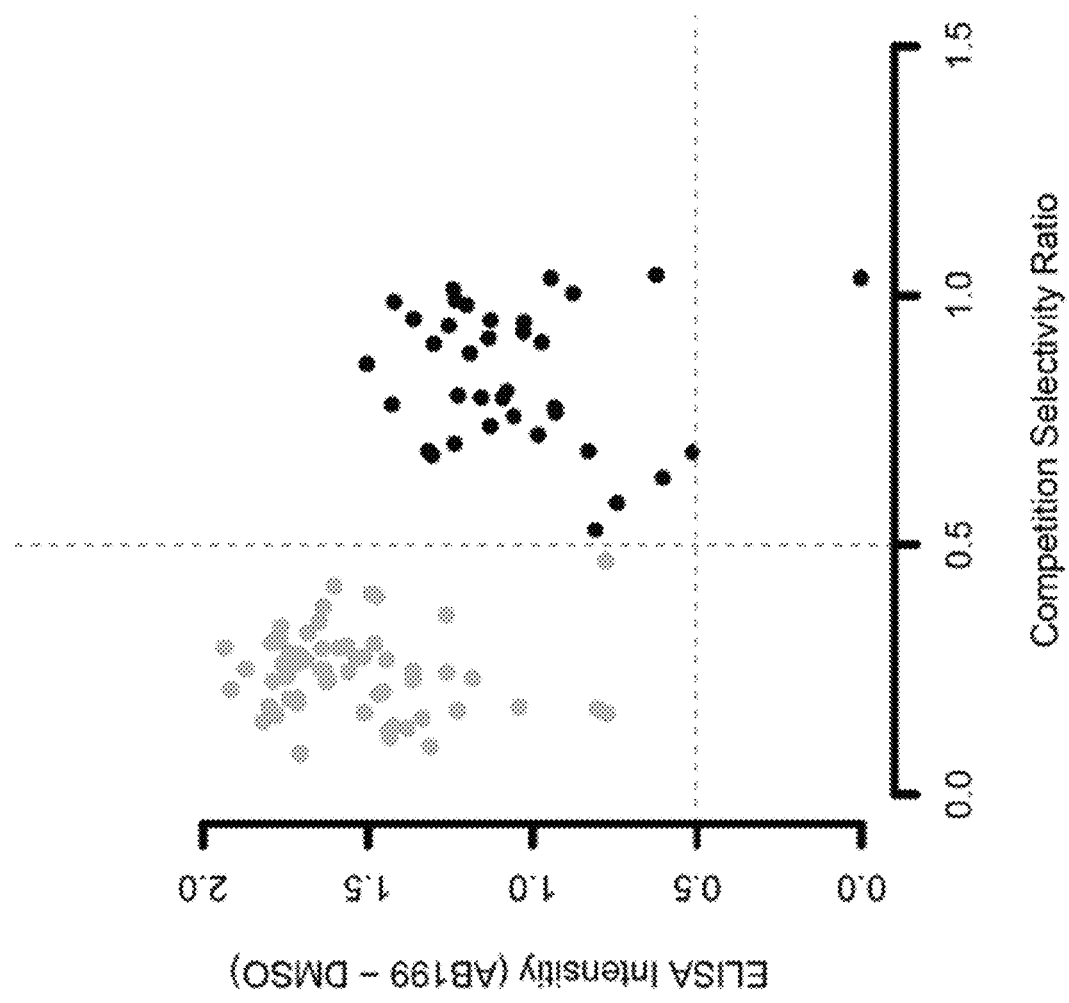
FIG. 15 shows competition ELISA of Fab-phage selected against BCL-2/ABT-199. The top hits (light grey) were sequenced to identify clones with unique sequences.

We have generated dimers using the same method described above, but with the protein Bcl-2 and the small molecule ABT-199. After selections, we performed phage competition ELISAs using the isolated Fab-phage from our selections in the presence or absence of ABT-199 (FIG. 15) to identify Fabs that selectively bound to BCL-2 in the presence of ABT-199. The best hits (in light grey) were sequenced to identify clones with unique sequences. The $K_d$ of all clones was <20 nM.

Example 9: FKBP/SLF Fab Dimers

Figure 17:
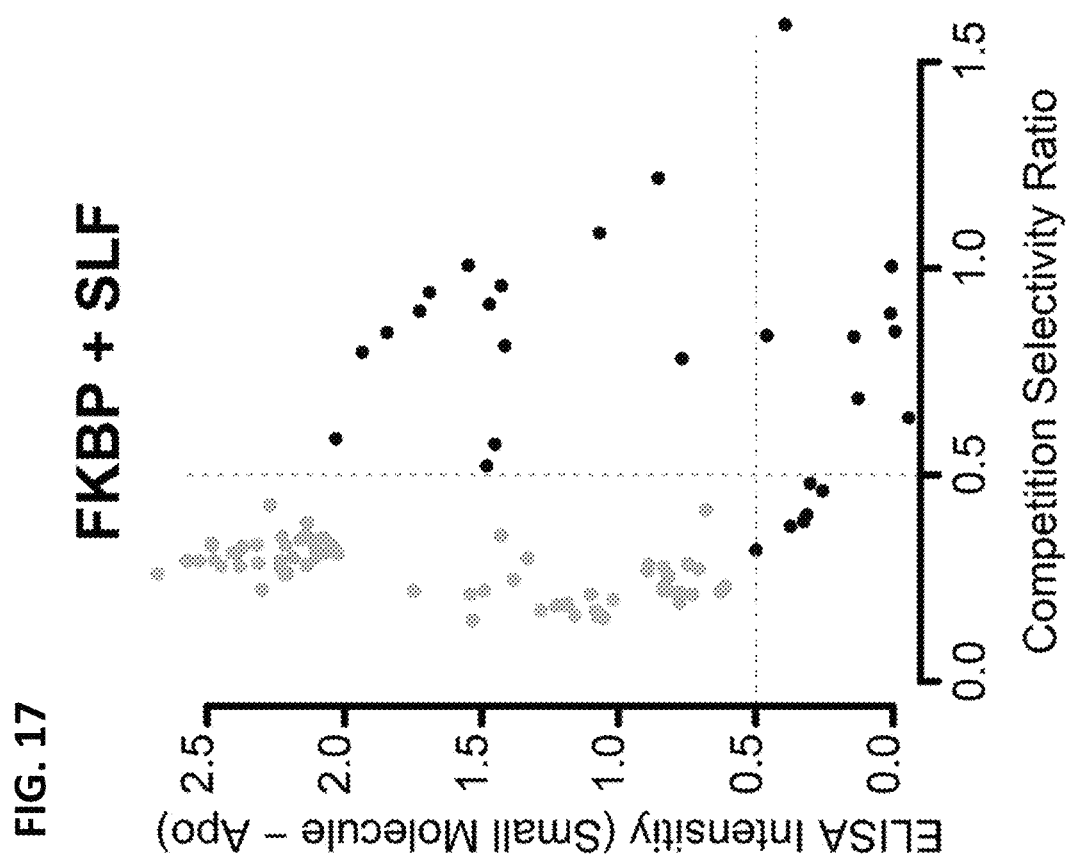
FIG. 17 shows competition ELISA of Fab-phage selected against FKBP/SLF. The top hits (light grey) were sequenced to identify clones with unique sequences.

We have generated dimers using the same method described above, but with the protein FKBP and the small molecule SLF. After selections, we performed phage competition ELISAs using the isolated Fab-phage from our selections in the presence or absence of SLF (FIG. 17) to identify Fabs that selectively bound to FKBP in the presence of SLF. The best hits (in light grey) were sequenced to identify clones with unique sequences. The $K_d$ of all clones was <20 nM.

Example 10: cIAP1/Small Molecule Fab Dimers

Figure 18:
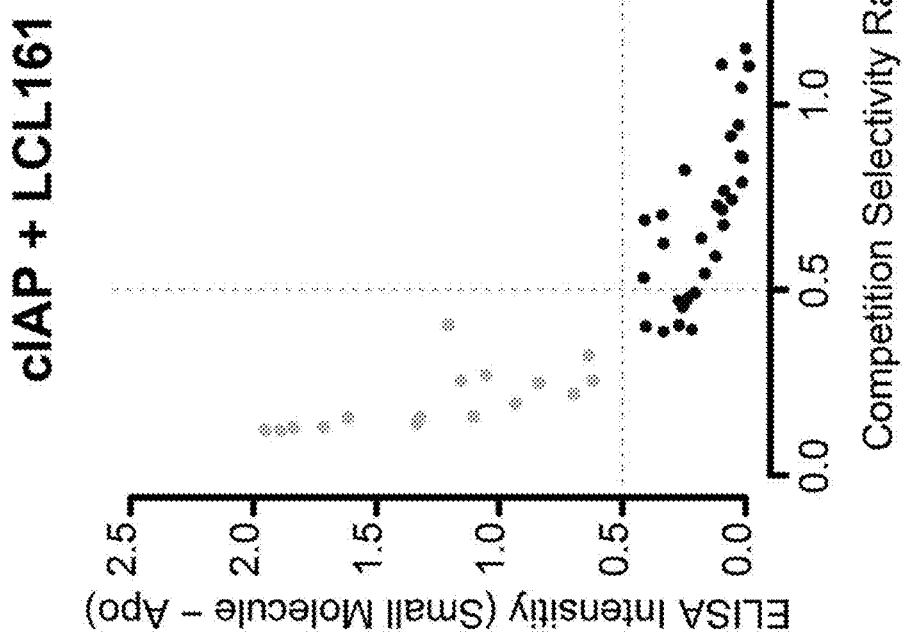
FIG. 18 shows competition ELISA of Fab-phage selected against cIAP1/GDC-0152, cIAP1/LCL161, cIAP1/AT406, and cIAP1/CUDC-427. The top hits (light grey) were sequenced to identify clones with unique sequences.
Figure 18:
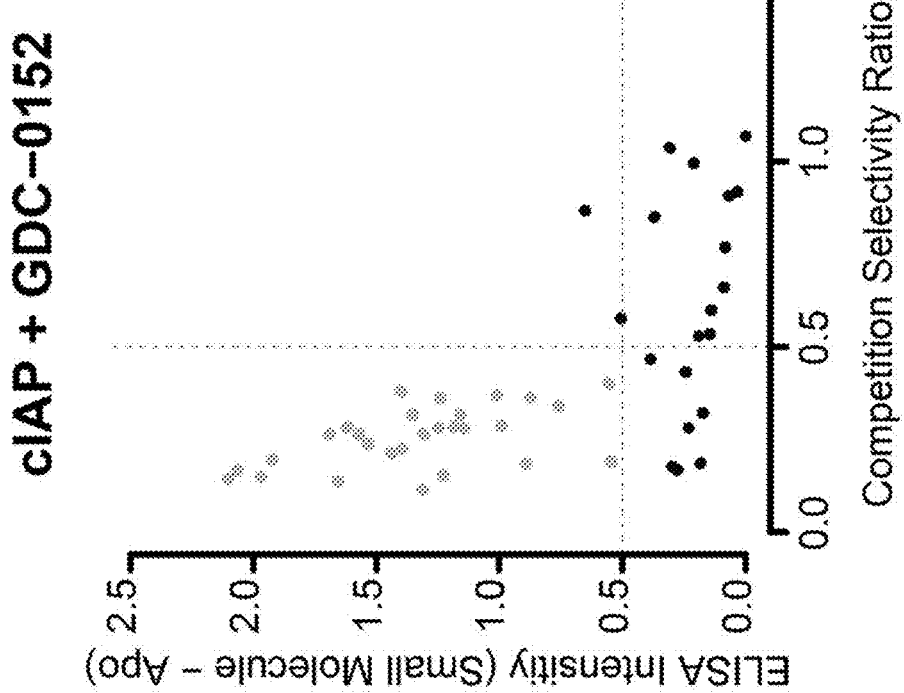

We have generated dimers using the same method described above, but with the protein cIAP1 and each of the small molecules GDC-0152, LCL-161, AT-406, and CUDC-427. After selections, we performed phage competition ELISAs using the isolated Fab-phage from our selections in the presence or absence of each of the small molecules (FIG. 18) to identify Fabs that selectively bound to cIAP1 in the presence of GDC-0152, LCL-161, AT-406, and CUDC-427. The best hits (in light grey) were sequenced to identify clones with unique sequences. The $K_d$ of all clones was <20 nM.

Example 11: Bispecific T Cell Engager

Figure 19B:
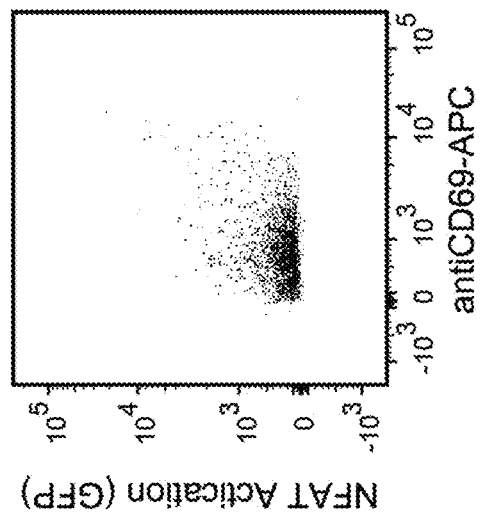
FIG. 19B shows flow cytometry analysis of T cell activation mediated by a bispecific T cell engager having Bcl-2 conjugated to an anti-CD3 antibody and antibody AZ21, AZ34, or AZ35 conjugated to an anti-CD19 antibody. When co-cultured with CD19+ K562 cells, addition of ABT-199 resulted in T cell activation, as evaluated by NFAT activation and CD69 expression, for each of the 3 bispecific T cell engagers.
Figure 19B:
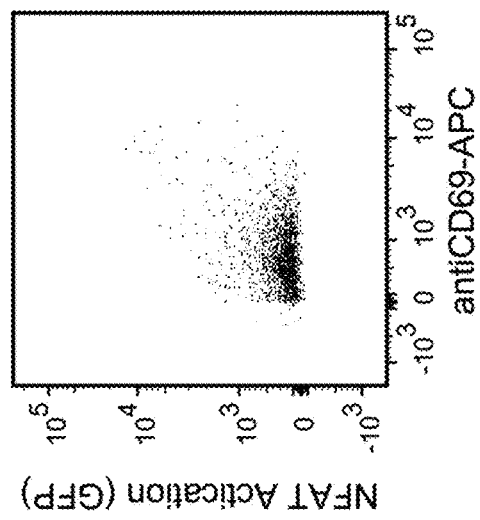
Figure 19B:
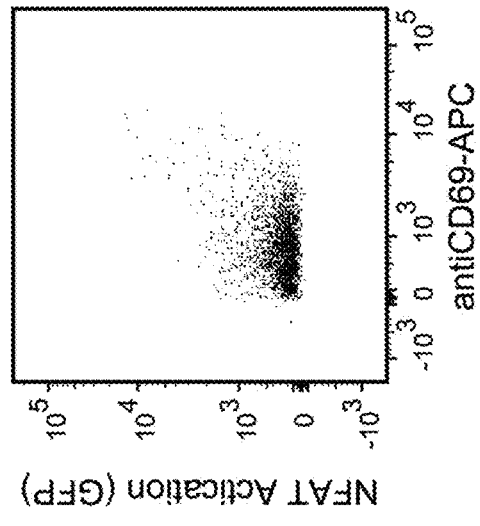
Figure 19B:
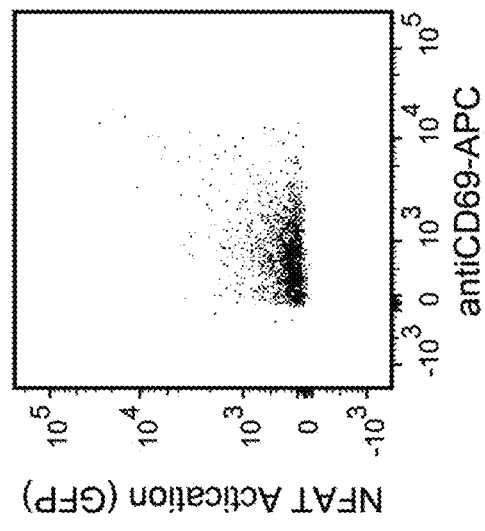
Figure 19B:
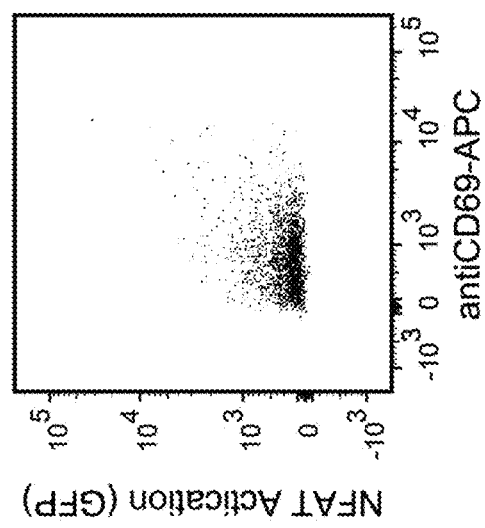
Figure 19B:
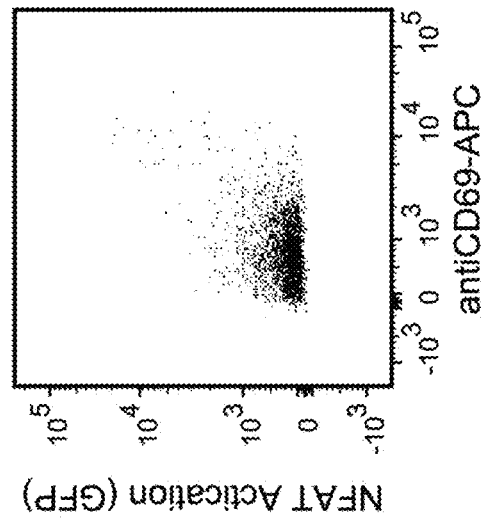
Figure 19B:
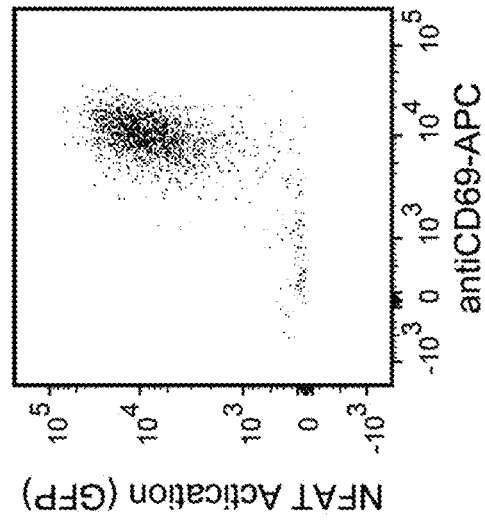
Figure 19B:
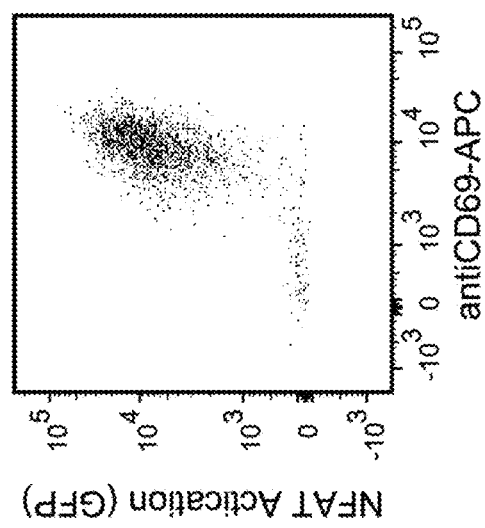
Figure 19B:
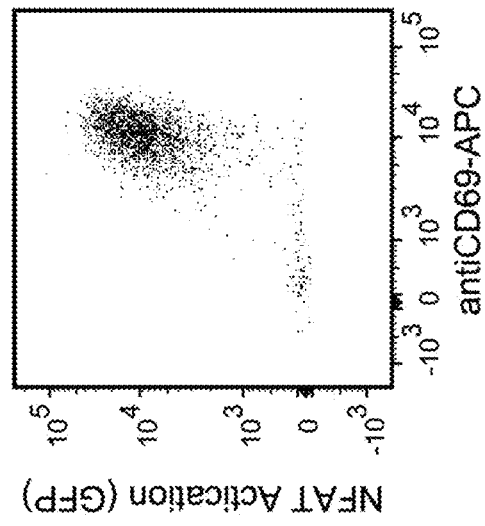
Figure 19C:
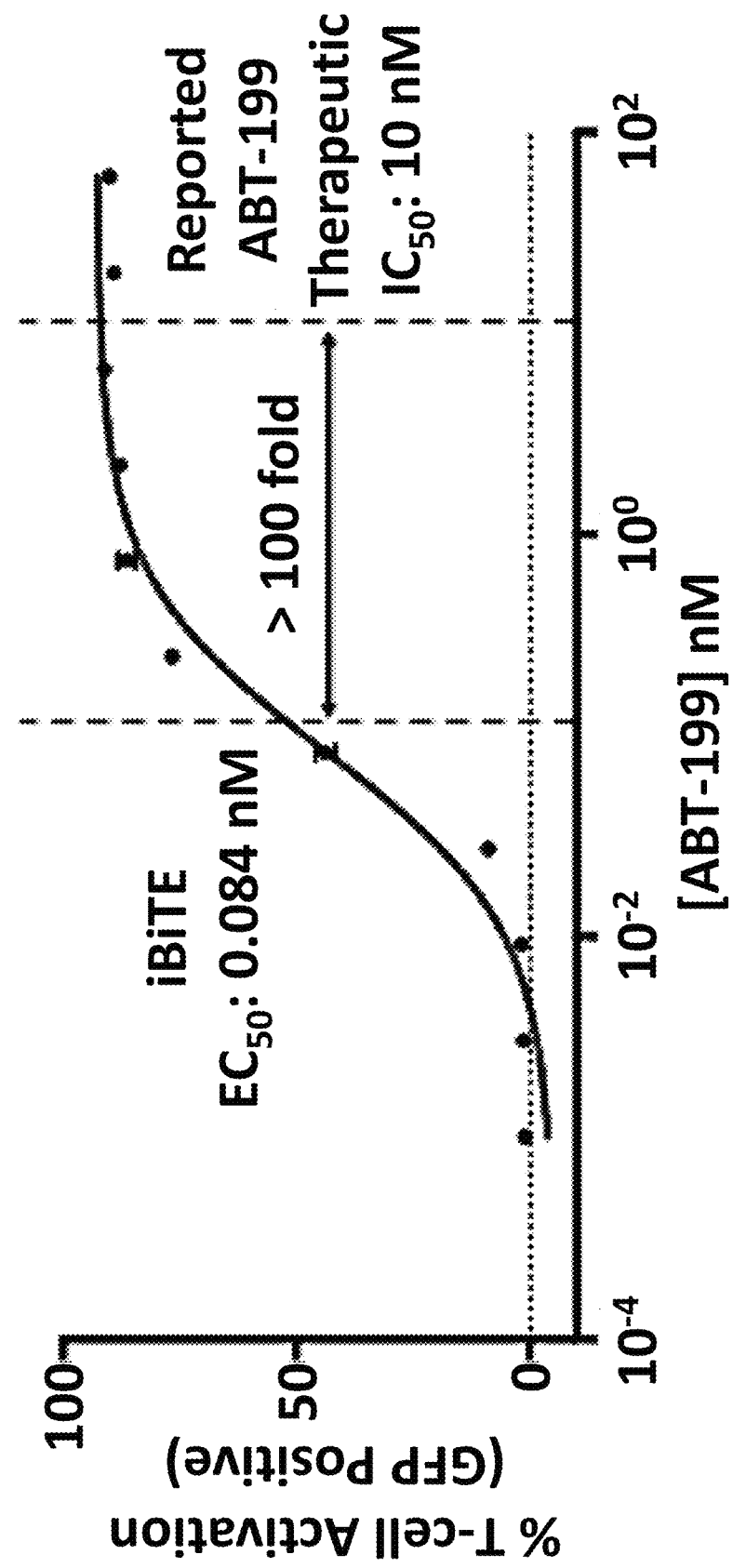
FIG. 19C shows the dose dependence of T cell activation on ABT-199 for a bispecific T cell engager having Bcl-2 conjugated to an anti-CD3 antibody and antibody AZ21 conjugated to an anti-CD19 antibody. T cell activation was evaluated by the percent of GFP-positive T cells, which indicates NFAT activation.

A representative embodiment of an AbCID-regulated inducible bispecific T cell engager is shown in FIG. 19A, having a first AbCID component conjugated to an anti-CD3 antibody and a second AbCID component conjugated to an antibody that recognizes a tumor specific antigen. Administration of the small molecule dimerizer allows for generation of the CID complex, resulting in recruitment of T cells to cancer cells expressing the tumor specific antigen. When co-cultured with CD19+K562 cells, dimerization of a bispecific T cell engager having Bcl-2 conjugated to an anti-CD3 antibody and either antibody AZ21, AZ34, or AZ35 conjugated to an anti-CD19 antibody upon addition of ABT-199 resulted in T-cell activation, as measured by activation of NFAT signaling (which results in GFP expression) and increased expression of CD69 (FIG. 19B). As shown in FIG. 19C, the level of T-cell activation (as measured by NFAT activation) mediated by a bispecific T cell engager having AZ21 conjugated to an anti-CD19 antibody and Bcl-2 conjugated to an anti-CD3 antibody was tunable by titration of ABT-199 concentration.

SEQUENCE LISTING

| SEQ ID NO | Sequence | Description |
|---|---|---|
| 1 | LSYSSM | FAB-AZ1 HC-CDR1 (BCL-xL + ABT-737) |
| 2 | IYSYYM | FAB-AZ2 HC-CDR1 (BCL-xL + ABT-737) |
| 3 | IYYSYM | FAB-AZ3 HC-CDR1 (BCL-xL + ABT-737) |
| 4 | IYSSSI | FAB-AZ4 HC-CDR1 (BCL-xL + ABT-737) |
| 5 | LYYYYI | FAB-AZ5 HC-CDR1 (BCL-xL + ABT-737) |
| 6 | LSYSYI | FAB-AZ6 HC-CDR1 (BCL-xL + ABT-737) |
| 7 | LSSYSM | FAB-AZ7 HC-CDR1 (BCL-xL + ABT-737) |
| 8 | ISYSSI | FAB-AZ8 HC-CDR1 (BCL-xL + ABT-737) |
| 9 | LYYSSI | FAB-AZ9 HC-CDR1 (BCL-xL + ABT-737) |
| 10 | LYSYSM | FAB-AZ10 HC-CDR1 (BCL-xL + ABT-737) |
| 11 | IYYYSM | FAB-AZ11 HC-CDR1 (BCL-2 + ABT-199) |
| 12 | LYYSSM | FAB-AZ13 HC-CDR1 (BCL-2 + ABT-199) |
| 13 | FSSSSI | FAB-AZ14 HC-CDR1 (BCL-2 + ABT-199) |
| 14 | LYYYSM | FAB-AZ15 HC-CDR1 (BCL-2 + ABT-199) |
| 15 | LYYYYM | FAB-AZ16 HC-CDR1 (BCL-2 + ABT-199) |
| 16 | ISYYSM | FAB-AZ17 HC-CDR1 (BCL-2 + ABT-199) |
| 17 | LSSSSM | FAB-AZ18 HC-CDR1 (BCL-2 + ABT-199) |

SEQUENCE LISTING

| SEQ ID NO | Sequence | Description |
| --- | --- | --- |
| 18 | ISYYYI | FAB-AZ19 HC-CDR1 (BCL-2 + ABT-199) |
| 19 | LYYYSI | FAB-AZ20 HC-CDR1 (BCL-2 + ABT-199) |
| 20 | IYSYYI | FAB-AZ23 HC-CDR1 (BCL-2 + ABT-199) |
| 21 | IYYSSI | FAB-AZ26 HC-CDR1 (BCL-2 + ABT-199) |
| 22 | IYSSSM | FAB-AZ29 HC-CDR1 (BCL-2 + ABT-199) |
| 23 | IYYSSM | FAB-AZ31 HC-CDR1 (BCL-2 + ABT-199) |
| 24 | LYYSYM | FAB-AZ36 HC-CDR1 (BCL-2 + ABT-199) |
| 25 | LSSSYI | FAB-AZ37 HC-CDR1 (BCL-2 + ABT-199) |
| 26 | FSYSSI | FAB-AZ40 HC-CDR1 (BCL-2 + ABT-199) |
| 27 | FSYYSI | FAB-AZ41 HC-CDR1 (BCL-2 + ABT-199) |
| 28 | ISSSYI | FAB-AZ42 HC-CDR1 (BCL-2 + ABT-199) |
| 29 | VYYYYI | FAB-AZ43 HC-CDR1 (BCL-2 + ABT-199) |
| 30 | VSYYSI | FAB-AZ44 HC-CDR1 (BCL-2 + ABT-263) |
| 31 | VSYSSI | FAB-AZ45 HC-CDR1 (BCL-2 + ABT-263) |
| 32 | VYSYSI | FAB-AZ46 HC-CDR1 (BCL-2 + ABT-263) |
| 33 | VSSSYI | FAB-AZ47 HC-CDR1 (BCL-2 + ABT-263) |
| 34 | IYYYYI | FAB-AZ49 HC-CDR1 (BCL-2 + ABT-263) |
| 35 | VSSYSI | FAB-AZ50 HC-CDR1 (BCL-2 + ABT-263) |
| 36 | ISSYSI | FAB-AZ52 HC-CDR1 (BCL-2 + ABT-263) |
| 37 | LSSSSI | FAB-AZ54 HC-CDR1 (BCL-2 + ABT-263) |
| 38 | VYYSSI | FAB-AZ59 HC-CDR1 (cIAP + LCL161) |
| 39 | VYYSYI | FAB-AZ60 HC-CDR1 (cIAP + LCL161) |
| 40 | FYYSSI | FAB-AZ62 HC-CDR1 (cIAP + LCL161) |
| 41 | FYSSI | FAB-AZ68 HC-CDR1 (cIAP + GDC-0152) |
| 42 | FSSYSI | FAB-AZ73 HC-CDR1 (cIAP + GDC-0152) |
| 43 | VSSSSI | FAB-AZ75 HC-CDR1 (cIAP + GDC-0152) |
| 44 | FSSSYI | FAB-AZ77 HC-CDR1 (cIAP + GDC-0152) |
| 45 | VYYYSI | FAB-AZ79 HC-CDR1 (cIAP + GDC-0152) |
| 46 | FSYYYT | FAB-AZ85 HC-CDR1 (cIAP + AT406) |
| 47 | VYSSSI | FAB-AZ91 HC-CDR1 (cIAP + AT406) |
| 48 | FYSSSI | FAB-AZ92 HC-CDR1 (cIAP + CUDC-427) |
| 49 | FYYSYI | FAB-AZ97 HC-CDR1 (cIAP + CUDC-427) |
| 50 | IYYYSI | FAB-AZ102 HC-CDR1 (cIAP + CUDC-427) |
| 51 | IYYYFI | FAB-AZ104 HC-CDR1 (cIAP + CUDC-427) |
| 52 | ISSSSI | FAB-AZ118 HC-CDR1 (Fab + Methotrexate) |
| 53 | SISPYSSYTS | FAB-AZ1 HC-CDR2 (BCL-xL + ABT-737) |
| 54 | YISPYYSYTS | FAB-AZ2 HC-CDR2 (BCL-xL + ABT-737) |

-continued

SEQUENCE LISTING

| SEQ ID NO | Sequence | Description |
|---|---|---|
| 55 | SIYPYYGYTY | FAB-AZ4 HC-CDR2 (BCL-xL + ABT-737) |
| 56 | SIYPSYGSTY | FAB-AZ5 HC-CDR2 (BCL-xL + ABT-737) |
| 57 | SIYSSSGSTY | FAB-AZ6 HC-CDR2 (BCL-xL + ABT-737) |
| 58 | SIYSYYGSTS | FAB-AZ7 HC-CDR2 (BCL-xL + ABT-737) |
| 59 | SISSYYGSTS | FAB-AZ8 HC-CDR2 (BCL-xL + ABT-737) |
| 60 | SISSSYGYTY | FAB-AZ9 HC-CDR2 (BCL-xL + ABT-737) |
| 61 | SISSYYSSTY | FAB-AZ10 HC-CDR2 (BCL-xL + ABT-737) |
| 62 | SIYPYYSYTY | FAB-AZ11 HC-CDR2 (BCL-2 + ABT-199) |
| 63 | SIYPYYGYTS | FAB-AZ12 HC-CDR2 (BCL-2 + ABT-199) |
| 64 | SISSYYGYTS | FAB-AZ13 HC-CDR2 (BCL-2 + ABT-199) |
| 65 | SISSYSGYTS | FAB-AZ14 HC-CDR2 (BCL-2 + ABT-199) |
| 66 | SIYSYYGYTY | FAB-AZ15 HC-CDR2 (BCL-2 + ABT-199) |
| 67 | SISPSYGYTS | FAB-AZ16 HC-CDR2 (BCL-2 + ABT-199) |
| 68 | YISSYSSYTY | FAB-AZ17 HC-CDR2 (BCL-2 + ABT-199) |
| 69 | YISPYSGYTS | FAB-AZ18 HC-CDR2 (BCL-2 + ABT-199) |
| 70 | SIYSSYSYTS | FAB-AZ19 HC-CDR2 (BCL-2 + ABT-199) |
| 71 | SISSSSGYTS | FAB-AZ20 HC-CDR2 (BCL-2 + ABT-199) |
| 72 | SISPYSSYTY | FAB-AZ21 HC-CDR2 (BCL-2 + ABT-199) |
| 73 | SISPYYGYTS | FAB-AZ22 HC-CDR2 (BCL-2 + ABT-199) |
| 74 | SISSYYSYTY | FAB-AZ23 HC-CDR2 (BCL-2 + ABT-199) |
| 75 | SISSYSGSTS | FAB-AZ31 HC-CDR2 (BCL-2 + ABT-199) |
| 76 | YISSYSGYTY | FAB-AZ35 HC-CDR2 (BCL-2 + ABT-199) |
| 77 | SIYPYYSSTY | FAB-AZ36 HC-CDR2 (BCL-2 + ABT-199) |
| 78 | YIYSYYGYTS | FAB-AZ37 HC-CDR2 (BCL-2 + ABT-199) |
| 79 | YISSYYSSTY | FAB-AZ38 HC-CDR2 (BCL-2 + ABT-199) |
| 80 | SISSYYGYTY | FAB-AZ41 HC-CDR2 (BCL-2 + ABT-199) |
| 81 | SIYSYYGSTY | FAB-AZ42 HC-CDR2 (BCL-2 + ABT-199) |
| 82 | SISSSSGSTS | FAB-AZ43 HC-CDR2 (BCL-2 + ABT-199) |
| 83 | SIYPYSGYTS | FAB-AZ44 HC-CDR2 (BCL-2 + ABT-263) |
| 84 | SISSYYGSTY | FAB-AZ45 HC-CDR2 (BCL-2 + ABT-263) |
| 85 | SIYSSYGYTY | FAB-AZ47 HC-CDR2 (BCL-2 + ABT-263) |
| 86 | SISSYSGYTY | FAB-AZ49 HC-CDR2 (BCL-2 + ABT-263) |
| 87 | SISSYSSYTS | FAB-AZ50 HC-CDR2 (BCL-2 + ABT-263) |
| 88 | SIYSYSGYTS | FAB-AZ55 HC-CDR2 (BCL-2 + ABT-263) |
| 89 | YISSYSGYTS | FAB-AZ56 HC-CDR2 (BCL-2 + ABT-263) |
| 90 | SISSSSGYTY | FAB-AZ60 HC-CDR2 (cIAP + LCL161) |
| 91 | SISPYYSSTS | FAB-AZ61 HC-CDR2 (cIAP + LCL161) |

| SEQ ID NO | Sequence | Description |
|---|---|---|
| 92 | SIYPSYSYTS | FAB-AZ62 HC-CDR2 (cIAP + LCL161) |
| 93 | SIYPSYGYTS | FAB-AZ63 HC-CDR2 (cIAP + LCL161) |
| 94 | SIYSYYGYTS | FAB-AZ66 HC-CDR2 (cIAP + GDC-0152) |
| 95 | SISSSYSYTS | FAB-AZ67 HC-CDR2 (cIAP + GDC-0152) |
| 96 | SISSSYGYTS | FAB-AZ68 HC-CDR2 (cIAP + GDC-0152) |
| 97 | SIYSSYGSTY | FAB-AZ72 HC-CDR2 (cIAP + GDC-0152) |
| 98 | SISPYYGSTY | FAB-AZ73 HC-CDR2 (cIAP + GDC-0152) |
| 99 | SIYPSSGYTY | FAB-AZ75 HC-CDR2 (cIAP + GDC-0152) |
| 100 | SIYSYSSSTY | FAB-AZ76 HC-CDR2 (cIAP + GDC-0152) |
| 101 | SISSSYGSTS | FAB-AZ77 HC-CDR2 (cIAP + GDC-0152) |
| 102 | SISPSSGSTS | FAB-AZ78 HC-CDR2 (cIAP + GDC-0152) |
| 103 | SISPYSGSTS | FAB-AZ82 HC-CDR2 (cIAP + AT406) |
| 104 | YTYSSSGYTY | FAB-AZ83 HC-CDR2 (cIAP + AT406) |
| 105 | SIYSYSGSTS | FAB-AZ92 HC-CDR2 (cIAP + CUDC-427) |
| 106 | SISPSYGSTS | FAB-AZ93 HC-CDR2 (cIAP + CUDC-427) |
| 107 | SIYSSYGYTS | FAB-AZ96 HC-CDR2 (cIAP + CUDC-427) |
| 108 | SIYPSSGYTS | FAB-AZ97 HC-CDR2 (cIAP + CUDC-427) |
| 109 | YISPSSGYTY | FAB-AZ98 HC-CDR2 (cIAP + CUDC-427) |
| 110 | SISSSYGSTY | FAB-AZ101 HC-CDR2 (cIAP + CUDC-427) |
| 111 | YIYPYSGSTS | FAB-AZ109 HC-CDR2 (FKBP + SLF) |
| 112 | YISSYYGSTY | FAB-AZ112 HC-CDR2 (FKBP + SLF) |
| 113 | GWVGM | FAB-AZ1 HC-CDR3 (BCL-xL + ABT-737) |
| 114 | GYPWYGM | FAB-AZ2 HC-CDR3 (BCL-xL + ABT-737) |
| 115 | YGYSYYYYGAL | FAB-AZ3 HC-CDR3 (BCL-xL + ABT-737) |
| 116 | SWWPYGM | FAB-AZ4 HC-CDR3 (BCL-xL + ABT-737) |
| 117 | ASVWFGWYVPSAM | FAB-AZ5 HC-CDR3 (BCL-xL + ABT-737) |
| 118 | GSHAGWAWFWYGM | FAB-AZ6 HC-CDR3 (BCL-xL + ABT-737) |
| 119 | YSPWVYYPYYGWYSGM | FAB-AZ7 HC-CDR3 (BCL-xL + ABT-737) |
| 120 | TVRGSKKPYFSGWAM | FAB-AZ8 HC-CDR3 (BCL-xL + ABT-737) |
| 121 | SHAWGWVYSYGM | FAB-AZ12 HC-CDR3 (BCL-2 + ABT-199) |
| 122 | SYGYWWGVYYSVAL | FAB-AZ13 HC-CDR3 (BCL-2 + ABT-199) |
| 123 | PSSGYYWGSHGYYGVAI | FAB-AZ14 HC-CDR3 (BCL-2 + ABT-199) |
| 124 | HSYWYACSAM | FAB-AZ16 HC-CDR3 (BCL-2 + ABT-199) |
| 125 | SYVHPYYWSYYAM | FAB-AZ17 HC-CDR3 (BCL-2 + ABT-199) |
| 126 | YSGSSGGSWFYWGL | FAB-AZ18 HC-CDR3 (BCL-2 + ABT-199) |
| 127 | SSVYWYYVYSGM | FAB-AZ19 HC-CDR3 (BCL-2 + ABT-199) |
| 128 | GYYSGSWWSYYPAF | FAB-AZ20 HC-CDR3 (BCL-2 + ABT-199) |

SEQUENCE LISTING

| SEQ ID NO | Sequence | Description |
|---|---|---|
| 129 | GYWSFYGM | FAB-AZ21 HC-CDR3 (BCL-2 + ABT-199) |
| 130 | SGYHAVYYGYYSYPWSL | FAB-AZ22 HC-CDR3 (BCL-2 + ABT-199) |
| 131 | GGYGFWGWWAL | FAB-AZ23 HC-CDR3 (BCL-2 + ABT-199) |
| 132 | AYGYWWSYPGAF | FAB-AZ25 HC-CDR3 (BCL-2 + ABT-199) |
| 133 | AVHYWSHAAHYGM | FAB-AZ26 HC-CDR3 (BCL-2 + ABT-199) |
| 134 | HSYWYASSAM | FAB-AZ27 HC-CDR3 (BCL-2 + ABT-199) |
| 135 | SGF | FAB-AZ28 HC-CDR3 (BCL-2 + ABT-199) |
| 136 | SFWYYAL | FAB-AZ29 HC-CDR3 (BCL-2 + ABT-199) |
| 137 | GGWFWGSGGYSSAF | FAB-AZ31 HC-CDR3 (BCL-2 + ABT-199) |
| 138 | GGWYWASGSYYGAM | FAB-AZ35 HC-CDR3 (BCL-2 + ABT-199) |
| 139 | SGGSGM | FAB-AZ36 HC-CDR3 (BCL-2 + ABT-199) |
| 140 | GSAYYGYGGWAYSSVGYAI | FAB-AZ37 HC-CDR3 (BCL-2 + ABT-199) |
| 141 | VPSYFYASYGM | FAB-AZ38 HC-CDR3 (BCL-2 + ABT-199) |
| 142 | TYWSYMGLYSPAM | FAB-AZ40 HC-CDR3 (BCL-2 + ABT-199) |
| 143 | YHQYAGM | FAB-AZ41 HC-CDR3 (BCL-2 + ABT-199) |
| 144 | TYYSGYYYSYFWSAL | FAB-AZ42 HC-CDR3 (BCL-2 + ABT-199) |
| 145 | YYMSWWGM | FAB-AZ43 HC-CDR3 (BCL-2 + ABT-199) |
| 146 | SYHYSWAM | FAB-AZ44 HC-CDR3 (BCL-2 + ABT-263) |
| 147 | SWGMWYYWQWPAI | FAB-AZ45 HC-CDR3 (BCL-2 + ABT-263) |
| 148 | SNGTWEWWSWWAL | FAB-AZ46 HC-CDR3 (BCL-2 + ABT-263) |
| 149 | SWVRKWGGYAWSVDYGGM | FAB-AZ47 HC-CDR3 (BCL-2 + ABT-263) |
| 150 | GNGMYWAI | FAB-AZ49 HC-CDR3 (BCL-2 + ABT-263) |
| 151 | YMGGWYSYMENHQWPEAL | FAB-AZ50 HC-CDR3 (BCL-2 + ABT-263) |
| 152 | YYYEGGM | FAB-AZ51 HC-CDR3 (BCL-2 + ABT-263) |
| 153 | QDHWYYYQWPAI | FAB-AZ52 HC-CDR3 (BCL-2 + ABT-263) |
| 154 | ASYYYAM | FAB-AZ53 HC-CDR3 (BCL-2 + ABT-263) |
| 155 | SYDTWYWWQYFAL | FAB-AZ54 HC-CDR3 (BCL-2 + ABT-263) |
| 156 | YSYSPGM | FAB-AZ55 HC-CDR3 (BCL-2 + ABT-263) |
| 157 | GYWPAL | FAB-AZ56 HC-CDR3 (BCL-2 + ABT-263) |
| 158 | SWGQWYWYQYYGF | FAB-AZ57 HC-CDR3 (BCL-2 + ABT-263) |
| 159 | YYYQGL | FAB-AZ58 HC-CDR3 (BCL-2 + ABT-263) |
| 160 | WYTYAHSYYYLMYYGSGM | FAB-AZ59 HC-CDR3 (cIAP + LCL161) |
| 161 | SYSYWAYFSYGM | FAB-AZ60 HC-CDR3 (cIAP + LCL161) |
| 162 | YMYYYAGWKYYSYGGFN | FAB-AZ61 HC-CDR3 (cIAP + LCL161) |
| 163 | WHYWVHYISGL | FAB-AZ62 HC-CDR3 (cIAP + LCL161) |
| 164 | LNYYNTYYLKYYYGSAL | FAB-AZ63 HC-CDR3 (cIAP + LCL161) |
| 165 | SSGYRYYWKWGVWSYNAI | FAB-AZ65 HC-CDR3 (cIAP + GDC-0152) |

-continued

SEQUENCE LISTING

| SEQ ID NO | Sequence | Description |
|---|---|---|
| 166 | YGYGGWSGYFDIYAL | FAB-AZ66 HC-CDR3 (cIAP + GDC-0152) |
| 167 | QWPYLYYYWGGL | FAB-AZ67 HC-CDR3 (cIAP + GDC-0152) |
| 168 | GSEWSYSGSWAPYGYGGL | FAB-AZ68 HC-CDR3 (cIAP + GDC-0152) |
| 169 | FLYYWHWMYKYPWMSGM | FAB-AZ69 HC-CDR3 (cIAP + GDC-0152) |
| 170 | YIQYGYLYHKYGI | FAB-AZ70 HC-CDR3 (cIAP + GDC-0152) |
| 171 | SSYSWYWYYYQRLWYSAM | FAB-AZ71 HC-CDR3 (cIAP + GDC-0152) |
| 172 | WNGAWYSYQGQWESIGGM | FAB-AZ72 HC-CDR3 (cIAP + GDC-0152) |
| 173 | GYFWPYYYQWHYEYSVAL | FAB-AZ73 HC-CDR3 (cIAP + GDC-0152) |
| 174 | SFYDVWYYGYYYMLGL | FAB-AZ74 HC-CDR3 (cIAP + GDC-0152) |
| 175 | STFSFYHSFWYPAYTGGM | FAB-AZ75 HC-CDR3 (cIAP + GDC-0152) |
| 176 | SSYSVYWAI | FAB-AZ76 HC-CDR3 (cIAP + GDC-0152) |
| 177 | SIHYYSYQQHYYIPKPYAF | FAB-AZ77 HC-CDR3 (cIAP + GDC-0152) |
| 178 | YGWRYWWWSQKYYVSEKGF | FAB-AZ78 HC-CDR3 (cIAP + GDC-0152) |
| 179 | SYPVTWGGYPAYGM | FAB-AZ79 HC-CDR3 (cIAP + GDC-0152) |
| 180 | ESWYHYWGMGFAYAGI | FAB-AZ80 HC-CDR3 (cIAP + GDC-0152) |
| 181 | YYYYFSGYQYMYGL | FAB-AZ81 HC-CDR3 (cIAP + AT406) |
| 182 | YAWYVYAWYRYWEAQAM | FAB-AZ82 HC-CDR3 (cIAP + AT406) |
| 183 | ASYYYRWWGWYDYGWAL | FAB-AZ83 HC-CDR3 (cIAP + AT406) |
| 184 | WGWSRYGSSGGF | FAB-AZ84 HC-CDR3 (cIAP + AT406) |
| 185 | QFWHFMSKGQWYHQAM | FAB-AZ85 HC-CDR3 (cIAP + AT406) |
| 186 | GSLWISWYIYYYQMGVGF | FAB-AZ86 HC-CDR3 (cIAP + AT406) |
| 187 | GGYYYSESRYGFGF | FAB-AZ87 HC-CDR3 (cIAP + AT406) |
| 188 | YTYYVKWAYYWSFYTSGL | FAB-AZ88 HC-CDR3 (cIAP + AT406) |
| 189 | SAWYYIHGGYGWAF | FAB-AZ89 HC-CDR3 (cIAP + AT406) |
| 190 | QPYYYYYQMSYHYGGL | FAB-AZ90 HC-CDR3 (cIAP + AT406) |
| 191 | YYHYMYSYSSKKYSYYAM | FAB-AZ91 HC-CDR3 (cIAP + AT406) |
| 192 | EMYFYKWSWYHYVSYDGL | FAB-AZ92 HC-CDR3 (cIAP + CUDC-427) |
| 193 | PGYSGWYWHHGF | FAB-AZ93 HC-CDR3 (cIAP + CUDC-427) |
| 194 | GSHYLYYYWYYKYGSAL | FAB-AZ94 HC-CDR3 (cIAP + CUDC-427) |
| 195 | YEYYYWYMSVSRYYLMAAL | FAB-AZ95 HC-CDR3 (cIAP + CUDC-427) |
| 196 | NSLYMHWSWNGYYFSSGM | FAB-AZ96 HC-CDR3 (cIAP + CUDC-427) |
| 197 | SGSGYEWYWMGM | FAB-AZ97 HC-CDR3 (cIAP + CUDC-427) |
| 198 | YSYTYYWGFQKYYSEYGM | FAB-AZ98 HC-CDR3 (cIAP + CUDC-427) |
| 199 | MYPWYYTYPWGF | FAB-AZ99 HC-CDR3 (cIAP + CUDC-427) |
| 200 | YQLYERYWYYSWPGGL | FAB-AZ100 HC-CDR3 (cIAP + CUDC-427) |
| 201 | SSGYGSKYGYYSGM | FAB-AZ101 HC-CDR3 (cIAP + CUDC-427) |
| 202 | EFWYYIYRDFYMLLSGL | FAB-AZ102 HC-CDR3 (cIAP + CUDC-427) |

| SEQ ID NO | Sequence | Description |
|---|---|---|
| 203 | YRYEYQWRGWYYVSFEAM | FAB-AZ103 HC-CDR3 (cIAP + CUDC-427) |
| 204 | YNYYGYSAEGWIYPGSAM | FAB-AZ104 HC-CDR3 (cIAP + CUDC-427) |
| 205 | GSWYSHYYEYYYQYGWAM | FAB-AZ105 HC-CDR3 (cIAP + CUDC-427) |
| 206 | EGYYYFWSYYFYSSYYAL | FAB-AZ106 HC-CDR3 (cIAP + CUDC-427) |
| 207 | MYHYFGASGWYMRYPQGI | FAB-AZ107 HC-CDR3 (FKBP + SLF) |
| 208 | YWGWEGM | FAB-AZ108 HC-CDR3 (FKBP + SLF) |
| 209 | YWYSAL | FAB-AZ109 HC-CDR3 (FKBP + SLF) |
| 210 | SPSYYWWYRWYYYGHAAF | FAB-AZ110 HC-CDR3 (FKBP + SLF) |
| 211 | YPYWGSVHGIGWTYYWAL | FAB-AZ111 HC-CDR3 (FKBP + SLF) |
| 212 | GPGYWHYSYYFYESFSAL | FAB-AZ112 HC-CDR3 (FKBP + SLF) |
| 213 | SYASGL | FAB-AZ118 HC-CDR3 (Fab + Methotrexate) |
| 214 | YYWGFPSLF | FAB-AZ1 LC-CDR3 (BCL-xL + ABT-737) |
| 215 | VSWAYPYLI | FAB-AZ2 LC-CDR3 (BCL-xL + ABT-737) |
| 216 | GWSGPWLI | FAB-AZ3 LC-CDR3 (BCL-xL + ABT-737) |
| 217 | VPAFPI | FAB-AZ4 LC-CDR3 (BCL-xL + ABT-737) |
| 218 | WPGWYPI | FAB-AZ5 LC-CDR3 (BCL-xL + ABT-737) |
| 219 | SSYSLI | FAB-AZ6 LC-CDR3 (BCL-xL + ABT-737) |
| 220 | SGWFFPF | FAB-AZ8 LC-CDR3 (BCL-xL + ABT-737) |
| 221 | SYYYYSGPI | FAB-AZ9 LC-CDR3 (BCL-xL + ABT-737) |
| 222 | SYYFYSGPI | FAB-AZ10 LC-CDR3 (BCL-xL + ABT-737) |
| 223 | YGVWAFLI | FAB-AZ11 LC-CDR3 (BCL-2 + ABT-199) |
| 224 | SASSWLI | FAB-AZ12 LC-CDR3 (BCL-2 + ABT-199) |
| 225 | GVSWFFSPI | FAB-AZ13 LC-CDR3 (BCL-2 + ABT-199) |
| 226 | SYGWPWYPF | FAB-AZ14 LC-CDR3 (BCL-2 + ABT-199) |
| 227 | SGSWGFLI | FAB-AZ15 LC-CDR3 (BCL-2 + ABT-199) |
| 228 | SWWYYPF | FAB-AZ16 LC-CDR3 (BCL-2 + ABT-199) |
| 229 | SWAGYPI | FAB-AZ17 LC-CDR3 (BCL-2 + ABT-I99) |
| 230 | YGGALI | FAB-AZ18 LC-CDR3 (BCL-2 + ABT-199) |
| 231 | SSSPF | FAB-AZ19 LC-CDR3 (BCL-2 + ABT-199) |
| 232 | WWFPI | FAB-AZ20 LC-CDR3 (BCL-2 + ABT-199) |
| 233 | YYAHYLF | FAB-AZ21 LC-CDR3 (BCL-2 + ABT-199) |
| 234 | GGVLI | FAB-AZ22 LC-CDR3 (BCL-2 + ABT-199) |
| 235 | YPSGLI | FAB-AZ23 LC-CDR3 (BCL-2 + ABT-199) |
| 236 | YSGWGFLI | FAB-AZ24 LC-CDR3 (BCL-2 + ABT-199) |
| 237 | SSGYYPI | FAB-AZ25 LC-CDR3 (BCL-2 + ABT-199) |
| 238 | SWYSLI | FAB-AZ26 LC-CDR3 (BCL-2 + ABT-199) |
| 239 | YASWYGALI | FAB-AZ28 LC-CDR3 (BCL-2 + ABT-199) |

SEQUENCE LISTING

| SEQ ID NO | Sequence | Description |
|---|---|---|
| 240 | SHAYYPF | FAB-AZ29 LC-CDR3 (BCL-2 + ABT-199) |
| 241 | SHYYGFLI | FAB-AZ30 LC-CDR3 (BCL-2 + ABT-199) |
| 242 | HHSLI | FAB-AZ31 LC-CDR3 (BCL-2 + ABT-199) |
| 243 | ASPWGFLI | FAB-AZ32 LC-CDR3 (BCL-2 + ABT-199) |
| 244 | SSHYGWLI | FAB-AZ33 LC-CDR3 (BCL-2 + ABT-199) |
| 245 | YGYSVLI | FAB-AZ35 LC-CDR3 (BCL-2 + ABT-199) |
| 246 | WSYPYSLI | FAB-AZ36 LC-CDR3 (BCL-2 + ABT-199) |
| 247 | SYYALI | FAB-AZ37 LC-CDR3 (BCL-2 + ABT-199) |
| 248 | YWFYSSPT | FAB-AZ38 LC-CDR3 (BCL-2 + ABT-199) |
| 249 | PSYWGFLT | FAB-AZ39 LC-CDR3 (BCL-2 + ABT-199) |
| 250 | YYESPI | FAB-AZ40 LC-CDR3 (BCL-2 + ABT-199) |
| 251 | SSWQPF | FAB-AZ41 LC-CDR3 (BCL-2 + ABT-199) |
| 252 | GWRGSLV | FAB-AZ42 LC-CDR3 (BCL-2 + ABT-199) |
| 253 | SSSSLI | FAB-AZ43 LC-CDR3 (BCL-2 + ABT-199) |
| 254 | SQYWYLF | FAB-AZ44 LC-CDR3 (BCL-2 + ABT-263) |
| 255 | YWHYSLI | FAB-AZ45 LC-CDR3 (BCL-2 + ABT-263) |
| 256 | SYYPMPF | FAB-AZ46 LC-CDR3 (BCL-2 + ABT-263) |
| 257 | SFFYLI | FAB-AZ47 LC-CDR3 (BCL-2 + ABT-263) |
| 258 | SGYYLI | FAB-AZ49 LC-CDR3 (BCL-2 + ABT-263) |
| 259 | MWDLSLI | FAB-AZ50 LC-CDR3 (BCL-2 + ABT-263) |
| 260 | SQRWYLI | FAB-AZ51 LC-CDR3 (BCL-2 + ABT-263) |
| 261 | YYYPFLI | FAB-AZ52 LC-CDR3 (BCL-2 + ABT-263) |
| 262 | YYYWYLI | FAB-AZ53 LC-CDR3 (BCL-2 + ABT-263) |
| 263 | SYYHLF | FAB-AZ54 LC-CDR3 (BCL-2 + ABT-263) |
| 264 | SYAWHLI | FAB-AZ55 LC-CDR3 (BCL-2 + ABT-263) |
| 265 | YGWLSPI | FAB-AZ56 LC-CDR3 (BCL-2 + ABT-263) |
| 266 | SYSSSPV | FAB-AZ57 LC-CDR3 (BCL-2 + ABT-263) |
| 267 | YQLWYLI | FAB-AZ58 LC-CDR3 (BCL-2 + ABT-263) |
| 268 | GSSTPI | FAB-AZ59 LC-CDR3 (cIAP + LCL161) |
| 269 | SGSVNGLI | FAB-AZ60 LC-CDR3 (cIAP + LCL161) |
| 270 | SDIYYPL | FAB-AZ61 LC-CDR3 (cIAP + LCL161) |
| 271 | VGGGLI | FAB-AZ62 LC-CDR3 (cIAP + LCL161) |
| 272 | EYWDLI | FAB-AZ63 LC-CDR3 (cIAP + LCL161) |
| 273 | SGMHQLI | FAB-AZ65 LC-CDR3 (cIAP + GDC-0152) |
| 274 | YYYWPI | FAB-AZ66 LC-CDR3 (cIAP + GDC-0152) |
| 275 | NSSSPI | FAB-AZ67 LC-CDR3 (cIAP + GDC-0152) |
| 276 | YSYSSLI | FAB-AZ68 LC-CDR3 (cIAP + GDC-0152) |

-continued

SEQUENCE LISTING

| SEQ ID NO | Sequence | Description |
|---|---|---|
| 277 | SSNFWSPV | FAB-AZ69 LC-CDR3 (cIAP + GDC-0152) |
| 278 | SYYMYPI | FAB-AZ70 LC-CDR3 (cIAP + GDC-0152) |
| 279 | SSYYPI | FAB-AZ71 LC-CDR3 (cIAP + GDC-0152) |
| 280 | SFFGPV | FAB-AZ73 LC-CDR3 (cIAP + GDC-0152) |
| 281 | SYYGVSPI | FAB-AZ75 LC-CDR3 (cIAP + GDC-0152) |
| 282 | PGSSSPI | FAB-AZ76 LC-CDR3 (cIAP + GDC-0152) |
| 283 | SYWFPI | FAB-AZ77 LC-CDR3 (cIAP + GDC-0152) |
| 284 | GSFYGDLI | FAB-AZ78 LC-CDR3 (cIAP + GDC-0152) |
| 285 | YWYWRPL | FAB-AZ79 LC-CDR3 (cIAP + GDC-0152) |
| 286 | SGSNSLI | FAB-AZ80 LC-CDR3 (cIAP + GDC-0152) |
| 287 | GSEYLI | FAB-AZ81 LC-CDR3 (cIAP + AT406) |
| 288 | SSGSPL | FAB-AZ82 LC-CDR3 (cIAP + AT406) |
| 289 | QYSPASPI | FAB-AZ83 LC-CDR3 (cIAP + AT406) |
| 290 | MSQSSYLI | FAB-AZ84 LC-CDR3 (cIAP + AT406) |
| 291 | AYYYPI | FAB-AZ85 LC-CDR3 (cIAP + AT406) |
| 292 | SYYGSLL | FAB-AZ90 LC-CDR3 (cIAP + AT406) |
| 293 | SLYMPL | FAB-AZ91 LC-CDR3 (cIAP + AT406) |
| 294 | AYTFPV | FAB-AZ93 LC-CDR3 (cIAP + CUDC-427) |
| 295 | YSSSLV | FAB-AZ96 LC-CDR3 (cIAP + CUDC-427) |
| 296 | IRSSPI | FAB-AZ97 LC-CDR3 (cIAP + CUDC-427) |
| 297 | YSYYGLI | FAB-AZ98 LC-CDR3 (cIAP + CUDC-427) |
| 298 | GYSYSLI | FAB-AZ99 LC-CDR3 (cIAP + CUDC-427) |
| 299 | SYWWLV | FAB-AZ100 LC-CDR3 (cIAP + CUDC-427) |
| 300 | SWVYYPI | FAB-AZ101 LC-CDR3 (cIAP + CUDC-427) |
| 301 | SESSPI | FAB-AZ103 LC-CDR3 (cIAP + CUDC-427) |
| 302 | YSYLFLV | FAB-AZ104 LC-CDR3 (cIAP + CUDC-427) |
| 303 | EYGPGLI | FAB-AZ105 LC-CDR3 (cIAP + CUDC-427) |
| 304 | SYSPALV | FAB-AZ107 LC-CDR3 (FKBP + SLF) |
| 305 | YFWWHLI | FAB-AZ108 LC-CDR3 (FKBP + SLF) |
| 306 | YYWSSPL | FAB-AZ109 LC-CDR3 (FKBP + SLF) |
| 307 | WQKWSGLI | FAB-AZ111 LC-CDR3 (FKBP + SLF) |
| 308 | WGSFHSLI | FAB-AZ112 LC-CDR3 (FKBP + SLF) |
| 309 | HYYFYWGPI | FAB-AZ118 LC-CDR3 (Fab + Methotrexate) |
| 310 | RASQSVSSAVA | LC-CDR1 |
| 311 | SASSLYS | LC-CDR2 |
| 312 | EISEVQLVESGGGLVQPGGSLRLSCAASGFNFSSS SIHWVRQAPGKGLEWVASISSSYGYTYYADSVK GRFTISADTSKNTAYLQMNSLRAEDTAVYYCAR TVRGSKKPYFSGWAMDYWGQGTLVTVSSASTK | Heavy Chain Scaffold |

SEQUENCE LISTING

| SEQ ID NO | Sequence | Description |
|---|---|---|
|  | GPSVFPLAPSSKSTSGGTAALGCLVKDYFPEPVT VSWNSGALTSGVHTFPAVLQSSGLYSLSSVVTVP SSSLGTQTYICNVNHKPSNTKVDKKVEPKSCDKT HTGGSHHHHHH |  |
| 313 | SDIQMTQSPSSLSASVGDRVTITCRASQSVSSAVA WYQQKPGKAPKLLIYSASSLYSGVPSRFSGSRSG TDFTLTISSLQPEDFATYYCQQSSYSLITFGQGTK VEIKRTVAAPSVFIFPPSDSQLKSGTASVVCLLNN FYPREAKVQWKVDNALQSGNSQESVTEQDSKDS TYSLSSTLTLSKADYEKHKVYACEVTHQGLSSPV TKSFNRGECGGSDYKDDDDK | Light Chain Scaffold |
| 314 | SQSNRELVVDFLSYKLSQKGYSWSQFSDVEENR TEAPEGTESEMETPSAINGNPSWHLADSPAVNGA TGHSSSLDAREVIPMAAVKQALREAGDEFELRY RRAFSDLTSQLHITPGTAYQSFEQVVNELFRDGV NWGRIVAFFSFGGALCVESVDKEMQVLVSRIAA WMATYLNDHLEPWIQENGGWDTFVELYGNNAA AESRKGQERFNRWFL | ABT-737-binding domain of Bcl-xL |
| 315 | AHAGRTGYDNREIVMKYIHYKLSQRGYEWDAG DVGAAPPGAAPAPGIFSSQPGHTPHPAASRDPVA RTSPLQTPAAPGAAAGPALSPVPPVVHLTLRQAG DDFSRRYRRDFAEMSSQLHLTPFTARGRFATVVE ELFRDGVNWGRIVAFFEFGGVMCVESVNREMSP LVDNIALWMTEYLNRHLHTWIQDNGGWDAFVE LYGPSMR | ABT-199/263-binding domain of Bcl-2 |
| 316 | GVQVETISPGDGRTFPKRGQTCVVHYTGMLEDG KKFDSSRDRNKPFKFMLGKQEVIRGWEEGVAQ MSVGQRAKLTISPDYAYGATGHPGIIPPHATLVF DVELLKLE | SLF-binding domain of FKBP |
| 317 | SLETLRFSISNLSMQTHAARMRTFMYWPSSVPVQ PEQLASAGFYYVGRNDDVKCFCCDGGLRCWES GDDPWVEHAKWFPRCEFLIRMKGQEFVDEIQGR YPHLLEQLLSTS | Smac mimetic-binding domain of cIAP1 |
| 318 | GFSITSPY | anti-Methotrexate Fab, HC-CDR1 |
| 319 | SYRGS | anti-Methotrexate Fab, HC-CDR2 |
| 320 | YGNYGAY | anti-Methotrexate Fab, HC-CDR3 |
| 321 | RSSQSIVHSNGNTYLE | anti-Methotrexate Fab, LC-CDR1 |
| 322 | KVSTRFS | anti-Methotrexate Fab, LC-CDR2 |
| 323 | FQGSHVPLT | anti-Methotrexate Fab, LC-CDR3 |
| 324 | GQVGRQLAIIGDDINR | Bak peptide |
| 325 | GGGGS | Gly4Ser |

What is claimed is:

1. A system comprising:
   (a) a first chemically-induced dimer (CID) component comprising (i) a first binding moiety that is a protein capable of interacting with a small molecule to form a complex; and (ii) a first adapter moiety linked to the first binding moiety; and
   (b) a second CID component comprising (i) a second binding moiety that is a protein that binds to the complex between the small molecule and the first binding moiety at a site of the complex comprising at least a portion of the small molecule and a portion of the first binding moiety; and (ii) a second adapter moiety linked to the second binding moiety;
   wherein the binding of the second binding moiety to the complex between the small molecule and the first binding moiety creates a dimer between the second CID component and the first CID component,
   wherein the first adapter moiety comprises a T cell antigen-binding moiety and the second adapter moiety comprises a target cell antigen-binding moiety; or the second adapter moiety comprises a T cell antigen-binding moiety and the first adapter moiety comprises a target cell antigen-binding moiety,
   wherein the target cell antigen-binding moiety is an extracellular antigen-binding moiety,
   wherein the first CID component comprises an ABT-199 binding domain comprising the amino acid sequence of SEQ ID NO:315; and
   wherein the second CID component comprises an antibody moiety comprising three heavy chain complementarity determining regions (CDRs) and three light chain CDRs of an antibody clone selected from antibody clone FAB-AZ11, FAB-AZ12, FAB-AZ13, FAB-AZ14, FAB-AZ15, FAB-AZ16, FAB-AZ17, FAB-AZ18, FAB-AZ19, FAB-AZ20, FAB-AZ21, FAB-AZ22, FAB-AZ23, FAB-AZ24, FAB-AZ25, FAB-AZ26, FAB-AZ27, FAB-AZ28, FAB-AZ29, FAB-AZ30, FAB-AZ31, FAB-AZ32, FAB-AZ33, FAB-AZ34, FAB-AZ35, FAB-AZ36, FAB-AZ37, FAB-AZ38, FAB-AZ39, FAB-AZ40, FAB-AZ41, FAB-AZ42, and FAB-AZ43.

2. The system of claim 1, wherein the second binding moiety binds to the complex between the small molecule and the first binding moiety with a dissociation constant (Kd) no more than ½₅₀ its Kd for each of an unbound form of the small molecule and an unbound form of the first binding moiety.

3. The system of claim 1, wherein the first binding moiety is a naturally occurring binding partner of the small molecule.

4. The system of claim 1, wherein when the second CID component and the first CID component are dimerized in the presence of the small molecule, the dimer formed is capable of binding a T cell and a target cell and redirecting the T cell to the target cell.

5. The system of claim 4, wherein the dimer formed is capable of modulating an immune response to the target cell.

6. The system of claim 4, wherein the T cell antigen is CD3.

7. The system of claim 1, wherein the first adapter moiety comprises the T cell antigen-binding moiety, and the second adapter moiety comprises the target cell antigen-binding moiety.

8. The system of claim 1, wherein the second adapter moiety comprises the T cell antigen-binding moiety, and the first adapter moiety comprises the target cell antigen-binding moiety.

9. The system of claim 1, wherein the second binding moiety is an antibody moiety.

10. A system comprising:
(a) a first chemically-induced dimer (CID) component comprising (i) a first binding moiety that is a protein capable of interacting with a small molecule to form a complex; and (ii) a first adapter moiety linked to the first binding moiety; and
(b) a second CID component comprising (i) a second binding moiety that is an antibody moiety that binds to the complex between the small molecule and the first binding moiety at a site of the complex comprising at least a portion of the small molecule and a portion of the first binding moiety; and (ii) a second adapter moiety linked to the second binding moiety;
wherein the binding of the second binding moiety to the complex between the small molecule and the first binding moiety creates a dimer between the second CID component and the first CID component,
wherein the first adapter moiety comprises a T cell antigen-binding moiety and the second adapter moiety comprises a target cell antigen-binding moiety; or the second adapter moiety comprises a T cell antigen-binding moiety and the first adapter moiety comprises a target cell antigen-binding moiety,
wherein the target cell antigen-binding moiety binds to a target antigen expressed on the surface of a target cell wherein the first CID component comprises an ABT-199 binding domain comprising the amino acid sequence of SEQ ID NO:315; and
wherein the second CID component comprises an antibody moiety comprising three heavy chain complementarity determining regions (CDRs) and three light chain CDRs of an antibody clone selected from antibody clone FAB-AZ11, FAB-AZ12, FAB-AZ13, FAB-AZ14, FAB-AZ15, FAB-AZ16, FAB-AZ17, FAB-AZ18, FAB-AZ19, FAB-AZ20, FAB-AZ21, FAB-AZ22, FAB-AZ23, FAB-AZ24, FAB-AZ25, FAB-AZ26, FAB-AZ27, FAB-AZ28, FAB-AZ29, FAB-AZ30, FAB-AZ31, FAB-AZ32, FAB-AZ33, FAB-AZ34, FAB-AZ35, FAB-AZ36, FAB-AZ37, FAB-AZ38, FAB-AZ39, FAB-AZ40, FAB-AZ41, FAB-AZ42, and FAB-AZ43.

11. A system comprising:
(a) a first chemically-induced dimer (CID) component comprising (i) a first binding moiety that is a protein capable of interacting with a small molecule to form a complex; and (ii) a first adapter moiety linked to the first binding moiety; and
(b) a second CID component comprising (i) a second binding moiety that is an antibody moiety that binds to the complex between the small molecule and the first binding moiety at a site of the complex comprising at least a portion of the small molecule and a portion of the first binding moiety; and (ii) a second adapter moiety linked to the second binding moiety;
wherein the binding of the second binding moiety to the complex between the small molecule and the first binding moiety creates a dimer between the second CID component and the first CID component,
wherein the first adapter moiety comprises a T cell antigen-binding moiety and the second adapter moiety comprises a target cell antigen-binding moiety; or the second adapter moiety comprises a T cell antigen-binding moiety and the first adapter moiety comprises a target cell antigen-binding moiety,
wherein the first CID component comprises an ABT-199 binding domain comprising the amino acid sequence of SEQ ID NO:315; and
wherein the second CID component comprises an antibody moiety comprising three heavy chain complementarity determining regions (CDRs) and three light chain CDRs of an antibody clone selected from antibody clone FAB-AZ11, FAB-AZ 12, FAB-AZ 13, FAB-AZ 14, FAB-AZ 15, FAB-AZ 16, FAB-AZ17, FAB-AZ18, FAB-AZ19, FAB-AZ20, FAB-AZ21, FAB-AZ22, FAB-AZ23, FAB-AZ24, FAB-AZ25, FAB-AZ26, FAB-AZ27, FAB-AZ28, FAB-AZ29, FAB-AZ30, FAB-AZ31, FAB-AZ32, FAB-AZ33, FAB-AZ34, FAB-AZ35, FAB-AZ36, FAB-AZ37, FAB-AZ38, FAB-AZ39, FAB-AZ40, FAB-AZ41, FAB-AZ42, and FAB-AZ43.

* * * * *

SEQUENCE LISTING

<160> NUMBER OF SEQ ID NOS: 325

<210> SEQ ID NO 1
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 1

Leu Ser Tyr Ser Ser Met
1               5

```
<210> SEQ ID NO 2
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 2

Ile Tyr Ser Tyr Tyr Met
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 3

Ile Tyr Tyr Ser Tyr Met
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 4

Ile Tyr Ser Ser Ser Ile
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 5

Leu Tyr Tyr Tyr Tyr Ile
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 6

Leu Ser Tyr Ser Tyr Ile
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 7

Leu Ser Ser Tyr Ser Met
1               5
```

```
<210> SEQ ID NO 8
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 8

Ile Ser Tyr Ser Ser Ile
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 9

Leu Tyr Tyr Ser Ser Ile
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 10

Leu Tyr Ser Tyr Ser Met
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 11

Ile Tyr Tyr Tyr Ser Met
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 12

Leu Tyr Tyr Ser Ser Met
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 13

Phe Ser Ser Ser Ser Ile
1               5
```

```
<210> SEQ ID NO 14
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 14

Leu Tyr Tyr Tyr Ser Met
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 15

Leu Tyr Tyr Tyr Tyr Met
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 16

Ile Ser Tyr Tyr Ser Met
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 17

Leu Ser Ser Ser Ser Met
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 18

Ile Ser Tyr Tyr Tyr Ile
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 19

Leu Tyr Tyr Tyr Ser Ile
1               5

<210> SEQ ID NO 20
```

```
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 20

Ile Tyr Ser Tyr Tyr Ile
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 21

Ile Tyr Tyr Ser Ser Ile
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 22

Ile Tyr Ser Ser Ser Met
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 23

Ile Tyr Tyr Ser Ser Met
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 24

Leu Tyr Tyr Ser Tyr Met
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 25

Leu Ser Ser Ser Tyr Ile
1               5

<210> SEQ ID NO 26
<211> LENGTH: 6
```

```
<212> TYPE: PRT
<213> ORGANISM: Artificial Sequence
<220> FEATURE:
<223> OTHER INFORMATION: Synthetic polypeptide

<400> SEQUENCE: 26

Phe Ser Tyr Ser Ser Ile
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 27

Phe Ser Tyr Tyr Ser Ile
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 28

Ile Ser Ser Ser Tyr Ile
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 29

Val Tyr Tyr Tyr Tyr Ile
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 30

Val Ser Tyr Tyr Ser Ile
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 31

Val Ser Tyr Ser Ser Ile
1               5

<210> SEQ ID NO 32
<211> LENGTH: 6
<212> TYPE: PRT
```

```
<213> ORGANISM: Artificial Sequence
<220> FEATURE:
<223> OTHER INFORMATION: Synthetic polypeptide

<400> SEQUENCE: 32

Val Tyr Ser Tyr Ser Ile
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 33

Val Ser Ser Ser Tyr Ile
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 34

Ile Tyr Tyr Tyr Tyr Ile
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 35

Val Ser Ser Tyr Ser Ile
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 36

Ile Ser Ser Tyr Ser Ile
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 37

Leu Ser Ser Ser Ser Ile
1               5

<210> SEQ ID NO 38
<211> LENGTH: 6
<212> TYPE: PRT
<213> ORGANISM: Artificial Sequence
```

```
<220> FEATURE:
<223> OTHER INFORMATION: Synthetic polypeptide

<400> SEQUENCE: 38

Val Tyr Tyr Ser Ser Ile
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 39

Val Tyr Tyr Ser Tyr Ile
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 40

Phe Tyr Tyr Ser Ser Ile
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 41

Phe Tyr Ser Ser Ile
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 42

Phe Ser Ser Tyr Ser Ile
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 43

Val Ser Ser Ser Ser Ile
1               5

<210> SEQ ID NO 44
<211> LENGTH: 6
<212> TYPE: PRT
<213> ORGANISM: Artificial Sequence
<220> FEATURE:
```

```
<223> OTHER INFORMATION: Synthetic polypeptide

<400> SEQUENCE: 44

Phe Ser Ser Ser Tyr Ile
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 45

Val Tyr Tyr Tyr Ser Ile
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 46

Phe Ser Tyr Tyr Tyr Ile
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 47

Val Tyr Ser Ser Ser Ile
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 48

Phe Tyr Ser Ser Ser Ile
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 49

Phe Tyr Tyr Ser Tyr Ile
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic polypeptide
```

<400> SEQUENCE: 50

Ile Tyr Tyr Tyr Ser Ile
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 51

Ile Tyr Tyr Tyr Phe Ile
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 52

Ile Ser Ser Ser Ser Ile
1               5

<210> SEQ ID NO 53
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 53

Ser Ile Ser Pro Tyr Ser Ser Tyr Thr Ser
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 54

Tyr Ile Ser Pro Tyr Tyr Ser Tyr Thr Ser
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 55

Ser Ile Tyr Pro Tyr Tyr Gly Tyr Thr Tyr
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic polypeptide

```
<400> SEQUENCE: 56

Ser Ile Tyr Pro Ser Tyr Gly Ser Thr Tyr
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 57

Ser Ile Tyr Ser Ser Ser Gly Ser Thr Tyr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 58

Ser Ile Tyr Ser Tyr Tyr Gly Ser Thr Ser
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 59

Ser Ile Ser Ser Tyr Tyr Gly Ser Thr Ser
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 60

Ser Ile Ser Ser Ser Tyr Gly Tyr Thr Tyr
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 61

Ser Ile Ser Ser Tyr Tyr Ser Ser Thr Tyr
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 62
```

```
Ser Ile Tyr Pro Tyr Tyr Ser Tyr Thr Tyr
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 63

Ser Ile Tyr Pro Tyr Tyr Gly Tyr Thr Ser
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 64

Ser Ile Ser Ser Tyr Tyr Gly Tyr Thr Ser
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 65

Ser Ile Ser Ser Tyr Ser Gly Tyr Thr Ser
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 66

Ser Ile Tyr Ser Tyr Tyr Gly Tyr Thr Tyr
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 67

Ser Ile Ser Pro Ser Tyr Gly Tyr Thr Ser
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 68
```

Tyr Ile Ser Ser Tyr Ser Ser Tyr Thr Tyr
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 69

Tyr Ile Ser Pro Tyr Ser Gly Tyr Thr Ser
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 70

Ser Ile Tyr Ser Ser Tyr Ser Tyr Thr Ser
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 71

Ser Ile Ser Ser Ser Ser Gly Tyr Thr Ser
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 72

Ser Ile Ser Pro Tyr Ser Ser Tyr Thr Tyr
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 73

Ser Ile Ser Pro Tyr Tyr Gly Tyr Thr Ser
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 74

Ser Ile Ser Ser Tyr Tyr Ser Tyr Thr Tyr

```
1               5                   10
```

<210> SEQ ID NO 75
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 75

```
Ser Ile Ser Ser Tyr Ser Gly Ser Thr Ser
1               5                   10
```

<210> SEQ ID NO 76
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 76

```
Tyr Ile Ser Ser Tyr Ser Gly Tyr Thr Tyr
1               5                   10
```

<210> SEQ ID NO 77
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 77

```
Ser Ile Tyr Pro Tyr Tyr Ser Ser Thr Tyr
1               5                   10
```

<210> SEQ ID NO 78
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 78

```
Tyr Ile Tyr Ser Tyr Tyr Gly Tyr Thr Ser
1               5                   10
```

<210> SEQ ID NO 79
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 79

```
Tyr Ile Ser Ser Tyr Tyr Ser Ser Thr Tyr
1               5                   10
```

<210> SEQ ID NO 80
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 80

```
Ser Ile Ser Ser Tyr Tyr Gly Tyr Thr Tyr
1               5                   10
```

```
<210> SEQ ID NO 81
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 81

Ser Ile Tyr Ser Tyr Tyr Gly Ser Thr Tyr
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 82

Ser Ile Ser Ser Ser Ser Gly Ser Thr Ser
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 83

Ser Ile Tyr Pro Tyr Ser Gly Tyr Thr Ser
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 84

Ser Ile Ser Ser Tyr Tyr Gly Ser Thr Tyr
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 85

Ser Ile Tyr Ser Ser Tyr Gly Tyr Thr Tyr
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 86

Ser Ile Ser Ser Tyr Ser Gly Tyr Thr Tyr
1               5                   10
```

<210> SEQ ID NO 87
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 87

Ser Ile Ser Ser Tyr Ser Ser Tyr Thr Ser
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 88

Ser Ile Tyr Ser Tyr Ser Gly Tyr Thr Ser
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 89

Tyr Ile Ser Ser Tyr Ser Gly Tyr Thr Ser
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 90

Ser Ile Ser Ser Ser Ser Gly Tyr Thr Tyr
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 91

Ser Ile Ser Pro Tyr Tyr Ser Ser Thr Ser
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 92

Ser Ile Tyr Pro Ser Tyr Ser Tyr Thr Ser
1               5                   10

```
<210> SEQ ID NO 93
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 93

Ser Ile Tyr Pro Ser Tyr Gly Tyr Thr Ser
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 94

Ser Ile Tyr Ser Tyr Tyr Gly Tyr Thr Ser
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 95

Ser Ile Ser Ser Ser Tyr Ser Tyr Thr Ser
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 96

Ser Ile Ser Ser Ser Tyr Gly Tyr Thr Ser
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 97

Ser Ile Tyr Ser Ser Tyr Gly Ser Thr Tyr
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 98

Ser Ile Ser Pro Tyr Tyr Gly Ser Thr Tyr
1               5                   10

<210> SEQ ID NO 99
```

```
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 99

Ser Ile Tyr Pro Ser Ser Gly Tyr Thr Tyr
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 100

Ser Ile Tyr Ser Tyr Ser Ser Ser Thr Tyr
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 101

Ser Ile Ser Ser Ser Tyr Gly Ser Thr Ser
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 102

Ser Ile Ser Pro Ser Ser Gly Ser Thr Ser
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 103

Ser Ile Ser Pro Tyr Ser Gly Ser Thr Ser
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 104

Tyr Ile Tyr Ser Ser Ser Gly Tyr Thr Tyr
1               5                   10

<210> SEQ ID NO 105
<211> LENGTH: 10
```

```
<212> TYPE: PRT
<213> ORGANISM: Artificial Sequence
<220> FEATURE:
<223> OTHER INFORMATION: Synthetic polypeptide

<400> SEQUENCE: 105

Ser Ile Tyr Ser Tyr Ser Gly Ser Thr Ser
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 106

Ser Ile Ser Pro Ser Tyr Gly Ser Thr Ser
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 107

Ser Ile Tyr Ser Ser Tyr Gly Tyr Thr Ser
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 108

Ser Ile Tyr Pro Ser Ser Gly Tyr Thr Ser
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 109

Tyr Ile Ser Pro Ser Ser Gly Tyr Thr Tyr
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 110

Ser Ile Ser Ser Ser Tyr Gly Ser Thr Tyr
1               5                   10

<210> SEQ ID NO 111
<211> LENGTH: 10
<212> TYPE: PRT
```

```
<213> ORGANISM: Artificial Sequence
<220> FEATURE:
<223> OTHER INFORMATION: Synthetic polypeptide

<400> SEQUENCE: 111

Tyr Ile Tyr Pro Tyr Ser Gly Ser Thr Ser
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 112

Tyr Ile Ser Ser Tyr Tyr Gly Ser Thr Tyr
1               5                   10

<210> SEQ ID NO 113
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 113

Gly Trp Val Gly Met
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 114

Gly Tyr Pro Trp Tyr Gly Met
1               5

<210> SEQ ID NO 115
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 115

Tyr Gly Tyr Ser Tyr Tyr Tyr Tyr Gly Ala Leu
1               5                   10

<210> SEQ ID NO 116
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 116

Ser Trp Trp Pro Tyr Gly Met
1               5

<210> SEQ ID NO 117
<211> LENGTH: 13
<212> TYPE: PRT
<213> ORGANISM: Artificial Sequence
```

```
<220> FEATURE:
<223> OTHER INFORMATION: Synthetic polypeptide

<400> SEQUENCE: 117

Ala Ser Val Trp Phe Gly Trp Tyr Val Pro Ser Ala Met
1               5                   10

<210> SEQ ID NO 118
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 118

Gly Ser His Ala His Gly Trp Ala Trp Phe Trp Tyr Gly Met
1               5                   10

<210> SEQ ID NO 119
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 119

Tyr Ser Pro Trp Val Tyr Tyr Pro Tyr Tyr Gly Trp Tyr Ser Gly Met
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 120

Thr Val Arg Gly Ser Lys Lys Pro Tyr Phe Ser Gly Trp Ala Met
1               5                   10                  15

<210> SEQ ID NO 121
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 121

Ser His Ala Trp Gly Trp Val Tyr Ser Tyr Gly Met
1               5                   10

<210> SEQ ID NO 122
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 122

Ser Tyr Gly Tyr Trp Trp Gly Val Tyr Tyr Ser Val Ala Leu
1               5                   10

<210> SEQ ID NO 123
<211> LENGTH: 17
<212> TYPE: PRT
<213> ORGANISM: Artificial Sequence
<220> FEATURE:
```

```
<223> OTHER INFORMATION: Synthetic polypeptide

<400> SEQUENCE: 123

Pro Ser Ser Gly Tyr Tyr Trp Gly Ser His Gly Tyr Tyr Gly Val Ala
1               5                   10                  15
Ile

<210> SEQ ID NO 124
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 124

His Ser Tyr Trp Tyr Ala Cys Ser Ala Met
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 125

Ser Tyr Val His Pro Tyr Tyr Trp Ser Tyr Tyr Ala Met
1               5                   10

<210> SEQ ID NO 126
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 126

Tyr Ser Gly Ser Ser Gly Gly Ser Trp Phe Tyr Trp Gly Leu
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 127

Ser Ser Val Tyr Trp Tyr Tyr Val Tyr Ser Gly Met
1               5                   10

<210> SEQ ID NO 128
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 128

Gly Tyr Tyr Ser Gly Ser Trp Trp Ser Tyr Tyr Pro Ala Phe
1               5                   10

<210> SEQ ID NO 129
<211> LENGTH: 8
<212> TYPE: PRT
<213> ORGANISM: Artificial Sequence
```

```
<220> FEATURE:
<223> OTHER INFORMATION: Synthetic polypeptide

<400> SEQUENCE: 129

Gly Tyr Trp Ser Phe Tyr Gly Met
1               5

<210> SEQ ID NO 130
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 130

Ser Gly Tyr His Ala Val Tyr Tyr Gly Tyr Tyr Ser Tyr Pro Trp Ser
1               5                   10                  15

Leu

<210> SEQ ID NO 131
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 131

Gly Gly Tyr Gly Phe Trp Gly Trp Trp Ala Leu
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 132

Ala Tyr Gly Tyr Trp Trp Ser Tyr Pro Gly Ala Phe
1               5                   10

<210> SEQ ID NO 133
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 133

Ala Val His Tyr Trp Ser His Ala Ala His Tyr Gly Met
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 134

His Ser Tyr Trp Tyr Ala Ser Ser Ala Met
1               5                   10

<210> SEQ ID NO 135
<211> LENGTH: 3
<212> TYPE: PRT
```

```
<213> ORGANISM: Artificial Sequence
<220> FEATURE:
<223> OTHER INFORMATION: Synthetic polypeptide

<400> SEQUENCE: 135

Ser Gly Phe
1

<210> SEQ ID NO 136
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 136

Ser Phe Trp Tyr Tyr Ala Leu
1               5

<210> SEQ ID NO 137
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 137

Gly Gly Trp Phe Trp Gly Ser Gly Gly Tyr Ser Ser Ala Phe
1               5                   10

<210> SEQ ID NO 138
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 138

Gly Gly Trp Tyr Trp Ala Ser Gly Ser Tyr Tyr Gly Ala Met
1               5                   10

<210> SEQ ID NO 139
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 139

Ser Gly Gly Ser Gly Met
1               5

<210> SEQ ID NO 140
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 140

Gly Ser Ala Tyr Tyr Gly Tyr Gly Gly Trp Tyr Ser Ser Val Gly
1               5                   10                  15

Tyr Ala Ile

<210> SEQ ID NO 141
<211> LENGTH: 11
```

```
<212> TYPE: PRT
<213> ORGANISM: Artificial Sequence
<220> FEATURE:
<223> OTHER INFORMATION: Synthetic polypeptide

<400> SEQUENCE: 141

Val Pro Ser Tyr Phe Tyr Ala Ser Tyr Gly Met
1               5                   10

<210> SEQ ID NO 142
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 142

Thr Tyr Trp Ser Tyr Met Gly Leu Tyr Ser Pro Ala Met
1               5                   10

<210> SEQ ID NO 143
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 143

Tyr His Gln Tyr Ala Gly Met
1               5

<210> SEQ ID NO 144
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 144

Thr Tyr Tyr Ser Gly Tyr Tyr Ser Tyr Phe Trp Ser Ala Leu
1               5                   10                  15

<210> SEQ ID NO 145
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 145

Tyr Tyr Met Ser Trp Trp Gly Met
1               5

<210> SEQ ID NO 146
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 146

Ser Tyr His Tyr Ser Trp Ala Met
1               5

<210> SEQ ID NO 147
<211> LENGTH: 13
<212> TYPE: PRT
```

```
<213> ORGANISM: Artificial Sequence
<220> FEATURE:
<223> OTHER INFORMATION: Synthetic polypeptide

<400> SEQUENCE: 147

Ser Trp Gly Met Trp Tyr Tyr Trp Gln Trp Pro Ala Ile
1               5                   10

<210> SEQ ID NO 148
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 148

Ser Asn Gly Thr Trp Glu Trp Trp Ser Trp Trp Ala Leu
1               5                   10

<210> SEQ ID NO 149
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 149

Ser Trp Val Arg Lys Trp Gly Gly Tyr Ala Trp Ser Val Asp Tyr Gly
1               5                   10                  15

Gly Met

<210> SEQ ID NO 150
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 150

Gly Asn Gly Met Tyr Trp Ala Ile
1               5

<210> SEQ ID NO 151
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 151

Tyr Met Gly Gly Trp Tyr Ser Tyr Met Glu Asn His Gln Trp Pro Glu
1               5                   10                  15

Ala Leu

<210> SEQ ID NO 152
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 152

Tyr Tyr Tyr Glu Gly Gly Met
1               5
```

-continued

```
<210> SEQ ID NO 153
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 153

Gln Asp His Trp Tyr Tyr Tyr Gln Trp Pro Ala Ile
1               5                   10

<210> SEQ ID NO 154
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 154

Ala Ser Tyr Tyr Tyr Ala Met
1               5

<210> SEQ ID NO 155
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 155

Ser Tyr Asp Thr Trp Tyr Trp Trp Gln Tyr Phe Ala Leu
1               5                   10

<210> SEQ ID NO 156
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 156

Tyr Ser Tyr Ser Pro Gly Met
1               5

<210> SEQ ID NO 157
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 157

Gly Tyr Trp Pro Ala Leu
1               5

<210> SEQ ID NO 158
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 158

Ser Trp Gly Gln Trp Tyr Trp Tyr Gln Tyr Tyr Gly Phe
1               5                   10

<210> SEQ ID NO 159
```

```
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 159

Tyr Tyr Tyr Gln Gly Leu
1               5

<210> SEQ ID NO 160
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 160

Trp Tyr Thr Tyr Ala His Ser Tyr Tyr Tyr Leu Met Tyr Tyr Gly Ser
1               5                   10                  15

Gly Met

<210> SEQ ID NO 161
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 161

Ser Tyr Ser Tyr Trp Ala Tyr Phe Ser Tyr Gly Met
1               5                   10

<210> SEQ ID NO 162
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 162

Tyr Met Tyr Tyr Tyr Ala Gly Trp Lys Tyr Tyr Ser Tyr Gly Gly Phe
1               5                   10                  15

Asn

<210> SEQ ID NO 163
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 163

Trp His Tyr Trp Val His Tyr Ile Ser Gly Leu
1               5                   10

<210> SEQ ID NO 164
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 164

Leu Asn Tyr Tyr Asn Thr Tyr Tyr Leu Lys Tyr Tyr Tyr Gly Ser Ala
1               5                   10                  15
```

Leu

<210> SEQ ID NO 165
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 165

Ser Ser Gly Tyr Arg Tyr Tyr Trp Lys Trp Gly Val Trp Ser Tyr Asn
1               5                   10                  15

Ala Ile

<210> SEQ ID NO 166
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 166

Tyr Gly Tyr Gly Gly Trp Ser Gly Tyr Phe Asp Ile Tyr Ala Leu
1               5                   10                  15

<210> SEQ ID NO 167
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 167

Gln Trp Pro Tyr Leu Tyr Tyr Tyr Trp Gly Gly Leu
1               5                   10

<210> SEQ ID NO 168
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 168

Gly Ser Glu Trp Ser Tyr Ser Gly Ser Trp Ala Pro Tyr Gly Tyr Gly
1               5                   10                  15

Gly Leu

<210> SEQ ID NO 169
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 169

Phe Leu Tyr Tyr Trp His Trp Met Tyr Lys Tyr Pro Trp Met Ser Gly
1               5                   10                  15

Met

<210> SEQ ID NO 170
<211> LENGTH: 13
<212> TYPE: PRT
<213> ORGANISM: Artificial Sequence

```
<220> FEATURE:
<223> OTHER INFORMATION: Synthetic polypeptide

<400> SEQUENCE: 170

Tyr Ile Gln Tyr Gly Tyr Leu Tyr His Lys Tyr Gly Ile
1               5                   10

<210> SEQ ID NO 171
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 171

Ser Ser Tyr Ser Trp Tyr Trp Tyr Tyr Gln Arg Leu Trp Tyr Ser
1               5                   10                  15

Ala Met

<210> SEQ ID NO 172
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 172

Trp Asn Gly Ala Trp Tyr Ser Tyr Gln Gly Gln Trp Glu Ser Ile Gly
1               5                   10                  15

Gly Met

<210> SEQ ID NO 173
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 173

Gly Tyr Phe Trp Pro Tyr Tyr Tyr Gln Trp His Tyr Glu Tyr Ser Val
1               5                   10                  15

Ala Leu

<210> SEQ ID NO 174
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 174

Ser Phe Tyr Asp Val Trp Tyr Gly Tyr Tyr Tyr Met Leu Gly Leu
1               5                   10                  15

<210> SEQ ID NO 175
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 175

Ser Thr Phe Ser Phe Tyr His Ser Phe Trp Tyr Pro Ala Tyr Thr Gly
1               5                   10                  15
```

Gly Met

<210> SEQ ID NO 176
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 176

Ser Ser Tyr Ser Val Tyr Trp Ala Ile
1               5

<210> SEQ ID NO 177
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 177

Ser Ile His Tyr Tyr Ser Tyr Gln Gln His Tyr Tyr Ile Pro Lys Pro
1               5                   10                  15

Tyr Ala Phe

<210> SEQ ID NO 178
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 178

Tyr Gly Trp Arg Tyr Trp Trp Trp Ser Gln Lys Tyr Tyr Val Ser Glu
1               5                   10                  15

Lys Gly Phe

<210> SEQ ID NO 179
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 179

Ser Tyr Pro Val Thr Trp Gly Gly Tyr Pro Ala Tyr Gly Met
1               5                   10

<210> SEQ ID NO 180
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 180

Glu Ser Trp Tyr His Tyr Trp Gly Met Gly Phe Ala Tyr Ala Gly Ile
1               5                   10                  15

<210> SEQ ID NO 181
<211> LENGTH: 14
<212> TYPE: PRT
<213> ORGANISM: Artificial Sequence
<220> FEATURE:
<223> OTHER INFORMATION: Synthetic polypeptide

```
<400> SEQUENCE: 181

Tyr Tyr Tyr Tyr Phe Ser Gly Tyr Gln Tyr Met Tyr Gly Leu
1               5                   10

<210> SEQ ID NO 182
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 182

Tyr Ala Trp Tyr Val Tyr Ala Trp Tyr Arg Tyr Trp Glu Ala Gln Ala
1               5                   10                  15

Met

<210> SEQ ID NO 183
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 183

Ala Ser Tyr Tyr Tyr Arg Trp Trp Gly Trp Tyr Asp Tyr Gly Trp Ala
1               5                   10                  15

Leu

<210> SEQ ID NO 184
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 184

Trp Gly Trp Ser Arg Tyr Gly Ser Ser Gly Gly Phe
1               5                   10

<210> SEQ ID NO 185
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 185

Gln Phe Trp His Phe Met Ser Lys Gly Gln Trp Tyr His Gln Ala Met
1               5                   10                  15

<210> SEQ ID NO 186
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 186

Gly Ser Leu Trp Ile Ser Trp Tyr Ile Tyr Tyr Gln Met Gly Val
1               5                   10                  15

Gly Phe

<210> SEQ ID NO 187
<211> LENGTH: 14
```

<212> TYPE: PRT
<213> ORGANISM: Artificial Sequence
<220> FEATURE:
<223> OTHER INFORMATION: Synthetic polypeptide

<400> SEQUENCE: 187

Gly Gly Tyr Tyr Tyr Ser Glu Ser Arg Tyr Gly Phe Gly Phe
1               5                   10

<210> SEQ ID NO 188
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 188

Tyr Thr Tyr Tyr Val Lys Trp Ala Tyr Tyr Trp Ser Phe Tyr Thr Ser
1               5                   10                  15

Gly Leu

<210> SEQ ID NO 189
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 189

Ser Ala Trp Tyr Tyr Ile His Gly Gly Tyr Gly Trp Ala Phe
1               5                   10

<210> SEQ ID NO 190
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 190

Gln Pro Tyr Tyr Tyr Tyr Gln Met Ser Tyr His Tyr Gly Gly Leu
1               5                   10                  15

<210> SEQ ID NO 191
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 191

Tyr Tyr His Tyr Met Tyr Ser Tyr Ser Ser Lys Lys Tyr Ser Tyr Tyr
1               5                   10                  15

Ala Met

<210> SEQ ID NO 192
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 192

Glu Met Tyr Phe Tyr Lys Trp Ser Trp Tyr His Tyr Val Ser Tyr Asp
1               5                   10                  15

Gly Leu

<210> SEQ ID NO 193
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 193

Pro Gly Tyr Ser Gly Trp Tyr Trp His His Gly Phe
1               5                   10

<210> SEQ ID NO 194
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 194

Gly Ser His Tyr Leu Tyr Tyr Tyr Trp Tyr Tyr Lys Tyr Gly Ser
1               5                   10                  15

Ala Leu

<210> SEQ ID NO 195
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 195

Tyr Glu Tyr Tyr Tyr Trp Tyr Met Ser Val Ser Arg Tyr Tyr Leu Met
1               5                   10                  15

Ala Ala Leu

<210> SEQ ID NO 196
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 196

Asn Ser Leu Tyr Met His Trp Ser Trp Asn Gly Tyr Tyr Phe Ser Ser
1               5                   10                  15

Gly Met

<210> SEQ ID NO 197
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 197

Ser Gly Ser Gly Tyr Glu Trp Tyr Trp Met Gly Met
1               5                   10

<210> SEQ ID NO 198
<211> LENGTH: 18
<212> TYPE: PRT
<213> ORGANISM: Artificial Sequence
<220> FEATURE:

```
<223> OTHER INFORMATION: Synthetic polypeptide

<400> SEQUENCE: 198

Tyr Ser Tyr Thr Tyr Tyr Trp Gly Phe Gln Lys Tyr Tyr Ser Glu Tyr
1               5                   10                  15

Gly Met

<210> SEQ ID NO 199
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 199

Met Tyr Pro Trp Tyr Tyr Thr Tyr Pro Trp Gly Phe
1               5                   10

<210> SEQ ID NO 200
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 200

Tyr Gln Leu Tyr Glu Arg Tyr Trp Tyr Tyr Ser Trp Pro Gly Gly Leu
1               5                   10                  15

<210> SEQ ID NO 201
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 201

Ser Ser Gly Tyr Gly Ser Lys Tyr Gly Tyr Tyr Ser Gly Met
1               5                   10

<210> SEQ ID NO 202
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 202

Glu Phe Trp Tyr Tyr Ile Tyr Arg Asp Phe Tyr Met Leu Leu Ser Gly
1               5                   10                  15

Leu

<210> SEQ ID NO 203
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 203

Tyr Arg Tyr Glu Tyr Gln Trp Arg Gly Trp Tyr Tyr Val Ser Phe Glu
1               5                   10                  15

Ala Met
```

-continued

```
<210> SEQ ID NO 204
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 204

Tyr Asn Tyr Tyr Gly Tyr Ser Ala Glu Gly Trp Ile Tyr Pro Gly Ser
1               5                   10                  15

Ala Met

<210> SEQ ID NO 205
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 205

Gly Ser Trp Tyr Ser His Tyr Tyr Glu Tyr Tyr Tyr Gln Tyr Gly Trp
1               5                   10                  15

Ala Met

<210> SEQ ID NO 206
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 206

Glu Gly Tyr Tyr Tyr Phe Trp Ser Tyr Tyr Phe Tyr Ser Ser Tyr Tyr
1               5                   10                  15

Ala Leu

<210> SEQ ID NO 207
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 207

Met Tyr His Tyr Phe Gly Ala Ser Gly Trp Tyr Met Arg Tyr Pro Gln
1               5                   10                  15

Gly Ile

<210> SEQ ID NO 208
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 208

Tyr Trp Gly Trp Glu Gly Met
1               5

<210> SEQ ID NO 209
<211> LENGTH: 6
<212> TYPE: PRT
<213> ORGANISM: Artificial Sequence
<220> FEATURE:
<223> OTHER INFORMATION: Synthetic polypeptide
```

```
<400> SEQUENCE: 209

Tyr Trp Tyr Ser Ala Leu
1               5

<210> SEQ ID NO 210
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 210

Ser Pro Ser Tyr Tyr Trp Trp Tyr Arg Trp Tyr Tyr Gly His Ala
1               5                   10                  15

Ala Phe

<210> SEQ ID NO 211
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 211

Tyr Pro Tyr Trp Gly Ser Val His Gly Ile Gly Trp Thr Tyr Tyr Trp
1               5                   10                  15

Ala Leu

<210> SEQ ID NO 212
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 212

Gly Pro Gly Tyr Trp His Tyr Ser Tyr Tyr Phe Tyr Glu Ser Phe Ser
1               5                   10                  15

Ala Leu

<210> SEQ ID NO 213
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 213

Ser Tyr Ala Ser Gly Leu
1               5

<210> SEQ ID NO 214
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 214

Tyr Tyr Trp Gly Phe Pro Ser Leu Phe
1               5

<210> SEQ ID NO 215
```

```
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 215

Val Ser Trp Ala Tyr Pro Tyr Leu Ile
1               5

<210> SEQ ID NO 216
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 216

Gly Trp Ser Gly Pro Trp Leu Ile
1               5

<210> SEQ ID NO 217
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 217

Val Pro Ala Phe Pro Ile
1               5

<210> SEQ ID NO 218
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 218

Trp Pro Gly Trp Tyr Pro Ile
1               5

<210> SEQ ID NO 219
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 219

Ser Ser Tyr Ser Leu Ile
1               5

<210> SEQ ID NO 220
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 220

Ser Gly Trp Phe Phe Pro Phe
1               5

<210> SEQ ID NO 221
<211> LENGTH: 9
```

```
<212> TYPE: PRT
<213> ORGANISM: Artificial Sequence
<220> FEATURE:
<223> OTHER INFORMATION: Synthetic polypeptide

<400> SEQUENCE: 221

Ser Tyr Tyr Tyr Tyr Ser Gly Pro Ile
1               5

<210> SEQ ID NO 222
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 222

Ser Tyr Tyr Phe Tyr Ser Gly Pro Ile
1               5

<210> SEQ ID NO 223
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 223

Tyr Gly Val Trp Ala Phe Leu Ile
1               5

<210> SEQ ID NO 224
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 224

Ser Ala Ser Ser Trp Leu Ile
1               5

<210> SEQ ID NO 225
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 225

Gly Val Ser Trp Phe Phe Ser Pro Ile
1               5

<210> SEQ ID NO 226
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 226

Ser Tyr Gly Trp Pro Trp Tyr Pro Phe
1               5

<210> SEQ ID NO 227
<211> LENGTH: 8
<212> TYPE: PRT
```

<213> ORGANISM: Artificial Sequence
<220> FEATURE:
<223> OTHER INFORMATION: Synthetic polypeptide

<400> SEQUENCE: 227

Ser Gly Ser Trp Gly Phe Leu Ile
1               5

<210> SEQ ID NO 228
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 228

Ser Trp Trp Tyr Tyr Pro Phe
1               5

<210> SEQ ID NO 229
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 229

Ser Trp Ala Gly Tyr Pro Ile
1               5

<210> SEQ ID NO 230
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 230

Tyr Gly Gly Ala Leu Ile
1               5

<210> SEQ ID NO 231
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 231

Ser Ser Ser Pro Phe
1               5

<210> SEQ ID NO 232
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 232

Trp Trp Phe Pro Ile
1               5

<210> SEQ ID NO 233
<211> LENGTH: 7
<212> TYPE: PRT
<213> ORGANISM: Artificial Sequence

```
<220> FEATURE:
<223> OTHER INFORMATION: Synthetic polypeptide

<400> SEQUENCE: 233

Tyr Tyr Ala His Tyr Leu Phe
1               5

<210> SEQ ID NO 234
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 234

Gly Gly Val Leu Ile
1               5

<210> SEQ ID NO 235
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 235

Tyr Pro Ser Gly Leu Ile
1               5

<210> SEQ ID NO 236
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 236

Tyr Ser Gly Trp Gly Phe Leu Ile
1               5

<210> SEQ ID NO 237
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 237

Ser Ser Gly Tyr Tyr Pro Ile
1               5

<210> SEQ ID NO 238
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 238

Ser Trp Tyr Ser Leu Ile
1               5

<210> SEQ ID NO 239
<211> LENGTH: 9
<212> TYPE: PRT
<213> ORGANISM: Artificial Sequence
<220> FEATURE:
```

<223> OTHER INFORMATION: Synthetic polypeptide

<400> SEQUENCE: 239

Tyr Ala Ser Trp Tyr Gly Ala Leu Ile
1               5

<210> SEQ ID NO 240
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 240

Ser His Ala Tyr Tyr Pro Phe
1               5

<210> SEQ ID NO 241
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 241

Ser His Tyr Tyr Gly Phe Leu Ile
1               5

<210> SEQ ID NO 242
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 242

His His Ser Leu Ile
1               5

<210> SEQ ID NO 243
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 243

Ala Ser Pro Trp Gly Phe Leu Ile
1               5

<210> SEQ ID NO 244
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 244

Ser Ser His Tyr Gly Trp Leu Ile
1               5

<210> SEQ ID NO 245
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 245

Tyr Gly Tyr Ser Val Leu Ile
1               5

<210> SEQ ID NO 246
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 246

Trp Ser Tyr Pro Tyr Ser Leu Ile
1               5

<210> SEQ ID NO 247
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 247

Ser Tyr Tyr Ala Leu Ile
1               5

<210> SEQ ID NO 248
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 248

Tyr Trp Phe Tyr Ser Ser Pro Ile
1               5

<210> SEQ ID NO 249
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 249

Pro Ser Tyr Trp Gly Phe Leu Ile
1               5

<210> SEQ ID NO 250
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 250

Tyr Tyr Glu Ser Pro Ile
1               5

<210> SEQ ID NO 251
<211> LENGTH: 6
<212> TYPE: PRT
<213> ORGANISM: Artificial Sequence
<220> FEATURE:
<223> OTHER INFORMATION: Synthetic polypeptide

```
<400> SEQUENCE: 251

Ser Ser Trp Gln Pro Phe
1               5

<210> SEQ ID NO 252
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 252

Gly Trp Arg Gly Ser Leu Val
1               5

<210> SEQ ID NO 253
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 253

Ser Ser Ser Ser Leu Ile
1               5

<210> SEQ ID NO 254
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 254

Ser Gln Tyr Trp Tyr Leu Phe
1               5

<210> SEQ ID NO 255
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 255

Tyr Trp His Tyr Ser Leu Ile
1               5

<210> SEQ ID NO 256
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 256

Ser Tyr Tyr Pro Met Pro Phe
1               5

<210> SEQ ID NO 257
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 257
```

```
Ser Phe Phe Tyr Leu Ile
1               5

<210> SEQ ID NO 258
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 258

Ser Gly Tyr Tyr Leu Ile
1               5

<210> SEQ ID NO 259
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 259

Met Trp Asp Leu Ser Leu Ile
1               5

<210> SEQ ID NO 260
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 260

Ser Gln Arg Trp Tyr Leu Ile
1               5

<210> SEQ ID NO 261
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 261

Tyr Tyr Tyr Pro Phe Leu Ile
1               5

<210> SEQ ID NO 262
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 262

Tyr Tyr Tyr Trp Tyr Leu Ile
1               5

<210> SEQ ID NO 263
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 263
```

```
Ser Tyr Tyr His Leu Phe
1               5

<210> SEQ ID NO 264
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 264

Ser Tyr Ala Trp His Leu Ile
1               5

<210> SEQ ID NO 265
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 265

Tyr Gly Trp Leu Ser Pro Ile
1               5

<210> SEQ ID NO 266
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 266

Ser Tyr Ser Ser Ser Pro Val
1               5

<210> SEQ ID NO 267
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 267

Tyr Gln Leu Trp Tyr Leu Ile
1               5

<210> SEQ ID NO 268
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 268

Gly Ser Ser Thr Pro Ile
1               5

<210> SEQ ID NO 269
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 269

Ser Gly Ser Val Asn Gly Leu Ile
```

```
1               5

<210> SEQ ID NO 270
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 270

Ser Asp Ile Tyr Tyr Pro Leu
1               5

<210> SEQ ID NO 271
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 271

Val Gly Gly Gly Leu Ile
1               5

<210> SEQ ID NO 272
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 272

Glu Tyr Trp Asp Leu Ile
1               5

<210> SEQ ID NO 273
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 273

Ser Gly Met His Gln Leu Ile
1               5

<210> SEQ ID NO 274
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 274

Tyr Tyr Tyr Trp Pro Ile
1               5

<210> SEQ ID NO 275
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 275

Asn Ser Ser Ser Ser Pro Ile
1               5
```

<210> SEQ ID NO 276
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 276

Tyr Ser Tyr Ser Ser Leu Ile
1               5

<210> SEQ ID NO 277
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 277

Ser Ser Asn Phe Trp Ser Pro Val
1               5

<210> SEQ ID NO 278
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 278

Ser Tyr Tyr Met Tyr Pro Ile
1               5

<210> SEQ ID NO 279
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 279

Ser Ser Tyr Tyr Pro Ile
1               5

<210> SEQ ID NO 280
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 280

Ser Phe Phe Gly Pro Val
1               5

<210> SEQ ID NO 281
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 281

Ser Tyr Tyr Gly Val Ser Pro Ile
1               5

```
<210> SEQ ID NO 282
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 282

Pro Gly Ser Ser Ser Pro Ile
1               5

<210> SEQ ID NO 283
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 283

Ser Tyr Trp Phe Pro Ile
1               5

<210> SEQ ID NO 284
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 284

Gly Ser Phe Tyr Gly Asp Leu Ile
1               5

<210> SEQ ID NO 285
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 285

Tyr Trp Tyr Trp Arg Pro Leu
1               5

<210> SEQ ID NO 286
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 286

Ser Gly Ser Asn Ser Leu Ile
1               5

<210> SEQ ID NO 287
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 287

Gly Ser Glu Tyr Leu Ile
1               5
```

```
<210> SEQ ID NO 288
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 288

Ser Ser Gly Ser Pro Leu
1               5

<210> SEQ ID NO 289
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 289

Gln Tyr Ser Pro Ala Ser Pro Ile
1               5

<210> SEQ ID NO 290
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 290

Met Ser Gln Ser Ser Tyr Leu Ile
1               5

<210> SEQ ID NO 291
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 291

Ala Tyr Tyr Tyr Pro Ile
1               5

<210> SEQ ID NO 292
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 292

Ser Tyr Tyr Gly Ser Leu Leu
1               5

<210> SEQ ID NO 293
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 293

Ser Leu Tyr Met Pro Leu
1               5

<210> SEQ ID NO 294
```

```
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 294

Ala Tyr Thr Phe Pro Val
1               5

<210> SEQ ID NO 295
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 295

Tyr Ser Ser Ser Leu Val
1               5

<210> SEQ ID NO 296
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 296

Ile Arg Ser Ser Pro Ile
1               5

<210> SEQ ID NO 297
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 297

Tyr Ser Tyr Tyr Gly Leu Ile
1               5

<210> SEQ ID NO 298
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 298

Gly Tyr Ser Tyr Ser Leu Ile
1               5

<210> SEQ ID NO 299
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 299

Ser Tyr Trp Trp Leu Val
1               5

<210> SEQ ID NO 300
<211> LENGTH: 7
```

```
<212> TYPE: PRT
<213> ORGANISM: Artificial Sequence
<220> FEATURE:
<223> OTHER INFORMATION: Synthetic polypeptide

<400> SEQUENCE: 300

Ser Trp Val Tyr Tyr Pro Ile
1               5

<210> SEQ ID NO 301
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 301

Ser Glu Ser Ser Pro Ile
1               5

<210> SEQ ID NO 302
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 302

Tyr Ser Tyr Leu Phe Leu Val
1               5

<210> SEQ ID NO 303
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 303

Glu Tyr Gly Pro Gly Leu Ile
1               5

<210> SEQ ID NO 304
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 304

Ser Tyr Ser Pro Ala Leu Val
1               5

<210> SEQ ID NO 305
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 305

Tyr Phe Trp Trp His Leu Ile
1               5

<210> SEQ ID NO 306
<211> LENGTH: 7
<212> TYPE: PRT
```

```
<213> ORGANISM: Artificial Sequence
<220> FEATURE:
<223> OTHER INFORMATION: Synthetic polypeptide

<400> SEQUENCE: 306

Tyr Tyr Trp Ser Ser Pro Leu
1               5

<210> SEQ ID NO 307
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 307

Trp Gln Lys Trp Ser Gly Leu Ile
1               5

<210> SEQ ID NO 308
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 308

Trp Gly Ser Phe His Ser Leu Ile
1               5

<210> SEQ ID NO 309
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 309

His Tyr Tyr Phe Tyr Trp Gly Pro Ile
1               5

<210> SEQ ID NO 310
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 310

Arg Ala Ser Gln Ser Val Ser Ser Ala Val Ala
1               5                   10

<210> SEQ ID NO 311
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 311

Ser Ala Ser Ser Leu Tyr Ser
1               5

<210> SEQ ID NO 312
<211> LENGTH: 246
<212> TYPE: PRT
<213> ORGANISM: Artificial Sequence
```

<220> FEATURE:
<223> OTHER INFORMATION: Synthetic polypeptide

<400> SEQUENCE: 312

Glu Ile Ser Glu Val Gln Leu Val Glu Ser Gly Gly Leu Val Gln
1               5                   10                  15

Pro Gly Gly Ser Leu Arg Leu Ser Cys Ala Ala Ser Gly Phe Asn Phe
            20                  25                  30

Ser Ser Ser Ile His Trp Val Arg Gln Ala Pro Gly Lys Gly Leu
        35                  40                  45

Glu Trp Val Ala Ser Ile Ser Ser Tyr Gly Tyr Thr Tyr Tyr Ala
    50                  55                  60

Asp Ser Val Lys Gly Arg Phe Thr Ile Ser Ala Asp Thr Ser Lys Asn
65                  70                  75                  80

Thr Ala Tyr Leu Gln Met Asn Ser Leu Arg Ala Glu Asp Thr Ala Val
                85                  90                  95

Tyr Tyr Cys Ala Arg Thr Val Arg Gly Ser Lys Lys Pro Tyr Phe Ser
            100                 105                 110

Gly Trp Ala Met Asp Tyr Trp Gly Gln Gly Thr Leu Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Gly Gly Ser
225                 230                 235                 240

His His His His His His
                245

<210> SEQ ID NO 313
<211> LENGTH: 226
<212> TYPE: PRT
<213> ORGANISM: Artificial Sequence
<220> FEATURE:
<223> OTHER INFORMATION: Synthetic polypeptide

<400> SEQUENCE: 313

Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Val Ser Ser
            20                  25                  30

Ala Val Ala Trp Tyr Gln Gln Lys Pro Gly Lys Ala Pro Lys Leu Leu
        35                  40                  45

Ile Tyr Ser Ala Ser Ser Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Ser Tyr Ser Leu 85                  90                  95
Ile Thr Phe Gly Gln Gly Thr Lys Val Glu Ile Lys Arg Thr Val Ala
                    100                 105                 110

Ala Pro Ser Val Phe Ile Phe Pro Pro Ser Asp Ser Gln Leu Lys Ser
                115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys Gly Gly Ser Asp Tyr Lys Asp Asp Asp
            210                 215                 220

Asp Lys
225

<210> SEQ ID NO 314
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 314

Ser Gln Ser Asn Arg Glu Leu Val Val Asp Phe Leu Ser Tyr Lys Leu
1               5                   10                  15

Ser Gln Lys Gly Tyr Ser Trp Ser Gln Phe Ser Asp Val Glu Glu Asn
                20                  25                  30

Arg Thr Glu Ala Pro Glu Gly Thr Glu Ser Glu Met Glu Thr Pro Ser
            35                  40                  45

Ala Ile Asn Gly Asn Pro Ser Trp His Leu Ala Asp Ser Pro Ala Val
        50                  55                  60

Asn Gly Ala Thr Gly His Ser Ser Ser Leu Asp Ala Arg Glu Val Ile
65                  70                  75                  80

Pro Met Ala Ala Val Lys Gln Ala Leu Arg Glu Ala Gly Asp Glu Phe
                85                  90                  95

Glu Leu Arg Tyr Arg Arg Ala Phe Ser Asp Leu Thr Ser Gln Leu His
                100                 105                 110

Ile Thr Pro Gly Thr Ala Tyr Gln Ser Phe Glu Gln Val Val Asn Glu
            115                 120                 125

Leu Phe Arg Asp Gly Val Asn Trp Gly Arg Ile Val Ala Phe Phe Ser
        130                 135                 140

Phe Gly Gly Ala Leu Cys Val Glu Ser Val Asp Lys Glu Met Gln Val
145                 150                 155                 160

Leu Val Ser Arg Ile Ala Ala Trp Met Ala Thr Tyr Leu Asn Asp His
                165                 170                 175

Leu Glu Pro Trp Ile Gln Glu Asn Gly Gly Trp Asp Thr Phe Val Glu
                180                 185                 190

Leu Tyr Gly Asn Asn Ala Ala Ala Glu Ser Arg Lys Gly Gln Glu Arg
            195                 200                 205

Phe Asn Arg Trp Phe Leu

<210> SEQ ID NO 315
<211> LENGTH: 206
<212> TYPE: PRT
<213> ORGANISM: Artificial Sequence
<220> FEATURE:
<223> OTHER INFORMATION: Synthetic polypeptide

<400> SEQUENCE: 315

```
Ala His Ala Gly Arg Thr Gly Tyr Asp Asn Arg Glu Ile Val Met Lys
1               5                   10                  15

Tyr Ile His Tyr Lys Leu Ser Gln Arg Gly Tyr Glu Trp Asp Ala Gly
            20                  25                  30

Asp Val Gly Ala Ala Pro Pro Gly Ala Ala Pro Ala Pro Gly Ile Phe
        35                  40                  45

Ser Ser Gln Pro Gly His Thr Pro His Pro Ala Ala Ser Arg Asp Pro
    50                  55                  60

Val Ala Arg Thr Ser Pro Leu Gln Thr Pro Ala Ala Pro Gly Ala Ala
65                  70                  75                  80

Ala Gly Pro Ala Leu Ser Pro Val Pro Pro Val Val His Leu Thr Leu
                85                  90                  95

Arg Gln Ala Gly Asp Asp Phe Ser Arg Arg Tyr Arg Arg Asp Phe Ala
            100                 105                 110

Glu Met Ser Ser Gln Leu His Leu Thr Pro Phe Thr Ala Arg Gly Arg
        115                 120                 125

Phe Ala Thr Val Val Glu Glu Leu Phe Arg Asp Gly Val Asn Trp Gly
    130                 135                 140

Arg Ile Val Ala Phe Phe Glu Phe Gly Gly Val Met Cys Val Glu Ser
145                 150                 155                 160

Val Asn Arg Glu Met Ser Pro Leu Val Asp Asn Ile Ala Leu Trp Met
                165                 170                 175

Thr Glu Tyr Leu Asn Arg His Leu His Thr Trp Ile Gln Asp Asn Gly
            180                 185                 190

Gly Trp Asp Ala Phe Val Glu Leu Tyr Gly Pro Ser Met Arg
        195                 200                 205
```

<210> SEQ ID NO 316
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 316

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95
```

```
Leu Val Phe Asp Val Glu Leu Leu Lys Leu Glu
            100                 105
```

<210> SEQ ID NO 317
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 317

```
Ser Leu Glu Thr Leu Arg Phe Ser Ile Ser Asn Leu Ser Met Gln Thr
1               5                   10                  15

His Ala Ala Arg Met Arg Thr Phe Met Tyr Trp Pro Ser Ser Val Pro
            20                  25                  30

Val Gln Pro Glu Gln Leu Ala Ser Ala Gly Phe Tyr Tyr Val Gly Arg
        35                  40                  45

Asn Asp Asp Val Lys Cys Phe Cys Cys Asp Gly Gly Leu Arg Cys Trp
    50                  55                  60

Glu Ser Gly Asp Asp Pro Trp Val Glu His Ala Lys Trp Phe Pro Arg
65                  70                  75                  80

Cys Glu Phe Leu Ile Arg Met Lys Gly Gln Gly Phe Val Asp Glu Ile
                85                  90                  95

Gln Gly Arg Tyr Pro His Leu Leu Glu Gln Leu Leu Ser Thr Ser
            100                 105                 110
```

<210> SEQ ID NO 318
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 318

```
Gly Phe Ser Ile Thr Ser Pro Tyr
1               5
```

<210> SEQ ID NO 319
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 319

```
Ser Tyr Arg Gly Ser
1               5
```

<210> SEQ ID NO 320
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 320

```
Tyr Gly Asn Tyr Gly Ala Tyr
1               5
```

<210> SEQ ID NO 321
<211> LENGTH: 16
<212> TYPE: PRT
<213> ORGANISM: Artificial Sequence
<220> FEATURE:

-continued

```
<223> OTHER INFORMATION: Synthetic polypeptide

<400> SEQUENCE: 321

Arg Ser Ser Gln Ser Ile Val His Ser Asn Gly Asn Thr Tyr Leu Glu
1               5                   10                  15

<210> SEQ ID NO 322
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 322

Lys Val Ser Thr Arg Phe Ser
1               5

<210> SEQ ID NO 323
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 323

Phe Gln Gly Ser His Val Pro Leu Thr
1               5

<210> SEQ ID NO 324
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 324

Gly Gln Val Gly Arg Gln Leu Ala Ile Ile Gly Asp Asp Ile Asn Arg
1               5                   10                  15

<210> SEQ ID NO 325
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 325

Gly Gly Gly Gly Ser
1               5
```